US012766192B2

(12) United States Patent
Fan et al.

(10) Patent No.: US 12,766,192 B2
(45) Date of Patent: Oct. 20, 2026

(54) ANTIBODIES AND CHIMERIC ANTIGEN RECEPTORS TARGETING GLYPICAN-3 (GPC3) AND METHODS OF USE THEREOF

(71) Applicants: Legend Biotech Ireland Limited, Dublin (IE); Legend Biotech USA Inc., Somerset, NJ (US)

(72) Inventors: Xiaohu Fan, Edmonton (CA); Jie Mao, Nanjing (CN); Qiuchuan Zhuang, Nanjing (CN); Ruixue Wang, Nanjing (CN)

(73) Assignees: Legend Biotech Ireland Limited, Dublin (IE); Legend Biotech USA Inc.

( * ) Notice: Subject to any disclaimer, the term of this patent is extended or adjusted under 35 U.S.C. 154(b) by 1064 days.

(21) Appl. No.: 17/798,541

(22) PCT Filed: Feb. 26, 2021

(86) PCT No.: PCT/CN2021/078203
§ 371 (c)(1),
(2) Date: Aug. 9, 2022

(87) PCT Pub. No.: WO2021/170100
PCT Pub. Date: Sep. 2, 2021

(65) Prior Publication Data

US 2023/0088461 A1 Mar. 23, 2023

(30) Foreign Application Priority Data

Feb. 27, 2020 (WO) ................ PCT/CN2020/076937

(51) Int. Cl.
*A61K 40/11* (2025.01)
*A61K 40/31* (2025.01)
(Continued)

(52) U.S. Cl.
CPC .............. *A61K 40/11* (2025.01); *A61K 40/31* (2025.01); *A61K 40/4261* (2025.01); *A61P 35/00* (2018.01)

(58) Field of Classification Search
CPC .... A61K 40/11; A61K 40/31; A61K 40/4261; A61K 2039/868; A61K 35/17;
(Continued)

(56) References Cited

U.S. PATENT DOCUMENTS 7,803,533 B2 9/2010 Nishimura et al.
8,497,355 B2 7/2013 Igawa et al.
(Continued)

FOREIGN PATENT DOCUMENTS

CN 105949324 9/2016
CN 106749675 5/2017
(Continued)

OTHER PUBLICATIONS

Koenig P, Lee CV, Walters BT, et al. Mutational landscape of antibody variable domains reveals a switch modulating the interdomain conformational dynamics and antigen binding. Proc Natl Acad Sci U S A. 2017;114(4):E486-E495. (Year: 2017).*
(Continued)

*Primary Examiner* — Joanne Hama
*Assistant Examiner* — Hannah Sunshine
(74) *Attorney, Agent, or Firm* — Fish & Richardson P.C.

(57) ABSTRACT

Provided are anti-glypican-3 (GPC3) antibodies or antigen binding fragments thereof, and a chimeric antigen receptor (CAR) that binds glypican-3 (GPC3) containing an anti-GPC3 antibody in an extracellular domain, a transmembrane domain, and an intracellular signaling domain. Immune effector cells transduced with the disclosed CAR constructs can be used for cancer immunotherapy.

23 Claims, 26 Drawing Sheets

Specification includes a Sequence Listing.

(51) Int. Cl.
*A61K 40/42* (2025.01)
*A61P 35/00* (2006.01)

(58) Field of Classification Search
CPC ............ A61K 39/001174; A61P 35/00; C07K 2317/24; C07K 2317/92; C07K 14/52; C07K 14/5434; C07K 14/7051; C07K 2317/622; C07K 2319/92; C07K 2317/565; C07K 2319/03; C07K 16/303; C07K 2317/73; C07K 2319/00; G01N 33/53; G01N 2333/4722; G01N 33/68
See application file for complete search history.

(56) References Cited

U.S. PATENT DOCUMENTS

| | | | |
|---|---|---|---|
| 11,819,553 B2 * | 11/2023 | Biechele | A61P 35/00 |
| 2007/0154964 A1 | 7/2007 | Wang et al. | |
| 2015/0147330 A1 | 5/2015 | Ho et al. | |
| 2017/0281683 A1 | 10/2017 | Heczey et al. | |
| 2019/0359698 A1 | 11/2019 | Tamada et al. | |

FOREIGN PATENT DOCUMENTS

| | | | |
|---|---|---|---|
| CN | 107428833 A | 12/2017 |
| CN | 107982538 | 5/2018 |
| CN | 109385400 | 2/2019 |
| CN | 109970859 | 7/2019 |
| CN | 110177876 | 8/2019 |
| CN | 110684120 | 1/2020 |
| CN | 111925445 | 11/2020 |
| CN | 112175085 | 1/2021 |
| EP | 2216046 A2 | 8/2010 |
| EP | 3825404 A1 | 5/2021 |
| JP | 2009-232848 A | 10/2009 |
| JP | 2017-522861 A | 8/2017 |
| KR | 20050020806 A | 3/2005 |
| WO | WO 2012145469 | 10/2012 |
| WO | WO 2013070468 | 5/2013 |
| WO | WO 2013181543 | 12/2013 |
| WO | WO 2014180306 | 11/2014 |
| WO | WO 2015179658 A2 | 11/2015 |
| WO | WO 2016036973 | 3/2016 |
| WO | WO 2016049459 | 3/2016 |
| WO | WO 2016086813 | 6/2016 |
| WO | WO 2017020812 | 2/2017 |
| WO | WO 2017041749 | 3/2017 |
| WO | WO 2017186121 | 11/2017 |
| WO | WO 2017196847 | 11/2017 |
| WO | WO 2018018958 | 2/2018 |
| WO | WO 2018059549 A1 | 4/2018 |
| WO | WO 2018131586 | 7/2018 |
| WO | WO 2018200586 A1 | 11/2018 |
| WO | WO 2019161174 A1 | 8/2019 |
| WO | WO 2020017479 | 1/2020 |
| WO | WO 2020017479 A1 | 1/2020 |
| WO | WO 2020118634 | 6/2020 |

OTHER PUBLICATIONS

Rabia LA, Desai AA, Jhajj HS, Tessier PM. Understanding and overcoming trade-offs between antibody affinity, specificity, stability and solubility. Biochem Eng J. Sep. 15, 2018;137:365-374. (Year: 2018).*
Ho et al., "Glypican-3: a new target for cancer immunotherapy," Eur J Cancer, Feb. 2011, 47(3):333-338.
Liu et al., "Armored Inducible Expression of IL-12 Enhances Antitumor Activity of Glypican-3-Targeted Chimeric Antigen Receptor-Engineered T Cells in Hepatocellular Carcinoma," The Journal of Immunology, May 29, 2019, 203(1): 198- 207 (including Supplementary materials).
PCT International Preliminary Report on Patentability in International Appln. No. PCT/CN2021/078203, mailed on Sep. 9, 2022, 7 pages.
PCT International Search Report and Written Opinion in International Appln. No. PCT/CN2021/078203, mailed on May 26, 2021, 13 pages.
Shirakawa et al., "Glypican-3 expression is correlated with poor prognosis in hepatocellular carcinoma," Cancer Sci., Aug. 2009, 100(8):1403-1407.
Adachi et al., "IL-7 and CCL19 expression in CAR-T cells improves immune cell infiltration and CAR-T cell survival in the tumor," Nat Biotechnol, Apr. 2018, Mar. 5, 2018, 36(4):346-351 (Advance Online Publication 13 pages).
Extended European Search Report in European Appln. No. 21759551.1, mailed on Jun. 12, 2024, 22 pages.
Kozani et al., "Recent Advances in Solid Tumor CAR-T Cell Therapy: Driving Tumor Cells From Hero to Zero?," Front Immunol, May 2022, vol. 13, Article 795164, 22 pages.
Ma et al., "Interleukin-23 engineering improves CART cell function in solid tumors," Nat Biotechnology, Apr. 2020, available online Feb. 3, 2020, 38(4):448-459 (Author Manuscript, 34 pages).
Pang et al., "IL-7 and CCL19-secreting CAR-T cell therapy for tumors with positive glypican-3 or mesothelin," J Hematol Oncol, Jul. 29, 2021, 14(1):118, 6 pages.
Partial Supplementary European Search Report in European Appln. No. 21759551.1, mailed on Mar. 22, 2024, 10 pages.
Wu et al., "Advances in immunotherapy for melanoma," Chin J Cell Mol Immunol, Feb. 18, 2016, 32(2):272-279 (with English Abstract).

* cited by examiner

SEQUENCE LISTING

```
<160> NUMBER OF SEQ ID NOS: 152

<210> SEQ ID NO 1
<211> LENGTH: 6
<212> TYPE: PRT
<213> ORGANISM: Artificial Sequence
<220> FEATURE:
<223> OTHER INFORMATION: HCDR1

<400> SEQUENCE: 1

Ser Gly Phe Ser Trp His
1               5


<210> SEQ ID NO 2
<211> LENGTH: 5
<212> TYPE: PRT
<213> ORGANISM: Artificial Sequence
<220> FEATURE:
<223> OTHER INFORMATION: HCDR1

<400> SEQUENCE: 2

Thr Tyr Gly Met Ser
1               5
```

<210> SEQ ID NO 3
<211> LENGTH: 5
<212> TYPE: PRT
<213> ORGANISM: Artificial Sequence
<220> FEATURE:
<223> OTHER INFORMATION: HCDR1

<400> SEQUENCE: 3

Asp Tyr Glu Met His
1               5

<210> SEQ ID NO 4
<211> LENGTH: 5
<212> TYPE: PRT
<213> ORGANISM: Artificial Sequence
<220> FEATURE:
<223> OTHER INFORMATION: HCDR1

<400> SEQUENCE: 4

Ala Tyr Glu Met His
1               5

<210> SEQ ID NO 5
<211> LENGTH: 5
<212> TYPE: PRT
<213> ORGANISM: Artificial Sequence
<220> FEATURE:
<223> OTHER INFORMATION: HCDR1

<400> SEQUENCE: 5

Ala Tyr Glu Met His
1               5

<210> SEQ ID NO 6
<211> LENGTH: 5
<212> TYPE: PRT
<213> ORGANISM: Artificial Sequence
<220> FEATURE:
<223> OTHER INFORMATION: HCDR1

<400> SEQUENCE: 6

Thr Tyr Asp Met Ser
1               5

<210> SEQ ID NO 7
<211> LENGTH: 5
<212> TYPE: PRT
<213> ORGANISM: Artificial Sequence
<220> FEATURE:
<223> OTHER INFORMATION: HCDR1

<400> SEQUENCE: 7

Thr Tyr Asp Met Ser
1               5

<210> SEQ ID NO 8
<211> LENGTH: 5
<212> TYPE: PRT
<213> ORGANISM: Artificial Sequence
<220> FEATURE:
<223> OTHER INFORMATION: HCDR1

<400> SEQUENCE: 8

Thr Tyr Gly Met Ser
1               5

<210> SEQ ID NO 9

<211> LENGTH: 5
<212> TYPE: PRT
<213> ORGANISM: Artificial Sequence
<220> FEATURE:
<223> OTHER INFORMATION: HCDR1

<400> SEQUENCE: 9

Asp Tyr Glu Met His
1               5

<210> SEQ ID NO 10
<211> LENGTH: 5
<212> TYPE: PRT
<213> ORGANISM: Artificial Sequence
<220> FEATURE:
<223> OTHER INFORMATION: HCDR1

<400> SEQUENCE: 10

Val Ser Pro Met Thr
1               5

<210> SEQ ID NO 11
<211> LENGTH: 16
<212> TYPE: PRT
<213> ORGANISM: Artificial Sequence
<220> FEATURE:
<223> OTHER INFORMATION: HCDR2

<400> SEQUENCE: 11

Phe Met Gln Tyr Ser Gly Asn Thr Asn Tyr Asn Pro Ser Leu Lys Ser
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: HCDR2

<400> SEQUENCE: 12

Tyr Ile Ser Ser Gly Gly Ala Thr Thr Tyr Tyr Pro Asp Ser Val Lys
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: HCDR2

<400> SEQUENCE: 13

Ala Ile Asp Pro Glu Thr Gly Ala Thr Ala Tyr Asn Gln Lys Phe Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: HCDR2

<400> SEQUENCE: 14

Gly Ile Asp Pro Glu Thr Gly Asn Thr Ala Tyr Ser Gln Lys Phe Lys
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: HCDR2

<400> SEQUENCE: 15

Gly Ile Asp Pro Glu Thr Gly Asn Thr Ala Tyr Ser Gln Asn Phe Lys
1 5 10 15

Gly

<210> SEQ ID NO 16
<211> LENGTH: 17
<212> TYPE: PRT
<213> ORGANISM: Artificial Sequence
<220> FEATURE:
<223> OTHER INFORMATION: HCDR2

<400> SEQUENCE: 16

Tyr Ile Ser Ser Gly Gly Ala Thr Thr Tyr Tyr Pro Asp Ser Val Lys
1 5 10 15

Gly

<210> SEQ ID NO 17
<211> LENGTH: 17
<212> TYPE: PRT
<213> ORGANISM: Artificial Sequence
<220> FEATURE:
<223> OTHER INFORMATION: HCDR2

<400> SEQUENCE: 17

Tyr Ile Ser Ser Gly Gly Asn Ser Pro Tyr Tyr Pro Gln Thr Val Lys
1 5 10 15

Gly

<210> SEQ ID NO 18
<211> LENGTH: 17
<212> TYPE: PRT
<213> ORGANISM: Artificial Sequence
<220> FEATURE:
<223> OTHER INFORMATION: HCDR2

<400> SEQUENCE: 18

Tyr Ile Ser Ser Gly Gly Ala Asn Thr Tyr Tyr Pro Asp Ser Val Lys
1 5 10 15

Gly

<210> SEQ ID NO 19
<211> LENGTH: 17
<212> TYPE: PRT
<213> ORGANISM: Artificial Sequence
<220> FEATURE:
<223> OTHER INFORMATION: HCDR2

<400> SEQUENCE: 19

Gly Ile Asp Pro Glu Thr Gly Asn Thr Ala Tyr Ser Gln Lys Phe Lys
1 5 10 15

Gly

<210> SEQ ID NO 20
<211> LENGTH: 17
<212> TYPE: PRT
<213> ORGANISM: Artificial Sequence
<220> FEATURE:
<223> OTHER INFORMATION: HCDR2

<400> SEQUENCE: 20

Leu Ile His Pro Tyr Asn Gly Asp Thr Thr Tyr Asn Gln Lys Phe Lys
1 5 10 15

Gly

<210> SEQ ID NO 21
<211> LENGTH: 9
<212> TYPE: PRT
<213> ORGANISM: Artificial Sequence
<220> FEATURE:
<223> OTHER INFORMATION: HCDR3

<400> SEQUENCE: 21

Arg Glu Glu Gly Ala Trp Phe Ala Tyr
1 5

<210> SEQ ID NO 22
<211> LENGTH: 11
<212> TYPE: PRT
<213> ORGANISM: Artificial Sequence
<220> FEATURE:
<223> OTHER INFORMATION: HCDR3

<400> SEQUENCE: 22

Leu Ser Ile Met Ile Arg Gly Trp Phe Ala Tyr
1 5 10

<210> SEQ ID NO 23
<211> LENGTH: 6
<212> TYPE: PRT
<213> ORGANISM: Artificial Sequence
<220> FEATURE:
<223> OTHER INFORMATION: HCDR3

<400> SEQUENCE: 23

Tyr Tyr Ser Phe Ala Tyr
1 5

<210> SEQ ID NO 24
<211> LENGTH: 6
<212> TYPE: PRT
<213> ORGANISM: Artificial Sequence
<220> FEATURE:
<223> OTHER INFORMATION: HCDR3

<400> SEQUENCE: 24

Tyr Tyr Ser Phe Ala Tyr
1 5

<210> SEQ ID NO 25
<211> LENGTH: 6
<212> TYPE: PRT
<213> ORGANISM: Artificial Sequence
<220> FEATURE:
<223> OTHER INFORMATION: HCDR3

<400> SEQUENCE: 25

Tyr Tyr Ser Phe Ala Tyr
1 5

<210> SEQ ID NO 26
<211> LENGTH: 11
<212> TYPE: PRT
<213> ORGANISM: Artificial Sequence
<220> FEATURE:
<223> OTHER INFORMATION: HCDR3

<400> SEQUENCE: 26

Leu Ser Leu Met Ile Arg Gly Trp Phe Ala Tyr
1 5 10

<210> SEQ ID NO 27
<211> LENGTH: 11
<212> TYPE: PRT
<213> ORGANISM: Artificial Sequence
<220> FEATURE:
<223> OTHER INFORMATION: HCDR3

<400> SEQUENCE: 27

Gln Asn Ile Ala Arg Arg Gly Ala Met Asp Phe
1 5 10

<210> SEQ ID NO 28
<211> LENGTH: 11
<212> TYPE: PRT
<213> ORGANISM: Artificial Sequence
<220> FEATURE:
<223> OTHER INFORMATION: HCDR3

<400> SEQUENCE: 28

Leu Ser Thr Leu Val Arg Gly Trp Phe Ala Tyr
1 5 10

<210> SEQ ID NO 29
<211> LENGTH: 6
<212> TYPE: PRT
<213> ORGANISM: Artificial Sequence
<220> FEATURE:
<223> OTHER INFORMATION: HCDR3

<400> SEQUENCE: 29

Tyr Tyr Ser Phe Ala Tyr
1 5

<210> SEQ ID NO 30
<211> LENGTH: 11
<212> TYPE: PRT
<213> ORGANISM: Artificial Sequence
<220> FEATURE:
<223> OTHER INFORMATION: HCDR3

<400> SEQUENCE: 30

Trp Gly Asn Tyr Tyr Pro Tyr Ala Met Asp Tyr
1 5 10

<210> SEQ ID NO 31
<211> LENGTH: 16
<212> TYPE: PRT
<213> ORGANISM: Artificial Sequence
<220> FEATURE:
<223> OTHER INFORMATION: LCDR1

<400> SEQUENCE: 31

Gly Ser Ser Gln Ser Leu Val His Ser Asn Gly Asn Thr Tyr Leu His
1 5 10 15

<210> SEQ ID NO 32
<211> LENGTH: 16
<212> TYPE: PRT
<213> ORGANISM: Artificial Sequence
<220> FEATURE:
<223> OTHER INFORMATION: LCDR1

<400> SEQUENCE: 32

Arg Ser Ser Gln Ser Leu Val His Ser Asn Gly Asn Thr Tyr Leu His
1 5 10 15

<210> SEQ ID NO 33
<211> LENGTH: 16
<212> TYPE: PRT
<213> ORGANISM: Artificial Sequence
<220> FEATURE:
<223> OTHER INFORMATION: LCDR1

<400> SEQUENCE: 33

Arg Ser Ser Gln Ser Phe Val His Ser Asn Gly Asn Thr Tyr Leu Gln
1 5 10 15

<210> SEQ ID NO 34
<211> LENGTH: 16
<212> TYPE: PRT
<213> ORGANISM: Artificial Sequence
<220> FEATURE:
<223> OTHER INFORMATION: LCDR1

<400> SEQUENCE: 34

Arg Ser Ser Gln Thr Ile Val His Ser Asn Gly Asn Thr Tyr Leu Glu
1 5 10 15

<210> SEQ ID NO 35
<211> LENGTH: 16
<212> TYPE: PRT
<213> ORGANISM: Artificial Sequence
<220> FEATURE:
<223> OTHER INFORMATION: LCDR1

<400> SEQUENCE: 35

Arg Ser Ser Gln Thr Ile Val His Ser Asn Gly Asn Thr Tyr Leu Glu
1 5 10 15

<210> SEQ ID NO 36
<211> LENGTH: 16
<212> TYPE: PRT
<213> ORGANISM: Artificial Sequence
<220> FEATURE:
<223> OTHER INFORMATION: LCDR1

<400> SEQUENCE: 36

Arg Ser Ser Gln Ser Leu Val His Ser Asn Gly Asn Thr Tyr Leu His
1 5 10 15

<210> SEQ ID NO 37
<211> LENGTH: 16
<212> TYPE: PRT
<213> ORGANISM: Artificial Sequence
<220> FEATURE:
<223> OTHER INFORMATION: LCDR1

<400> SEQUENCE: 37

Thr Ser Ser Gln Ser Leu Leu His Ser Asn Gly Asn Thr Tyr Leu His
1 5 10 15

<210> SEQ ID NO 38

<211> LENGTH: 16
<212> TYPE: PRT
<213> ORGANISM: Artificial Sequence
<220> FEATURE:
<223> OTHER INFORMATION: LCDR1

<400> SEQUENCE: 38

Arg Ser Ser Gln Ser Leu Val His Ser Asn Gly Asn Thr Tyr Leu His
1 5 10 15

<210> SEQ ID NO 39
<211> LENGTH: 16
<212> TYPE: PRT
<213> ORGANISM: Artificial Sequence
<220> FEATURE:
<223> OTHER INFORMATION: LCDR1

<400> SEQUENCE: 39

Arg Ser Ser Gln Thr Ile Val His Ser Asn Gly Asn Thr Tyr Leu Glu
1 5 10 15

<210> SEQ ID NO 40
<211> LENGTH: 11
<212> TYPE: PRT
<213> ORGANISM: Artificial Sequence
<220> FEATURE:
<223> OTHER INFORMATION: LCDR1

<400> SEQUENCE: 40

Lys Ala Ser Gln Asn Val Arg Ser Thr Val Ala
1 5 10

<210> SEQ ID NO 41
<211> LENGTH: 7
<212> TYPE: PRT
<213> ORGANISM: Artificial Sequence
<220> FEATURE:
<223> OTHER INFORMATION: LCDR2

<400> SEQUENCE: 41

Lys Val Ser Asn Arg Phe Ser
1 5

<210> SEQ ID NO 42
<211> LENGTH: 7
<212> TYPE: PRT
<213> ORGANISM: Artificial Sequence
<220> FEATURE:
<223> OTHER INFORMATION: LCDR2

<400> SEQUENCE: 42

Lys Val Ser Asn Arg Phe Ser
1 5

<210> SEQ ID NO 43
<211> LENGTH: 7
<212> TYPE: PRT
<213> ORGANISM: Artificial Sequence
<220> FEATURE:
<223> OTHER INFORMATION: LCDR2

<400> SEQUENCE: 43

Lys Val Ser Asn Arg Phe Ser
1 5

<210> SEQ ID NO 44
<211> LENGTH: 7

<212> TYPE: PRT
<213> ORGANISM: Artificial Sequence
<220> FEATURE:
<223> OTHER INFORMATION: LCDR2

<400> SEQUENCE: 44

Lys Val Ser Asn Arg Phe Ser
1 5

<210> SEQ ID NO 45
<211> LENGTH: 7
<212> TYPE: PRT
<213> ORGANISM: Artificial Sequence
<220> FEATURE:
<223> OTHER INFORMATION: LCDR2

<400> SEQUENCE: 45

Lys Val Ser Asn Arg Phe Ser
1 5

<210> SEQ ID NO 46
<211> LENGTH: 7
<212> TYPE: PRT
<213> ORGANISM: Artificial Sequence
<220> FEATURE:
<223> OTHER INFORMATION: LCDR2

<400> SEQUENCE: 46

Lys Val Ser Asn Arg Phe Ser
1 5

<210> SEQ ID NO 47
<211> LENGTH: 7
<212> TYPE: PRT
<213> ORGANISM: Artificial Sequence
<220> FEATURE:
<223> OTHER INFORMATION: LCDR2

<400> SEQUENCE: 47

Lys Val Ser Asn Arg Phe Ser
1 5

<210> SEQ ID NO 48
<211> LENGTH: 7
<212> TYPE: PRT
<213> ORGANISM: Artificial Sequence
<220> FEATURE:
<223> OTHER INFORMATION: LCDR2

<400> SEQUENCE: 48

Lys Val Ser Asn Arg Phe Ser
1 5

<210> SEQ ID NO 49
<211> LENGTH: 7
<212> TYPE: PRT
<213> ORGANISM: Artificial Sequence
<220> FEATURE:
<223> OTHER INFORMATION: LCDR2

<400> SEQUENCE: 49

Lys Val Ser Asn Arg Phe Ser
1 5

<210> SEQ ID NO 50
<211> LENGTH: 7
<212> TYPE: PRT

<213> ORGANISM: Artificial Sequence
<220> FEATURE:
<223> OTHER INFORMATION: LCDR2

<400> SEQUENCE: 50

Leu Thr Ser Asn Arg His Thr
1               5

<210> SEQ ID NO 51
<211> LENGTH: 9
<212> TYPE: PRT
<213> ORGANISM: Artificial Sequence
<220> FEATURE:
<223> OTHER INFORMATION: LCDR3

<400> SEQUENCE: 51

Ser Gln Ser Thr His Phe Pro Phe Thr
1               5

<210> SEQ ID NO 52
<211> LENGTH: 9
<212> TYPE: PRT
<213> ORGANISM: Artificial Sequence
<220> FEATURE:
<223> OTHER INFORMATION: LCDR3

<400> SEQUENCE: 52

Ser Gln Ser Thr His Val Pro Tyr Thr
1               5

<210> SEQ ID NO 53
<211> LENGTH: 9
<212> TYPE: PRT
<213> ORGANISM: Artificial Sequence
<220> FEATURE:
<223> OTHER INFORMATION: LCDR3

<400> SEQUENCE: 53

Phe Gln Gly Ser His Val Pro Tyr Thr
1               5

<210> SEQ ID NO 54
<211> LENGTH: 9
<212> TYPE: PRT
<213> ORGANISM: Artificial Sequence
<220> FEATURE:
<223> OTHER INFORMATION: LCDR3

<400> SEQUENCE: 54

Phe Gln Val Ser His Val Pro Tyr Thr
1               5

<210> SEQ ID NO 55
<211> LENGTH: 9
<212> TYPE: PRT
<213> ORGANISM: Artificial Sequence
<220> FEATURE:
<223> OTHER INFORMATION: LCDR3

<400> SEQUENCE: 55

Phe Gln Val Ser His Val Pro Tyr Thr
1               5

<210> SEQ ID NO 56
<211> LENGTH: 9
<212> TYPE: PRT
<213> ORGANISM: Artificial Sequence

<220> FEATURE:
<223> OTHER INFORMATION: LCDR3

<400> SEQUENCE: 56

Ser Gln Ser Thr His Val Pro Tyr Thr
1 5

<210> SEQ ID NO 57
<211> LENGTH: 9
<212> TYPE: PRT
<213> ORGANISM: Artificial Sequence
<220> FEATURE:
<223> OTHER INFORMATION: LCDR3

<400> SEQUENCE: 57

Ser Gln Ser Thr His Val Pro Pro Thr
1 5

<210> SEQ ID NO 58
<211> LENGTH: 9
<212> TYPE: PRT
<213> ORGANISM: Artificial Sequence
<220> FEATURE:
<223> OTHER INFORMATION: LCDR3

<400> SEQUENCE: 58

Ser Gln Ser Thr His Val Pro Tyr Thr
1 5

<210> SEQ ID NO 59
<211> LENGTH: 9
<212> TYPE: PRT
<213> ORGANISM: Artificial Sequence
<220> FEATURE:
<223> OTHER INFORMATION: LCDR3

<400> SEQUENCE: 59

Phe Gln Val Ser His Val Pro Tyr Thr
1 5

<210> SEQ ID NO 60
<211> LENGTH: 9
<212> TYPE: PRT
<213> ORGANISM: Artificial Sequence
<220> FEATURE:
<223> OTHER INFORMATION: LCDR3

<400> SEQUENCE: 60

Leu Gln His Trp Asn Tyr Pro Tyr Thr
1 5

<210> SEQ ID NO 61
<211> LENGTH: 118
<212> TYPE: PRT
<213> ORGANISM: Artificial Sequence
<220> FEATURE:
<223> OTHER INFORMATION: LAb19301 VH

<400> SEQUENCE: 61

Asp Val Gln Leu Gln Glu Ser Gly Pro Asp Leu Val Lys Pro Ser Gln
1 5 10 15

Ser Leu Ser Leu Thr Cys Thr Val Thr Gly Tyr Ser Ile Thr Ser Gly
20 25 30

Phe Ser Trp His Trp Ile Arg Gln Phe Pro Gly His Lys Leu Glu Trp
35 40 45

Met Gly Phe Met Gln Tyr Ser Gly Asn Thr Asn Tyr Asn Pro Ser Leu
    50                  55                  60

Lys Ser Arg Ile Ser Phe Thr Arg Asp Thr Ser Lys Asn Gln Phe Phe
65                  70                  75                  80

Leu Gln Leu Lys Ser Val Thr Pro Glu Asp Thr Ala Thr Tyr Tyr Cys
                85                  90                  95

Ala Arg Arg Glu Glu Gly Ala Trp Phe Ala Tyr Trp Gly Gln Gly Thr
            100                 105                 110

Leu Val Thr Val Ser Ala
        115

<210> SEQ ID NO 62
<211> LENGTH: 120
<212> TYPE: PRT
<213> ORGANISM: Artificial Sequence
<220> FEATURE:
<223> OTHER INFORMATION: LAb19302 VH

<400> SEQUENCE: 62

Ala Val Gln Leu Val Glu Ser Gly Gly Gly Leu Val Arg Pro Gly Gly
1               5                   10                  15

Ser Leu Lys Leu Ser Cys Ala Ala Ser Gly Phe Ala Phe Ser Thr Tyr
            20                  25                  30

Gly Met Ser Trp Val Arg Gln Thr Pro Glu Thr Arg Leu Glu Trp Val
        35                  40                  45

Ala Tyr Ile Ser Ser Gly Gly Ala Thr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Leu Ser Ile Met Ile Arg Gly Trp Phe Ala Tyr Trp Gly Gln
            100                 105                 110

Gly Thr Leu Val Thr Val Ser Ala
        115                 120

<210> SEQ ID NO 63
<211> LENGTH: 115
<212> TYPE: PRT
<213> ORGANISM: Artificial Sequence
<220> FEATURE:
<223> OTHER INFORMATION: LAb19303 VH

<400> SEQUENCE: 63

Gln Val Gln Leu Gln Gln Ser Gly Ala Glu Leu Val Arg Pro Gly Ala
1               5                   10                  15

Ser Val Thr Leu Ser Cys Glu Ala Ser Gly Tyr Thr Phe Asn Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Ala Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Thr Arg Tyr Tyr Ser Phe Ala Tyr Trp Gly Gln Gly Thr Leu Val Thr
            100                 105                 110

```
Val Ser Ala
        115


<210> SEQ ID NO 64
<211> LENGTH: 115
<212> TYPE: PRT
<213> ORGANISM: Artificial Sequence
<220> FEATURE:
<223> OTHER INFORMATION: LAb19304 VH

<400> SEQUENCE: 64

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Ala Tyr
            20                  25                  30

Glu Met His Trp Val Lys Gln Thr Pro Val His Gly Leu Glu Trp Ile
        35                  40                  45

Gly Gly Ile Asp Pro Glu Thr Gly Asn Thr Ala Tyr Ser Gln Lys Phe
    50                  55                  60

Lys Gly Lys Ala Thr Leu Thr Ala Asp Lys Ser Ser Ser Thr Ala Tyr
65                  70                  75                  80

Met Glu Val Arg Ser Leu Thr Ser Glu Asp Ser Ala Val Tyr Tyr Cys
                85                  90                  95

Ser Arg Tyr Tyr Ser Phe Ala Tyr Trp Gly Gln Gly Thr Leu Val Thr
            100                 105                 110

Val Ser Ala
        115


<210> SEQ ID NO 65
<211> LENGTH: 115
<212> TYPE: PRT
<213> ORGANISM: Artificial Sequence
<220> FEATURE:
<223> OTHER INFORMATION: LAb19305 VH

<400> SEQUENCE: 65

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Ala Tyr
            20                  25                  30

Glu Met His Trp Val Lys Gln Thr Pro Val Tyr Gly Leu Glu Trp Ile
        35                  40                  45

Gly Gly Ile Asp Pro Glu Thr Gly Asn Thr Ala Tyr Ser Gln Asn Phe
    50                  55                  60

Lys Gly Lys Ala Thr Leu Thr Ala Asp Lys Ser Ser Ser Thr Ala Tyr
65                  70                  75                  80

Met Glu Val Arg Ser Leu Thr Ser Glu Asp Ser Ala Val Tyr Tyr Cys
                85                  90                  95

Ser Arg Tyr Tyr Ser Phe Ala Tyr Trp Gly Gln Gly Thr Leu Val Thr
            100                 105                 110

Val Ser Ala
        115


<210> SEQ ID NO 66
<211> LENGTH: 120
<212> TYPE: PRT
<213> ORGANISM: Artificial Sequence
<220> FEATURE:
<223> OTHER INFORMATION: LAb19306 VH
```

<400> SEQUENCE: 66

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Thr Tyr
            20                  25                  30

Asp Met Ser Trp Val Arg Gln Thr Pro Glu Arg Arg Leu Glu Trp Val
        35                  40                  45

Ala Tyr Ile Ser Ser Gly Gly Ala Thr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Ser Leu Met Ile Arg Gly Trp Phe Ala Tyr Trp Gly Gln
            100                 105                 110

Gly Thr Leu Val Thr Val Ser Ala
        115                 120
```

<210> SEQ ID NO 67
<211> LENGTH: 120
<212> TYPE: PRT
<213> ORGANISM: Artificial Sequence
<220> FEATURE:
<223> OTHER INFORMATION: LAb19307 VH

<400> SEQUENCE: 67

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Ala Phe Gly Thr Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Asn Ser Pro Tyr Tyr Pro Gln Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gln Asn Ile Ala Arg Arg Gly Ala Met Asp Phe Trp Gly Gln
            100                 105                 110

Gly Ala Ser Val Thr Val Ser Ser
        115                 120
```

<210> SEQ ID NO 68
<211> LENGTH: 120
<212> TYPE: PRT
<213> ORGANISM: Artificial Sequence
<220> FEATURE:
<223> OTHER INFORMATION: LAb19308 VH

<400> SEQUENCE: 68

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ile Thr Tyr
            20                  25                  30

Gly Met Ser Trp Val Arg Gln Thr Pro Glu Lys Arg Leu Glu Trp Val
        35                  40                  45
```

```
Ala Tyr Ile Ser Ser Gly Gly Ala Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Leu Ser Thr Leu Val Arg Gly Trp Phe Ala Tyr Trp Gly Gln
            100                 105                 110

Gly Thr Leu Val Thr Val Ser Ala
        115                 120


<210> SEQ ID NO 69
<211> LENGTH: 115
<212> TYPE: PRT
<213> ORGANISM: Artificial Sequence
<220> FEATURE:
<223> OTHER INFORMATION: LAb19309 VH

<400> SEQUENCE: 69

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Ile Asp Pro Glu Thr Gly Asn Thr Ala Tyr Ser Gln Lys Phe
    50                  55                  60

Lys Gly Lys Ala Thr Leu Thr Ala Asp Lys Ser Ser Ser Thr Ala Tyr
65                  70                  75                  80

Met Glu Val Arg Ser Leu Thr Ser Glu Asp Ser Ala Val Tyr Tyr Cys
                85                  90                  95

Thr Arg Tyr Tyr Ser Phe Ala Tyr Trp Gly Gln Gly Thr Leu Val Thr
            100                 105                 110

Val Ser Ala
        115


<210> SEQ ID NO 70
<211> LENGTH: 120
<212> TYPE: PRT
<213> ORGANISM: Artificial Sequence
<220> FEATURE:
<223> OTHER INFORMATION: LAb19310 VH

<400> SEQUENCE: 70

Glu Val Gln Leu Gln Gln Ser Gly Pro Glu Leu Val Lys Pro Gly Pro
1               5                   10                  15

Ser Leu Lys Ile Ser Cys Lys Ala Ser Gly Tyr Ser Phe Thr Val Ser
            20                  25                  30

Pro Met Thr Trp Val Lys Gln Ser His Gly Lys Asn Leu Glu Trp Ile
        35                  40                  45

Gly Leu Ile His Pro Tyr Asn Gly Asp Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Trp Gly Asn Tyr Tyr Pro Tyr Ala Met Asp Tyr Trp Gly Gln
```

```
            100                 105                 110

Gly Thr Ser Val Thr Val Ser Ser
        115                 120


<210> SEQ ID NO 71
<211> LENGTH: 112
<212> TYPE: PRT
<213> ORGANISM: Artificial Sequence
<220> FEATURE:
<223> OTHER INFORMATION: LAb19301 VL

<400> SEQUENCE: 71

Asp Val Val Met Thr Gln Thr Pro Leu Ser Leu Pro Val Ser Leu Gly
1               5                   10                  15

Asp Gln Ala Ser Ile Ser Cys Gly Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Phe Thr Phe Gly Ser Gly Thr Lys Leu Glu Ile Lys
            100                 105                 110


<210> SEQ ID NO 72
<211> LENGTH: 112
<212> TYPE: PRT
<213> ORGANISM: Artificial Sequence
<220> FEATURE:
<223> OTHER INFORMATION: LAb19302 VL

<400> SEQUENCE: 72

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110


<210> SEQ ID NO 73
<211> LENGTH: 112
<212> TYPE: PRT
<213> ORGANISM: Artificial Sequence
<220> FEATURE:
<223> OTHER INFORMATION: LAb19303 VL

<400> SEQUENCE: 73

Asp Val Leu Met Thr Gln Thr Pro Leu Ser Leu Pro Val Ser Leu Gly
1               5                   10                  15
```

```
Asp Gln Ala Ser Ile Ser Cys Arg Ser Ser Gln Ser Phe Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110


<210> SEQ ID NO 74
<211> LENGTH: 112
<212> TYPE: PRT
<213> ORGANISM: Artificial Sequence
<220> FEATURE:
<223> OTHER INFORMATION: LAb19304 VL

<400> SEQUENCE: 74

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110


<210> SEQ ID NO 75
<211> LENGTH: 112
<212> TYPE: PRT
<213> ORGANISM: Artificial Sequence
<220> FEATURE:
<223> OTHER INFORMATION: LAb19305 VL

<400> SEQUENCE: 75

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
```

100 105 110

<210> SEQ ID NO 76
<211> LENGTH: 112
<212> TYPE: PRT
<213> ORGANISM: Artificial Sequence
<220> FEATURE:
<223> OTHER INFORMATION: LAb19306 VL

<400> SEQUENCE: 76

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Tyr Thr Phe Gly Gly Gly Thr Lys Leu Glu Ile Lys
100 105 110

<210> SEQ ID NO 77
<211> LENGTH: 112
<212> TYPE: PRT
<213> ORGANISM: Artificial Sequence
<220> FEATURE:
<223> OTHER INFORMATION: LAb19307 VL

<400> SEQUENCE: 77

Asp Val Val Leu Thr Gln Ser Pro Leu Ser Gln Pro Val Ser Leu Gly
1 5 10 15

Asp Gln Ala Ser Ile Ser Cys Thr Ser Ser Gln Ser Leu Leu His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Pro Thr Phe Gly Gly Gly Thr Lys Leu Glu Ile Lys
100 105 110

<210> SEQ ID NO 78
<211> LENGTH: 112
<212> TYPE: PRT
<213> ORGANISM: Artificial Sequence
<220> FEATURE:
<223> OTHER INFORMATION: LAb19308 VL

<400> SEQUENCE: 78

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

```
Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110


<210> SEQ ID NO 79
<211> LENGTH: 112
<212> TYPE: PRT
<213> ORGANISM: Artificial Sequence
<220> FEATURE:
<223> OTHER INFORMATION: LAb19309 VL

<400> SEQUENCE: 79

Asp Val Leu Met Thr Gln Thr Pro Leu Ser Leu Pro Val Asn Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110


<210> SEQ ID NO 80
<211> LENGTH: 107
<212> TYPE: PRT
<213> ORGANISM: Artificial Sequence
<220> FEATURE:
<223> OTHER INFORMATION: LAb19310 VL

<400> SEQUENCE: 80

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Ser Thr
            20                  25                  30

Val Ala Trp Tyr Gln Gln Lys Pro Gly Gln Ser Pro Lys Ala Leu Ile
        35                  40                  45

Tyr Leu Thr Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Tyr
                85                  90                  95

Thr Phe Gly Gly Gly Thr Lys Leu Glu Ile Lys
            100                 105
```

<210> SEQ ID NO 81
<211> LENGTH: 248
<212> TYPE: PRT
<213> ORGANISM: Artificial Sequence
<220> FEATURE:
<223> OTHER INFORMATION: LAb19301 scFv

<400> SEQUENCE: 81

```
Asp Val Val Met Thr Gln Thr Pro Leu Ser Leu Pro Val Ser Leu Gly
1               5                   10                  15

Asp Gln Ala Ser Ile Ser Cys Gly Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Phe Thr Phe Gly Ser Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Asp Val Gln Leu Gln Glu Ser Gly Pro Asp Leu Val Lys Pro
    130                 135                 140

Ser Gln Ser Leu Ser Leu Thr Cys Thr Val Thr Gly Tyr Ser Ile Thr
145                 150                 155                 160

Ser Gly Phe Ser Trp His Trp Ile Arg Gln Phe Pro Gly His Lys Leu
                165                 170                 175

Glu Trp Met Gly Phe Met Gln Tyr Ser Gly Asn Thr Asn Tyr Asn Pro
            180                 185                 190

Ser Leu Lys Ser Arg Ile Ser Phe Thr Arg Asp Thr Ser Lys Asn Gln
        195                 200                 205

Phe Phe Leu Gln Leu Lys Ser Val Thr Pro Glu Asp Thr Ala Thr Tyr
    210                 215                 220

Tyr Cys Ala Arg Arg Glu Glu Gly Ala Trp Phe Ala Tyr Trp Gly Gln
225                 230                 235                 240

Gly Thr Leu Val Thr Val Ser Ala
                245
```

<210> SEQ ID NO 82
<211> LENGTH: 250
<212> TYPE: PRT
<213> ORGANISM: Artificial Sequence
<220> FEATURE:
<223> OTHER INFORMATION: LAb19302 scFv

<400> SEQUENCE: 82

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Ala Val Gln Leu Val Glu Ser Gly Gly Gly Leu Val Arg Pro
    130                 135                 140

Gly Gly Ser Leu Lys Leu Ser Cys Ala Ala Ser Gly Phe Ala Phe Ser
145                 150                 155                 160

Thr Tyr Gly Met Ser Trp Val Arg Gln Thr Pro Glu Thr Arg Leu Glu
                165                 170                 175

Trp Val Ala Tyr Ile Ser Ser Gly Gly Ala Thr Thr Tyr Tyr Pro Asp
            180                 185                 190

Ser Val Lys Gly Arg Phe Thr Ile Ser Arg Asp Asn Ala Lys Asn Thr
        195                 200                 205

Leu Tyr Leu Gln Met Ser Ser Leu Lys Ser Glu Asp Thr Ala Met Tyr
    210                 215                 220

Tyr Cys Ala Ser Leu Ser Ile Met Ile Arg Gly Trp Phe Ala Tyr Trp
225                 230                 235                 240

Gly Gln Gly Thr Leu Val Thr Val Ser Ala
                245                 250


<210> SEQ ID NO 83
<211> LENGTH: 245
<212> TYPE: PRT
<213> ORGANISM: Artificial Sequence
<220> FEATURE:
<223> OTHER INFORMATION: LAb19303 scFv

<400> SEQUENCE: 83

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Phe Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Gln Val Gln Leu Gln Gln Ser Gly Ala Glu Leu Val Arg Pro
    130                 135                 140

Gly Ala Ser Val Thr Leu Ser Cys Glu Ala Ser Gly Tyr Thr Phe Asn
145                 150                 155                 160

Asp Tyr Glu Met His Trp Val Lys Gln Thr Pro Val His Gly Leu Glu
                165                 170                 175
```

```
Trp Ile Gly Ala Ile Asp Pro Glu Thr Gly Ala Thr Ala Tyr Asn Gln
            180                 185                 190

Lys Phe Lys Gly Lys Ala Thr Leu Thr Ala Asp Lys Ser Ser Ser Thr
        195                 200                 205

Ala Tyr Met Glu Leu Arg Ser Leu Thr Ser Glu Asp Thr Ala Val Tyr
    210                 215                 220

Tyr Cys Thr Arg Tyr Tyr Ser Phe Ala Tyr Trp Gly Gln Gly Thr Leu
225                 230                 235                 240

Val Thr Val Ser Ala
                245
```

<210> SEQ ID NO 84
<211> LENGTH: 245
<212> TYPE: PRT
<213> ORGANISM: Artificial Sequence
<220> FEATURE:
<223> OTHER INFORMATION: LAb19304 scFv

<400> SEQUENCE: 84

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Gln Val Gln Leu Gln Gln Ser Gly Ala Glu Leu Val Arg Pro
    130                 135                 140

Gly Ala Ser Val Thr Leu Ser Cys Lys Ala Ser Gly Tyr Thr Phe Thr
145                 150                 155                 160

Ala Tyr Glu Met His Trp Val Lys Gln Thr Pro Val His Gly Leu Glu
                165                 170                 175

Trp Ile Gly Gly Ile Asp Pro Glu Thr Gly Asn Thr Ala Tyr Ser Gln
            180                 185                 190

Lys Phe Lys Gly Lys Ala Thr Leu Thr Ala Asp Lys Ser Ser Ser Thr
        195                 200                 205

Ala Tyr Met Glu Val Arg Ser Leu Thr Ser Glu Asp Ser Ala Val Tyr
    210                 215                 220

Tyr Cys Ser Arg Tyr Tyr Ser Phe Ala Tyr Trp Gly Gln Gly Thr Leu
225                 230                 235                 240

Val Thr Val Ser Ala
                245
```

<210> SEQ ID NO 85
<211> LENGTH: 245
<212> TYPE: PRT
<213> ORGANISM: Artificial Sequence
<220> FEATURE:

<223> OTHER INFORMATION: LAb19305 scFv

<400> SEQUENCE: 85

Asp Val Leu Met Thr Gln Thr Pro Leu Ser Leu Pro Val Ser Leu Gly
1 5 10 15

Asp Gln Ala Ser Ile Ser Cys Arg Ser Ser Gln Thr Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Val
85 90 95

Ser His Val Pro Tyr Thr Phe Gly Gly Gly Thr Lys Leu Glu Ile Lys
100 105 110

Gly Ser Thr Ser Gly Ser Gly Lys Pro Gly Ser Gly Glu Gly Ser Thr
115 120 125

Lys Gly Gln Val Gln Leu Gln Gln Ser Gly Ala Glu Leu Val Arg Pro
130 135 140

Gly Ala Ser Val Thr Leu Ser Cys Lys Ala Ser Gly Tyr Thr Phe Thr
145 150 155 160

Ala Tyr Glu Met His Trp Val Lys Gln Thr Pro Val Tyr Gly Leu Glu
165 170 175

Trp Ile Gly Gly Ile Asp Pro Glu Thr Gly Asn Thr Ala Tyr Ser Gln
180 185 190

Asn Phe Lys Gly Lys Ala Thr Leu Thr Ala Asp Lys Ser Ser Ser Thr
195 200 205

Ala Tyr Met Glu Val Arg Ser Leu Thr Ser Glu Asp Ser Ala Val Tyr
210 215 220

Tyr Cys Ser Arg Tyr Tyr Ser Phe Ala Tyr Trp Gly Gln Gly Thr Leu
225 230 235 240

Val Thr Val Ser Ala
245

<210> SEQ ID NO 86
<211> LENGTH: 250
<212> TYPE: PRT
<213> ORGANISM: Artificial Sequence
<220> FEATURE:
<223> OTHER INFORMATION: LAb19306 scFv

<400> SEQUENCE: 86

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

```
Thr His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Glu Val Gln Leu Val Glu Ser Gly Gly Gly Leu Val Lys Pro
    130                 135                 140

Gly Gly Ser Leu Lys Leu Ser Cys Ala Ala Ser Gly Phe Ala Phe Ser
145                 150                 155                 160

Thr Tyr Asp Met Ser Trp Val Arg Gln Thr Pro Glu Arg Arg Leu Glu
                165                 170                 175

Trp Val Ala Tyr Ile Ser Ser Gly Gly Ala Thr Thr Tyr Tyr Pro Asp
            180                 185                 190

Ser Val Lys Gly Arg Phe Thr Ile Ser Arg Asp Asn Ala Lys Asn Thr
        195                 200                 205

Leu Tyr Leu Gln Met Ser Ser Leu Lys Ser Glu Asp Thr Ala Met Tyr
    210                 215                 220

Tyr Cys Ala Arg Leu Ser Leu Met Ile Arg Gly Trp Phe Ala Tyr Trp
225                 230                 235                 240

Gly Gln Gly Thr Leu Val Thr Val Ser Ala
                245                 250


<210> SEQ ID NO 87
<211> LENGTH: 250
<212> TYPE: PRT
<213> ORGANISM: Artificial Sequence
<220> FEATURE:
<223> OTHER INFORMATION: LAb19307 scFv

<400> SEQUENCE: 87

Asp Val Val Leu Thr Gln Ser Pro Leu Ser Gln Pro Val Ser Leu Gly
1               5                   10                  15

Asp Gln Ala Ser Ile Ser Cys Thr Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Glu Val Gln Leu Val Glu Ser Gly Gly Asp Leu Val Lys Pro
    130                 135                 140

Gly Gly Ser Leu Lys Leu Ser Cys Ala Ala Ser Gly Phe Ala Phe Gly
145                 150                 155                 160

Thr Tyr Asp Met Ser Trp Val Arg Gln Thr Pro Glu Lys Arg Leu Glu
                165                 170                 175

Trp Val Ala Tyr Ile Ser Ser Gly Gly Asn Ser Pro Tyr Tyr Pro Gln
            180                 185                 190

Thr Val Lys Gly Arg Phe Thr Ile Ser Arg Asp Asn Ala Lys Asn Thr
        195                 200                 205
```

```
Leu Tyr Leu Gln Met Ser Ser Leu Lys Ser Glu Asp Thr Ala Met Tyr
    210                 215                 220

Tyr Cys Ala Arg Gln Asn Ile Ala Arg Arg Gly Ala Met Asp Phe Trp
225                 230                 235                 240

Gly Gln Gly Ala Ser Val Thr Val Ser Ser
                245                 250


<210> SEQ ID NO 88
<211> LENGTH: 250
<212> TYPE: PRT
<213> ORGANISM: Artificial Sequence
<220> FEATURE:
<223> OTHER INFORMATION: LAb19308 scFv

<400> SEQUENCE: 88

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Glu Val Gln Leu Val Glu Ser Gly Gly Gly Leu Val Lys Pro
    130                 135                 140

Gly Gly Ser Leu Lys Leu Ser Cys Ala Ala Ser Gly Phe Ala Phe Ile
145                 150                 155                 160

Thr Tyr Gly Met Ser Trp Val Arg Gln Thr Pro Glu Lys Arg Leu Glu
                165                 170                 175

Trp Val Ala Tyr Ile Ser Ser Gly Gly Ala Asn Thr Tyr Tyr Pro Asp
            180                 185                 190

Ser Val Lys Gly Arg Phe Thr Ile Ser Arg Asp Asn Ala Lys Asn Thr
        195                 200                 205

Leu Tyr Leu Gln Met Ser Ser Leu Lys Ser Glu Asp Thr Ala Met Tyr
    210                 215                 220

Tyr Cys Ala Ser Leu Ser Thr Leu Val Arg Gly Trp Phe Ala Tyr Trp
225                 230                 235                 240

Gly Gln Gly Thr Leu Val Thr Val Ser Ala
                245                 250


<210> SEQ ID NO 89
<211> LENGTH: 245
<212> TYPE: PRT
<213> ORGANISM: Artificial Sequence
<220> FEATURE:
<223> OTHER INFORMATION: LAb19309 scFv

<400> SEQUENCE: 89

Asp Val Leu Met Thr Gln Thr Pro Leu Ser Leu Pro Val Asn Leu Gly
```

```
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Gln Val Gln Leu Gln Gln Ser Gly Ala Glu Leu Val Arg Pro
    130                 135                 140

Gly Ala Ser Val Thr Leu Ser Cys Lys Ala Ser Gly Tyr Thr Phe Thr
145                 150                 155                 160

Asp Tyr Glu Met His Trp Val Lys Gln Thr Pro Val His Gly Leu Glu
                165                 170                 175

Trp Ile Gly Gly Ile Asp Pro Glu Thr Gly Asn Thr Ala Tyr Ser Gln
            180                 185                 190

Lys Phe Lys Gly Lys Ala Thr Leu Thr Ala Asp Lys Ser Ser Ser Thr
        195                 200                 205

Ala Tyr Met Glu Val Arg Ser Leu Thr Ser Glu Asp Ser Ala Val Tyr
    210                 215                 220

Tyr Cys Thr Arg Tyr Tyr Ser Phe Ala Tyr Trp Gly Gln Gly Thr Leu
225                 230                 235                 240

Val Thr Val Ser Ala
                245
```

<210> SEQ ID NO 90
<211> LENGTH: 245
<212> TYPE: PRT
<213> ORGANISM: Artificial Sequence
<220> FEATURE:
<223> OTHER INFORMATION: LAb19310 scFv

<400> SEQUENCE: 90

```
Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Ser Thr
            20                  25                  30

Val Ala Trp Tyr Gln Gln Lys Pro Gly Gln Ser Pro Lys Ala Leu Ile
        35                  40                  45

Tyr Leu Thr Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Tyr
                85                  90                  95

Thr Phe Gly Gly Gly Thr Lys Leu Glu Ile Lys Gly Ser Thr Ser Gly
            100                 105                 110

Ser Gly Lys Pro Gly Ser Gly Glu Gly Ser Thr Lys Gly Glu Val Gln
```

```
        115                 120                 125

Leu Gln Gln Ser Gly Pro Glu Leu Val Lys Pro Gly Pro Ser Leu Lys
    130                 135                 140

Ile Ser Cys Lys Ala Ser Gly Tyr Ser Phe Thr Val Ser Pro Met Thr
145                 150                 155                 160

Trp Val Lys Gln Ser His Gly Lys Asn Leu Glu Trp Ile Gly Leu Ile
                165                 170                 175

His Pro Tyr Asn Gly Asp Thr Thr Tyr Asn Gln Lys Phe Lys Gly Lys
            180                 185                 190

Ala Thr Leu Thr Val Asp Lys Ser Ser Ser Thr Ala Tyr Met Glu Leu
        195                 200                 205

Leu Ser Leu Thr Ser Glu Asp Ser Ala Val Tyr Tyr Cys Ala Arg Trp
    210                 215                 220

Gly Asn Tyr Tyr Pro Tyr Ala Met Asp Tyr Trp Gly Gln Gly Thr Ser
225                 230                 235                 240

Val Thr Val Ser Ser
                245


<210> SEQ ID NO 91
<211> LENGTH: 473
<212> TYPE: PRT
<213> ORGANISM: Artificial Sequence
<220> FEATURE:
<223> OTHER INFORMATION: LIC19301 CAR

<400> SEQUENCE: 91

Asp Val Val Met Thr Gln Thr Pro Leu Ser Leu Pro Val Ser Leu Gly
1               5                   10                  15

Asp Gln Ala Ser Ile Ser Cys Gly Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Phe Thr Phe Gly Ser Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Asp Val Gln Leu Gln Glu Ser Gly Pro Asp Leu Val Lys Pro
    130                 135                 140

Ser Gln Ser Leu Ser Leu Thr Cys Thr Val Thr Gly Tyr Ser Ile Thr
145                 150                 155                 160

Ser Gly Phe Ser Trp His Trp Ile Arg Gln Phe Pro Gly His Lys Leu
                165                 170                 175

Glu Trp Met Gly Phe Met Gln Tyr Ser Gly Asn Thr Asn Tyr Asn Pro
            180                 185                 190

Ser Leu Lys Ser Arg Ile Ser Phe Thr Arg Asp Thr Ser Lys Asn Gln
        195                 200                 205

Phe Phe Leu Gln Leu Lys Ser Val Thr Pro Glu Asp Thr Ala Thr Tyr
    210                 215                 220

Tyr Cys Ala Arg Arg Glu Glu Gly Ala Trp Phe Ala Tyr Trp Gly Gln
```

```
225                 230                 235                 240

Gly Thr Leu Val Thr Val Ser Ala Thr Ser Thr Thr Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
        275                 280                 285

Gly Leu Asp Phe Ala Cys Asp Ile Tyr Ile Trp Ala Pro Leu Ala Gly
    290                 295                 300

Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470


<210> SEQ ID NO 92
<211> LENGTH: 475
<212> TYPE: PRT
<213> ORGANISM: Artificial Sequence
<220> FEATURE:
<223> OTHER INFORMATION: LIC19302 CAR

<400> SEQUENCE: 92

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
```

```
        115                 120                 125

Lys Gly Ala Val Gln Leu Val Glu Ser Gly Gly Gly Leu Val Arg Pro
    130                 135                 140

Gly Gly Ser Leu Lys Leu Ser Cys Ala Ala Ser Gly Phe Ala Phe Ser
145                 150                 155                 160

Thr Tyr Gly Met Ser Trp Val Arg Gln Thr Pro Glu Thr Arg Leu Glu
                165                 170                 175

Trp Val Ala Tyr Ile Ser Ser Gly Gly Ala Thr Thr Tyr Tyr Pro Asp
            180                 185                 190

Ser Val Lys Gly Arg Phe Thr Ile Ser Arg Asp Asn Ala Lys Asn Thr
        195                 200                 205

Leu Tyr Leu Gln Met Ser Ser Leu Lys Ser Glu Asp Thr Ala Met Tyr
    210                 215                 220

Tyr Cys Ala Ser Leu Ser Ile Met Ile Arg Gly Trp Phe Ala Tyr Trp
225                 230                 235                 240

Gly Gln Gly Thr Leu Val Thr Val Ser Ala Thr Ser Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475


<210> SEQ ID NO 93
<211> LENGTH: 470
<212> TYPE: PRT
<213> ORGANISM: Artificial Sequence
<220> FEATURE:
<223> OTHER INFORMATION: LIC19303 CAR

<400> SEQUENCE: 93

Asp Val Leu Met Thr Gln Thr Pro Leu Ser Leu Pro Val Ser Leu Gly
```

```
1               5                   10                  15

Asp Gln Ala Ser Ile Ser Cys Arg Ser Ser Gln Ser Phe Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Gln Val Gln Leu Gln Gln Ser Gly Ala Glu Leu Val Arg Pro
    130                 135                 140

Gly Ala Ser Val Thr Leu Ser Cys Glu Ala Ser Gly Tyr Thr Phe Asn
145                 150                 155                 160

Asp Tyr Glu Met His Trp Val Lys Gln Thr Pro Val His Gly Leu Glu
                165                 170                 175

Trp Ile Gly Ala Ile Asp Pro Glu Thr Gly Ala Thr Ala Tyr Asn Gln
            180                 185                 190

Lys Phe Lys Gly Lys Ala Thr Leu Thr Ala Asp Lys Ser Ser Ser Thr
        195                 200                 205

Ala Tyr Met Glu Leu Arg Ser Leu Thr Ser Glu Asp Thr Ala Val Tyr
    210                 215                 220

Tyr Cys Thr Arg Tyr Tyr Ser Phe Ala Tyr Trp Gly Gln Gly Thr Leu
225                 230                 235                 240

Val Thr Val Ser Ala Thr Ser Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430
```

Gly Met Lys Gly Glu Arg Arg Arg Gly Lys Gly His Asp Gly Leu Tyr
435 440 445

Gln Gly Leu Ser Thr Ala Thr Lys Asp Thr Tyr Asp Ala Leu His Met
450 455 460

Gln Ala Leu Pro Pro Arg
465 470

<210> SEQ ID NO 94
<211> LENGTH: 470
<212> TYPE: PRT
<213> ORGANISM: Artificial Sequence
<220> FEATURE:
<223> OTHER INFORMATION: LIC19304 CAR

<400> SEQUENCE: 94

Asp Val Leu Met Thr Gln Thr Pro Leu Ser Leu Pro Val Ser Leu Gly
1 5 10 15

Asp Gln Ala Ser Ile Ser Cys Arg Ser Ser Gln Thr Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Val
85 90 95

Ser His Val Pro Tyr Thr Phe Gly Gly Gly Thr Lys Leu Glu Ile Lys
100 105 110

Gly Ser Thr Ser Gly Ser Gly Lys Pro Gly Ser Gly Glu Gly Ser Thr
115 120 125

Lys Gly Gln Val Gln Leu Gln Gln Ser Gly Ala Glu Leu Val Arg Pro
130 135 140

Gly Ala Ser Val Thr Leu Ser Cys Lys Ala Ser Gly Tyr Thr Phe Thr
145 150 155 160

Ala Tyr Glu Met His Trp Val Lys Gln Thr Pro Val His Gly Leu Glu
165 170 175

Trp Ile Gly Gly Ile Asp Pro Glu Thr Gly Asn Thr Ala Tyr Ser Gln
180 185 190

Lys Phe Lys Gly Lys Ala Thr Leu Thr Ala Asp Lys Ser Ser Ser Thr
195 200 205

Ala Tyr Met Glu Val Arg Ser Leu Thr Ser Glu Asp Ser Ala Val Tyr
210 215 220

Tyr Cys Ser Arg Tyr Tyr Ser Phe Ala Tyr Trp Gly Gln Gly Thr Leu
225 230 235 240

Val Thr Val Ser Ala Thr Ser Thr Thr Thr Pro Ala Pro Arg Pro Pro
245 250 255

Thr Pro Ala Pro Thr Ile Ala Ser Gln Pro Leu Ser Leu Arg Pro Glu
260 265 270

Ala Cys Arg Pro Ala Ala Gly Gly Ala Val His Thr Arg Gly Leu Asp
275 280 285

Phe Ala Cys Asp Ile Tyr Ile Trp Ala Pro Leu Ala Gly Thr Cys Gly
290 295 300

Val Leu Leu Leu Ser Leu Val Ile Thr Leu Tyr Cys Lys Arg Gly Arg
305 310 315 320

Lys Lys Leu Leu Tyr Ile Phe Lys Gln Pro Phe Met Arg Pro Val Gln
325 330 335

Thr Thr Gln Glu Glu Asp Gly Cys Ser Cys Arg Phe Pro Glu Glu Glu
340 345 350

Glu Gly Gly Cys Glu Leu Arg Val Lys Phe Ser Arg Ser Ala Asp Ala
355 360 365

Pro Ala Tyr Gln Gln Gly Gln Asn Gln Leu Tyr Asn Glu Leu Asn Leu
370 375 380

Gly Arg Arg Glu Glu Tyr Asp Val Leu Asp Lys Arg Arg Gly Arg Asp
385 390 395 400

Pro Glu Met Gly Gly Lys Pro Arg Arg Lys Asn Pro Gln Glu Gly Leu
405 410 415

Tyr Asn Glu Leu Gln Lys Asp Lys Met Ala Glu Ala Tyr Ser Glu Ile
420 425 430

Gly Met Lys Gly Glu Arg Arg Arg Gly Lys Gly His Asp Gly Leu Tyr
435 440 445

Gln Gly Leu Ser Thr Ala Thr Lys Asp Thr Tyr Asp Ala Leu His Met
450 455 460

Gln Ala Leu Pro Pro Arg
465 470

<210> SEQ ID NO 95
<211> LENGTH: 470
<212> TYPE: PRT
<213> ORGANISM: Artificial Sequence
<220> FEATURE:
<223> OTHER INFORMATION: LIC19305 CAR

<400> SEQUENCE: 95

Asp Val Leu Met Thr Gln Thr Pro Leu Ser Leu Pro Val Ser Leu Gly
1 5 10 15

Asp Gln Ala Ser Ile Ser Cys Arg Ser Ser Gln Thr Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Val
85 90 95

Ser His Val Pro Tyr Thr Phe Gly Gly Gly Thr Lys Leu Glu Ile Lys
100 105 110

Gly Ser Thr Ser Gly Ser Gly Lys Pro Gly Ser Gly Glu Gly Ser Thr
115 120 125

Lys Gly Gln Val Gln Leu Gln Gln Ser Gly Ala Glu Leu Val Arg Pro
130 135 140

Gly Ala Ser Val Thr Leu Ser Cys Lys Ala Ser Gly Tyr Thr Phe Thr
145 150 155 160

Ala Tyr Glu Met His Trp Val Lys Gln Thr Pro Val Tyr Gly Leu Glu
165 170 175

Trp Ile Gly Gly Ile Asp Pro Glu Thr Gly Asn Thr Ala Tyr Ser Gln
180 185 190

Asn Phe Lys Gly Lys Ala Thr Leu Thr Ala Asp Lys Ser Ser Ser Thr
195 200 205

```
Ala Tyr Met Glu Val Arg Ser Leu Thr Ser Glu Asp Ser Ala Val Tyr
    210                 215                 220

Tyr Cys Ser Arg Tyr Tyr Ser Phe Ala Tyr Trp Gly Gln Gly Thr Leu
225                 230                 235                 240

Val Thr Val Ser Ala Thr Ser Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470


<210> SEQ ID NO 96
<211> LENGTH: 475
<212> TYPE: PRT
<213> ORGANISM: Artificial Sequence
<220> FEATURE:
<223> OTHER INFORMATION: LIC19306 CAR

<400> SEQUENCE: 96

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95
```

```
Thr His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Glu Val Gln Leu Val Glu Ser Gly Gly Gly Leu Val Lys Pro
    130                 135                 140

Gly Gly Ser Leu Lys Leu Ser Cys Ala Ala Ser Gly Phe Ala Phe Ser
145                 150                 155                 160

Thr Tyr Asp Met Ser Trp Val Arg Gln Thr Pro Glu Arg Arg Leu Glu
                165                 170                 175

Trp Val Ala Tyr Ile Ser Ser Gly Gly Ala Thr Thr Tyr Tyr Pro Asp
            180                 185                 190

Ser Val Lys Gly Arg Phe Thr Ile Ser Arg Asp Asn Ala Lys Asn Thr
        195                 200                 205

Leu Tyr Leu Gln Met Ser Ser Leu Lys Ser Glu Asp Thr Ala Met Tyr
    210                 215                 220

Tyr Cys Ala Arg Leu Ser Leu Met Ile Arg Gly Trp Phe Ala Tyr Trp
225                 230                 235                 240

Gly Gln Gly Thr Leu Val Thr Val Ser Ala Thr Ser Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475
```

<210> SEQ ID NO 97
<211> LENGTH: 475
<212> TYPE: PRT
<213> ORGANISM: Artificial Sequence
<220> FEATURE:

<223> OTHER INFORMATION: LIC19307 CAR

<400> SEQUENCE: 97

```
Asp Val Val Leu Thr Gln Ser Pro Leu Ser Gln Pro Val Ser Leu Gly
1               5                   10                  15

Asp Gln Ala Ser Ile Ser Cys Thr Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Glu Val Gln Leu Val Glu Ser Gly Gly Asp Leu Val Lys Pro
    130                 135                 140

Gly Gly Ser Leu Lys Leu Ser Cys Ala Ala Ser Gly Phe Ala Phe Gly
145                 150                 155                 160

Thr Tyr Asp Met Ser Trp Val Arg Gln Thr Pro Glu Lys Arg Leu Glu
                165                 170                 175

Trp Val Ala Tyr Ile Ser Ser Gly Gly Asn Ser Pro Tyr Tyr Pro Gln
            180                 185                 190

Thr Val Lys Gly Arg Phe Thr Ile Ser Arg Asp Asn Ala Lys Asn Thr
        195                 200                 205

Leu Tyr Leu Gln Met Ser Ser Leu Lys Ser Glu Asp Thr Ala Met Tyr
    210                 215                 220

Tyr Cys Ala Arg Gln Asn Ile Ala Arg Arg Gly Ala Met Asp Phe Trp
225                 230                 235                 240

Gly Gln Gly Ala Ser Val Thr Val Ser Ser Thr Ser Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400
```

```
Arg Arg Gly Arg Asp Pro Glu Met Gly Gly Lys Pro Arg Arg Lys Asn
            405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475


<210> SEQ ID NO 98
<211> LENGTH: 475
<212> TYPE: PRT
<213> ORGANISM: Artificial Sequence
<220> FEATURE:
<223> OTHER INFORMATION: LIC19308 CAR

<400> SEQUENCE: 98

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Glu Val Gln Leu Val Glu Ser Gly Gly Gly Leu Val Lys Pro
    130                 135                 140

Gly Gly Ser Leu Lys Leu Ser Cys Ala Ala Ser Gly Phe Ala Phe Ile
145                 150                 155                 160

Thr Tyr Gly Met Ser Trp Val Arg Gln Thr Pro Glu Lys Arg Leu Glu
                165                 170                 175

Trp Val Ala Tyr Ile Ser Ser Gly Gly Ala Asn Thr Tyr Tyr Pro Asp
            180                 185                 190

Ser Val Lys Gly Arg Phe Thr Ile Ser Arg Asp Asn Ala Lys Asn Thr
        195                 200                 205

Leu Tyr Leu Gln Met Ser Ser Leu Lys Ser Glu Asp Thr Ala Met Tyr
    210                 215                 220

Tyr Cys Ala Ser Leu Ser Thr Leu Val Arg Gly Trp Phe Ala Tyr Trp
225                 230                 235                 240

Gly Gln Gly Thr Leu Val Thr Val Ser Ala Thr Ser Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285
```

```
Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475


<210> SEQ ID NO 99
<211> LENGTH: 470
<212> TYPE: PRT
<213> ORGANISM: Artificial Sequence
<220> FEATURE:
<223> OTHER INFORMATION: LIC19309 CAR

<400> SEQUENCE: 99

Asp Val Leu Met Thr Gln Thr Pro Leu Ser Leu Pro Val Asn Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Gln Val Gln Leu Gln Gln Ser Gly Ala Glu Leu Val Arg Pro
    130                 135                 140

Gly Ala Ser Val Thr Leu Ser Cys Lys Ala Ser Gly Tyr Thr Phe Thr
145                 150                 155                 160

Asp Tyr Glu Met His Trp Val Lys Gln Thr Pro Val His Gly Leu Glu
                165                 170                 175
```

Trp Ile Gly Gly Ile Asp Pro Glu Thr Gly Asn Thr Ala Tyr Ser Gln
180 185 190

Lys Phe Lys Gly Lys Ala Thr Leu Thr Ala Asp Lys Ser Ser Ser Thr
195 200 205

Ala Tyr Met Glu Val Arg Ser Leu Thr Ser Glu Asp Ser Ala Val Tyr
210 215 220

Tyr Cys Thr Arg Tyr Tyr Ser Phe Ala Tyr Trp Gly Gln Gly Thr Leu
225 230 235 240

Val Thr Val Ser Ala Thr Ser Thr Thr Thr Pro Ala Pro Arg Pro Pro
245 250 255

Thr Pro Ala Pro Thr Ile Ala Ser Gln Pro Leu Ser Leu Arg Pro Glu
260 265 270

Ala Cys Arg Pro Ala Ala Gly Gly Ala Val His Thr Arg Gly Leu Asp
275 280 285

Phe Ala Cys Asp Ile Tyr Ile Trp Ala Pro Leu Ala Gly Thr Cys Gly
290 295 300

Val Leu Leu Leu Ser Leu Val Ile Thr Leu Tyr Cys Lys Arg Gly Arg
305 310 315 320

Lys Lys Leu Leu Tyr Ile Phe Lys Gln Pro Phe Met Arg Pro Val Gln
325 330 335

Thr Thr Gln Glu Glu Asp Gly Cys Ser Cys Arg Phe Pro Glu Glu Glu
340 345 350

Glu Gly Gly Cys Glu Leu Arg Val Lys Phe Ser Arg Ser Ala Asp Ala
355 360 365

Pro Ala Tyr Gln Gln Gly Gln Asn Gln Leu Tyr Asn Glu Leu Asn Leu
370 375 380

Gly Arg Arg Glu Glu Tyr Asp Val Leu Asp Lys Arg Arg Gly Arg Asp
385 390 395 400

Pro Glu Met Gly Gly Lys Pro Arg Arg Lys Asn Pro Gln Glu Gly Leu
405 410 415

Tyr Asn Glu Leu Gln Lys Asp Lys Met Ala Glu Ala Tyr Ser Glu Ile
420 425 430

Gly Met Lys Gly Glu Arg Arg Arg Gly Lys Gly His Asp Gly Leu Tyr
435 440 445

Gln Gly Leu Ser Thr Ala Thr Lys Asp Thr Tyr Asp Ala Leu His Met
450 455 460

Gln Ala Leu Pro Pro Arg
465 470

<210> SEQ ID NO 100
<211> LENGTH: 470
<212> TYPE: PRT
<213> ORGANISM: Artificial Sequence
<220> FEATURE:
<223> OTHER INFORMATION: LIC19310 CAR

<400> SEQUENCE: 100

Asp Ile Val Met Thr Gln Ser Gln Lys Phe Met Ser Thr Ser Val Gly
1 5 10 15

Asp Arg Val Ser Ile Thr Cys Lys Ala Ser Gln Asn Val Arg Ser Thr
20 25 30

Val Ala Trp Tyr Gln Gln Lys Pro Gly Gln Ser Pro Lys Ala Leu Ile
35 40 45

Tyr Leu Thr Ser Asn Arg His Thr Gly Val Pro Asp Arg Phe Thr Gly
50 55 60

```
Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Tyr
                85                  90                  95

Thr Phe Gly Gly Gly Thr Lys Leu Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Gln Gln Ser Gly Pro Glu Leu Val Lys Pro Gly Pro Ser Leu Lys
    130                 135                 140

Ile Ser Cys Lys Ala Ser Gly Tyr Ser Phe Thr Val Ser Pro Met Thr
145                 150                 155                 160

Trp Val Lys Gln Ser His Gly Lys Asn Leu Glu Trp Ile Gly Leu Ile
                165                 170                 175

His Pro Tyr Asn Gly Asp Thr Thr Tyr Asn Gln Lys Phe Lys Gly Lys
            180                 185                 190

Ala Thr Leu Thr Val Asp Lys Ser Ser Ser Thr Ala Tyr Met Glu Leu
        195                 200                 205

Leu Ser Leu Thr Ser Glu Asp Ser Ala Val Tyr Tyr Cys Ala Arg Trp
    210                 215                 220

Gly Asn Tyr Tyr Pro Tyr Ala Met Asp Tyr Trp Gly Gln Gly Thr Ser
225                 230                 235                 240

Val Thr Val Ser Ser Thr Ser Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470
```

<210> SEQ ID NO 101
<211> LENGTH: 21
<212> TYPE: PRT
<213> ORGANISM: Artificial Sequence
<220> FEATURE:
<223> OTHER INFORMATION: CD8alpha signal peptide

<400> SEQUENCE: 101

Met Ala Leu Pro Val Thr Ala Leu Leu Leu Pro Leu Ala Leu Leu Leu
1 5 10 15

His Ala Ala Arg Pro
20

<210> SEQ ID NO 102
<211> LENGTH: 45
<212> TYPE: PRT
<213> ORGANISM: Artificial Sequence
<220> FEATURE:
<223> OTHER INFORMATION: CD8alpha hinge domain

<400> SEQUENCE: 102

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 103
<211> LENGTH: 24
<212> TYPE: PRT
<213> ORGANISM: Artificial Sequence
<220> FEATURE:
<223> OTHER INFORMATION: CD8alpha transmembrane domain

<400> SEQUENCE: 103

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 104
<211> LENGTH: 42
<212> TYPE: PRT
<213> ORGANISM: Artificial Sequence
<220> FEATURE:
<223> OTHER INFORMATION: CD137 cytoplasmic domain

<400> SEQUENCE: 104

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 105
<211> LENGTH: 112
<212> TYPE: PRT
<213> ORGANISM: Artificial Sequence
<220> FEATURE:
<223> OTHER INFORMATION: CD3zeta cytoplasmic domain

<400> SEQUENCE: 105

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 106
<211> LENGTH: 541
<212> TYPE: PRT
<213> ORGANISM: Artificial Sequence
<220> FEATURE:
<223> OTHER INFORMATION: GPC3 fusion protein

<400> SEQUENCE: 106

Gln Pro Pro Pro Pro Pro Pro Asp Ala Thr Cys His Gln Val Arg Ser
1 5 10 15

Phe Phe Gln Arg Leu Gln Pro Gly Leu Lys Trp Val Pro Glu Thr Pro
20 25 30

Val Pro Gly Ser Asp Leu Gln Val Cys Leu Pro Lys Gly Pro Thr Cys
35 40 45

Cys Ser Arg Lys Met Glu Glu Lys Tyr Gln Leu Thr Ala Arg Leu Asn
50 55 60

Met Glu Gln Leu Leu Gln Ser Ala Ser Met Glu Leu Lys Phe Leu Ile
65 70 75 80

Ile Gln Asn Ala Ala Val Phe Gln Glu Ala Phe Glu Ile Val Val Arg
85 90 95

His Ala Lys Asn Tyr Thr Asn Ala Met Phe Lys Asn Asn Tyr Pro Ser
100 105 110

Leu Thr Pro Gln Ala Phe Glu Phe Val Gly Glu Phe Phe Thr Asp Val
115 120 125

Ser Leu Tyr Ile Leu Gly Ser Asp Ile Asn Val Asp Asp Met Val Asn
130 135 140

Glu Leu Phe Asp Ser Leu Phe Pro Val Ile Tyr Thr Gln Leu Met Asn
145 150 155 160

Pro Gly Leu Pro Asp Ser Ala Leu Asp Ile Asn Glu Cys Leu Arg Gly
165 170 175

Ala Arg Arg Asp Leu Lys Val Phe Gly Asn Phe Pro Lys Leu Ile Met
180 185 190

Thr Gln Val Ser Lys Ser Leu Gln Val Thr Arg Ile Phe Leu Gln Ala
195 200 205

Leu Asn Leu Gly Ile Glu Val Ile Asn Thr Thr Asp His Leu Lys Phe
210 215 220

Ser Lys Asp Cys Gly Arg Met Leu Thr Arg Met Trp Tyr Cys Ser Tyr
225 230 235 240

Cys Gln Gly Leu Met Met Val Lys Pro Cys Gly Gly Tyr Cys Asn Val
245 250 255

```
Val Met Gln Gly Cys Met Ala Gly Val Val Glu Ile Asp Lys Tyr Trp
            260                 265                 270

Arg Glu Tyr Ile Leu Ser Leu Glu Glu Leu Val Asn Gly Met Tyr Arg
        275                 280                 285

Ile Tyr Asp Met Glu Asn Val Leu Leu Gly Leu Phe Ser Thr Ile His
    290                 295                 300

Asp Ser Ile Gln Tyr Val Gln Lys Asn Ala Gly Lys Leu Thr Thr Thr
305                 310                 315                 320

Ile Gly Lys Leu Cys Ala His Ser Gln Gln Arg Gln Tyr Arg Phe Ala
                325                 330                 335

Tyr Tyr Pro Glu Asp Leu Phe Ile Asp Lys Lys Val Leu Lys Val Ala
            340                 345                 350

His Val Glu His Glu Glu Thr Leu Ser Ser Arg Arg Arg Glu Leu Ile
        355                 360                 365

Gln Lys Leu Lys Ser Phe Ile Ser Phe Tyr Ser Ala Leu Pro Gly Tyr
    370                 375                 380

Ile Cys Ser His Ser Pro Val Ala Glu Asn Asp Thr Leu Cys Trp Asn
385                 390                 395                 400

Gly Gln Glu Leu Val Glu Arg Tyr Ser Gln Lys Ala Ala Arg Asn Gly
                405                 410                 415

Met Lys Asn Gln Phe Asn Leu His Glu Leu Lys Met Lys Gly Pro Glu
            420                 425                 430

Pro Val Val Ser Gln Ile Ile Asp Lys Leu Lys His Ile Asn Gln Leu
        435                 440                 445

Leu Arg Thr Met Ser Met Pro Lys Gly Arg Val Leu Asp Lys Asn Leu
    450                 455                 460

Asp Glu Glu Gly Phe Glu Ser Gly Asp Cys Gly Asp Asp Glu Asp Glu
465                 470                 475                 480

Cys Ile Gly Gly Ser Gly Asp Gly Met Ile Lys Val Lys Asn Gln Leu
                485                 490                 495

Arg Phe Leu Ala Glu Leu Ala Tyr Asp Leu Asp Val Asp Asp Ala Pro
            500                 505                 510

Gly Asn Ser Gln Gln Ala Thr Pro Lys Asp Asn Glu Ile Ser Thr Phe
        515                 520                 525

His Asn Leu Gly Asn Val His His His His His His His
    530                 535                 540


<210> SEQ ID NO 107
<211> LENGTH: 494
<212> TYPE: PRT
<213> ORGANISM: Artificial Sequence
<220> FEATURE:
<223> OTHER INFORMATION: LIC19301 CAR

<400> SEQUENCE: 107

Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
            20                  25                  30

Pro Val Ser Leu Gly Asp Gln Ala Ser Ile Ser Cys Gly Ser Ser Gln
        35                  40                  45

Ser Leu Val His Ser Asn Gly Asn Thr Tyr Leu His Trp Tyr Leu Gln
    50                  55                  60

Lys Pro Gly Gln Ser Pro Lys Leu Leu Ile Tyr Lys Val Ser Asn Arg
65                  70                  75                  80
```

```
Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Phe Pro Phe Thr Phe Gly Ser Gly Thr
        115                 120                 125

Lys Leu Glu Ile Lys Gly Ser Thr Ser Gly Ser Gly Lys Pro Gly Ser
    130                 135                 140

Gly Glu Gly Ser Thr Lys Gly Asp Val Gln Leu Gln Glu Ser Gly Pro
145                 150                 155                 160

Asp Leu Val Lys Pro Ser Gln Ser Leu Ser Leu Thr Cys Thr Val Thr
                165                 170                 175

Gly Tyr Ser Ile Thr Ser Gly Phe Ser Trp His Trp Ile Arg Gln Phe
            180                 185                 190

Pro Gly His Lys Leu Glu Trp Met Gly Phe Met Gln Tyr Ser Gly Asn
        195                 200                 205

Thr Asn Tyr Asn Pro Ser Leu Lys Ser Arg Ile Ser Phe Thr Arg Asp
    210                 215                 220

Thr Ser Lys Asn Gln Phe Phe Leu Gln Leu Lys Ser Val Thr Pro Glu
225                 230                 235                 240

Asp Thr Ala Thr Tyr Tyr Cys Ala Arg Arg Glu Glu Gly Ala Trp Phe
                245                 250                 255

Ala Tyr Trp Gly Gln Gly Thr Leu Val Thr Val Ser Ala Thr Ser Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 108
<211> LENGTH: 496
<212> TYPE: PRT
<213> ORGANISM: Artificial Sequence
<220> FEATURE:
<223> OTHER INFORMATION: LIC19302 CAR

<400> SEQUENCE: 108

```
Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Ser Asn Gly Asn Thr Tyr Leu His Trp Tyr Leu Gln
    50                  55                  60

Lys Pro Gly Gln Ser Pro Lys Val Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Val Pro Tyr Thr Phe Gly Gly Gly Thr
        115                 120                 125

Lys Leu Glu Ile Lys Gly Ser Thr Ser Gly Ser Gly Lys Pro Gly Ser
    130                 135                 140

Gly Glu Gly Ser Thr Lys Gly Ala Val Gln Leu Val Glu Ser Gly Gly
145                 150                 155                 160

Gly Leu Val Arg Pro Gly Gly Ser Leu Lys Leu Ser Cys Ala Ala Ser
                165                 170                 175

Gly Phe Ala Phe Ser Thr Tyr Gly Met Ser Trp Val Arg Gln Thr Pro
            180                 185                 190

Glu Thr Arg Leu Glu Trp Val Ala Tyr Ile Ser Ser Gly Gly Ala Thr
        195                 200                 205

Thr Tyr Tyr Pro Asp Ser Val Lys Gly Arg Phe Thr Ile Ser Arg Asp
    210                 215                 220

Asn Ala Lys Asn Thr Leu Tyr Leu Gln Met Ser Ser Leu Lys Ser Glu
225                 230                 235                 240

Asp Thr Ala Met Tyr Tyr Cys Ala Ser Leu Ser Ile Met Ile Arg Gly
                245                 250                 255

Trp Phe Ala Tyr Trp Gly Gln Gly Thr Leu Val Thr Val Ser Ala Thr
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
```

```
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495


<210> SEQ ID NO 109
<211> LENGTH: 491
<212> TYPE: PRT
<213> ORGANISM: Artificial Sequence
<220> FEATURE:
<223> OTHER INFORMATION: LIC19303 CAR

<400> SEQUENCE: 109

Met Ala Leu Pro Val Thr Ala Leu Leu Leu Pro Leu Ala Leu Leu Leu
1               5                   10                  15

His Ala Ala Arg Pro Asp Val Leu Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Phe Val His Ser Asn Gly Asn Thr Tyr Leu Gln Trp Tyr Leu Gln
    50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Tyr Cys Phe Gln Gly Ser His Val Pro Tyr Thr Phe Gly Gly Gly Thr
        115                 120                 125

Lys Leu Glu Ile Lys Gly Ser Thr Ser Gly Ser Gly Lys Pro Gly Ser
    130                 135                 140

Gly Glu Gly Ser Thr Lys Gly Gln Val Gln Leu Gln Gln Ser Gly Ala
145                 150                 155                 160

Glu Leu Val Arg Pro Gly Ala Ser Val Thr Leu Ser Cys Glu Ala Ser
                165                 170                 175

Gly Tyr Thr Phe Asn Asp Tyr Glu Met His Trp Val Lys Gln Thr Pro
            180                 185                 190

Val His Gly Leu Glu Trp Ile Gly Ala Ile Asp Pro Glu Thr Gly Ala
        195                 200                 205

Thr Ala Tyr Asn Gln Lys Phe Lys Gly Lys Ala Thr Leu Thr Ala Asp
    210                 215                 220

Lys Ser Ser Ser Thr Ala Tyr Met Glu Leu Arg Ser Leu Thr Ser Glu
225                 230                 235                 240

Asp Thr Ala Val Tyr Tyr Cys Thr Arg Tyr Tyr Ser Phe Ala Tyr Trp
```

```
                245                 250                 255

Gly Gln Gly Thr Leu Val Thr Val Ser Ala Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 110
<211> LENGTH: 491
<212> TYPE: PRT
<213> ORGANISM: Artificial Sequence
<220> FEATURE:
<223> OTHER INFORMATION: LIC19304 CAR

<400> SEQUENCE: 110

Met Ala Leu Pro Val Thr Ala Leu Leu Leu Pro Leu Ala Leu Leu Leu
1               5                   10                  15

His Ala Ala Arg Pro Asp Val Leu Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Thr Ile Val His Ser Asn Gly Asn Thr Tyr Leu Glu Trp Tyr Leu Gln
    50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Tyr Cys Phe Gln Val Ser His Val Pro Tyr Thr Phe Gly Gly Gly Thr
```

```
        115                 120                 125

Lys Leu Glu Ile Lys Gly Ser Thr Ser Gly Ser Gly Lys Pro Gly Ser
    130                 135                 140

Gly Glu Gly Ser Thr Lys Gly Gln Val Gln Leu Gln Gln Ser Gly Ala
145                 150                 155                 160

Glu Leu Val Arg Pro Gly Ala Ser Val Thr Leu Ser Cys Lys Ala Ser
                165                 170                 175

Gly Tyr Thr Phe Thr Ala Tyr Glu Met His Trp Val Lys Gln Thr Pro
            180                 185                 190

Val His Gly Leu Glu Trp Ile Gly Gly Ile Asp Pro Glu Thr Gly Asn
        195                 200                 205

Thr Ala Tyr Ser Gln Lys Phe Lys Gly Lys Ala Thr Leu Thr Ala Asp
    210                 215                 220

Lys Ser Ser Ser Thr Ala Tyr Met Glu Val Arg Ser Leu Thr Ser Glu
225                 230                 235                 240

Asp Ser Ala Val Tyr Tyr Cys Ser Arg Tyr Tyr Ser Phe Ala Tyr Trp
                245                 250                 255

Gly Gln Gly Thr Leu Val Thr Val Ser Ala Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

```
<210> SEQ ID NO 111
<211> LENGTH: 491
<212> TYPE: PRT
<213> ORGANISM: Artificial Sequence
<220> FEATURE:
<223> OTHER INFORMATION: LIC19305 CAR
```

<400> SEQUENCE: 111

Met Ala Leu Pro Val Thr Ala Leu Leu Leu Pro Leu Ala Leu Leu Leu
1 5 10 15

His Ala Ala Arg Pro Asp Val Leu Met Thr Gln Thr Pro Leu Ser Leu
20 25 30

Pro Val Ser Leu Gly Asp Gln Ala Ser Ile Ser Cys Arg Ser Ser Gln
35 40 45

Thr Ile Val His Ser Asn Gly Asn Thr Tyr Leu Glu Trp Tyr Leu Gln
50 55 60

Lys Pro Gly Gln Ser Pro Lys Leu Leu Ile Tyr Lys Val Ser Asn Arg
65 70 75 80

Phe Ser Gly Val Pro Asp Arg Phe Ser Gly Ser Gly Ser Gly Thr Asp
85 90 95

Phe Thr Leu Lys Ile Ser Arg Val Glu Ala Glu Asp Leu Gly Val Tyr
100 105 110

Tyr Cys Phe Gln Val Ser His Val Pro Tyr Thr Phe Gly Gly Gly Thr
115 120 125

Lys Leu Glu Ile Lys Gly Ser Thr Ser Gly Ser Gly Lys Pro Gly Ser
130 135 140

Gly Glu Gly Ser Thr Lys Gly Gln Val Gln Leu Gln Gln Ser Gly Ala
145 150 155 160

Glu Leu Val Arg Pro Gly Ala Ser Val Thr Leu Ser Cys Lys Ala Ser
165 170 175

Gly Tyr Thr Phe Thr Ala Tyr Glu Met His Trp Val Lys Gln Thr Pro
180 185 190

Val Tyr Gly Leu Glu Trp Ile Gly Gly Ile Asp Pro Glu Thr Gly Asn
195 200 205

Thr Ala Tyr Ser Gln Asn Phe Lys Gly Lys Ala Thr Leu Thr Ala Asp
210 215 220

Lys Ser Ser Ser Thr Ala Tyr Met Glu Val Arg Ser Leu Thr Ser Glu
225 230 235 240

Asp Ser Ala Val Tyr Tyr Cys Ser Arg Tyr Tyr Ser Phe Ala Tyr Trp
245 250 255

Gly Gln Gly Thr Leu Val Thr Val Ser Ala Thr Ser Thr Thr Thr Pro
260 265 270

Ala Pro Arg Pro Pro Thr Pro Ala Pro Thr Ile Ala Ser Gln Pro Leu
275 280 285

Ser Leu Arg Pro Glu Ala Cys Arg Pro Ala Ala Gly Gly Ala Val His
290 295 300

Thr Arg Gly Leu Asp Phe Ala Cys Asp Ile Tyr Ile Trp Ala Pro Leu
305 310 315 320

Ala Gly Thr Cys Gly Val Leu Leu Leu Ser Leu Val Ile Thr Leu Tyr
325 330 335

Cys Lys Arg Gly Arg Lys Lys Leu Leu Tyr Ile Phe Lys Gln Pro Phe
340 345 350

Met Arg Pro Val Gln Thr Thr Gln Glu Glu Asp Gly Cys Ser Cys Arg
355 360 365

Phe Pro Glu Glu Glu Glu Gly Gly Cys Glu Leu Arg Val Lys Phe Ser
370 375 380

Arg Ser Ala Asp Ala Pro Ala Tyr Gln Gln Gly Gln Asn Gln Leu Tyr
385 390 395 400

Asn Glu Leu Asn Leu Gly Arg Arg Glu Glu Tyr Asp Val Leu Asp Lys
405 410 415

Arg Arg Gly Arg Asp Pro Glu Met Gly Gly Lys Pro Arg Arg Lys Asn
420 425 430

Pro Gln Glu Gly Leu Tyr Asn Glu Leu Gln Lys Asp Lys Met Ala Glu
435 440 445

Ala Tyr Ser Glu Ile Gly Met Lys Gly Glu Arg Arg Arg Gly Lys Gly
450 455 460

His Asp Gly Leu Tyr Gln Gly Leu Ser Thr Ala Thr Lys Asp Thr Tyr
465 470 475 480

Asp Ala Leu His Met Gln Ala Leu Pro Pro Arg
485 490

<210> SEQ ID NO 112
<211> LENGTH: 496
<212> TYPE: PRT
<213> ORGANISM: Artificial Sequence
<220> FEATURE:
<223> OTHER INFORMATION: LIC19306 CAR

<400> SEQUENCE: 112

Met Ala Leu Pro Val Thr Ala Leu Leu Leu Pro Leu Ala Leu Leu Leu
1 5 10 15

His Ala Ala Arg Pro Asp Val Val Met Thr Gln Thr Pro Leu Ser Leu
20 25 30

Pro Val Ser Leu Gly Asp Gln Ala Ser Ile Ser Cys Arg Ser Ser Gln
35 40 45

Ser Leu Val His Ser Asn Gly Asn Thr Tyr Leu His Trp Tyr Leu Gln
50 55 60

Lys Pro Gly Gln Ser Pro Lys Leu Leu Ile Tyr Lys Val Ser Asn Arg
65 70 75 80

Phe Ser Gly Val Pro Asp Arg Phe Ser Gly Ser Gly Ser Gly Thr Asp
85 90 95

Phe Thr Leu Lys Ile Ser Arg Val Glu Ala Glu Asp Leu Gly Val Tyr
100 105 110

Phe Cys Ser Gln Ser Thr His Val Pro Tyr Thr Phe Gly Gly Gly Thr
115 120 125

Lys Leu Glu Ile Lys Gly Ser Thr Ser Gly Ser Gly Lys Pro Gly Ser
130 135 140

Gly Glu Gly Ser Thr Lys Gly Glu Val Gln Leu Val Glu Ser Gly Gly
145 150 155 160

Gly Leu Val Lys Pro Gly Gly Ser Leu Lys Leu Ser Cys Ala Ala Ser
165 170 175

Gly Phe Ala Phe Ser Thr Tyr Asp Met Ser Trp Val Arg Gln Thr Pro
180 185 190

Glu Arg Arg Leu Glu Trp Val Ala Tyr Ile Ser Ser Gly Gly Ala Thr
195 200 205

Thr Tyr Tyr Pro Asp Ser Val Lys Gly Arg Phe Thr Ile Ser Arg Asp
210 215 220

Asn Ala Lys Asn Thr Leu Tyr Leu Gln Met Ser Ser Leu Lys Ser Glu
225 230 235 240

Asp Thr Ala Met Tyr Tyr Cys Ala Arg Leu Ser Leu Met Ile Arg Gly
245 250 255

Trp Phe Ala Tyr Trp Gly Gln Gly Thr Leu Val Thr Val Ser Ala Thr
260 265 270

Ser Thr Thr Thr Pro Ala Pro Arg Pro Pro Thr Pro Ala Pro Thr Ile
275 280 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 113
<211> LENGTH: 496
<212> TYPE: PRT
<213> ORGANISM: Artificial Sequence
<220> FEATURE:
<223> OTHER INFORMATION: LIC19307 CAR

<400> SEQUENCE: 113

Met Ala Leu Pro Val Thr Ala Leu Leu Leu Pro Leu Ala Leu Leu Leu
1               5                   10                  15

His Ala Ala Arg Pro Asp Val Val Leu Thr Gln Ser Pro Leu Ser Gln
            20                  25                  30

Pro Val Ser Leu Gly Asp Gln Ala Ser Ile Ser Cys Thr Ser Ser Gln
        35                  40                  45

Ser Leu Leu His Ser Asn Gly Asn Thr Tyr Leu His Trp Tyr Leu Gln
    50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Val Pro Pro Thr Phe Gly Gly Gly Thr
        115                 120                 125

Lys Leu Glu Ile Lys Gly Ser Thr Ser Gly Ser Gly Lys Pro Gly Ser
    130                 135                 140

Gly Glu Gly Ser Thr Lys Gly Glu Val Gln Leu Val Glu Ser Gly Gly
145                 150                 155                 160

```
Asp Leu Val Lys Pro Gly Gly Ser Leu Lys Leu Ser Cys Ala Ala Ser
                165                 170                 175

Gly Phe Ala Phe Gly Thr Tyr Asp Met Ser Trp Val Arg Gln Thr Pro
            180                 185                 190

Glu Lys Arg Leu Glu Trp Val Ala Tyr Ile Ser Ser Gly Gly Asn Ser
        195                 200                 205

Pro Tyr Tyr Pro Gln Thr Val Lys Gly Arg Phe Thr Ile Ser Arg Asp
    210                 215                 220

Asn Ala Lys Asn Thr Leu Tyr Leu Gln Met Ser Ser Leu Lys Ser Glu
225                 230                 235                 240

Asp Thr Ala Met Tyr Tyr Cys Ala Arg Gln Asn Ile Ala Arg Arg Gly
                245                 250                 255

Ala Met Asp Phe Trp Gly Gln Gly Ala Ser Val Thr Val Ser Ser Thr
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

<210> SEQ ID NO 114
<211> LENGTH: 496
<212> TYPE: PRT
<213> ORGANISM: Artificial Sequence
<220> FEATURE:
<223> OTHER INFORMATION: LIC19308 CAR

<400> SEQUENCE: 114

```
Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
            20                  25                  30
```

```
Pro Val Ser Leu Gly Asp Gln Ala Ser Ile Ser Cys Arg Ser Ser Gln
        35                  40                  45

Ser Leu Val His Ser Asn Gly Asn Thr Tyr Leu His Trp Tyr Leu Gln
    50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Val Pro Tyr Thr Phe Gly Gly Gly Thr
        115                 120                 125

Lys Leu Glu Ile Lys Gly Ser Thr Ser Gly Ser Gly Lys Pro Gly Ser
    130                 135                 140

Gly Glu Gly Ser Thr Lys Gly Glu Val Gln Leu Val Glu Ser Gly Gly
145                 150                 155                 160

Gly Leu Val Lys Pro Gly Gly Ser Leu Lys Leu Ser Cys Ala Ala Ser
                165                 170                 175

Gly Phe Ala Phe Ile Thr Tyr Gly Met Ser Trp Val Arg Gln Thr Pro
            180                 185                 190

Glu Lys Arg Leu Glu Trp Val Ala Tyr Ile Ser Ser Gly Gly Ala Asn
        195                 200                 205

Thr Tyr Tyr Pro Asp Ser Val Lys Gly Arg Phe Thr Ile Ser Arg Asp
    210                 215                 220

Asn Ala Lys Asn Thr Leu Tyr Leu Gln Met Ser Ser Leu Lys Ser Glu
225                 230                 235                 240

Asp Thr Ala Met Tyr Tyr Cys Ala Ser Leu Ser Thr Leu Val Arg Gly
                245                 250                 255

Trp Phe Ala Tyr Trp Gly Gln Gly Thr Leu Val Thr Val Ser Ala Thr
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445
```

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 115
<211> LENGTH: 491
<212> TYPE: PRT
<213> ORGANISM: Artificial Sequence
<220> FEATURE:
<223> OTHER INFORMATION: LIC19309 CAR

<400> SEQUENCE: 115

Met Ala Leu Pro Val Thr Ala Leu Leu Leu Pro Leu Ala Leu Leu Leu
1               5                   10                  15

His Ala Ala Arg Pro Asp Val Leu Met Thr Gln Thr Pro Leu Ser Leu
            20                  25                  30

Pro Val Asn Leu Gly Asp Gln Ala Ser Ile Ser Cys Arg Ser Ser Gln
        35                  40                  45

Thr Ile Val His Ser Asn Gly Asn Thr Tyr Leu Glu Trp Tyr Leu Gln
    50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Arg Ile Ser Arg Val Glu Ala Glu Asp Leu Gly Val Tyr
            100                 105                 110

Tyr Cys Phe Gln Val Ser His Val Pro Tyr Thr Phe Gly Gly Gly Thr
        115                 120                 125

Lys Leu Glu Ile Lys Gly Ser Thr Ser Gly Ser Gly Lys Pro Gly Ser
    130                 135                 140

Gly Glu Gly Ser Thr Lys Gly Gln Val Gln Leu Gln Gln Ser Gly Ala
145                 150                 155                 160

Glu Leu Val Arg Pro Gly Ala Ser Val Thr Leu Ser Cys Lys Ala Ser
                165                 170                 175

Gly Tyr Thr Phe Thr Asp Tyr Glu Met His Trp Val Lys Gln Thr Pro
            180                 185                 190

Val His Gly Leu Glu Trp Ile Gly Gly Ile Asp Pro Glu Thr Gly Asn
        195                 200                 205

Thr Ala Tyr Ser Gln Lys Phe Lys Gly Lys Ala Thr Leu Thr Ala Asp
    210                 215                 220

Lys Ser Ser Ser Thr Ala Tyr Met Glu Val Arg Ser Leu Thr Ser Glu
225                 230                 235                 240

Asp Ser Ala Val Tyr Tyr Cys Thr Arg Tyr Tyr Ser Phe Ala Tyr Trp
                245                 250                 255

Gly Gln Gly Thr Leu Val Thr Val Ser Ala Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

```
Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 116
<211> LENGTH: 490
<212> TYPE: PRT
<213> ORGANISM: Artificial Sequence
<220> FEATURE:
<223> OTHER INFORMATION: LIC19310 CAR

<400> SEQUENCE: 116

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Gln Lys Phe Met
            20                  25                  30

Ser Thr Ser Val Gly Asp Arg Val Ser Ile Thr Cys Lys Ala Ser Gln
        35                  40                  45

Asn Val Arg Ser Thr Val Ala Trp Tyr Gln Gln Lys Pro Gly Gln Ser
    50                  55                  60

Pro Lys Ala Leu Ile Tyr Leu Thr Ser Asn Arg His Thr Gly Val Pro
65                  70                  75                  80

Asp Arg Phe Thr Gly Ser Gly Ser Gly Thr Asp Phe Thr Leu Thr Ile
                85                  90                  95

Ser Asn Val Gln Ser Glu Asp Leu Ala Asp Tyr Phe Cys Leu Gln His
            100                 105                 110

Trp Asn Tyr Pro Tyr Thr Phe Gly Gly Gly Thr Lys Leu Glu Ile Lys
        115                 120                 125

Gly Ser Thr Ser Gly Ser Gly Lys Pro Gly Ser Gly Glu Gly Ser Thr
    130                 135                 140

Lys Gly Glu Val Gln Leu Gln Gln Ser Gly Pro Glu Leu Val Lys Pro
145                 150                 155                 160

Gly Pro Ser Leu Lys Ile Ser Cys Lys Ala Ser Gly Tyr Ser Phe Thr
                165                 170                 175

Val Ser Pro Met Thr Trp Val Lys Gln Ser His Gly Lys Asn Leu Glu
            180                 185                 190
```

```
Trp Ile Gly Leu Ile His Pro Tyr Asn Gly Asp Thr Thr Tyr Asn Gln
        195                 200                 205

Lys Phe Lys Gly Lys Ala Thr Leu Thr Val Asp Lys Ser Ser Ser Thr
    210                 215                 220

Ala Tyr Met Glu Leu Leu Ser Leu Thr Ser Glu Asp Ser Ala Val Tyr
225                 230                 235                 240

Tyr Cys Ala Arg Trp Gly Asn Tyr Tyr Pro Tyr Ala Met Asp Tyr Trp
                245                 250                 255

Gly Gln Gly Thr Ser Val Thr Val Ser Ser Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro
                485                 490
```

<210> SEQ ID NO 117
<211> LENGTH: 115
<212> TYPE: PRT
<213> ORGANISM: Artificial Sequence
<220> FEATURE:
<223> OTHER INFORMATION: 9VH1

<400> SEQUENCE: 117

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Arg Leu Glu Trp Met
        35                  40                  45

Gly Gly Ile Asp Pro Glu Thr Gly Asn Thr Ala Tyr Ser Gln Lys Phe
    50                  55                  60
```

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Tyr Tyr Ser Phe Ala Tyr Trp Gly Gln Gly Thr Leu Val Thr
100 105 110

Val Ser Ser
115

<210> SEQ ID NO 118
<211> LENGTH: 115
<212> TYPE: PRT
<213> ORGANISM: Artificial Sequence
<220> FEATURE:
<223> OTHER INFORMATION: 9VH2

<400> SEQUENCE: 118

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Asp Tyr
20 25 30

Glu Met His Trp Val Gln Gln Ala Pro Gly Lys Gly Leu Glu Trp Met
35 40 45

Gly Gly Ile Asp Pro Glu Thr Gly Asn Thr Ala Tyr Ser Gln Lys Phe
50 55 60

Lys Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Thr Tyr Tyr Ser Phe Ala Tyr Trp Gly Gln Gly Thr Leu Val Thr
100 105 110

Val Ser Ser
115

<210> SEQ ID NO 119
<211> LENGTH: 115
<212> TYPE: PRT
<213> ORGANISM: Artificial Sequence
<220> FEATURE:
<223> OTHER INFORMATION: 9VH3

<400> SEQUENCE: 119

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Glu Met His Trp Val Arg Gln Ala Thr Gly Gln Gly Leu Glu Trp Met
35 40 45

Gly Gly Ile Asp Pro Glu Thr Gly Asn Thr Ala Tyr Ser Gln Lys Phe
50 55 60

Lys Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Tyr Tyr Ser Phe Ala Tyr Trp Gly Gln Gly Thr Leu Val Thr
100 105 110

Val Ser Ser
115

<210> SEQ ID NO 120
<211> LENGTH: 115
<212> TYPE: PRT
<213> ORGANISM: Artificial Sequence
<220> FEATURE:
<223> OTHER INFORMATION: 5VH1

<400> SEQUENCE: 120

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ala Tyr
20 25 30

Glu Met His Trp Val Arg Gln Ala Pro Gly Gln Arg Leu Glu Trp Met
35 40 45

Gly Gly Ile Asp Pro Glu Thr Gly Asn Thr Ala Tyr Ser Gln Asn Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Tyr Tyr Ser Phe Ala Tyr Trp Gly Gln Gly Thr Leu Val Thr
100 105 110

Val Ser Ser
115

<210> SEQ ID NO 121
<211> LENGTH: 115
<212> TYPE: PRT
<213> ORGANISM: Artificial Sequence
<220> FEATURE:
<223> OTHER INFORMATION: 5VH2

<400> SEQUENCE: 121

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ala Tyr
20 25 30

Glu Met His Trp Val Arg Gln Ala Pro Gly Gln Gly Leu Glu Trp Met
35 40 45

Gly Gly Ile Asp Pro Glu Thr Gly Asn Thr Ala Tyr Ser Gln Asn Phe
50 55 60

Lys Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Tyr Tyr Ser Phe Ala Tyr Trp Gly Gln Gly Thr Leu Val Thr
100 105 110

Val Ser Ser
115

<210> SEQ ID NO 122
<211> LENGTH: 115
<212> TYPE: PRT
<213> ORGANISM: Artificial Sequence
<220> FEATURE:
<223> OTHER INFORMATION: 5VH3

<400> SEQUENCE: 122

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ala Tyr
20 25 30

Glu Met His Trp Val Gln Gln Ala Pro Gly Lys Gly Leu Glu Trp Met
35 40 45

Gly Gly Ile Asp Pro Glu Thr Gly Asn Thr Ala Tyr Ser Gln Asn Phe
50 55 60

Lys Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Thr Tyr Tyr Ser Phe Ala Tyr Trp Gly Gln Gly Thr Leu Val Thr
100 105 110

Val Ser Ser
115

<210> SEQ ID NO 123
<211> LENGTH: 112
<212> TYPE: PRT
<213> ORGANISM: Artificial Sequence
<220> FEATURE:
<223> OTHER INFORMATION: VL1

<400> SEQUENCE: 123

Asp Val Val Met Thr Gln Ser Pro Leu Ser Leu Pro Val Thr Leu Gly
1 5 10 15

Gln Pro Ala Ser Ile Ser Cys Arg Ser Ser Gln Thr Ile Val His Ser
20 25 30

Asn Gly Asn Thr Tyr Leu Glu Trp Phe Gln Gln Arg Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Val
85 90 95

Ser His Val Pro Tyr Thr Phe Gly Gly Gly Thr Lys Leu Glu Ile Lys
100 105 110

<210> SEQ ID NO 124
<211> LENGTH: 112
<212> TYPE: PRT
<213> ORGANISM: Artificial Sequence
<220> FEATURE:
<223> OTHER INFORMATION: VL2

<400> SEQUENCE: 124

Asp Ile Val Met Thr Gln Ser Pro Leu Ser Leu Pro Val Thr Pro Gly
1 5 10 15

Glu Pro Ala Ser Ile Ser Cys Arg Ser Ser Gln Thr Ile Val His Ser
20 25 30

Asn Gly Asn Thr Tyr Leu Glu Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

```
Ser Arg Val Glu Ala Glu Asp Val Gly Val Tyr Tyr Cys Phe Gln Val
                85                  90                  95

Ser His Val Pro Tyr Thr Phe Gly Gly Gly Thr Lys Leu Glu Ile Lys
            100                 105                 110


<210> SEQ ID NO 125
<211> LENGTH: 112
<212> TYPE: PRT
<213> ORGANISM: Artificial Sequence
<220> FEATURE:
<223> OTHER INFORMATION: VL3

<400> SEQUENCE: 125

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Thr Ile Val His Ser
            20                  25                  30

Asn Gly Asn Thr Tyr Leu Glu Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe Gln Val
                85                  90                  95

Ser His Val Pro Tyr Thr Phe Gly Gly Gly Thr Lys Leu Glu Ile Lys
            100                 105                 110


<210> SEQ ID NO 126
<211> LENGTH: 107
<212> TYPE: PRT
<213> ORGANISM: Artificial Sequence
<220> FEATURE:
<223> OTHER INFORMATION: hIgKCL

<400> SEQUENCE: 126

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 127
<211> LENGTH: 330
<212> TYPE: PRT
<213> ORGANISM: Artificial Sequence
<220> FEATURE:
<223> OTHER INFORMATION: hIgG1CH

<400> SEQUENCE: 127
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 128
<211> LENGTH: 245
<212> TYPE: PRT
<213> ORGANISM: Artificial Sequence
<220> FEATURE:
<223> OTHER INFORMATION: LAb9VH1VL3 scFv

<400> SEQUENCE: 128

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Thr Ile Val His Ser
            20                  25                  30
```

```
Asn Gly Asn Thr Tyr Leu Glu Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe Gln Val
                85                  90                  95

Ser His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Gln Val Gln Leu Val Gln Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Asp Tyr Glu Met His Trp Val Arg Gln Ala Pro Gly Gln Arg Leu Glu
                165                 170                 175

Trp Met Gly Gly Ile Asp Pro Glu Thr Gly Asn Thr Ala Tyr Ser Gln
            180                 185                 190

Lys Phe Lys Gly Arg Val Thr Ile Thr Arg Asp Thr Ser Ala Ser Thr
        195                 200                 205

Ala Tyr Met Glu Leu Ser Ser Leu Arg Ser Glu Asp Thr Ala Val Tyr
    210                 215                 220

Tyr Cys Ala Arg Tyr Tyr Ser Phe Ala Tyr Trp Gly Gln Gly Thr Leu
225                 230                 235                 240

Val Thr Val Ser Ser
                245
```

<210> SEQ ID NO 129
<211> LENGTH: 245
<212> TYPE: PRT
<213> ORGANISM: Artificial Sequence
<220> FEATURE:
<223> OTHER INFORMATION: LAb9VH3VL2 scFv

<400> SEQUENCE: 129

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gly Gly Thr Lys Leu Glu Ile Lys
            100                 105                 110

Gly Ser Thr Ser Gly Ser Gly Lys Pro Gly Ser Gly Glu Gly Ser Thr
        115                 120                 125

Lys Gly Gln Val Gln Leu Val Gln Ser Gly Ala Glu Val Lys Lys Pro
    130                 135                 140
```

```
Gly Ala Ser Val Lys Val Ser Cys Lys Ala Ser Gly Tyr Thr Phe Thr
145                 150                 155                 160

Asp Tyr Glu Met His Trp Val Arg Gln Ala Thr Gly Gln Gly Leu Glu
                165                 170                 175

Trp Met Gly Gly Ile Asp Pro Glu Thr Gly Asn Thr Ala Tyr Ser Gln
            180                 185                 190

Lys Phe Lys Gly Arg Val Thr Met Thr Arg Asn Thr Ser Ile Ser Thr
        195                 200                 205

Ala Tyr Met Glu Leu Ser Ser Leu Arg Ser Glu Asp Thr Ala Val Tyr
    210                 215                 220

Tyr Cys Ala Arg Tyr Tyr Ser Phe Ala Tyr Trp Gly Gln Gly Thr Leu
225                 230                 235                 240

Val Thr Val Ser Ser
                245


<210> SEQ ID NO 130
<211> LENGTH: 491
<212> TYPE: PRT
<213> ORGANISM: Artificial Sequence
<220> FEATURE:
<223> OTHER INFORMATION: huLIC19309a CAR

<400> SEQUENCE: 130

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Asp Ser Leu
            20                  25                  30

Ala Val Ser Leu Gly Glu Arg Ala Thr Ile Asn Cys Arg Ser Ser Gln
        35                  40                  45

Thr Ile Val His Ser Asn Gly Asn Thr Tyr Leu Glu Trp Tyr Gln Gln
    50                  55                  60

Lys Pro Gly Gln Pro Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Phe Gln Val Ser His Val Pro Tyr Thr Phe Gly Gly Gly Thr
        115                 120                 125

Lys Leu Glu Ile Lys Gly Ser Thr Ser Gly Ser Gly Lys Pro Gly Ser
    130                 135                 140

Gly Glu Gly Ser Thr Lys Gly Gln Val Gln Leu Val Gln Ser Gly Ala
145                 150                 155                 160

Glu Val Lys Lys Pro Gly Ala Ser Val Lys Val Ser Cys Lys Ala Ser
                165                 170                 175

Gly Tyr Thr Phe Thr Asp Tyr Glu Met His Trp Val Arg Gln Ala Pro
            180                 185                 190

Gly Gln Arg Leu Glu Trp Met Gly Gly Ile Asp Pro Glu Thr Gly Asn
        195                 200                 205

Thr Ala Tyr Ser Gln Lys Phe Lys Gly Arg Val Thr Ile Thr Arg Asp
    210                 215                 220

Thr Ser Ala Ser Thr Ala Tyr Met Glu Leu Ser Ser Leu Arg Ser Glu
225                 230                 235                 240

Asp Thr Ala Val Tyr Tyr Cys Ala Arg Tyr Tyr Ser Phe Ala Tyr Trp
                245                 250                 255
```

```
Gly Gln Gly Thr Leu Val Thr Val Ser Ser Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 131
<211> LENGTH: 491
<212> TYPE: PRT
<213> ORGANISM: Artificial Sequence
<220> FEATURE:
<223> OTHER INFORMATION: huLIC19309b CAR (H93 CAR)

<400> SEQUENCE: 131

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Thr Ile Val His Ser Asn Gly Asn Thr Tyr Leu Glu Trp Tyr Leu Gln
    50                  55                  60

Lys Pro Gly Gln Ser Pro Gln Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Phe Gln Val Ser His Val Pro Tyr Thr Phe Gly Gly Gly Thr
        115                 120                 125
```

```
Lys Leu Glu Ile Lys Gly Ser Thr Ser Gly Ser Gly Lys Pro Gly Ser
    130                 135                 140

Gly Glu Gly Ser Thr Lys Gly Gln Val Gln Leu Val Gln Ser Gly Ala
145                 150                 155                 160

Glu Val Lys Lys Pro Gly Ala Ser Val Lys Val Ser Cys Lys Ala Ser
                165                 170                 175

Gly Tyr Thr Phe Thr Asp Tyr Glu Met His Trp Val Arg Gln Ala Thr
            180                 185                 190

Gly Gln Gly Leu Glu Trp Met Gly Gly Ile Asp Pro Glu Thr Gly Asn
        195                 200                 205

Thr Ala Tyr Ser Gln Lys Phe Lys Gly Arg Val Thr Met Thr Arg Asn
    210                 215                 220

Thr Ser Ile Ser Thr Ala Tyr Met Glu Leu Ser Ser Leu Arg Ser Glu
225                 230                 235                 240

Asp Thr Ala Val Tyr Tyr Cys Ala Arg Tyr Tyr Ser Phe Ala Tyr Trp
                245                 250                 255

Gly Gln Gly Thr Leu Val Thr Val Ser Ser Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 132
<211> LENGTH: 18
<212> TYPE: PRT
<213> ORGANISM: Artificial Sequence
<220> FEATURE:
<223> OTHER INFORMATION: “whitlow” linker

<400> SEQUENCE: 132

Gly Ser Thr Ser Gly Ser Gly Lys Pro Gly Ser Gly Glu Gly Ser Thr
1               5                   10                  15

Lys Gly

<210> SEQ ID NO 133
<211> LENGTH: 962
<212> TYPE: PRT
<213> ORGANISM: Artificial Sequence
<220> FEATURE:
<223> OTHER INFORMATION: H93M CAR amino acid

<400> SEQUENCE: 133

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Thr Ile Val His Ser Asn Gly Asn Thr Tyr Leu Glu Trp Tyr Leu Gln
    50                  55                  60

Lys Pro Gly Gln Ser Pro Gln Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Phe Gln Val Ser His Val Pro Tyr Thr Phe Gly Gly Gly Thr
        115                 120                 125

Lys Leu Glu Ile Lys Gly Ser Thr Ser Gly Ser Gly Lys Pro Gly Ser
    130                 135                 140

Gly Glu Gly Ser Thr Lys Gly Gln Val Gln Leu Val Gln Ser Gly Ala
145                 150                 155                 160

Glu Val Lys Lys Pro Gly Ala Ser Val Lys Val Ser Cys Lys Ala Ser
                165                 170                 175

Gly Tyr Thr Phe Thr Asp Tyr Glu Met His Trp Val Arg Gln Ala Thr
            180                 185                 190

Gly Gln Gly Leu Glu Trp Met Gly Gly Ile Asp Pro Glu Thr Gly Asn
        195                 200                 205

Thr Ala Tyr Ser Gln Lys Phe Lys Gly Arg Val Thr Met Thr Arg Asn
    210                 215                 220

Thr Ser Ile Ser Thr Ala Tyr Met Glu Leu Ser Ser Leu Arg Ser Glu
225                 230                 235                 240

Asp Thr Ala Val Tyr Tyr Cys Ala Arg Tyr Tyr Ser Phe Ala Tyr Trp
                245                 250                 255

Gly Gln Gly Thr Leu Val Thr Val Ser Ser Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe

```
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Val Asn Gly Ser Gly
                485                 490                 495

Ala Thr Asn Phe Ser Leu Leu Lys Gln Ala Gly Asp Val Glu Glu Asn
            500                 505                 510

Pro Gly Pro Met Cys His Gln Gln Leu Val Ile Ser Trp Phe Ser Leu
        515                 520                 525

Val Phe Leu Ala Ser Pro Leu Val Ala Ile Trp Glu Leu Lys Lys Asp
    530                 535                 540

Val Tyr Val Val Glu Leu Asp Trp Tyr Pro Asp Ala Pro Gly Glu Met
545                 550                 555                 560

Val Val Leu Thr Cys Asp Thr Pro Glu Glu Asp Gly Ile Thr Trp Thr
                565                 570                 575

Leu Asp Gln Ser Ser Glu Val Leu Gly Ser Gly Lys Thr Leu Thr Ile
            580                 585                 590

Gln Val Lys Glu Phe Gly Asp Ala Gly Gln Tyr Thr Cys His Lys Gly
        595                 600                 605

Gly Glu Val Leu Ser His Ser Leu Leu Leu Leu His Lys Lys Glu Asp
    610                 615                 620

Gly Ile Trp Ser Thr Asp Ile Leu Lys Asp Gln Lys Glu Pro Lys Asn
625                 630                 635                 640

Lys Thr Phe Leu Arg Cys Glu Ala Lys Asn Tyr Ser Gly Arg Phe Thr
                645                 650                 655

Cys Trp Trp Leu Thr Thr Ile Ser Thr Asp Leu Thr Phe Ser Val Lys
            660                 665                 670

Ser Ser Arg Gly Ser Ser Asp Pro Gln Gly Val Thr Cys Gly Ala Ala
        675                 680                 685

Thr Leu Ser Ala Glu Arg Val Arg Gly Asp Asn Lys Glu Tyr Glu Tyr
    690                 695                 700

Ser Val Glu Cys Gln Glu Asp Ser Ala Cys Pro Ala Ala Glu Glu Ser
705                 710                 715                 720

Leu Pro Ile Glu Val Met Val Asp Ala Val His Lys Leu Lys Tyr Glu
                725                 730                 735

Asn Tyr Thr Ser Ser Phe Phe Ile Arg Asp Ile Ile Lys Pro Asp Pro
            740                 745                 750

Pro Lys Asn Leu Gln Leu Lys Pro Leu Lys Asn Ser Arg Gln Val Glu
        755                 760                 765
```

```
Val Ser Trp Glu Tyr Pro Asp Thr Trp Ser Thr Pro His Ser Tyr Phe
    770                 775                 780

Ser Leu Thr Phe Cys Val Gln Val Gln Gly Lys Ser Lys Arg Glu Lys
785                 790                 795                 800

Lys Asp Arg Val Phe Thr Asp Lys Thr Ser Ala Thr Val Ile Cys Arg
                805                 810                 815

Lys Asn Ala Ser Ile Ser Val Arg Ala Gln Asp Arg Tyr Tyr Ser Ser
            820                 825                 830

Ser Trp Ser Glu Trp Ala Ser Val Pro Cys Ser Gly Ser Gly Glu Gly
        835                 840                 845

Arg Gly Ser Leu Leu Thr Cys Gly Asp Val Glu Glu Asn Pro Gly Pro
    850                 855                 860

Met Ala Leu Leu Leu Ala Leu Ser Leu Leu Val Leu Trp Thr Ser Pro
865                 870                 875                 880

Ala Pro Thr Leu Ser Gly Thr Asn Asp Ala Glu Asp Cys Cys Leu Ser
                885                 890                 895

Val Thr Gln Lys Pro Ile Pro Gly Tyr Ile Val Arg Asn Phe His Tyr
            900                 905                 910

Leu Leu Ile Lys Asp Gly Cys Arg Val Pro Ala Val Val Phe Thr Thr
        915                 920                 925

Leu Arg Gly Arg Gln Leu Cys Ala Pro Pro Asp Gln Pro Trp Val Glu
    930                 935                 940

Arg Ile Ile Gln Arg Leu Gln Arg Thr Ser Ala Lys Met Lys Arg Arg
945                 950                 955                 960

Ser Ser
```

<210> SEQ ID NO 134
<211> LENGTH: 447
<212> TYPE: PRT
<213> ORGANISM: Artificial Sequence
<220> FEATURE:
<223> OTHER INFORMATION: IL12p40-T2A-CCL-19

<400> SEQUENCE: 134

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160
```

Gly Ser Ser Asp Pro Gln Gly Val Thr Cys Gly Ala Ala Thr Leu Ser
165 170 175

Ala Glu Arg Val Arg Gly Asp Asn Lys Glu Tyr Glu Tyr Ser Val Glu
180 185 190

Cys Gln Glu Asp Ser Ala Cys Pro Ala Ala Glu Glu Ser Leu Pro Ile
195 200 205

Glu Val Met Val Asp Ala Val His Lys Leu Lys Tyr Glu Asn Tyr Thr
210 215 220

Ser Ser Phe Phe Ile Arg Asp Ile Ile Lys Pro Asp Pro Pro Lys Asn
225 230 235 240

Leu Gln Leu Lys Pro Leu Lys Asn Ser Arg Gln Val Glu Val Ser Trp
245 250 255

Glu Tyr Pro Asp Thr Trp Ser Thr Pro His Ser Tyr Phe Ser Leu Thr
260 265 270

Phe Cys Val Gln Val Gln Gly Lys Ser Lys Arg Glu Lys Lys Asp Arg
275 280 285

Val Phe Thr Asp Lys Thr Ser Ala Thr Val Ile Cys Arg Lys Asn Ala
290 295 300

Ser Ile Ser Val Arg Ala Gln Asp Arg Tyr Tyr Ser Ser Ser Trp Ser
305 310 315 320

Glu Trp Ala Ser Val Pro Cys Ser Gly Ser Gly Glu Gly Arg Gly Ser
325 330 335

Leu Leu Thr Cys Gly Asp Val Glu Glu Asn Pro Gly Pro Met Ala Leu
340 345 350

Leu Leu Ala Leu Ser Leu Leu Val Leu Trp Thr Ser Pro Ala Pro Thr
355 360 365

Leu Ser Gly Thr Asn Asp Ala Glu Asp Cys Cys Leu Ser Val Thr Gln
370 375 380

Lys Pro Ile Pro Gly Tyr Ile Val Arg Asn Phe His Tyr Leu Leu Ile
385 390 395 400

Lys Asp Gly Cys Arg Val Pro Ala Val Val Phe Thr Thr Leu Arg Gly
405 410 415

Arg Gln Leu Cys Ala Pro Pro Asp Gln Pro Trp Val Glu Arg Ile Ile
420 425 430

Gln Arg Leu Gln Arg Thr Ser Ala Lys Met Lys Arg Arg Ser Ser
435 440 445

<210> SEQ ID NO 135
<211> LENGTH: 328
<212> TYPE: PRT
<213> ORGANISM: Artificial Sequence
<220> FEATURE:
<223> OTHER INFORMATION: Human IL12p40

<400> SEQUENCE: 135

Met Cys His Gln Gln Leu Val Ile Ser Trp Phe Ser Leu Val Phe Leu
1 5 10 15

Ala Ser Pro Leu Val Ala Ile Trp Glu Leu Lys Lys Asp Val Tyr Val
20 25 30

Val Glu Leu Asp Trp Tyr Pro Asp Ala Pro Gly Glu Met Val Val Leu
35 40 45

Thr Cys Asp Thr Pro Glu Glu Asp Gly Ile Thr Trp Thr Leu Asp Gln
50 55 60

Ser Ser Glu Val Leu Gly Ser Gly Lys Thr Leu Thr Ile Gln Val Lys
65 70 75 80

```
Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

<210> SEQ ID NO 136
<211> LENGTH: 98
<212> TYPE: PRT
<213> ORGANISM: Artificial Sequence
<220> FEATURE:
<223> OTHER INFORMATION: Human CCL-19

<400> SEQUENCE: 136

```
Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser
```

<210> SEQ ID NO 137
<211> LENGTH: 2886
<212> TYPE: DNA
<213> ORGANISM: Artificial Sequence
<220> FEATURE:
<223> OTHER INFORMATION: H93M CAR nucleic acid

<400> SEQUENCE: 137
atggccctgc ctgtgaccgc tctgctgctg cctctggctc tgctgctgca cgctgcccgc 60
cctgacattg tgatgaccca gtctcccctg tccctgccag tgacccctgg agagccagcc 120
tccatctctt gcaggagctc ccagaccatc gtgcacagca acggcaatac atacctggag 180
tggtatctgc agaagcccgg ccagtcccct cagctgctga tctacaaggt gtctaacagg 240
ttcagcggag tgccagaccg ctttagcgga tccggatctg gcaccgattt cacactgaag 300
atctctagag tggaggccga ggacgtgggc gtgtactatt gcttccaggt gagccacgtg 360
ccatatacct ttggcggcgg cacaaagctg gagatcaagg gcagcacctc cggatctggc 420
aagccaggat ccggagaggg atctacaaag ggacaggtgc agctggtgca gagcggagca 480
gaggtgaaga agcctggagc cagcgtgaag gtgtcctgta aggcctctgg ctacaccttc 540
acagactatg agatgcactg ggtgcggcag gcaaccggac agggcctgga gtggatggga 600
ggaatcgacc cagagacagg caacacagcc tactcccaga agtttaaggg ccgggtgacc 660
atgacaagaa ataccagcat ctccacagcc tatatggagc tgtctagcct gagatctgag 720
gatacagccg tgtactattg tgctcgctac tattcctttg cctactgggg acaggggaca 780
ctggtcaccg tctcatcaac tagtaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg caaacggggc 1020
agaaagaaac tcctgtatat attcaaacaa ccatttatga gaccagtaca aactactcaa 1080
gaggaagatg gctgtagctg ccgatttcca gaagaagaag aaggaggatg tgaactgaga 1140
gtgaagttca gcaggagcgc agacgccccc gcgtaccagc agggccagaa ccagctctat 1200
aacgagctca atctaggacg aagagaggag tacgatgttt tggacaagag acgtggccgg 1260
gaccctgaga tggggggaaa gccgagaagg aagaaccctc aggaaggcct gtacaatgaa 1320
ctgcagaaag ataagatggc ggaggcctac agtgagattg ggatgaaagg cgagcgccgg 1380
aggggcaagg ggcacgatgg cctttaccag ggtctcagta cagccaccaa ggacacctac 1440
gacgcccttc acatgcaggc cctgccccct cgcgttaacg gcagcggagc tacaaacttc 1500
agtcttctaa aacaggctgg tgacgtggag gagaatcccg gccctatgtg ccatcagcag 1560
ctggtcattt cttggttctc tctggtgttt ctggctagtc ctctggtcgc tatttgggaa 1620
ctgaaaaaag atgtgtacgt ggtggagctg gactggtatc cagatgcacc aggagagatg 1680
gtggtgctga cctgcgacac acccgaggag gatggcatca cctggacact ggaccagagc 1740
tccgaggtgc tgggaagcgg caagaccctg acaatccagg tgaaggagtt cggcgatgcc 1800
ggccagtaca catgtcacaa gggcggcgag gtgctgtctc acagcctgct gctgctgcac 1860
aagaaggagg acggcatctg gtccacagac atcctgaagg atcagaagga gcctaagaac 1920
aagaccttcc tgcggtgcga ggccaagaat tattctggcc ggttcacctg ttggtggctg 1980
accacaatct ctaccgacct gaccttcagc gtgaagtcta gccggggctc ctctgatcca 2040
cagggagtga catgcggagc agccaccctg agcgccgagc gggtgagagg cgacaacaag 2100
gagtacgagt atagcgtgga gtgccaggag gattccgcct gtccagcagc agaggagtcc 2160
ctgcctatcg aagtgatggt ggacgccgtg cacaagctga agtacgagaa ttatacaagc 2220
tccttcttta tcagggacat catcaagcca gatcccccta agaacctgca gctgaagccc 2280
ctgaagaatt cccgccaggt ggaggtgtct tgggagtacc ctgatacctg gtccacacca 2340
cacagctatt tctccctgac cttttgcgtg caggtgcagg gcaagtctaa gagggagaag 2400
aaggaccgcg tgttcaccga taagacaagc gccaccgtga tctgtcggaa gaacgcctcc 2460
atctctgtgc gggctcagga ccgatattac tcatcatcat ggagtgaatg ggcctcagtg 2520
ccttgctcag gcagtggaga gggcagagga agtctgctaa catgcggtga cgtcgaggag 2580
aatcctggcc caatggctct gctgctggca ctgagtctgc tggtcctgtg gacatcacct 2640
gcacctaccc tgagtggaac taatgacgct gaagattgtt gcctgagcgt gacccagaag 2700
ccaatccccg gctacatcgt gaggaacttc cactatctgc tgatcaagga cggatgcagg 2760
gtgcctgcag tggtgtttac cacactgcgg ggcagacagc tgtgcgcacc acctgatcag 2820
ccctgggtcg agagaattat tcagagactg cagcgcacct cagctaagat gaaacgccgc 2880
tcaagt 2886

<210> SEQ ID NO 138
<211> LENGTH: 22
<212> TYPE: PRT
<213> ORGANISM: Artificial Sequence
<220> FEATURE:
<223> OTHER INFORMATION: P2A

<400> SEQUENCE: 138

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 139
<211> LENGTH: 21
<212> TYPE: PRT
<213> ORGANISM: Artificial Sequence
<220> FEATURE:
<223> OTHER INFORMATION: T2A

<400> SEQUENCE: 139

Gly Ser Gly Glu Gly Arg Gly Ser Leu Leu Thr Cys Gly Asp Val Glu
1 5 10 15

Glu Asn Pro Gly Pro
20

<210> SEQ ID NO 140
<211> LENGTH: 6
<212> TYPE: DNA
<213> ORGANISM: Artificial Sequence
<220> FEATURE:
<223> OTHER INFORMATION: MluI restriction site

<400> SEQUENCE: 140 acgcgt 6

<210> SEQ ID NO 141
<211> LENGTH: 6
<212> TYPE: DNA
<213> ORGANISM: Artificial Sequence
<220> FEATURE:
<223> OTHER INFORMATION: SpeI restriction site

<400> SEQUENCE: 141 actagt 6

<210> SEQ ID NO 142
<211> LENGTH: 6
<212> TYPE: DNA
<213> ORGANISM: Artificial Sequence
<220> FEATURE:
<223> OTHER INFORMATION: EcoRI restriction site

<400> SEQUENCE: 142 gaattc 6

<210> SEQ ID NO 143
<211> LENGTH: 6
<212> TYPE: DNA
<213> ORGANISM: Artificial Sequence
<220> FEATURE:
<223> OTHER INFORMATION: HpaI restriction site

<400> SEQUENCE: 143 gttaac 6

<210> SEQ ID NO 144
<211> LENGTH: 464
<212> TYPE: PRT
<213> ORGANISM: Artificial Sequence
<220> FEATURE:
<223> OTHER INFORMATION: 9VH1-hIgG1CH

<400> SEQUENCE: 144

```
Met Gly Trp Ser Trp Ile Leu Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Val Arg Gln Ala Pro Gly Gln Arg Leu
    50                  55                  60

Glu Trp Met Gly Gly Ile Asp Pro Glu Thr Gly Asn Thr Ala Tyr Ser
65                  70                  75                  80

Gln Lys Phe Lys Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Tyr Tyr Ser Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
```

```
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460


<210> SEQ ID NO 145
<211> LENGTH: 464
<212> TYPE: PRT
<213> ORGANISM: Artificial Sequence
<220> FEATURE:
<223> OTHER INFORMATION: 9VH2-hIgG1CH

<400> SEQUENCE: 145

Met Gly Trp Ser Trp Ile Leu Leu Phe Leu Leu Ser Val Thr Ala Gly
1               5                   10                  15

Val His Ser Glu Val Gln Leu Val Gln Ser Gly Ala Glu Val Lys Lys
            20                  25                  30

Pro Gly Ala Thr Val Lys Ile Ser Cys Lys Val Ser Gly Tyr Thr Phe
        35                  40                  45

Thr Asp Tyr Glu Met His Trp Val Gln Gln Ala Pro Gly Lys Gly Leu
    50                  55                  60

Glu Trp Met Gly Gly Ile Asp Pro Glu Thr Gly Asn Thr Ala Tyr Ser
65                  70                  75                  80

Gln Lys Phe Lys Gly Arg Val Thr Ile Thr Ala Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Thr Tyr Tyr Ser Phe Ala Tyr Trp Gly Gln Gly Thr
```

115 120 125

Leu Val Thr Val Ser Ser Ala Ser Thr Lys Gly Pro Ser Val Phe Pro
130 135 140

Leu Ala Pro Ser Ser Lys Ser Thr Ser Gly Gly Thr Ala Ala Leu Gly
145 150 155 160

Cys Leu Val Lys Asp Tyr Phe Pro Glu Pro Val Thr Val Ser Trp Asn
165 170 175

Ser Gly Ala Leu Thr Ser Gly Val His Thr Phe Pro Ala Val Leu Gln
180 185 190

Ser Ser Gly Leu Tyr Ser Leu Ser Ser Val Val Thr Val Pro Ser Ser
195 200 205

Ser Leu Gly Thr Gln Thr Tyr Ile Cys Asn Val Asn His Lys Pro Ser
210 215 220

Asn Thr Lys Val Asp Lys Lys Val Glu Pro Lys Ser Cys Asp Lys Thr
225 230 235 240

His Thr Cys Pro Pro Cys Pro Ala Pro Glu Leu Leu Gly Gly Pro Ser
245 250 255

Val Phe Leu Phe Pro Pro Lys Pro Lys Asp Thr Leu Met Ile Ser Arg
260 265 270

Thr Pro Glu Val Thr Cys Val Val Val Asp Val Ser His Glu Asp Pro
275 280 285

Glu Val Lys Phe Asn Trp Tyr Val Asp Gly Val Glu Val His Asn Ala
290 295 300

Lys Thr Lys Pro Arg Glu Glu Gln Tyr Asn Ser Thr Tyr Arg Val Val
305 310 315 320

Ser Val Leu Thr Val Leu His Gln Asp Trp Leu Asn Gly Lys Glu Tyr
325 330 335

Lys Cys Lys Val Ser Asn Lys Ala Leu Pro Ala Pro Ile Glu Lys Thr
340 345 350

Ile Ser Lys Ala Lys Gly Gln Pro Arg Glu Pro Gln Val Tyr Thr Leu
355 360 365

Pro Pro Ser Arg Asp Glu Leu Thr Lys Asn Gln Val Ser Leu Thr Cys
370 375 380

Leu Val Lys Gly Phe Tyr Pro Ser Asp Ile Ala Val Glu Trp Glu Ser
385 390 395 400

Asn Gly Gln Pro Glu Asn Asn Tyr Lys Thr Thr Pro Pro Val Leu Asp
405 410 415

Ser Asp Gly Ser Phe Phe Leu Tyr Ser Lys Leu Thr Val Asp Lys Ser
420 425 430

Arg Trp Gln Gln Gly Asn Val Phe Ser Cys Ser Val Met His Glu Ala
435 440 445

Leu His Asn His Tyr Thr Gln Lys Ser Leu Ser Leu Ser Pro Gly Lys
450 455 460

<210> SEQ ID NO 146
<211> LENGTH: 464
<212> TYPE: PRT
<213> ORGANISM: Artificial Sequence
<220> FEATURE:
<223> OTHER INFORMATION: 9VH3-hIgG1CH

<400> SEQUENCE: 146

Met Gly Trp Ser Trp Ile Leu Leu Phe Leu Leu Ser Val Thr Ala Gly
1 5 10 15

Val His Ser Gln Val Gln Leu Val Gln Ser Gly Ala Glu Val Lys Lys

```
            20                  25                  30

Pro Gly Ala Ser Val Lys Val Ser Cys Lys Ala Ser Gly Tyr Thr Phe
        35                  40                  45

Thr Asp Tyr Glu Met His Trp Val Arg Gln Ala Thr Gly Gln Gly Leu
    50                  55                  60

Glu Trp Met Gly Gly Ile Asp Pro Glu Thr Gly Asn Thr Ala Tyr Ser
65                  70                  75                  80

Gln Lys Phe Lys Gly Arg Val Thr Met Thr Arg Asn Thr Ser Ile Ser
                85                  90                  95

Thr Ala Tyr Met Glu Leu Ser Ser Leu Arg Ser Glu Asp Thr Ala Val
            100                 105                 110

Tyr Tyr Cys Ala Arg Tyr Tyr Ser Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445
```

```
Leu His Asn His Tyr Thr Gln Lys Ser Leu Ser Leu Ser Pro Gly Lys
    450                 455                 460


<210> SEQ ID NO 147
<211> LENGTH: 463
<212> TYPE: PRT
<213> ORGANISM: Artificial Sequence
<220> FEATURE:
<223> OTHER INFORMATION: 5VH1-hIgG1CH

<400> SEQUENCE: 147

Met Gly Trp Ser Trp Ile Leu Leu Phe Leu Leu Ser Val Thr Ala Gly
1               5                   10                  15

Val His Gln Val Gln Leu Val Gln Ser Gly Ala Glu Val Lys Lys Pro
            20                  25                  30

Gly Ala Ser Val Lys Val Ser Cys Lys Ala Ser Gly Tyr Thr Phe Thr
        35                  40                  45

Ala Tyr Glu Met His Trp Val Arg Gln Ala Pro Gly Gln Arg Leu Glu
    50                  55                  60

Trp Met Gly Gly Ile Asp Pro Glu Thr Gly Asn Thr Ala Tyr Ser Gln
65                  70                  75                  80

Asn Phe Lys Gly Arg Val Thr Ile Thr Arg Asp Thr Ser Ala Ser Thr
                85                  90                  95

Ala Tyr Met Glu Leu Ser Ser Leu Arg Ser Glu Asp Thr Ala Val Tyr
            100                 105                 110

Tyr Cys Ala Arg Tyr Tyr Ser Phe Ala Tyr Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350
```

Ser Lys Ala Lys Gly Gln Pro Arg Glu Pro Gln Val Tyr Thr Leu Pro
355 360 365

Pro Ser Arg Asp Glu Leu Thr Lys Asn Gln Val Ser Leu Thr Cys Leu
370 375 380

Val Lys Gly Phe Tyr Pro Ser Asp Ile Ala Val Glu Trp Glu Ser Asn
385 390 395 400

Gly Gln Pro Glu Asn Asn Tyr Lys Thr Thr Pro Pro Val Leu Asp Ser
405 410 415

Asp Gly Ser Phe Phe Leu Tyr Ser Lys Leu Thr Val Asp Lys Ser Arg
420 425 430

Trp Gln Gln Gly Asn Val Phe Ser Cys Ser Val Met His Glu Ala Leu
435 440 445

His Asn His Tyr Thr Gln Lys Ser Leu Ser Leu Ser Pro Gly Lys
450 455 460

<210> SEQ ID NO 148
<211> LENGTH: 463
<212> TYPE: PRT
<213> ORGANISM: Artificial Sequence
<220> FEATURE:
<223> OTHER INFORMATION: 5VH2-hIgG1CH

<400> SEQUENCE: 148

Met Gly Trp Ser Trp Ile Leu Leu Phe Leu Leu Ser Val Thr Ala Gly
1 5 10 15

Val His Gln Val Gln Leu Val Gln Ser Gly Ala Glu Val Lys Lys Pro
20 25 30

Gly Ala Ser Val Lys Val Ser Cys Lys Ala Ser Gly Tyr Thr Phe Thr
35 40 45

Ala Tyr Glu Met His Trp Val Arg Gln Ala Pro Gly Gln Gly Leu Glu
50 55 60

Trp Met Gly Gly Ile Asp Pro Glu Thr Gly Asn Thr Ala Tyr Ser Gln
65 70 75 80

Asn Phe Lys Gly Arg Val Thr Met Thr Arg Asp Thr Ser Thr Ser Thr
85 90 95

Val Tyr Met Glu Leu Ser Ser Leu Arg Ser Glu Asp Thr Ala Val Tyr
100 105 110

Tyr Cys Ala Arg Tyr Tyr Ser Phe Ala Tyr Trp Gly Gln Gly Thr Leu
115 120 125

Val Thr Val Ser Ser Ala Ser Thr Lys Gly Pro Ser Val Phe Pro Leu
130 135 140

Ala Pro Ser Ser Lys Ser Thr Ser Gly Gly Thr Ala Ala Leu Gly Cys
145 150 155 160

Leu Val Lys Asp Tyr Phe Pro Glu Pro Val Thr Val Ser Trp Asn Ser
165 170 175

Gly Ala Leu Thr Ser Gly Val His Thr Phe Pro Ala Val Leu Gln Ser
180 185 190

Ser Gly Leu Tyr Ser Leu Ser Ser Val Val Thr Val Pro Ser Ser Ser
195 200 205

Leu Gly Thr Gln Thr Tyr Ile Cys Asn Val Asn His Lys Pro Ser Asn
210 215 220

Thr Lys Val Asp Lys Lys Val Glu Pro Lys Ser Cys Asp Lys Thr His
225 230 235 240

Thr Cys Pro Pro Cys Pro Ala Pro Glu Leu Leu Gly Gly Pro Ser Val
245 250 255

Phe Leu Phe Pro Pro Lys Pro Lys Asp Thr Leu Met Ile Ser Arg Thr
260 265 270

Pro Glu Val Thr Cys Val Val Val Asp Val Ser His Glu Asp Pro Glu
275 280 285

Val Lys Phe Asn Trp Tyr Val Asp Gly Val Glu Val His Asn Ala Lys
290 295 300

Thr Lys Pro Arg Glu Glu Gln Tyr Asn Ser Thr Tyr Arg Val Val Ser
305 310 315 320

Val Leu Thr Val Leu His Gln Asp Trp Leu Asn Gly Lys Glu Tyr Lys
325 330 335

Cys Lys Val Ser Asn Lys Ala Leu Pro Ala Pro Ile Glu Lys Thr Ile
340 345 350

Ser Lys Ala Lys Gly Gln Pro Arg Glu Pro Gln Val Tyr Thr Leu Pro
355 360 365

Pro Ser Arg Asp Glu Leu Thr Lys Asn Gln Val Ser Leu Thr Cys Leu
370 375 380

Val Lys Gly Phe Tyr Pro Ser Asp Ile Ala Val Glu Trp Glu Ser Asn
385 390 395 400

Gly Gln Pro Glu Asn Asn Tyr Lys Thr Thr Pro Pro Val Leu Asp Ser
405 410 415

Asp Gly Ser Phe Phe Leu Tyr Ser Lys Leu Thr Val Asp Lys Ser Arg
420 425 430

Trp Gln Gln Gly Asn Val Phe Ser Cys Ser Val Met His Glu Ala Leu
435 440 445

His Asn His Tyr Thr Gln Lys Ser Leu Ser Leu Ser Pro Gly Lys
450 455 460

<210> SEQ ID NO 149
<211> LENGTH: 463
<212> TYPE: PRT
<213> ORGANISM: Artificial Sequence
<220> FEATURE:
<223> OTHER INFORMATION: 5VH3-hIgG1CH

<400> SEQUENCE: 149

Met Gly Trp Ser Trp Ile Leu Leu Phe Leu Leu Ser Val Thr Ala Gly
1 5 10 15

Val His Glu Val Gln Leu Val Gln Ser Gly Ala Glu Val Lys Lys Pro
20 25 30

Gly Ala Thr Val Lys Ile Ser Cys Lys Val Ser Gly Tyr Thr Phe Thr
35 40 45

Ala Tyr Glu Met His Trp Val Gln Gln Ala Pro Gly Lys Gly Leu Glu
50 55 60

Trp Met Gly Gly Ile Asp Pro Glu Thr Gly Asn Thr Ala Tyr Ser Gln
65 70 75 80

Asn Phe Lys Gly Arg Val Thr Ile Thr Ala Asp Thr Ser Thr Asp Thr
85 90 95

Ala Tyr Met Glu Leu Ser Ser Leu Arg Ser Glu Asp Thr Ala Val Tyr
100 105 110

Tyr Cys Ala Thr Tyr Tyr Ser Phe Ala Tyr Trp Gly Gln Gly Thr Leu
115 120 125

Val Thr Val Ser Ser Ala Ser Thr Lys Gly Pro Ser Val Phe Pro Leu
130 135 140

Ala Pro Ser Ser Lys Ser Thr Ser Gly Gly Thr Ala Ala Leu Gly Cys
145 150 155 160

Leu Val Lys Asp Tyr Phe Pro Glu Pro Val Thr Val Ser Trp Asn Ser
165 170 175

Gly Ala Leu Thr Ser Gly Val His Thr Phe Pro Ala Val Leu Gln Ser
180 185 190

Ser Gly Leu Tyr Ser Leu Ser Ser Val Val Thr Val Pro Ser Ser Ser
195 200 205

Leu Gly Thr Gln Thr Tyr Ile Cys Asn Val Asn His Lys Pro Ser Asn
210 215 220

Thr Lys Val Asp Lys Lys Val Glu Pro Lys Ser Cys Asp Lys Thr His
225 230 235 240

Thr Cys Pro Pro Cys Pro Ala Pro Glu Leu Leu Gly Gly Pro Ser Val
245 250 255

Phe Leu Phe Pro Pro Lys Pro Lys Asp Thr Leu Met Ile Ser Arg Thr
260 265 270

Pro Glu Val Thr Cys Val Val Val Asp Val Ser His Glu Asp Pro Glu
275 280 285

Val Lys Phe Asn Trp Tyr Val Asp Gly Val Glu Val His Asn Ala Lys
290 295 300

Thr Lys Pro Arg Glu Glu Gln Tyr Asn Ser Thr Tyr Arg Val Val Ser
305 310 315 320

Val Leu Thr Val Leu His Gln Asp Trp Leu Asn Gly Lys Glu Tyr Lys
325 330 335

Cys Lys Val Ser Asn Lys Ala Leu Pro Ala Pro Ile Glu Lys Thr Ile
340 345 350

Ser Lys Ala Lys Gly Gln Pro Arg Glu Pro Gln Val Tyr Thr Leu Pro
355 360 365

Pro Ser Arg Asp Glu Leu Thr Lys Asn Gln Val Ser Leu Thr Cys Leu
370 375 380

Val Lys Gly Phe Tyr Pro Ser Asp Ile Ala Val Glu Trp Glu Ser Asn
385 390 395 400

Gly Gln Pro Glu Asn Asn Tyr Lys Thr Thr Pro Pro Val Leu Asp Ser
405 410 415

Asp Gly Ser Phe Phe Leu Tyr Ser Lys Leu Thr Val Asp Lys Ser Arg
420 425 430

Trp Gln Gln Gly Asn Val Phe Ser Cys Ser Val Met His Glu Ala Leu
435 440 445

His Asn His Tyr Thr Gln Lys Ser Leu Ser Leu Ser Pro Gly Lys
450 455 460

<210> SEQ ID NO 150
<211> LENGTH: 238
<212> TYPE: PRT
<213> ORGANISM: Artificial Sequence
<220> FEATURE:
<223> OTHER INFORMATION: VL1-hIgKCL

<400> SEQUENCE: 150

Met Gly Trp Ser Trp Ile Leu Leu Phe Leu Leu Ser Val Thr Ala Gly
1 5 10 15

Val His Ser Asp Val Val Met Thr Gln Ser Pro Leu Ser Leu Pro Val
20 25 30

Thr Leu Gly Gln Pro Ala Ser Ile Ser Cys Arg Ser Ser Gln Thr Ile
35 40 45

Val His Ser Asn Gly Asn Thr Tyr Leu Glu Trp Phe Gln Gln Arg Pro
50 55 60

```
Gly Gln Ser Pro Arg Arg Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Phe Gln Val Ser His Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 151
<211> LENGTH: 238
<212> TYPE: PRT
<213> ORGANISM: Artificial Sequence
<220> FEATURE:
<223> OTHER INFORMATION: VL2-hIgKCL

<400> SEQUENCE: 151

Met Gly Trp Ser Trp Ile Leu Leu Phe Leu Leu Ser Val Thr Ala Gly
1               5                   10                  15

Val His Ser Asp Ile Val Met Thr Gln Ser Pro Leu Ser Leu Pro Val
            20                  25                  30

Thr Pro Gly Glu Pro Ala Ser Ile Ser Cys Arg Ser Ser Gln Thr Ile
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Phe Gln Val Ser His Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190
```

```
Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 152
<211> LENGTH: 238
<212> TYPE: PRT
<213> ORGANISM: Artificial Sequence
<220> FEATURE:
<223> OTHER INFORMATION: VL3- hIgKCL

<400> SEQUENCE: 152

Met Gly Trp Ser Trp Ile Leu Leu Phe Leu Leu Ser Val Thr Ala Gly
1               5                   10                  15

Val His Ser Asp Ile Val Met Thr Gln Ser Pro Asp Ser Leu Ala Val
            20                  25                  30

Ser Leu Gly Glu Arg Ala Thr Ile Asn Cys Arg Ser Ser Gln Thr Ile
        35                  40                  45

Val His Ser Asn Gly Asn Thr Tyr Leu Glu Trp Tyr Gln Gln Lys Pro
    50                  55                  60

Gly Gln Pro Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Phe Gln Val Ser His Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

ANTIBODIES AND CHIMERIC ANTIGEN RECEPTORS TARGETING GLYPICAN-3 (GPC3) AND METHODS OF USE THEREOF

CROSS-REFERENCE TO RELATED APPLICATIONS

This application is a U.S. National Stage Application under 35 U.S.C. § 371 of International Patent Application No. PCT/CN2021/078203, filed on Feb. 26, 2021, which claims benefit of priority of International Patent Application No. PCT/CN2020/076937 filed on Feb. 27, 2020, the content of each of which is incorporated by reference herein in its entirety.

SEQUENCE LISTING

This application incorporates by reference a Sequence Listing submitted with this application as a text format, entitled "14651-019-228_SEQ_LISTING" created on Feb. 23, 2021 having a size of 226,307 bytes.

1. FIELD

The present disclosure relates to the fields of antibodies, chimeric antigen receptors and engineered immune cells that target GPC3, and methods of use thereof.

2. BACKGROUND

Glypican-3 (GPC3), a 65-kDa protein of 580 amino acids, is a heparan sulfate proteoglycan anchored to the cell membrane by glycosylphosphatidylinositol. Bound to the two heparan sulfate chains are various important proteins, including fibroblast growth factor and Wnt. The heparan chains are not yet fully defined in terms of function, but are believed to control the association of the bound proteins to the corresponding receptors. GPC3 is expressed in hepatocellular carcinoma (HCC), ovarian clear cell carcinoma (OCCC), melanomas, lung squamous cell carcinomas, hepatoblastomas, nephroblastomas (Wilms' tumors), and yolk sac tumors, as well as in certain stomach cancers, for example, gastric cancers that produce α-fetoprotein. The exact function of secreted and membrane-anchored GPC3 in these cancers is not entirely clear, but it is demonstrated to involve in neoplastic transformation, e.g., in HCC (Shirakawa H., et al, Cancer Sci. 2009; 100:1403-1407). Strikingly, the protein is nearly absent in all other cancer forms. Based on these characteristics, GPC3 is a potentially ideal target for cancer immunotherapy. There is a need in the art for new anti-GPC3 antibodies and immunotherapies, such as GPC3 CAR-T therapies.

3. SUMMARY

In one aspect, provided herein is an antibody or antigen binding fragment thereof that binds glypican-3 (GPC3), comprising an HCDR1 selected from the group consisting of SEQ ID NOs: 1-10, an HCDR2 selected from the group consisting of SEQ ID NOs: 11-20, and an HCDR3 selected from the group consisting of SEQ ID NOs: 21-30; and a LCDR1 selected from the group consisting of SEQ ID NOs: 31-40, a LCDR2 selected from the group consisting of SEQ ID NOs: 41-50, and a LCDR3 selected from the group consisting of SEQ ID NOs: 51-60.

In some embodiments, in the antibody or antigen binding fragment provided herein. (i) the HCDR1 comprises the amino acid sequence of SEQ ID NO: 1, the HCDR2 comprises the amino acid sequence of SEQ ID NO: 11, the HCDR3 comprises the amino acid sequence of SEQ ID NO: 21, the LCDR1 comprises the amino acid sequence of SEQ ID NO: 31, the LCDR2 comprises the amino acid sequence of SEQ ID NO: 41, and the LCDR3 comprises the amino acid sequence of SEQ ID NO: 51, or (ii) the HCDR1 comprises the amino acid sequence of SEQ ID NO: 2, the HCDR2 comprises the amino acid sequence of SEQ ID NO: 12, the HCDR3 comprises the amino acid sequence of SEQ ID NO: 22, the LCDR1 comprises the amino acid sequence of SEQ ID NO: 32, the LCDR2 comprises the amino acid sequence of SEQ ID NO: 42, and the LCDR3 comprises the amino acid sequence of SEQ ID NO: 52, or (iii) the HCDR1 comprises the amino acid sequence of SEQ ID NO: 3, the HCDR2 comprises the amino acid sequence of SEQ ID NO: 13, the HCDR3 comprises the amino acid sequence of SEQ ID NO: 23, the LCDR1 comprises the amino acid sequence of SEQ ID NO: 33, the LCDR2 comprises the amino acid sequence of SEQ ID NO: 43, and the LCDR3 comprises the amino acid sequence of SEQ ID NO: 53, or (iv) the HCDR1 comprises the amino acid sequence of SEQ ID NO: 4, the HCDR2 comprises the amino acid sequence of SEQ ID NO: 14, the HCDR3 comprises the amino acid sequence of SEQ ID NO: 24, the LCDR1 comprises the amino acid sequence of SEQ ID NO: 34, the LCDR2 comprises the amino acid sequence of SEQ ID NO: 44, and the LCDR3 comprises the amino acid sequence of SEQ ID NO: 54, or (v) the HCDR1 comprises the amino acid sequence of SEQ ID NO: 5, the HCDR2 comprises the amino acid sequence of SEQ ID NO: 15, the HCDR3 comprises the amino acid sequence of SEQ ID NO: 25, the LCDR1 comprises the amino acid sequence of SEQ ID NO: 35, the LCDR2 comprises the amino acid sequence of SEQ ID NO: 45, and the LCDR3 comprises the amino acid sequence of SEQ ID NO: 55, or (vi) the HCDR1 comprises the amino acid sequence of SEQ ID NO: 6, the HCDR2 comprises the amino acid sequence of SEQ ID NO: 16, the HCDR3 comprises the amino acid sequence of SEQ ID NO: 26, the LCDR1 comprises the amino acid sequence of SEQ ID NO: 36, the LCDR2 comprises the amino acid sequence of SEQ ID NO: 46, and the LCDR3 comprises the amino acid sequence of SEQ ID NO: 56, or (vii) the HCDR1 comprises the amino acid sequence of SEQ ID NO: 7, the HCDR2 comprises the amino acid sequence of SEQ ID NO: 17, the HCDR3 comprises the amino acid sequence of SEQ ID NO: 27, the LCDR1 comprises the amino acid sequence of SEQ ID NO: 37, the LCDR2 comprises the amino acid sequence of SEQ ID NO: 47, and the LCDR3 comprises the amino acid sequence of SEQ ID NO: 57, or (viii) the HCDR1 comprises the amino acid sequence of SEQ ID NO: 8, the HCDR2 comprises the amino acid sequence of SEQ ID NO: 18, the HCDR3 comprises the amino acid sequence of SEQ ID NO: 28, the LCDR1 comprises the amino acid sequence of SEQ ID NO: 38, the LCDR2 comprises the amino acid sequence of SEQ ID NO: 48, and the LCDR3 comprises the amino acid sequence of SEQ ID NO: 58, or (ix) the HCDR1 comprises the amino acid sequence of SEQ ID NO: 9, the HCDR2 comprises the amino acid sequence of SEQ ID NO: 19, the HCDR3 comprises the amino acid sequence of SEQ ID NO: 29, the LCDR1 comprises the amino acid sequence of SEQ ID NO: 39, the LCDR2 comprises the amino acid sequence of SEQ ID NO: 49, and the LCDR3 comprises the amino acid sequence of SEQ ID NO: 59, or (x) the HCDR1 comprises the amino acid sequence of SEQ ID NO: 10, the HCDR2 comprises the amino acid sequence of SEQ ID NO: 20, the HCDR3 comprises the amino acid sequence of SEQ ID NO: 30, the LCDR1 comprises the amino acid sequence of SEQ ID NO: 40, the LCDR2 comprises the amino acid sequence of SEQ ID NO: 50, and the LCDR3 comprises the amino acid sequence of SEQ ID NO: 60.

In some embodiments, the antibody or antigen binding fragment provided herein comprises (i) a VH domain comprising an amino acid sequence having at least 80% identity to the amino acid sequence of SEQ ID NO: 61 and a VL domain comprising an amino acid sequence having at least 80% identity to the amino acid sequence of SEQ ID NO: 71, or (ii) a VH domain comprising an amino acid sequence having at least 80% identity to the amino acid sequence of SEQ ID NO: 62 and a VL domain comprising an amino acid sequence having at least 80% identity to the amino acid sequence of SEQ ID NO: 72, or (iii) a VH domain comprising an amino acid sequence having at least 80% identity to the amino acid sequence of SEQ ID NO: 63 and a VL domain comprising an amino acid sequence having at least 80% identity to the amino acid sequence of SEQ ID NO: 73, or (iv) a VH domain comprising an amino acid sequence having at least 80% identity to the amino acid sequence of SEQ ID NO: 64 and a VL domain comprising an amino acid sequence having at least 80% identity to the amino acid sequence of SEQ ID NO: 74, or (v) a VH domain comprising an amino acid sequence having at least 80% identity to the amino acid sequence of SEQ ID NO: 65 and a VL domain comprising an amino acid sequence having at least 80% identity to the amino acid sequence of SEQ ID NO: 75, or (vi) a VH domain comprising an amino acid sequence having at least 80% identity to the amino acid sequence of SEQ ID NO: 66 and a VL domain comprising an amino acid sequence having at least 80% identity to the amino acid sequence of SEQ ID NO: 76, or (vii) a VH domain comprising an amino acid sequence having at least 80% identity to the amino acid sequence of SEQ ID NO: 67 and a VL domain comprising an amino acid sequence having at least 80% identity to the amino acid sequence of SEQ ID NO: 77, or (viii) a VH domain comprising an amino acid sequence having at least 80% identity to the amino acid sequence of SEQ ID NO: 68 and a VL domain comprising an amino acid sequence having at least 80% identity to the amino acid sequence of SEQ ID NO: 78, or (ix) a VH domain comprising an amino acid sequence having at least 80% identity to the amino acid sequence of SEQ ID NO: 69 and a VL domain comprising an amino acid sequence having at least 80% identity to the amino acid sequence of SEQ ID NO: 79, or (x) a VH domain comprising an amino acid sequence having at least 80% identity to the amino acid sequence of SEQ ID NO: 70 and a VL domain comprising an amino acid sequence having at least 80% identity to the amino acid sequence of SEQ ID NO: 80, or (xi) a VH domain comprising an amino acid sequence having at least 80% identity to the amino acid sequence of SEQ ID NO: 117 and a VL domain comprising an amino acid sequence having at least 80% identity to the amino acid sequence of SEQ ID NO: 123, or (xii) a VH domain comprising an amino acid sequence having at least 80% identity to the amino acid sequence of SEQ ID NO: 118 and a VL domain comprising an amino acid sequence having at least 80% identity to the amino acid sequence of SEQ ID NO: 123, or (xiii) a VH domain comprising an amino acid sequence having at least 80% identity to the amino acid sequence of SEQ ID NO: 119 and a VL domain comprising an amino acid sequence having at least 80% identity to the amino acid sequence of SEQ ID NO: 123, or (xiv) a VH domain comprising an amino acid sequence having at least 80% identity to the amino acid sequence of SEQ ID NO: 120 and a VL domain comprising an amino acid sequence having at least 80% identity to the amino acid sequence of SEQ ID NO: 123, or (xv) a VH domain comprising an amino acid sequence having at least 80% identity to the amino acid sequence of SEQ ID NO: 121 and a VL domain comprising an amino acid sequence having at least 80% identity to the amino acid sequence of SEQ ID NO: 123, or (xvi) a VH domain comprising an amino acid sequence having at least 80% identity to the amino acid sequence of SEQ ID NO: 122 and a VL domain comprising an amino acid sequence having at least 80% identity to the amino acid sequence of SEQ ID NO: 123, or (xvii) a VH domain comprising an amino acid sequence having at least 80% identity to the amino acid sequence of SEQ ID NO: 117 and a VL domain comprising an amino acid sequence having at least 80% identity to the amino acid sequence of SEQ ID NO: 124, or (xviii) a VH domain comprising an amino acid sequence having at least 80% identity to the amino acid sequence of SEQ ID NO: 118 and a VL domain comprising an amino acid sequence having at least 80% identity to the amino acid sequence of SEQ ID NO: 124, or (xix) a VH domain comprising an amino acid sequence having at least 80% identity to the amino acid sequence of SEQ ID NO: 119 and a VL domain comprising an amino acid sequence having at least 80% identity to the amino acid sequence of SEQ ID NO: 124, or (xx) a VH domain comprising an amino acid sequence having at least 80% identity to the amino acid sequence of SEQ ID NO: 120 and a VL domain comprising an amino acid sequence having at least 80% identity to the amino acid sequence of SEQ ID NO: 124, or (xxi) a VH domain comprising an amino acid sequence having at least 80% identity to the amino acid sequence of SEQ ID NO: 121 and a VL domain comprising an amino acid sequence having at least 80% identity to the amino acid sequence of SEQ ID NO: 124, or (xxii) a VH domain comprising an amino acid sequence having at least 80% identity to the amino acid sequence of SEQ ID NO: 122 and a VL domain comprising an amino acid sequence having at least 80% identity to the amino acid sequence of SEQ ID NO: 124, or (xxiii) a VH domain comprising an amino acid sequence having at least 80% identity to the amino acid sequence of SEQ ID NO: 117 and a VL domain comprising an amino acid sequence having at least 80% identity to the amino acid sequence of SEQ ID NO: 125, or (xxiv) a VH domain comprising an amino acid sequence having at least 80% identity to the amino acid sequence of SEQ ID NO: 118 and a VL domain comprising an amino acid sequence having at least 80% identity to the amino acid sequence of SEQ ID NO: 125, or (xxv) a VH domain comprising an amino acid sequence having at least 80% identity to the amino acid sequence of SEQ ID NO: 119 and a VL domain comprising an amino acid sequence having at least 80% identity to the amino acid sequence of SEQ ID NO: 125, or (xxvi) a VH domain comprising an amino acid sequence having at least 80% identity to the amino acid sequence of SEQ ID NO: 120 and a VL domain comprising an amino acid sequence having at least 80% identity to the amino acid sequence of SEQ ID NO: 125, or (xxvii) a VH domain comprising an amino acid sequence having at least 80% identity to the amino acid sequence of SEQ ID NO: 121 and a VL domain comprising an amino acid sequence having at least 80% identity to the amino acid sequence of SEQ ID NO: 125, or (xxviii) a VH domain comprising an amino acid sequence having at least 80% identity to the amino acid sequence of SEQ ID NO: 122 and a VL domain comprising an amino acid sequence having at least 80% identity to the amino acid sequence of SEQ ID NO: 125.

In some embodiments, the antibody or antigen binding fragment provided herein comprises (i) a VH domain comprising the amino acid sequence of SEQ ID NO: 61 and a VL domain comprising the amino acid sequence of SEQ ID NO: 71, or (ii) a VH domain comprising the amino acid sequence of SEQ ID NO: 62 and a VL domain comprising the amino acid sequence of SEQ ID NO: 72, or (iii) a VH domain comprising the amino acid sequence of SEQ ID NO: 63 and a VL domain comprising the amino acid sequence of SEQ ID NO: 73, or (iv) a VH domain comprising the amino acid sequence of SEQ ID NO: 64 and a VL domain comprising the amino acid sequence of SEQ ID NO: 74, or (v) a VH domain comprising the amino acid sequence of SEQ ID NO: 65 and a VL domain comprising the amino acid sequence of SEQ ID NO: 75, or (vi) a VH domain comprising the amino acid sequence of SEQ ID NO: 66 and a VL domain comprising the amino acid sequence of SEQ ID NO: 76, or (vii) a VH domain comprising the amino acid sequence of SEQ ID NO: 67 and a VL domain comprising the amino acid sequence of SEQ ID NO: 77, or (viii) a VH domain comprising the amino acid sequence of SEQ ID NO: 68 and a VL domain comprising the amino acid sequence of SEQ ID NO: 78, or (ix) a VH domain comprising the amino acid sequence of SEQ ID NO: 69 and a VL domain comprising the amino acid sequence of SEQ ID NO: 79, or (x) a VH domain comprising the amino acid sequence of SEQ ID NO: 70 and a VL domain comprising the amino acid sequence of SEQ ID NO: 80, or (xi) a VH domain comprising the amino acid sequence of SEQ ID NO: 117 and a VL domain comprising the amino acid sequence of SEQ ID NO: 123, or (xii) a VH domain comprising the amino acid sequence of SEQ ID NO: 118 and a VL domain comprising the amino acid sequence of SEQ ID NO: 123, or (xiii) a VH domain comprising the amino acid sequence of SEQ ID NO: 119 and a VL domain comprising the amino acid sequence of SEQ ID NO: 123, or (xiv) a VH domain comprising the amino acid sequence of SEQ ID NO: 120 and a VL domain comprising the amino acid sequence of SEQ ID NO: 123, or (xv) a VH domain comprising the amino acid sequence of SEQ ID NO: 121 and a VL domain comprising the amino acid sequence of SEQ ID NO: 123, or (xvi) a VH domain comprising the amino acid sequence of SEQ ID NO: 122 and a VL domain comprising the amino acid sequence of SEQ ID NO: 123, or (xvii) a VH domain comprising the amino acid sequence of SEQ ID NO: 117 and a VL domain comprising the amino acid sequence of SEQ ID NO: 124, or (xviii) a VH domain comprising the amino acid sequence of SEQ ID NO: 118 and a VL domain comprising the amino acid sequence of SEQ ID NO: 124, or (xix) a VH domain comprising the amino acid sequence of SEQ ID NO: 119 and a VL domain comprising the amino acid sequence of SEQ ID NO: 124, or (xx) a VH domain comprising the amino acid sequence of SEQ ID NO: 120 and a VL domain comprising the amino acid sequence of SEQ ID NO: 124, or (xxi) a VH domain comprising the amino acid sequence of SEQ ID NO: 121 and a VL domain comprising the amino acid sequence of SEQ ID NO: 124, or (xxii) a VH domain comprising the amino acid sequence of SEQ ID NO: 122 and a VL domain comprising the amino acid sequence of SEQ ID NO: 124, or (xxiii) a VH domain comprising the amino acid sequence of SEQ ID NO: 117 and a VL domain comprising the amino acid sequence of SEQ ID NO: 125, or (xxiv) a VH domain comprising the amino acid sequence of SEQ ID NO: 118 and a VL domain comprising the amino acid sequence of SEQ ID NO: 125, or (xxV) a VH domain comprising the amino acid sequence of SEQ ID NO: 119 and a VL domain comprising the amino acid sequence of SEQ ID NO: 125, or (xxvi) a VH domain comprising the amino acid sequence of SEQ ID NO: 120 and a VL domain comprising the amino acid sequence of SEQ ID NO: 125, or (xxvii) a VH domain comprising the amino acid sequence of SEQ ID NO: 121 and a VL domain comprising the amino acid sequence of SEQ ID NO: 125, or (xxviii) a VH domain comprising the amino acid sequence of SEQ ID NO: 122 and a VL domain comprising the amino acid sequence of SEQ ID NO: 125.

In some embodiments, the antibody or antigen binding fragment is a Fab fragment, a Fab' fragment, a F(ab)'2 fragment, a single chain variable fragment (scFv), or a disulfide stabilized variable fragment (dsFv).

In some embodiments, the antibody or antigen binding fragment provided herein comprises the amino acid sequence having at least 80% identity to any one of SEQ ID NOs: 81-90, 128, and 129.

In some embodiments, the antibody is an IgG. In some embodiments, the antibody is a humanized antibody.

In another aspect, provided herein is a nucleic acid molecule encoding the antibody or antigen binding fragment provided herein. In yet another aspect, provided herein is a vector comprising the nucleic acid molecule provided herein.

In yet another aspect, provided herein is a host cell transformed with the vector provided herein.

In yet another aspect, provided herein is a composition comprising a therapeutically effective amount of the antibody or antigen binding fragment, the nucleic acid molecule, or the vector provided herein, and a pharmaceutically acceptable carrier.

In yet another aspect, provided herein is a method of treating a patient who has cancer that expresses GPC3, comprising administering to the patient the composition provided herein, wherein optionally the cancer is selected from the group consisting of hepatocellular carcinoma (HCC), melanoma, ovarian clear cell carcinoma (OCCC), volk sac tumor (YST), neuroblastoma, hepatoblastoma, nephroblastoma (Wilms' tumor), squamous cell carcinoma of the lung, adenocarcinoma of the lung, large-cell lung carcinoma, small cell lung cancer, testicular nonseminomatous germ cell tumor, liposarcoma, cervical intraepithelial neoplasia, adenoma of the adrenal gland, schwannoma, embryonal tumor, gastric carcinoma, colorectal carcinoma, thyroid cancer, and esophageal cancer.

In yet another aspect, provided herein is a method of detecting GPC3 in a tissue sample, comprising contacting the tissue sample with the antibody or antigen binding fragment provided herein; and detecting binding of the antibody to the tissue sample, wherein an increase in binding of the antibody to the tissue sample as compared to binding of the antibody to a control sample detects GPC3 in the tissue sample.

In some embodiments, the antibody is directly labeled with a detectable marker.

In some embodiments, the method further comprises contacting a second antibody that specifically binds the antibody with the tissue sample, and detecting the binding of the second antibody, wherein an increase in binding of the second antibody to the tissue sample as compared to binding of the second antibody to a control sample detects GPC3 in the tissue sample. In some embodiments, the tissue sample comprises cells of hepatocellular carcinoma (HCC), melanoma, ovarian clear cell carcinoma (OCCC), volk sac tumor (YST), neuroblastoma, hepatoblastoma, nephroblastoma (Wilms' tumor), squamous cell carcinoma of the lung, adenocarcinoma of the lung, large-cell lung carcinoma, small cell lung cancer, testicular nonseminomatous germ cell tumor, liposarcoma, cervical intraepithelial neoplasia, adenoma of the adrenal gland, schwannoma, embryonal tumor, gastric carcinoma, colorectal carcinoma, thyroid cancer, and/or esophageal cancer.

In yet another aspect, provided herein is a chimeric antigen receptor (CAR), comprising a polypeptide comprising: (a) an extracellular antigen binding domain comprising the antibody or antigen binding fragment provided herein; (b) a transmembrane domain; and (c) an intracellular signaling domain.

In some embodiments, the antibody or antigen binding fragment is an scFv.

In some embodiments, the CAR provided herein further comprises a signal peptide located at the N-terminus of the polypeptide. In some embodiments, the signal peptide is derived from a molecule selected from the group consisting of CD8α, GM-CSF receptor α, and IgG1 heavy chain.

In some embodiments, the CAR further comprises a hinge domain located between the C-terminus of the extracellular antigen binding domain and the N-terminus of the transmembrane domain. In some embodiments, the hinge domain is derived from CD8α.

In some embodiments, the transmembrane domain is derived from a molecule selected from the group consisting of CD8α, CD4, CD28, CD137, CD80, CD86, CD152 and PD1.

In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, HVEM, ICOS, Myd88, LFA-1, ICOS, CD2, CD7, LIGHT, NKG2C, B7-H3, Ligands of CD83 and a combination thereof.

In some embodiments, the intracellular signaling domain comprises a primary intracellular signaling domain of an immune effector cell. In some embodiments, the primary intracellular signaling domain is derived from CD3ζ.

In some embodiments, the CAR provided herein comprises a polypeptide comprising (i) the amino acid sequence of SEQ ID NO: 91, or (ii) the amino acid sequence of SEQ ID NO: 92, or (iii) the amino acid sequence of SEQ ID NO: 93, or (iv) the amino acid sequence of SEQ ID NO: 94, or (v) the amino acid sequence of SEQ ID NO: 95, or (vi) the amino acid sequence of SEQ ID NO: 96, or (vii) the amino acid sequence of SEQ ID NO: 97, or (viii) the amino acid sequence of SEQ ID NO: 98, or (ix) the amino acid sequence of SEQ ID NO: 99, or (x) the amino acid sequence of SEQ ID NO: 100, or (xi) the amino acid sequence of SEQ ID NO: 107, or (xii) the amino acid sequence of SEQ ID NO: 108, or (xiii) the amino acid sequence of SEQ ID NO: 109, or (xiv) the amino acid sequence of SEQ ID NO: 110, or (xv) the amino acid sequence of SEQ ID NO: 111, or (xvi) the amino acid sequence of SEQ ID NO: 112, or (xvii) the amino acid sequence of SEQ ID NO: 113, or (xviii) the amino acid sequence of SEQ ID NO: 114, or (xix) the amino acid sequence of SEQ ID NO: 115, or (xx) the amino acid sequence of SEQ ID NO: 116, or (xxi) the amino acid sequence of SEQ ID NO: 130, or (xxii) the amino acid sequence of SEQ ID NO: 131.

In another aspect, provided herein is a polypeptide comprising the CAR provided herein, and at least one of p40 subunit of IL-12 and CCL-19. In some embodiments, the p40) is human p40) comprising the amino acid sequence of SEQ ID NO: 135, and the CCL-19 is human CCL-19 comprising the amino acid sequence of SEQ ID NO: 136. In some embodiments, p40 and CCL-19 are linked by a first self-cleaving peptide. In some embodiments, the first self-cleaving peptide is a 2A self-cleaving peptide T2A fragment comprising the amino acid sequence of SEQ ID NO: 139. In some embodiments, p40 subunit of IL-12 and CCL-19 are present in a domain comprising the amino acid sequence of SEQ ID NO: 134. In some embodiments, the CAR is linked to the domain by a second self-cleaving peptide. In some embodiments, the second self-cleaving peptide is a 2A self-cleaving peptide P2A fragment comprising the amino acid sequence of SEQ ID NO: 138. In a specific embodiment, provided herein is a polypeptide comprising the amino acid sequence of SEQ ID NO: 133.

In yet another aspect, provided herein is a nucleic acid molecule encoding the CAR or polypeptide provided herein. In yet another aspect, provided herein is a vector comprising the nucleic acid molecule. In some embodiments, the vector is a viral vector or a non-viral vector.

In yet another aspect, provided herein is a host cell transformed with the vector provided herein. In some embodiments, the host cell is an immune effector cell selected from a group consisting of T cell, NK cell, peripheral blood mononuclear cell (PBMC), hematopoietic stem cell, pluripotent stem cell, an embryonic stem cell, and a combination thereof. In a specific embodiment, the immune effector cell is a T cell.

In yet another aspect, provided herein is an immune effector cell expressing the CAR provided herein, exogenously introduced p40, and exogenously introduced CCL-19.

In yet another aspect, provided herein is a composition comprising a therapeutically effective amount of the host cell or the immune effector cell provided herein, and a pharmaceutically acceptable carrier.

In yet another aspect, provided herein is a method of treating a patient who has cancer that expresses GPC3, comprising administering to the patient the composition provided herein, wherein the cancer is optionally selected from the group consisting of hepatocellular carcinoma (HCC), melanoma, ovarian clear cell carcinoma (OCCC), yolk sac tumor (YST), neuroblastoma, hepatoblastoma, nephroblastoma (Wilms' tumor), squamous cell carcinoma of the lung, adenocarcinoma of the lung, large-cell lung carcinoma, small cell lung cancer, testicular nonseminomatous germ cell tumor, liposarcoma, cervical intraepithelial neoplasia, adenoma of the adrenal gland, schwannoma, embryonal tumor, gastric carcinoma, colorectal carcinoma, thyroid cancer, and esophageal cancer.

In some embodiments, the host cell or the immune effector cell is obtained from the patient. In other embodiments, the host cell or the immune effector cell is obtained from a healthy donor.

In some embodiments, the antibody or antigen binding fragment or CAR provided herein binds to GPC3 that comprises the amino acid sequence of at least one selected from GenBank Accession numbers: NM_001164617 and NP_001158089, NM_004484 and NP_004475, NM_001164618 and NP_001158090, and NM_001164619 and NP_001158091.

4. BRIEF DESCRIPTION OF THE FIGURES

FIG. 1 shows the expression levels of LIC19301-LIC19310 CAR-T cells.

FIG. 2 shows in vitro cytotoxicity of CAR-T cells of LIC19301-LIC19310 against GPC3 positive cell lines with different ratio of E/T. E/T refers to the ratio of effective cell to target cell. UnT refers to T cells un-electroporated with CAR.

FIG. 3 shows in vitro cytotoxicity of CAR-T cells of LIC19301-LIC19310 against GPC3 negative cell lines with different ratio of E/T. E/T refers to the ratio of effective cell to target cell. UnT refers to T cells un-electroporated with CAR.

Figure 7:
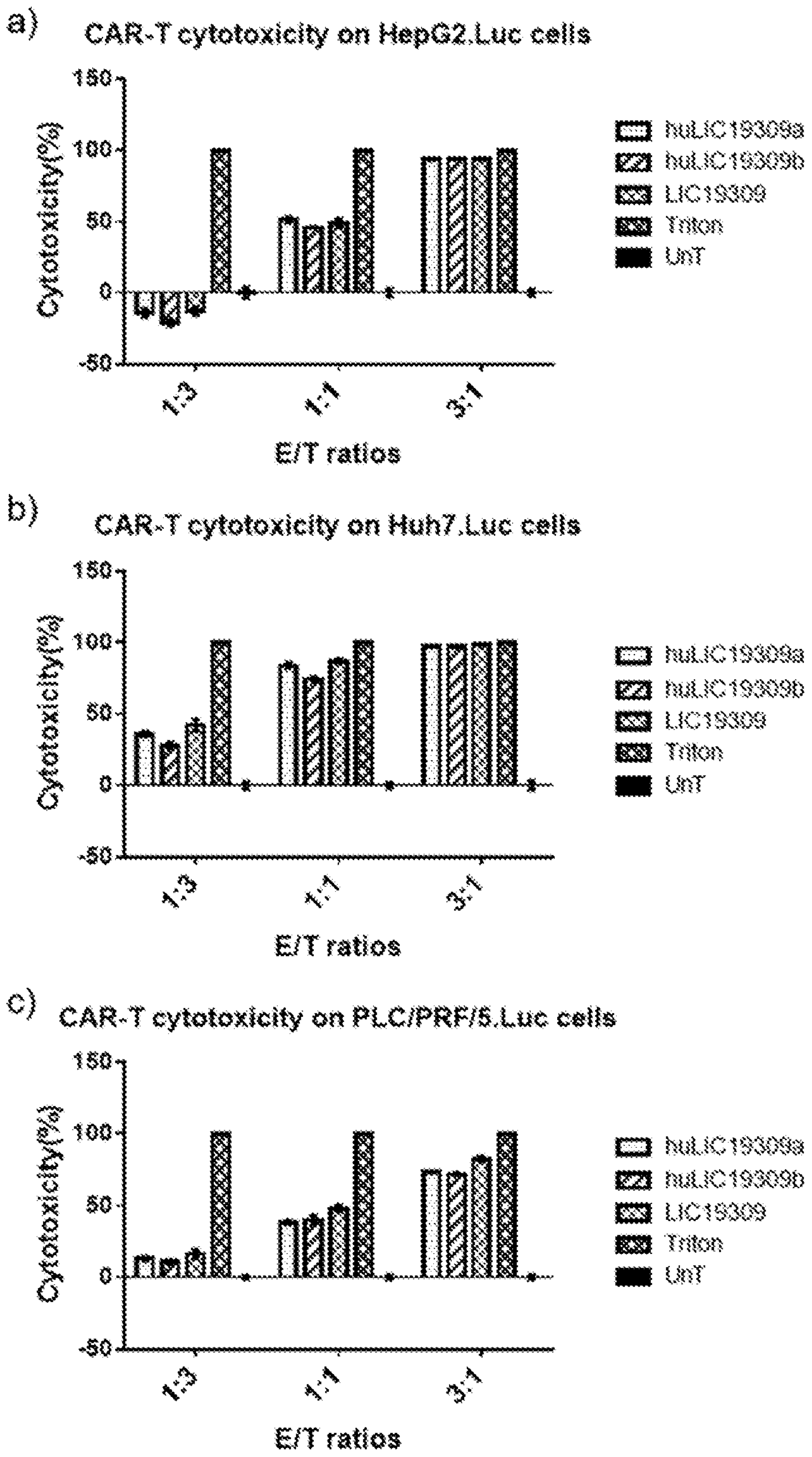

FIG. 7 shows in vitro cytotoxicity of humanized CAR-T cells and LIC19309 CAR-T cells against GPC3 positive cell lines with different ratio of E/T. E/T refers to the ratio of effective cell to target cell. UnT refers to T cells un-transfected with CAR.

Figure 8:
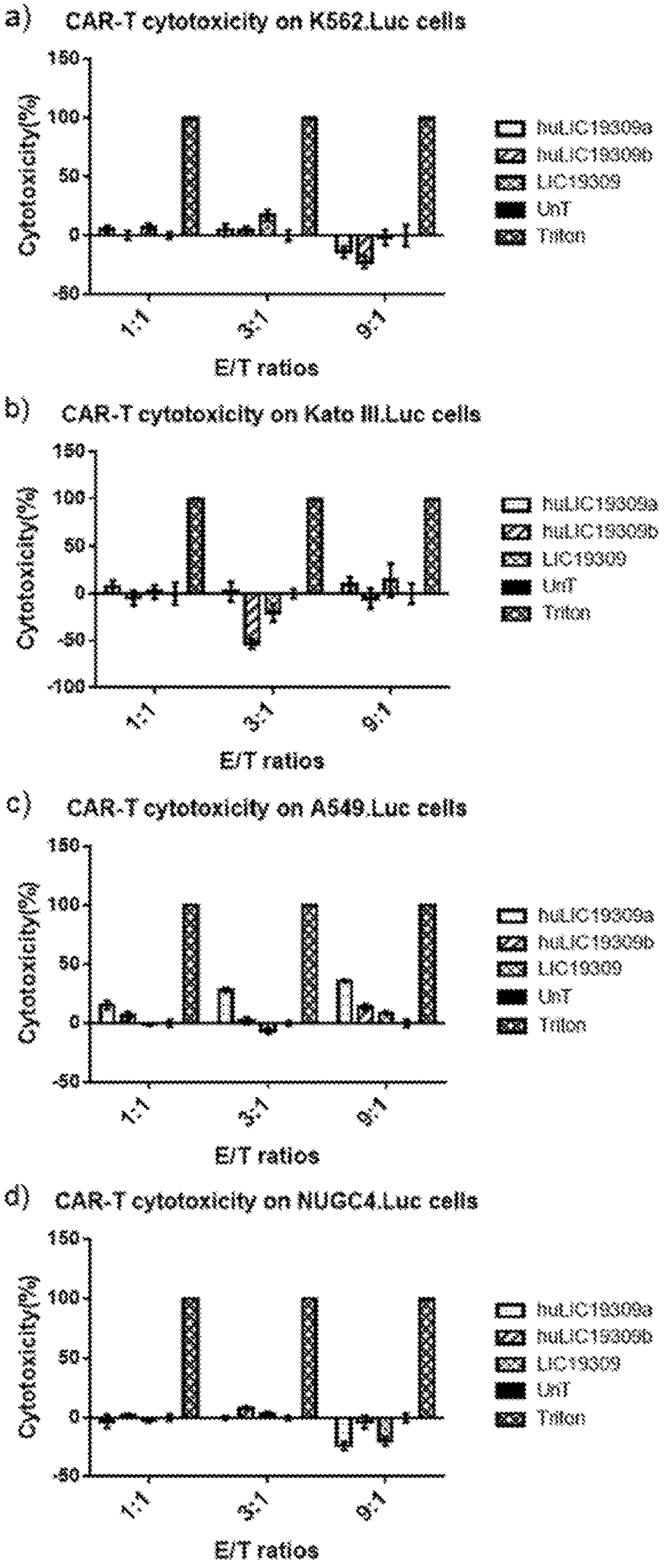

FIG. 8 shows in vitro cytotoxicity of humanized CAR-T cells and LIC19309 CAR-T cells against GPC3 negative cell lines with different ratio of E/T. E/T refers to the ratio of effective cell to target cell. UnT refers to T cells un-transfected with CAR.

Figure 9:
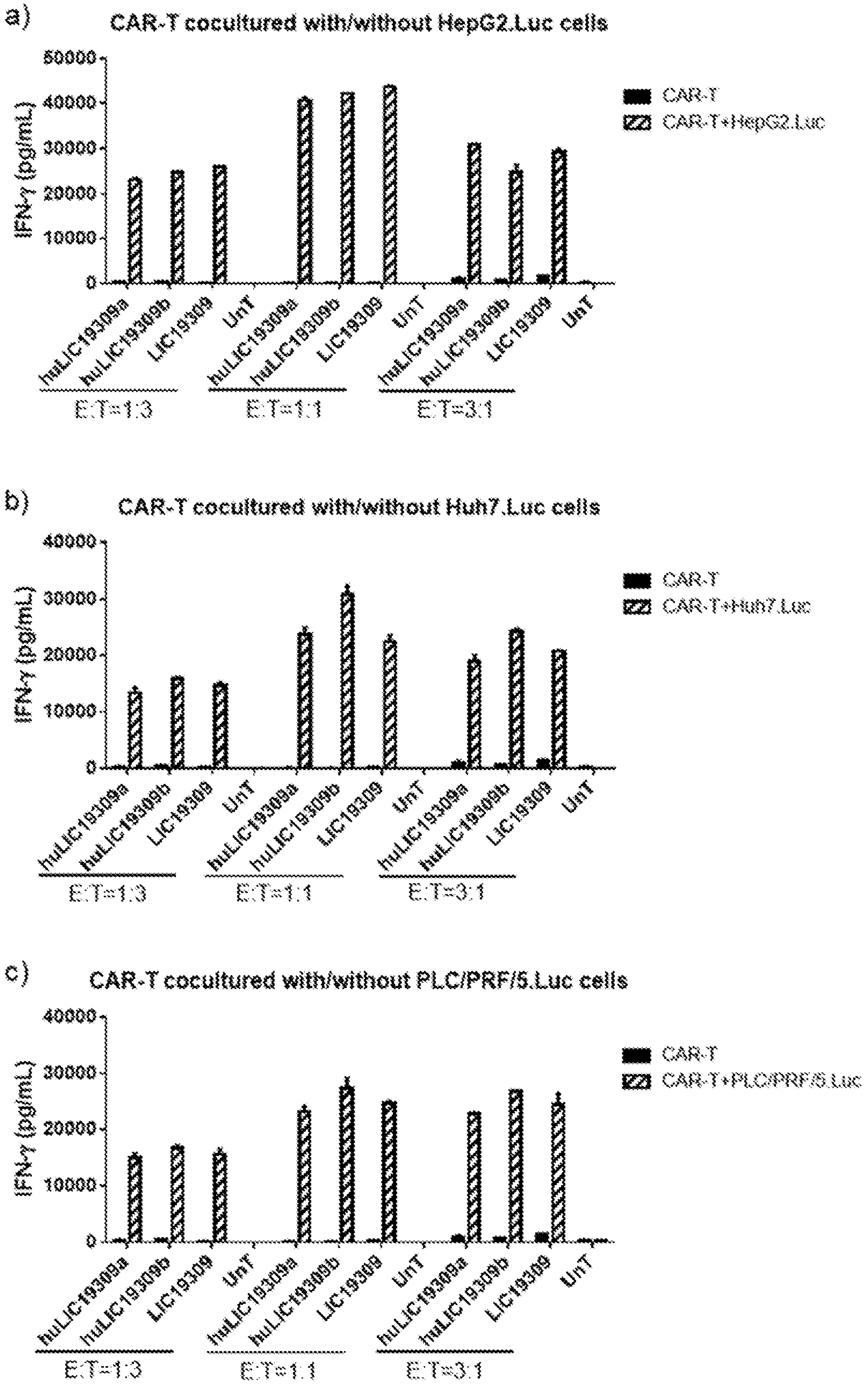

FIG. 9 shows IFN-γ secretion of humanized CAR-T cells and LIC19309 CAR-T cells before and after being co-cultured with HepG2, Huh7 or PLC/PRF/5 cell lines with different ratio of E/T for 20 hours. UnT refers to T cells un-transfected with CAR.

Figure 10:
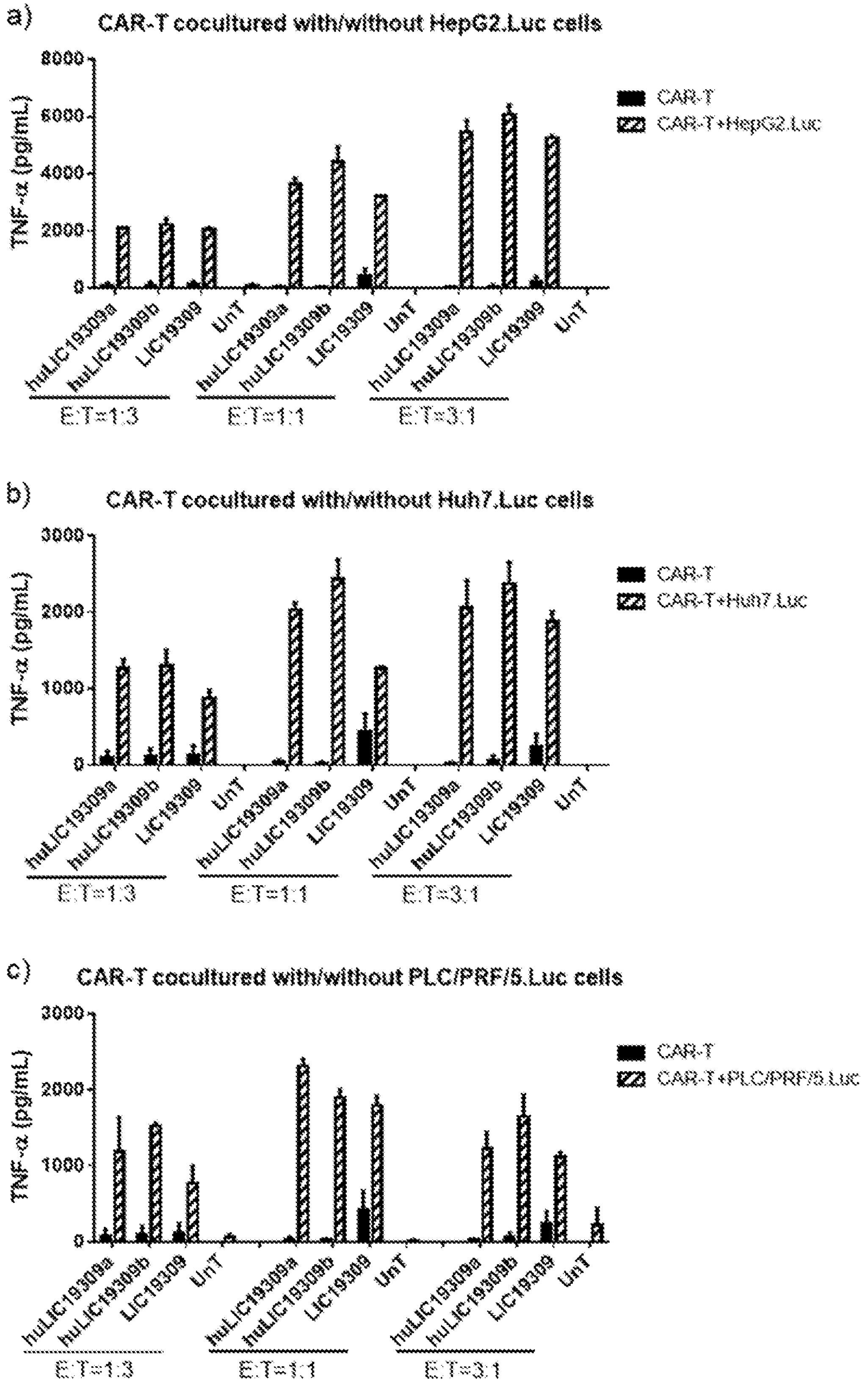

FIG. 10 shows TNF-α secretion of humanized CAR-T cells and LIC19309 CAR-T cells before and after being co-cultured with HepG2, Huh7 or PLC/PRF/5 cell lines with different ratio of E/T for 20 hours. UnT refers to T cells un-transfected with CAR.

Figure 11:
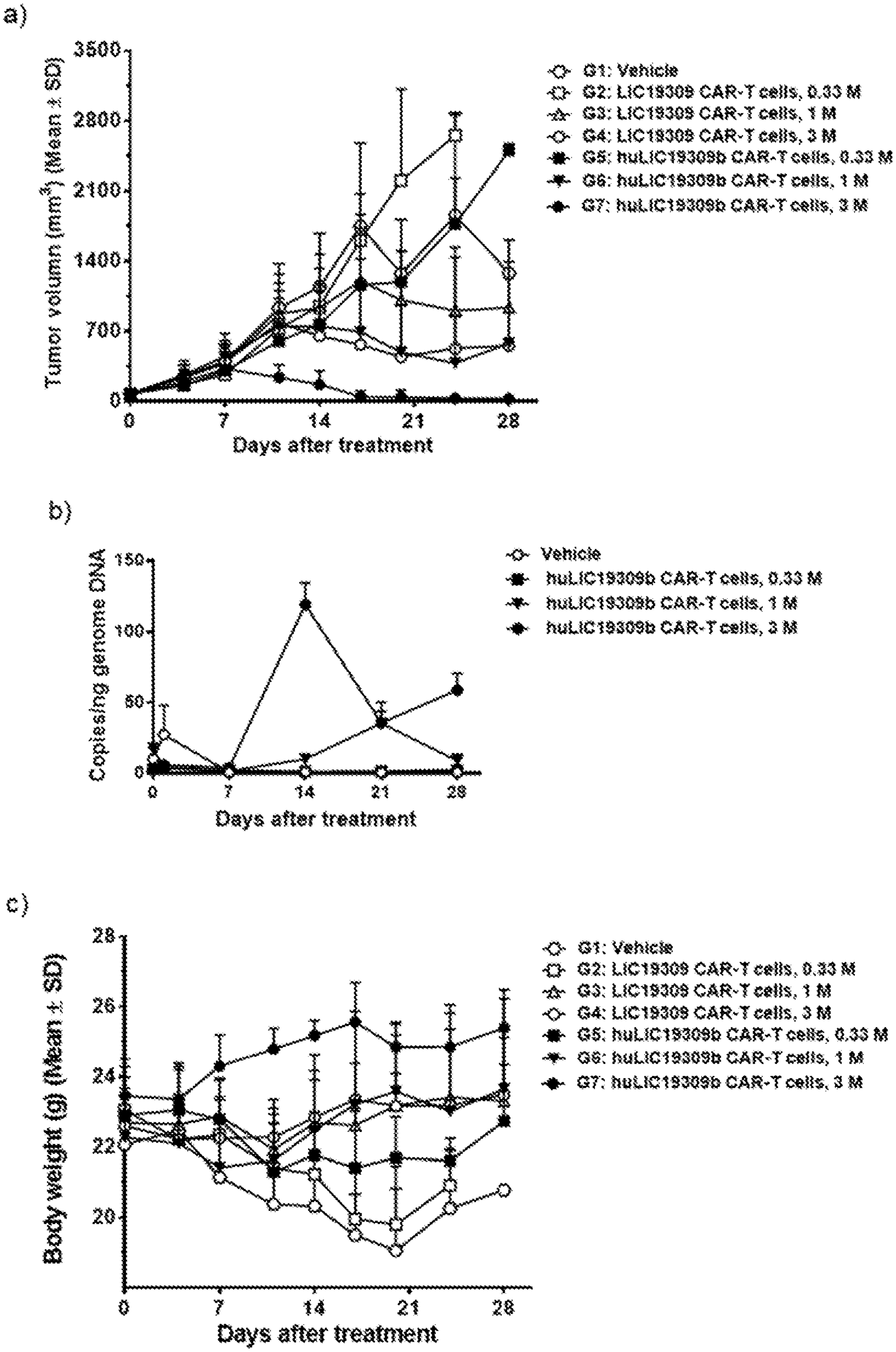

FIG. 11 shows the antitumor activity of humanized CAR-T cells following administration to NCG mice engrafted with Huh7 cells.

Figure 12:
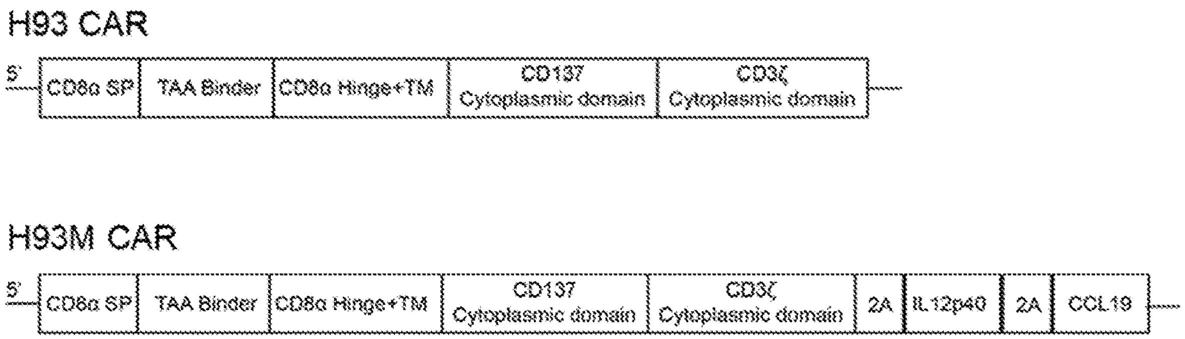

FIG. 12 shows the structures of H93 CAR and H93M CAR. SP refers to the signal peptide. TM refers to the transmembrane domain. TAA Binder refers to antigen binding domain or the binder of a tumor-associated antigen (i.e. anti-GPC3 scFv).

Figure 13:
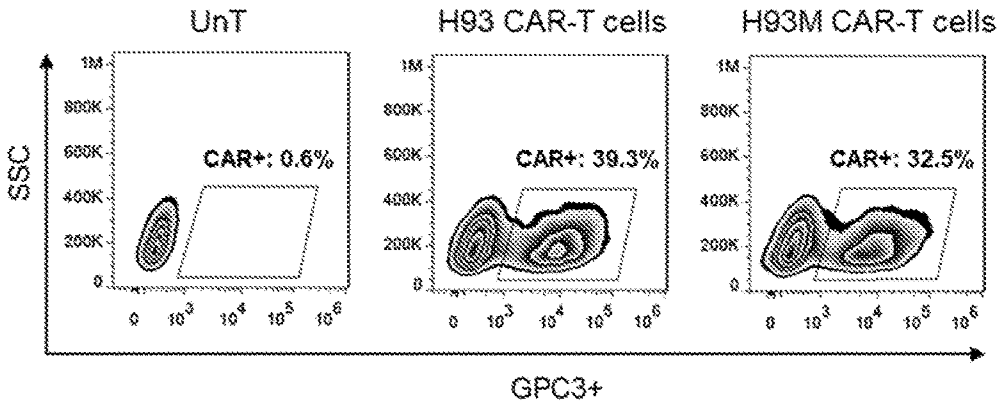

FIG. 13 shows the positive rates of H93 CAR-T cells and H93M CAR-T cells expressing humanized anti-GPC3 scFv CAR. UnT refers to T cells un-transduced with CAR.

Figure 14A:
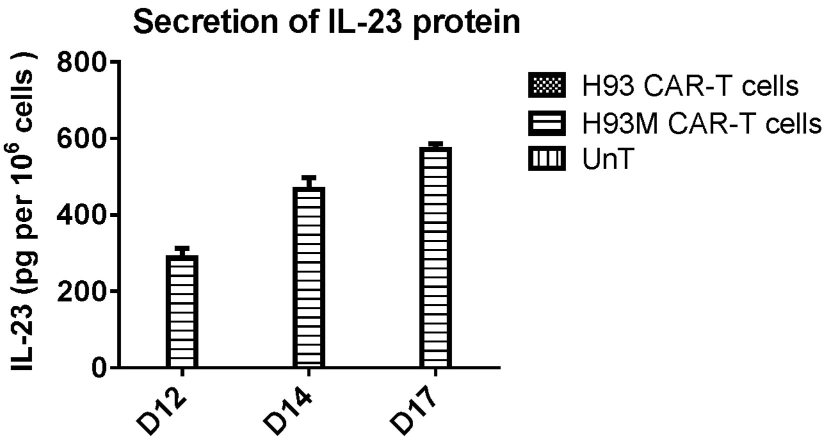
Figure 14B:
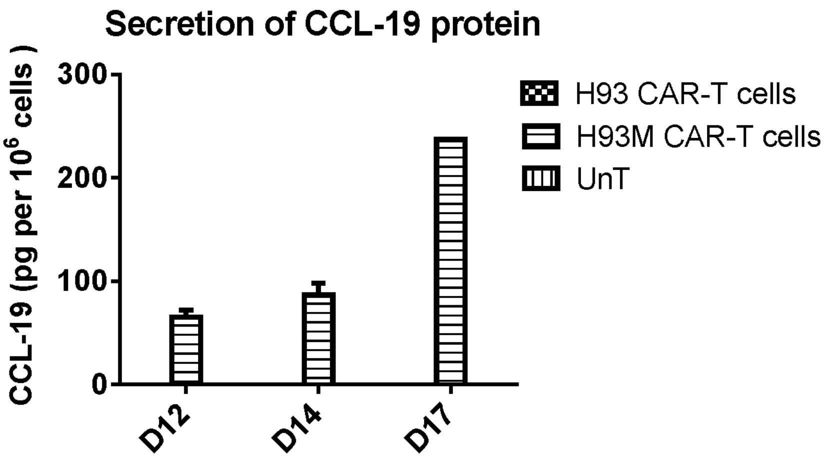

FIGS. 14A-14B show the production of IL-23 (FIG. 14A) and CCL-19 (FIG. 14B) proteins of CAR-T cells cultured in normal condition (RPMI-1640+300 IU/mL IL-2).

Figure 15A:
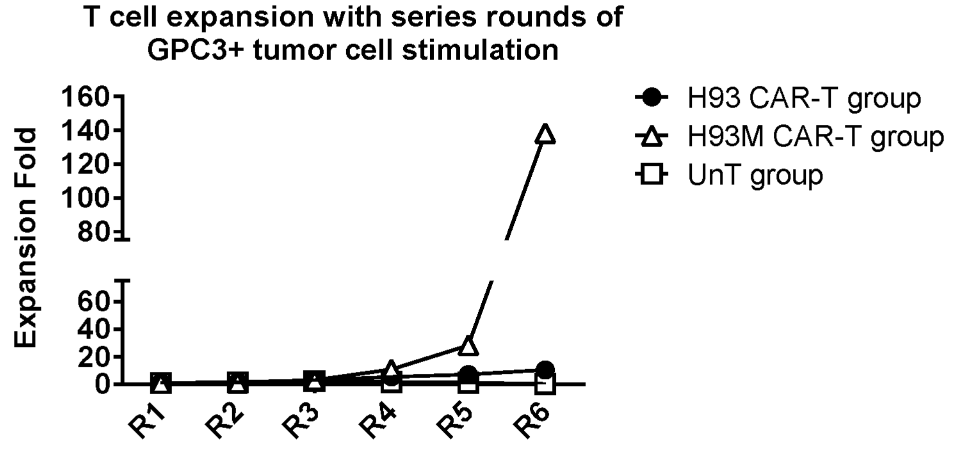
Figure 15B:
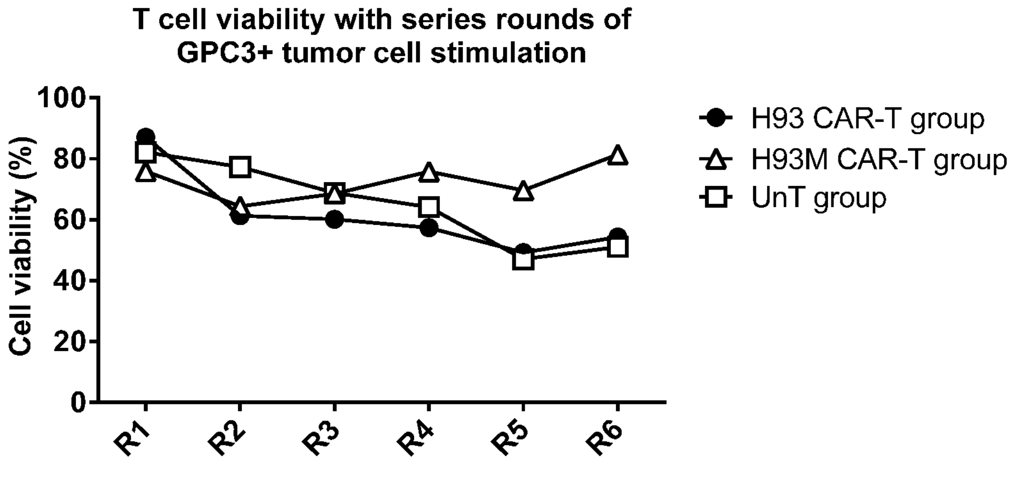

FIGS. 15A-15B show the expansion of CAR-T cells in the re-challenge assay. Cells were stimulated overnight with PLC/PRF/5 cells at a 1:1 E/T ratio every 2 days. The expansion fold (FIG. 15A) and viability (FIG. 15B) of T cells were recorded at the end of each round.

Figure 16A:
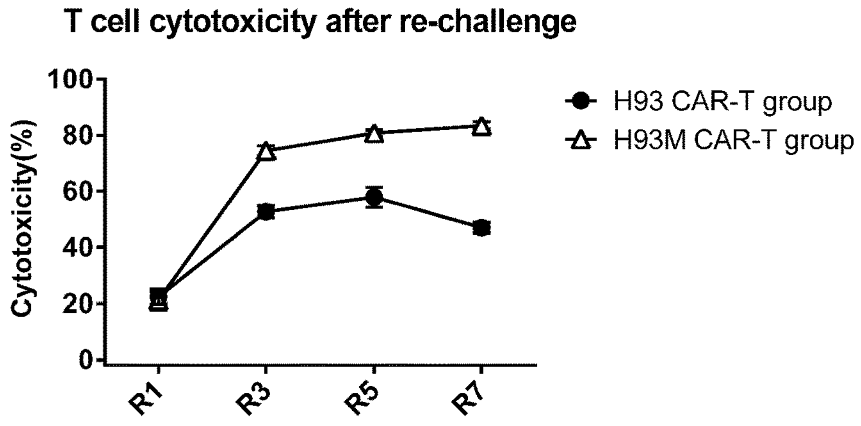
Figure 16B:
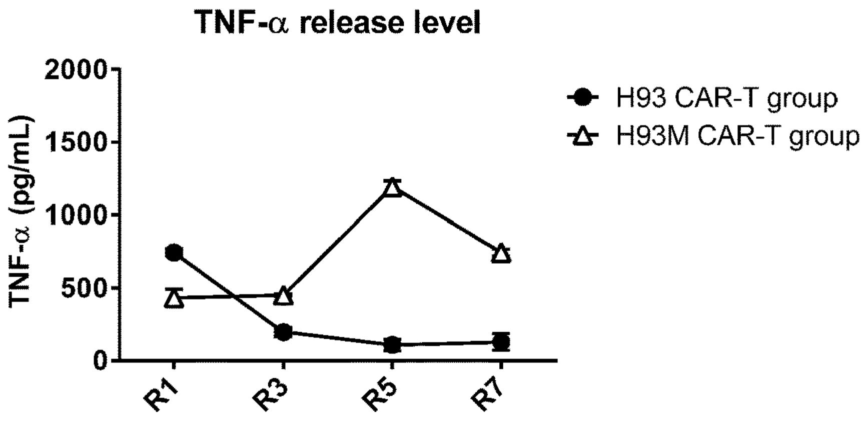
Figure 16C:
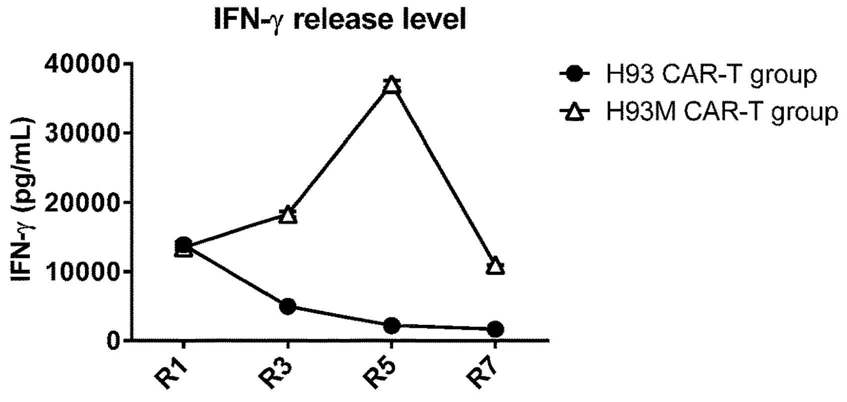

FIGS. 16A-16C show in vitro cytotoxicity (FIG. 16A), TNF-α release level (FIG. 16B) and IFN-γ release level (FIG. 16C) of CAR-T cells against GPC3 positive cell line with 1:1 E/T ratio after being treated with different stimulation rounds in the re-challenge assay.

Figure 17:
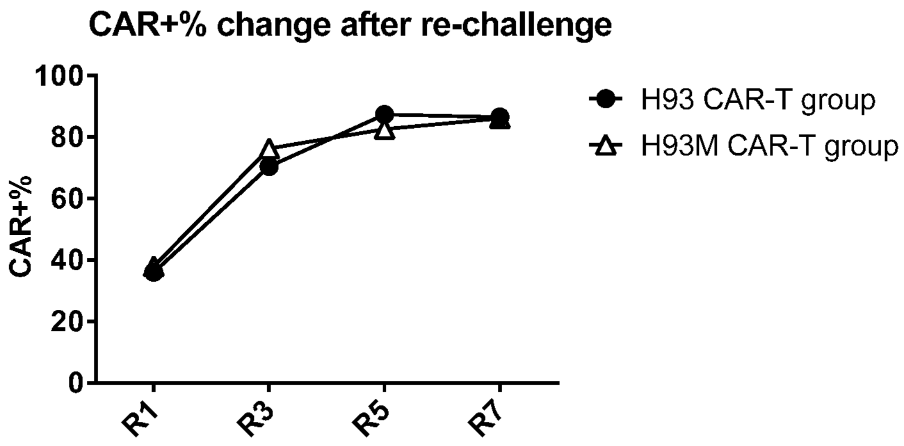

FIG. 17 shows the positive ratio of CAR-T cells after being treated with different stimulation rounds in the re-challenge assay.

FIGS. 18A-18D show the expression of PD-1 (FIG. 18A and FIG. 18B) and LAG3 (FIG. 18C and FIG. 18D) in CAR-T cells 24 hours after each stimulation round in the re-challenge assay.

Figure 19A:
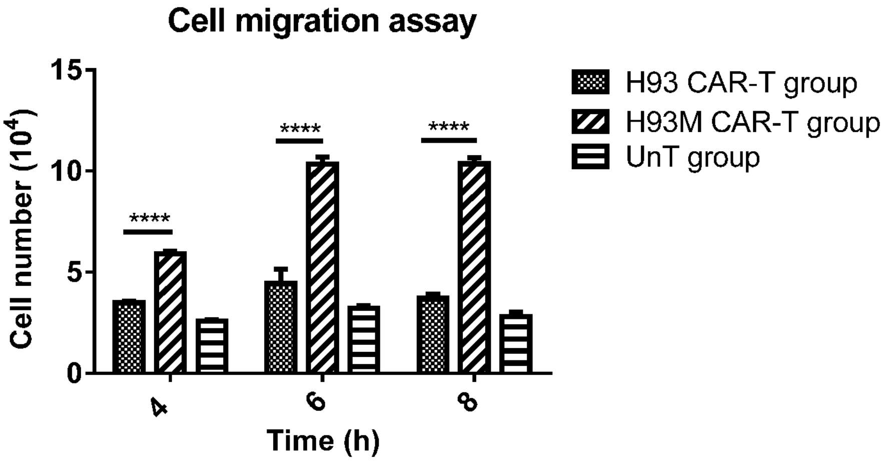
Figure 19B:
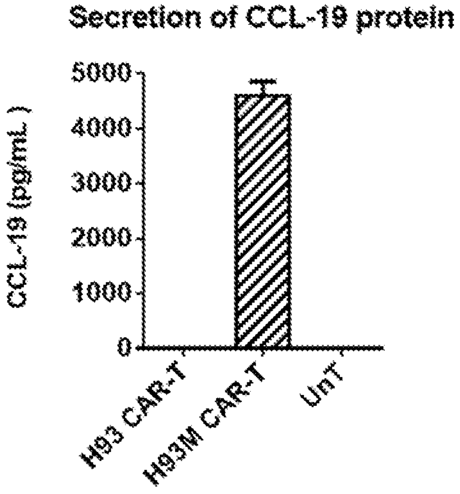

FIGS. 19A-19B show cell migration assay of CAR-T cells performed by 96-well transwell chambers. Different CAR-T cells were co-cultured with PLC/PRF/5 cells at 1:1 E/F ratio for 30 hours and the cell culture supernatant was collected and added to lower chamber. The T cell number of lower chamber migrating from the upper chamber after 4, 6, 8 hours were quantified (FIG. 19A), as well as the concentration of CCL-19 in co-culture supernatant (FIG. 19B).

FIGS. 20A-20D show the anti-tumor effects of CAR-T cells in NCG mouse xenograft model. NCG mice were inoculated subcutaneously with Huh7 cells, and treated with CAR-T cells at 0.2 M dosage and 0.6 M dosage (i.v.) (n=4 mice per group). The volume of tumors (FIG. 20A and FIG. 20B) and CAR copy number (FIG. 20C and FIG. 20D) in genomic DNA of NCG mice peripheral blood were assessed.

Figure 21A:
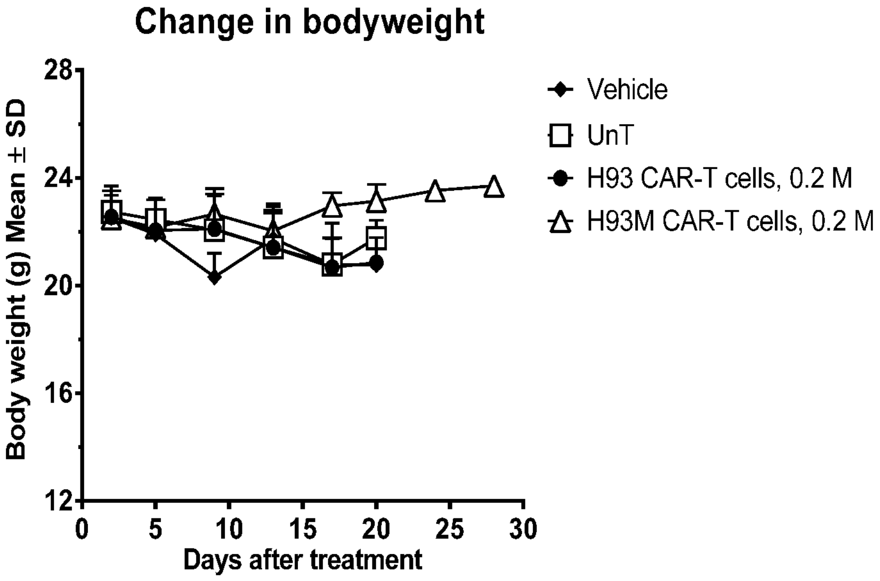
Figure 21B:
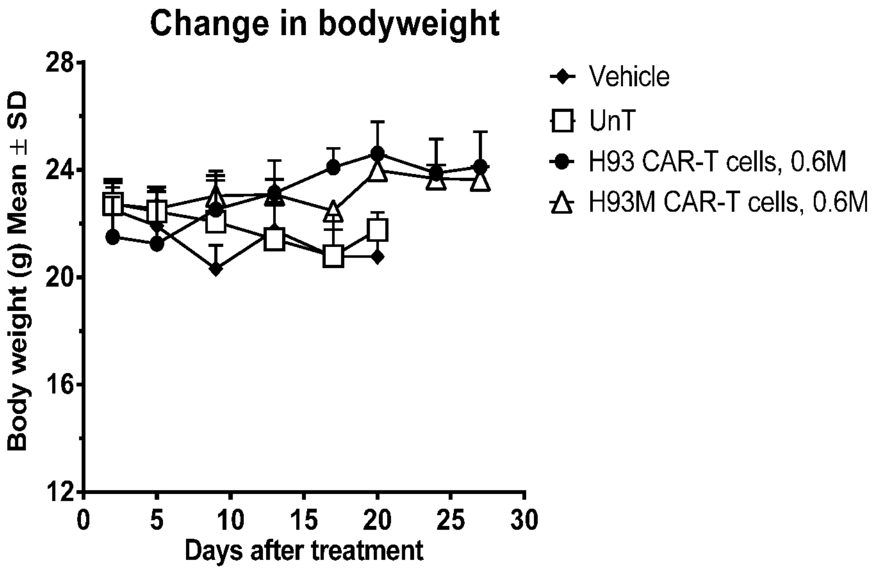

FIGS. 21A-21B show the weight change of mice treated with CAR-T cells at 0.2 M (FIG. 21A) and 0.6 M (FIG. 21B) dosages (n=4 mice per group) in NCG mouse xenograft model.

FIGS. 22A-22D show the level of IL-23 protein (FIG. 22A and FIG. 22B) and IFN-γ protein (FIG. 22C and FIG. 22D) in NCG mice peripheral blood after treated with 0.2 M or 0.6 M dosage CAR-T cells (n=3 mice per group).

Figure 23:
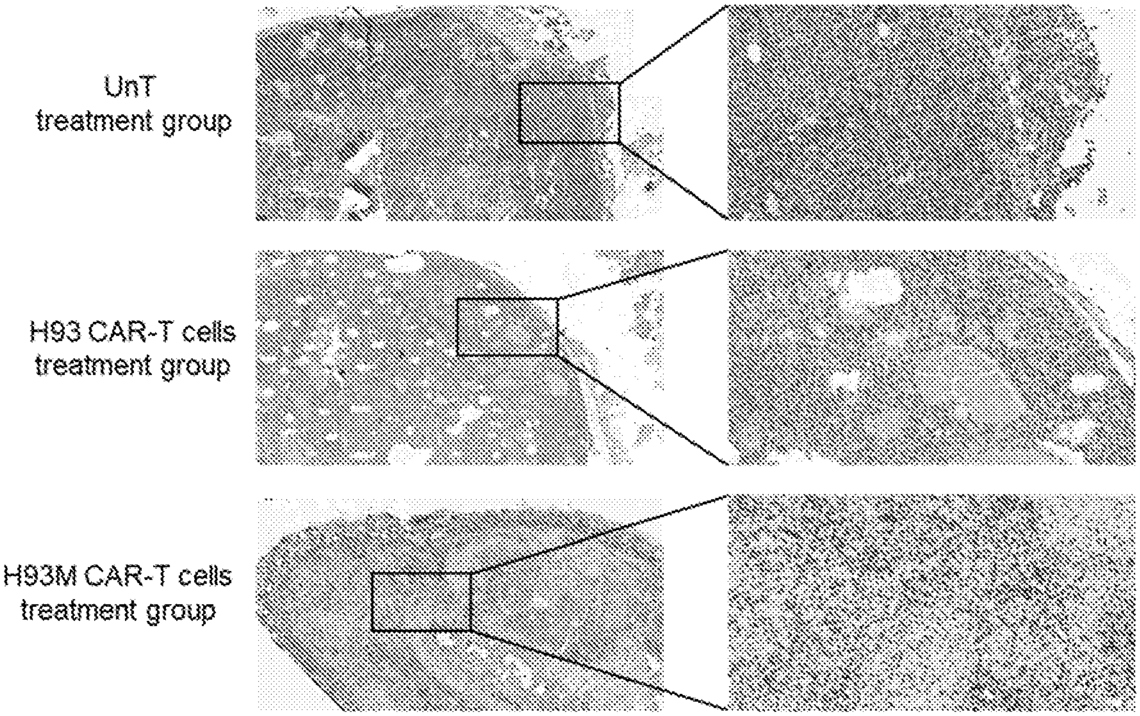

FIG. 23 shows the infiltration of T cells in tumor tissues of mice treated with 0.2 M UnT. H93 CAR-T cells or H93M CAR-T cells at the endpoint of the animal experiment (n=3) in NCG mouse xenograft model. Tumor tissues were fixed with formalin, embedded in paraffin and used for immunohistochemistry (IHC) to detect the infiltration of T cells which were stained by 3,3-Diaminobenzidine (DAB). The images were obtained by 3D HISTECH (DRNJIER). The right column shows the enlarged area of the black rectangle.

Figure 24:
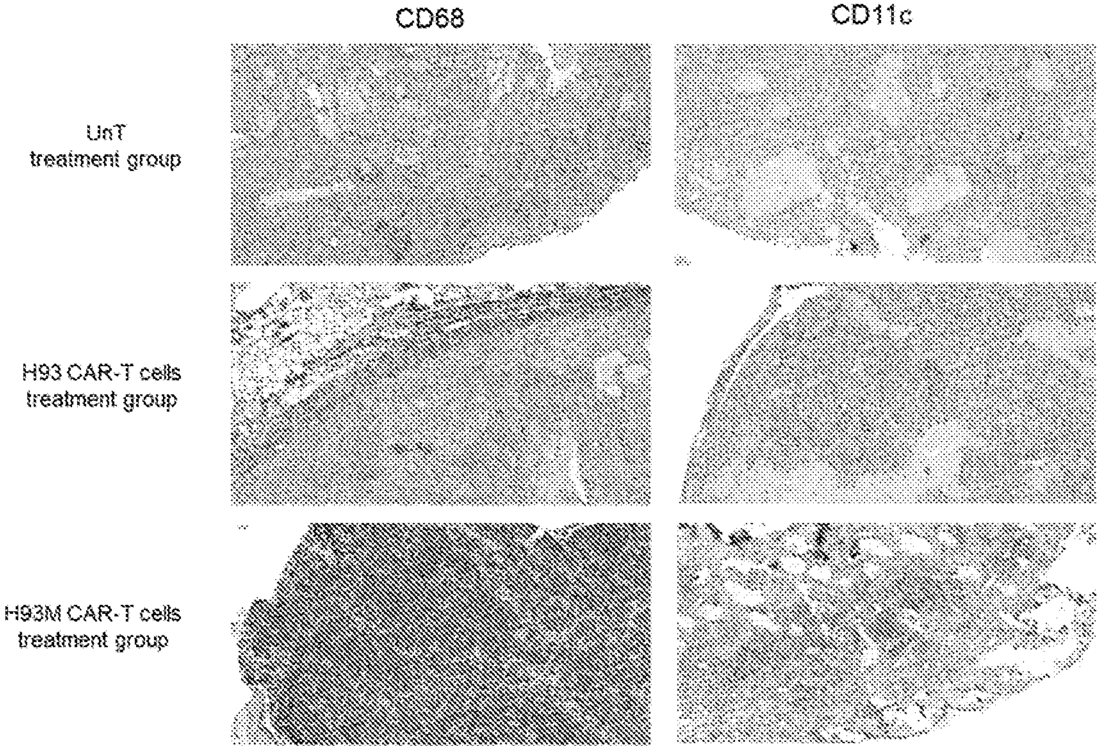

FIG. 24 shows the recruitment of mouse macrophage and mouse dendritic cell in tumor tissues after treated with 0.2 M UnT. H93 CAR-T cells or H93M CAR-T cells in NCG mouse xenograft model. At the endpoint of the animal experiment, tumor tissues were fixed with formalin, embedded in paraffin and used for immunohistochemistry (IHC). Macrophage with CD68 (left column) and dendritic cell with CD11c (right column) were stained by 3,3'-Diaminobenzidine (DAB). The images were obtained by 3D HISTECH (DRNJIER).

5. DETAILED DESCRIPTION

The present disclosure is based in part on the novel antibodies and chimeric antigen receptors that bind to GPC3 or engineered cells comprising same, and improved properties thereof.

5.1. Definitions

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual (3d ed. 2001); Current Protocols in Molecular Biology (Ausubel et al. eds., 2003); Therapeutic Monoclonal Antibodies: From Bench to Clinic (An ed. 2009); Monoclonal Antibodies: *Methods and Protocols* (Albitar ed. 2010); and *Antibody Engineering* Vols 1 and 2 (Kontermann and Dübel eds., 2d ed. 2010). Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "antibody." "immunoglobulin." or "Ig" is used interchangeably herein, and is used in the broadest sense and specifically covers, for example, monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments thereof (e.g., domain antibodies), as described below. An antibody can be human, humanized, chimeric and/or affinity matured, as well as an antibody from other species, for example, mouse, rabbit, llama, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70) kDa) and one light chain (about 25 kDa), each amino-terminal portion of each chain includes a variable region of about 100 to about 130 or more amino acids, and each carboxy-terminal portion of each chain includes a constant region. See, e.g., *Antibody Engineering* (Borrebaeck ed., 2d ed. 1995); and Kuby, *Immunology* (3d ed. 1997). Antibodies also include, but are not limited to, synthetic antibodies, recombinantly produced antibodies, antibodies including from Camelidae species (e.g., llama or alpaca) or their humanized variants, intrabodies, anti-idiotypic (anti-Id) antibodies, and functional fragments (e.g., antigen binding fragments) of any of the above, which refers to a portion of an antibody heavy or light chain polypeptide that retains some or all of the binding activity of the antibody from which the fragment was derived. Non-limiting examples of functional fragments (e.g., antigen binding fragments) include single-chain Fvs (scFv) (e.g., including monospecific, bispecific, etc.). Fab fragments. F(ab') fragments. $F(ab)_2$ fragments. $F(ab)_2$ fragments, disulfide-linked Fvs (dsFv). Fd fragments. Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to an antigen (e.g., one or more CDRs of an antibody). Such antibody fragments can be found in, for example. Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224; Pluckthun and Skerra, 1989. Meth. Enzymol. 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgAQ1, and IgA2) of immunoglobulin molecule. Antibodies may be agonistic antibodies or antagonistic antibodies. Antibodies may be neither agonistic nor antagonistic.

An "antigen" is a structure to which an antibody can selectively bind. A target antigen may be a polypeptide, carbohydrate, nucleic acid, lipid, hapten, or other naturally occurring or synthetic compound. In some embodiments, the target antigen is a polypeptide. In certain embodiments, an antigen is associated with a cell, for example, is present on or in a cell.

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as an antigen, is the affinity of the antibody or functional fragment for that epitope. The ratio of dissociation rate ($k_{off}$) to association rate ($k_{on}$) of a binding molecule (e.g., an antibody) to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the avidity.

In connection with the binding molecules described herein terms such as "bind to," "that specifically bind to," and analogous terms are also used interchangeably herein and refer to binding molecules of antigen binding domains that specifically bind to an antigen, such as a polypeptide. A binding molecule or antigen binding domain that binds to or specifically binds to an antigen can be identified, for example, by immunoassays, Octet®, Biacore®, or other techniques known to those of skill in the art. In some embodiments, a binding molecule or antigen binding domain binds to or specifically binds to an antigen when it binds to an antigen with higher affinity than to any cross-reactive antigen as determined using experimental techniques, such as radioimmunoassay (RIA) and enzyme linked immunosorbent assay (ELISA). Typically, a specific or selective reaction will be at least twice background signal or noise and may be more than 10 times background. See, e.g.,

*Fundamental Immunology* 332-36 (Paul ed., 2d ed. 1989) for a discussion regarding binding specificity. In certain embodiments, the extent of binding of a binding molecule or antigen binding domain to a "non-target" protein is less than about 10% of the binding of the binding molecule or antigen binding domain to its particular target antigen, for example, as determined by fluorescence activated cell sorting (FACS) analysis or RIA. A binding molecule or antigen binding domain that binds to an antigen includes one that is capable of binding the antigen with sufficient affinity such that the binding molecule is useful, for example, as a therapeutic and/or diagnostic agent in targeting the antigen. In certain embodiments, a binding molecule or antigen binding domain that binds to an antigen has a dissociation constant ($K_D$) of less than or equal to 1 μM, 800 nM, 600 nM, 550 nM, 500 nM, 300 nM, 250 nM, 100 nM, 50 nM, 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, a binding molecule or antigen binding domain binds to an epitope of an antigen that is conserved among the antigen from different species.

In certain embodiments, the binding molecules or antigen binding domains can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55). Chimeric sequences may include humanized sequences.

In certain embodiments, the binding molecules or antigen binding domains can comprise portions of "humanized" forms of nonhuman (e.g., camelid, murine, non-human primate) antibodies that include sequences from human immunoglobulins (e.g., recipient antibody) in which the native CDR residues are replaced by residues from the corresponding CDR of a nonhuman species (e.g., donor antibody) such as camelid, mouse, rat, rabbit, or nonhuman primate having the desired specificity, affinity, and capacity. In some instances, one or more FR region residues of the human immunoglobulin sequences are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., Nature 321: 522-25 (1986); Riechmann et al., Nature 332:323-29 (1988); Presta, Curr. Op. Struct. Biol. 2:593-96 (1992); Carter et al., Proc. Natl. Acad. Sci. USA 89:4285-89 (1992); U.S. Pat. Nos. 6,800,738; 6,719,971; 6,639,055; 6,407,213; and 6,054,297.

In certain embodiments, the binding molecules or antigen binding domains can comprise portions of a "fully human antibody" or "human antibody," wherein the terms are used interchangeably herein and refer to an antibody that comprises a human variable region and, for example, a human constant region. The binding molecules may comprise an antibody sequence. In specific embodiments, the terms refer to an antibody that comprises a variable region and constant region of human origin. "Fully human" antibodies, in certain embodiments, can also encompass antibodies which bind polypeptides and are encoded by nucleic acid sequences which are naturally occurring somatic variants of human germline immunoglobulin nucleic acid sequence. The term "fully human antibody" includes antibodies having variable and constant regions corresponding to human germline immunoglobulin sequences as described by Kabat et al. (See Kabat et al. (1991) *Sequences of Proteins of Immunological Interest*. Fifth Edition. U.S. Department of Health and Human Services. NIH Publication No. 91-3242). A "human antibody" is one that possesses an amino acid sequence which corresponds to that of an antibody produced by a human and/or has been made using any of the techniques for making human antibodies. This definition of a human antibody specifically excludes a humanized antibody comprising non-human antigen-binding residues. Human antibodies can be produced using various techniques known in the art, including phage-display libraries (Hoogenboom and Winter. J. Mol. Biol. 227:381 (1991); Marks et al., J. Mol. Biol. 222:581 (1991)) and yeast display libraries (Chao et al., Nature Protocols 1:755-68 (2006)). Also available for the preparation of human monoclonal antibodies are methods described in Cole et al., *Monoclonal Antibodies and Cancer Therapy* 77 (1985); Boerner et al., J. Immunol. 147(1); 86-95 (1991); and van Dijk and van de Winkel, Curr. Opin. Pharmacol, 5:368-74 (2001). Human antibodies can be prepared by administering the antigen to a transgenic animal that has been modified to produce such antibodies in response to antigenic challenge, but whose endogenous loci have been disabled. e.g., mice (see. e.g., Jakobovits, Curr. Opin. Biotechnol. 6(5):561-66 (1995); Brüggemann and Taussing, Curr. Opin. Biotechnol. 8(4):455-58 (1997); and U.S. Pat. Nos. 6,075,181 and 6,150,584 regarding XENOMOUSE™ technology). See also, for example. Li et al., Proc. Natl. Acad. Sci. USA 103:3557-62 (2006) regarding human antibodies generated via a human B-cell hybridoma technology.

In certain embodiments, the binding molecules or antigen binding domains can comprise portions of a "recombinant human antibody." wherein the phrase includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see. e.g., Taylor. L. D. et al., *Nucl. Acids Res.* 20:6287-6295 (1992)) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat. E. A. et al. (1991) *Sequences of Proteins of Immunological Interest*. Fifth Edition. U.S. Department of Health and Human Services. NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In certain embodiments, the binding molecules or antigen binding domains can comprise a portion of a "monoclonal antibody," wherein the term as used herein refers to an antibody obtained from a population of substantially homogeneous antibodies, e.g., the individual antibodies comprising the population are identical except for possible naturally occurring mutations that may be present in minor amounts or well-known post-translational modifications such as amino acid isomerization or deamidation, methionine oxidation or asparagine or glutamine deamidation, each monoclonal antibody will typically recognize a single epitope on the antigen. In specific embodiments, a "monoclonal antibody," as used herein, is an antibody produced by a single hybridoma or other cell. The term "monoclonal" is not limited to any particular method for making the antibody. For example, the monoclonal antibodies useful in the present disclosure may be prepared by the hybridoma methodology first described by Kohler et al., Nature 256:495 (1975), or may be made using recombinant DNA methods in bacterial or eukaryotic animal or plant cells (see. e.g., U.S. Pat. No. 4,816,567). The "monoclonal antibodies" may also be isolated from phage antibody libraries using the techniques described in Clackson et al., Nature 352:624-28 (1991) and Marks et al., J. Mol. Biol. 222:581-97 (1991), for example. Other methods for the preparation of clonal cell lines and of monoclonal antibodies expressed thereby are well known in the art. See. e.g., *Short Protocols in Molecular Biology* (Ausubel et al. eds., 5th ed. 2002).

A typical 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the $\alpha$ and $\gamma$ chains and four CH domains for $\mu$ and $\varepsilon$ isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic and Clinical Immunology* 71 (Stites et al. eds., 8th ed. 1994); and *Immunobiology* (Janeway et al. eds., 5th ed. 2001).

The term "Fab" or "Fab region" refers to an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability according to the present disclosure. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders as described in more detail the sections below.

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a $\beta$ sheet configuration, connected by three hypervariable regions, which form loops connecting, and in some cases form part of, the $\beta$ sheet structure. The hypervariable regions in each chain are held together in close proximity by the FRs and, with the hypervariable regions from the other chain, contribute to the formation of the antigen-binding site of antibodies (see. e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering according to Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types. (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450) amino acids, while μ and ε contain approximately 550) amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains.

As used herein, the terms "hypervariable region." "HVR," "Complementarity Determining Region," and "CDR" are used interchangeably. A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. CDR1, CDR2 and CDR3 in VH domain are also referred to as HCDR1, HCDR2 and HCDR3, respectively. CDR1, CDR2 and CDR3 in VL domain are also referred to as LCDR1, LCDR2 and LCDR3, respectively. Accordingly, CDRs are variable region sequences interspersed within the framework region sequences.

CDR regions are well known to those skilled in the art and have been defined by well-known numbering systems. For example, the Kabat Complementarity Determining Regions (CDRs) are based on sequence variability and are the most commonly used (see. e.g., Kabat et al., supra; Nick Deschacht et al., J Immunol 2010; 184:5696-5704). Chothia refers instead to the location of the structural loops (see. e.g., Chothia and Lesk, J. Mol. Biol. 196:901-17 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see. e.g., *Antibody Engineering* Vol. 2 (Kontermann and Dübel eds., 2d ed. 2010))). The "contact" hypervariable regions are based on an analysis of the available complex crystal structures. Another universal numbering system that has been developed and widely adopted is ImMunoGeneTics (IMGT) Information System® (Lafranc et al., Dev. Comp. Immunol. 27(1):55-77 (2003)). IMGT is an integrated information system specializing in immunoglobulins (IG), T-cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Plückthun, J. Mol. Biol. 309:657-70 (2001). Correspondence between the numbering system, including, for example, the Kabat numbering and the IMGT unique numbering system, is well known to one skilled in the art (see. e.g., Kabat, supra; Chothia and Lesk, supra; Martin, supra; Lefranc et al., supra). The residues from each of these hypervariable regions or CDRs are exemplified in Table 1 below.

TABLE 1

Exemplary CDRs According to Various Numbering Systems

| Loop | Kabat | AbM | Chothia | Contact | IMGT |
|---|---|---|---|---|---|
| CDR L1 | L24--L34 | L24--L34 | L26--L32 or L24--L34 | L30--L36 | L27--L38 |
| CDR L2 | L50--L56 | L50--L56 | L50--L52 or L50--L56 | L46--L55 | L56--L65 |
| CDR L3 | L89--L97 | L89--L97 | L91--L96 or L89--L97 | L89--L96 | L105--L117 |
| CDR H1 | H31--H35B (Kabat Numbering) | H26--H35B | H26--H32 . . . 34 | H30--H35B | H27--H38 |
| CDR H1 | H31--H35 (Chothia Numbering) | H26--H35 | H26--H32 | H30--H35 | |
| CDR H2 | H50--H65 | H50--H58 | H53--H55 or H52--H56 | H47--H58 | H56--H65 |
| CDR H3 | H95--H102 | H95--H102 | H96--H101 or H95--H102 | H93--H101 | H105--H117 |

The boundaries of a given CDR may vary depending on the scheme used for identification. Thus, unless otherwise specified, the terms "CDR" and "complementary determining region" of a given antibody or region thereof, such as a variable region, as well as individual CDRs (e.g., CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the IMGT, Kabat, Chothia, or Contact method. In other cases, the particular amino acid sequence of a CDR is given. It should be noted CDR regions may also be defined by a combination of various numbering systems, e.g., a combination of Kabat and Chothia numbering systems, or a combination of Kabat and IMGT numbering systems. Therefore, the term such as "a CDR1 as set forth in a specific VH" includes any CDR1 as defined by the exemplary CDR numbering systems described above, but is not limited thereby. Once a variable region (e.g., a VH or VL) is given, those skilled in the art would understand that CDRs within the region can be defined by different numbering systems or combinations thereof.

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A "functional Fc region" possesses an "effector function" of a native sequence Fc region. Exemplary "effector functions" include C1q binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays known to those skilled in the art. A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith.

As used herein, an "epitope" is a term in the art and refers to a localized region of an antigen to which a binding molecule (e.g., an antibody) can specifically bind. An epitope can be a linear epitope or a conformational, nonlinear, or discontinuous epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, a binding molecule binds to a group of amino acids regardless of whether they are folded in a natural three dimensional protein structure. In other embodiments, a binding molecule requires amino acid residues making up the epitope to exhibit a particular conformation (e.g., bend, twist, turn or fold) in order to recognize and bind the epitope.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The term "specificity" refers to selective recognition of an antigen binding protein (such as a CAR or an antibody) for a particular epitope of an antigen. Natural antibodies, for example, are monospecific. The term "multispecific" as used herein denotes that an antigen binding protein (such as a CAR or an antibody) has two or more antigen-binding sites of which at least two bind different antigens. "Bispecific" as used herein denotes that an antigen binding protein (such as a CAR or an antibody) has two different antigen-binding specificities. The term "monospecific" CAR as used herein denotes an antigen binding protein (such as a CAR or an antibody) that has one or more binding sites each of which bind the same antigen.

The term "valent" as used herein denotes the presence of a specified number of binding sites in an antigen binding protein (such as a CAR or an antibody). A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein (such as a CAR or an antibody).

"Chimeric antigen receptor" or "CAR" as used herein refers to genetically engineered receptors, which can be used to graft one or more antigen specificity onto immune effector cells, such as T cells. Some CARs are also known as "artificial T-cell receptors," "chimeric T cell receptors," or "chimeric immune receptors." In some embodiments, the CAR comprises an extracellular antigen binding domain specific for one or more antigens (such as tumor antigens), a transmembrane domain, and an intracellular signaling domain of a T cell and/or other receptors. "CAR-T cell" refers to a T cell that expresses a CAR.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies or other members of the immunoglobulin superfamily, in certain embodiments, a "polypeptide" can occur as a single chain or as two or more associated chains.

"Polynucleotide" or "nucleic acid." as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces a binding molecule of the present disclosure may include a parent hybridoma cell, as well as bacterial and eukaryotic host cells into which nucleic acids encoding the antibodies have been introduced. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule. Specifically, an "isolated" nucleic acid molecule encoding a CAR or an antibody described herein is a nucleic acid molecule that is identified and separated from at least one contaminant nucleic acid molecule with which it is ordinarily associated in the environment in which it was produced.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

As used herein, the term "operatively linked," and similar phrases (e.g., genetically fused), when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

The term "vector" refers to a substance that is used to carry or include a nucleic acid sequence, including for example, a nucleic acid sequence encoding a binding molecule (e.g., an antibody) as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product and it is further understood that expression levels can be optimized to obtain sufficient expression using methods well known in the art.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "autologous" is meant to refer to any material derived from the same individual to whom it is later to be re-introduced into the individual.

"Allogeneic" refers to a graft derived from a different individual of the same species.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "pharmaceutically acceptable" as used herein means being approved by a regulatory agency of the Federal or a state government, or listed in *United States Pharmacopeia, European Pharmacopeia*, or other generally recognized Pharmacopeia for use in animals, and more particularly in humans.

"Excipient" means a pharmaceutically-acceptable material, composition, or vehicle, such as a liquid or solid filler, diluent, solvent, or encapsulating material. Excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. The term "excipient" can also refer to a diluent, adjuvant (e.g., Freunds' adjuvant (complete or incomplete) or vehicle.

In some embodiments, excipients are pharmaceutically acceptable excipients. Examples of pharmaceutically acceptable excipients include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. Other examples of pharmaceutically acceptable excipients are described in Remington and Gennaro, Remington's Pharmaceutical Sciences (18th ed. 1990).

In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC; Boca Raton, FL, 2009. In some embodiments, pharmaceutically acceptable excipients are nontoxic to the cell or mammal being exposed thereto at the dosages and concentrations employed. In some embodiments, a pharmaceutically acceptable excipient is an aqueous pH buffered solution.

In some embodiments, excipients are sterile liquids, such as water and oils, including those of petroleum, animal, vegetable, or synthetic origin, such as peanut oil, soy bean oil, mineral oil, sesame oil, and the like. Water is an exemplary excipient when a composition (e.g., a pharmaceutical composition) is administered intravenously. Saline solutions and aqueous dextrose and glycerol solutions can also be employed as liquid excipients, particularly for injectable solutions. An excipient can also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard excipients such as pharmaceutical grades of mannitol, lactose, starch, magnesium stearate, sodium saccharine, cellulose, magnesium carbonate, etc.

Compositions, including pharmaceutical compounds, may contain a binding molecule (e.g., an antibody), for example, in isolated or purified form, together with a suitable amount of excipients.

The term "effective amount" or "therapeutically effective amount" as used herein refers to the amount of an antibody or a therapeutic molecule comprising an agent and the antibody or pharmaceutical composition provided herein which is sufficient to result in the desired outcome.

The terms "subject" and "patient" may be used interchangeably. As used herein, in certain embodiments, a subject is a mammal, such as a non-primate or a primate (e.g., human). In specific embodiments, the subject is a human. In one embodiment, the subject is a mammal, e.g., a human, diagnosed with a disease or disorder. In another embodiment, the subject is a mammal, e.g., a human, at risk of developing a disease or disorder.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art.

As used herein, the terms "treat," "treatment" and "treating" refer to the reduction or amelioration of the progression, severity, and/or duration of a disease or condition resulting from the administration of one or more therapies. Treating may be determined by assessing whether there has been a decrease, alleviation and/or mitigation of one or more symptoms associated with the underlying disorder such that an improvement is observed with the patient, despite that the patient may still be afflicted with the underlying disorder. The term "treating" includes both managing and ameliorating the disease. The terms "manage," "managing." and "management" refer to the beneficial effects that a subject derives from a therapy which does not necessarily result in a cure of the disease.

The terms "prevent," "preventing," and "prevention" refer to reducing the likelihood of the onset (or recurrence) of a disease, disorder, condition, or associated symptom(s) (e.g., diabetes or a cancer).

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

"GPC3 associated disease or disorder" as used herein refers to a disease or disorder that comprises a cell or tissue in which GPC3 is expressed or overexpressed. In some embodiments, GPC3 associated disease or disorder comprises a cell on which GPC3 is abnormally expressed. In other embodiments, GPC3 associated disease or disorder comprises a cell in or on which GPC3 is deficient in at least one of its activities.

The terms "about" and "approximately" mean within 20%, within 15%, within 10%, within 9%, within 8%, within 7%, within 6%, within 5%, within 4%, within 3%, within 2%, within 1%, or less of a given value or range.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "between" as used in a phrase as such "between A and B" or "between A-B" refers to a range including both A and B.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

5.2. GPC3 Binding Molecules

5.2.1. Antibodies that Bind to GPC3

In one aspect, provided herein are antibodies capable of binding to Glypican-3 (GPC3). GPC3 is a member of the glypican family of heparan sulfate (HS) proteoglycans that are attached to the cell surface by a glycosylphosphatidylinositol anchor (Filmus and Selleck, J Clin Invest 108: 497-501, 2001). The GPC3 gene codes for a core protein of approximately 70 kD, which can be cleaved by furin to produce an N-terminal 40 kD fragment and a C-terminal 30 kD fragment. Two HS chains are attached on the C-terminal portion of GPC3. GPC3 and other glypican family proteins play a role in cell division and cell growth regulation. GPC3 is highly expressed in HCC and some other human cancers including melanoma, squamous cell carcinomas of the lung, and clear cell carcinomas of the ovary (Ho and Kim, Eur J Cancer 47(3):333-338, 2011), but is not expressed in normal tissues. GPC3 is also known as SGB, DGSX, MXR7, SDYS, SGBS, OCI-5, SGBSI and GTR2-2. There are four known isoforms of human GPC3 (isoforms 1-4). Nucleic acid and amino acid sequences of the four isoforms of GPC3 are known, including GenBank Accession numbers: NM_001164617 and NP_001158089 (isoform 1); NM_004484 and NP_004475 (isoform 2); NM_001164618 and NP_001158090 (isoform 3); and NM_001164619 and NP_001158091 (isoform 4). In some embodiments, the anti-GPC3 antibody provided herein can bind to any of the above four isoforms. In some embodiments, the antibodies provided herein bind to human GPC3. In some embodiments, the anti-GPC3 antibody provided herein modulates one or more GPC3 activities. In some embodiments, the anti-GPC3 antibody provided herein is an antagonist antibody.

In some embodiments, the anti-GPC3 antibody provided herein binds to GPC3 (e.g., human GPC3) with a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). A variety of methods of measuring binding affinity are known in the art, any of which can be used for purposes of the present disclosure, including by RIA, for example, performed with the Fab version of an antibody of interest and its antigen (Chen et al., 1999. J. Mol Biol 293:865-81); by biolayer interferometry (BLI) or surface plasmon resonance (SPR) assays by Octet®, using, for example, an Octet® Red96 system, or by Biacore®, using, for example, a Biacore® TM-2000 or a Biacore® TM-3000. An "on-rate" or "rate of association" or "association rate" or "kon" may also be determined with the same biolayer interferometry (BLI) or surface plasmon resonance (SPR) techniques described above using, for example, the Octet® Red96, the Biacore® TM-2000, or the Biacore® TM-3000 system.

In some embodiments, the anti-GPC3 antibodies provide herein are those described in Section 6 below. Thus, in some embodiments, the antibody provided herein comprises one or more CDR sequences of any one of SEQ ID NOs: 61-80 and 117-125. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-GPC3 antibody is humanized. In some embodiments, the anti-GPC3 antibody comprises an acceptor human framework, e.g., a human immunoglobulin framework or a human consensus framework.

In some embodiments, the anti-GPC3 antibody provided herein comprises HCDR1, HCDR2, and HCDR3 as set forth in SEQ ID NO: 61. In some embodiments, the anti-GPC3 antibody provided herein comprises HCDR1, HCDR2, and HCDR3 as set forth in SEQ ID NO: 62. In some embodiments, the anti-GPC3 antibody provided herein comprises HCDR1, HCDR2, and HCDR3 as set forth in SEQ ID NO: 63. In some embodiments, the anti-GPC3 antibody provided herein comprises HCDR1, HCDR2, and HCDR3 as set forth in SEQ ID NO: 64. In some embodiments, the anti-GPC3 antibody provided herein comprises HCDR1, HCDR2, and HCDR3 as set forth in SEQ ID NO: 65. In some embodiments, the anti-GPC3 antibody provided herein comprises HCDR1, HCDR2, and HCDR3 as set forth in SEQ ID NO: 66. In some embodiments, the anti-GPC3 antibody provided herein comprises HCDR1, HCDR2, and HCDR3 as set forth in SEQ ID NO: 67. In some embodiments, the anti-GPC3 antibody provided herein comprises HCDR1, HCDR2, and HCDR3 as set forth in SEQ ID NO: 68. In some embodiments, the anti-GPC3 antibody provided herein comprises HCDR1, HCDR2, and HCDR3 as set forth in SEQ ID NO: 69. In some embodiments, the anti-GPC3 antibody provided herein comprises HCDR1, HCDR2, and HCDR3 as set forth in SEQ ID NO: 70. In some embodiments, the anti-GPC3 antibody provided herein comprises HCDR1, HCDR2, and HCDR3 as set forth in SEQ ID NO: 117. In some embodiments, the anti-GPC3 antibody provided herein comprises HCDR1, HCDR2, and HCDR3 as set forth in SEQ ID NO: 118. In some embodiments, the anti-GPC3 antibody provided herein comprises HCDR1, HCDR2, and HCDR3 as set forth in SEQ ID NO: 119. In some embodiments, the anti-GPC3 antibody provided herein comprises HCDR1, HCDR2, and HCDR3 as set forth in SEQ ID NO: 120. In some embodiments, the anti-GPC3 antibody provided herein comprises HCDR1, HCDR2, and HCDR3 as set forth in SEQ ID NO: 121. In some embodiments, the anti-GPC3 antibody provided herein comprises HCDR1, HCDR2, and HCDR3 as set forth in SEQ ID NO: 122. CDR sequences can be determined according to well-known numbering systems or a combination thereof. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering.

In some embodiments, the anti-GPC3 antibody provided herein comprises LCDR1, LCDR2, and LCDR3 as set forth in SEQ ID NO: 71. In some embodiments, the anti-GPC3 antibody provided herein comprises LCDR1, LCDR2, and LCDR3 as set forth in SEQ ID NO: 72. In some embodiments, the anti-GPC3 antibody provided herein comprises LCDR1, LCDR2, and LCDR3 as set forth in SEQ ID NO: 73. In some embodiments, the anti-GPC3 antibody provided herein comprises LCDR1, LCDR2, and LCDR3 as set forth in SEQ ID NO: 74. In some embodiments, the anti-GPC3 antibody provided herein comprises LCDR1, LCDR2, and LCDR3 as set forth in SEQ ID NO: 75. In some embodiments, the anti-GPC3 antibody provided herein comprises LCDR1, LCDR2, and LCDR3 as set forth in SEQ ID NO: 76. In some embodiments, the anti-GPC3 antibody provided herein comprises LCDR1, LCDR2, and LCDR3 as set forth in SEQ ID NO: 77. In some embodiments, the anti-GPC3 antibody provided herein comprises LCDR1, LCDR2, and LCDR3 as set forth in SEQ ID NO: 78. In some embodiments, the anti-GPC3 antibody provided herein comprises LCDR1, LCDR2, and LCDR3 as set forth in SEQ ID NO: 79. In some embodiments, the anti-GPC3 antibody provided herein comprises LCDR1, LCDR2, and LCDR3 as set forth in SEQ ID NO: 80. In some embodiments, the anti-GPC3 antibody provided herein comprises LCDR1, LCDR2, and LCDR3 as set forth in SEQ ID NO: 123. In some embodiments, the anti-GPC3 antibody provided herein comprises LCDR1, LCDR2, and LCDR3 as set forth in SEQ ID NO: 124. In some embodiments, the anti-GPC3 antibody provided herein comprises LCDR1, LCDR2, and LCDR3 as set forth in SEQ ID NO: 125. CDR sequences can be determined according to well-known numbering systems or a combination thereof. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering.

In some embodiments, an antibody is provided that comprises HCDR1, HCDR2, and HCDR3 as set forth in SEQ ID NO: 61 and LCDR1, LCDR2, and LCDR3 as set forth in SEQ ID NO: 71. In some embodiments, an antibody is provided that comprises HCDR1, HCDR2, and HCDR3 as set forth in SEQ ID NO: 62 and LCDR1, LCDR2, and LCDR3 as set forth in SEQ ID NO: 72. In some embodiments, an antibody is provided that comprises HCDR1, HCDR2, and HCDR3 as set forth in SEQ ID NO: 63 and LCDR1, LCDR2, and LCDR3 as set forth in SEQ ID NO: 73. In some embodiments, an antibody is provided that comprises HCDR1, HCDR2, and HCDR3 as set forth in SEQ ID NO: 64 and LCDR1, LCDR2, and LCDR3 as set forth in SEQ ID NO: 74. In some embodiments, an antibody is provided that comprises HCDR1, HCDR2, and HCDR3 as set forth in SEQ ID NO: 65 and LCDR1, LCDR2, and LCDR3 as set forth in SEQ ID NO: 75. In some embodiments, an antibody is provided that comprises HCDR1, HCDR2, and HCDR3 as set forth in SEQ ID NO: 66 and LCDR1, LCDR2, and LCDR3 as set forth in SEQ ID NO: 76. In some embodiments, an antibody is provided that comprises HCDR1, HCDR2, and HCDR3 as set forth in SEQ ID NO: 67 and LCDR1, LCDR2, and LCDR3 as set forth in SEQ ID NO: 77. In some embodiments, an antibody is provided that comprises HCDR1, HCDR2, and HCDR3 as set forth in SEQ ID NO: 68 and LCDR1, LCDR2, and LCDR3 as set forth in SEQ ID NO: 78. In some embodiments, an antibody is provided that comprises HCDR1, HCDR2, and HCDR3 as set forth in SEQ ID NO: 69 and LCDR1, LCDR2, and LCDR3 as set forth in SEQ ID NO: 79. In some embodiments, an antibody is provided that comprises HCDR1, HCDR2, and HCDR3 as set forth in SEQ ID NO: 70 and LCDR1, LCDR2, and LCDR3 as set forth in SEQ ID NO: 80. In some embodiments, an antibody is provided that comprises HCDR1, HCDR2, and HCDR3 as set forth in SEQ ID NO: 117 and LCDR1, LCDR2, and LCDR3 as set forth in SEQ ID NO: 123. In some embodiments, an antibody is provided that comprises HCDR1, HCDR2, and HCDR3 as set forth in SEQ ID NO: 118 and LCDR1, LCDR2, and LCDR3 as set forth in SEQ ID NO: 123. In some embodiments, an antibody is provided that comprises HCDR1, HCDR2, and HCDR3 as set forth in SEQ ID NO: 119 and LCDR1, LCDR2, and LCDR3 as set forth in SEQ ID NO: 123. In some embodiments, an antibody is provided that comprises HCDR1, HCDR2, and HCDR3 as set forth in SEQ ID NO: 120 and LCDR1, LCDR2, and LCDR3 as set forth in SEQ ID NO: 123. In some embodiments, an antibody is provided that comprises HCDR1, HCDR2, and HCDR3 as set forth in SEQ ID NO: 121 and LCDR1, LCDR2, and LCDR3 as set forth in SEQ ID NO: 123. In some embodiments, an antibody is provided that comprises HCDR1, HCDR2, and HCDR3 as set forth in SEQ ID NO: 122 and LCDR1, LCDR2, and LCDR3 as set forth in SEQ ID NO: 123. In some embodiments, an antibody is provided that comprises HCDR1, HCDR2, and HCDR3 as set forth in SEQ ID NO: 117 and LCDR1, LCDR2, and LCDR3 as set forth in SEQ ID NO: 124. In some embodiments, an antibody is provided that comprises HCDR1, HCDR2, and HCDR3 as set forth in SEQ ID NO: 118 and LCDR1, LCDR2, and LCDR3 as set forth in SEQ ID NO: 124. In some embodiments, an antibody is provided that comprises HCDR1, HCDR2, and HCDR3 as set forth in SEQ ID NO: 119 and LCDR1, LCDR2, and LCDR3 as set forth in SEQ ID NO: 124. In some embodiments, an antibody is provided that comprises HCDR1, HCDR2, and HCDR3 as set forth in SEQ ID NO: 120 and LCDR1, LCDR2, and LCDR3 as set forth in SEQ ID NO: 124. In some embodiments, an antibody is provided that comprises HCDR1, HCDR2, and HCDR3 as set forth in SEQ ID NO: 121 and LCDR1, LCDR2, and LCDR3 as set forth in SEQ ID NO: 124. In some embodiments, an antibody is provided that comprises HCDR1, HCDR2, and HCDR3 as set forth in SEQ ID NO: 122 and LCDR1, LCDR2, and LCDR3 as set forth in SEQ ID NO: 124. In some embodiments, an antibody is provided that comprises HCDR1, HCDR2, and HCDR3 as set forth in SEQ ID NO: 117 and LCDR1, LCDR2, and LCDR3 as set forth in SEQ ID NO: 125. In some embodiments, an antibody is provided that comprises HCDR1, HCDR2, and HCDR3 as set forth in SEQ ID NO: 118 and LCDR1, LCDR2, and LCDR3 as set forth in SEQ ID NO: 125. In some embodiments, an antibody is provided that comprises HCDR1, HCDR2, and HCDR3 as set forth in SEQ ID NO: 119 and LCDR1, LCDR2, and LCDR3 as set forth in SEQ ID NO: 125. In some embodiments, an antibody is provided that comprises HCDR1, HCDR2, and HCDR3 as set forth in SEQ ID NO: 120 and LCDR1, LCDR2, and LCDR3 as set forth in SEQ ID NO: 125. In some embodiments, an antibody is provided that comprises HCDR1, HCDR2, and HCDR3 as set forth in SEQ ID NO: 121 and LCDR1, LCDR2, and LCDR3 as set forth in SEQ ID NO: 125. In some embodiments, an antibody is provided that comprises HCDR1, HCDR2, and HCDR3 as set forth in SEQ ID NO: 122 and LCDR1, LCDR2, and LCDR3 as set forth in SEQ ID NO: 125. CDR sequences can be determined according to well-known numbering systems or a combination thereof. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering.

In other embodiments, provided herein is an antibody that binds to GPC3 comprising a HCDR1 comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identity to any of SEQ ID NOs: 1-10; (ii) a HCDR2 comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identity to any of SEQ ID NOs: 11-20, (iii) a HCDR3 comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identity to any of SEQ ID NOs: 21-30; (iv) a LCDR1 comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identity to any of SEQ ID NOs: 31-40; (v) a LCDR2 comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identity to any of SEQ ID NOs: 41-50; and/or (vi) a LCDR3 comprising an amino acid sequence having at least 75%, 80%, 85%, 86%, 87%, 88%, 89%, 90%, 91%, 92%, 93%, 94%, 95%, 96%, 97%, 98%, 99%, 100% sequence identity to any of SEQ ID NOs: 51-60. In some embodiments, the anti-GPC3 antibody is humanized. In some embodiments, the anti-GPC3 antibody comprises an acceptor human framework, e.g., a human immunoglobulin framework or a human consensus framework.

In some more specific embodiments, the antibody or antigen binding fragment provided herein comprises an HCDR1 comprising the amino acid sequence of SEQ ID NO: 1, an HCDR2 comprising the amino acid sequence of SEQ ID NO: 11, and an HCDR3 comprising the amino acid sequence of SEQ ID NO: 21, and a LCDR1 comprising the amino acid sequence of SEQ ID NO: 31, a LCDR2 comprising the amino acid sequence of SEQ ID NO: 41, and a LCDR3 comprising the amino acid sequence of SEQ ID NO: 51.

In some more specific embodiments, the antibody or antigen binding fragment provided herein comprises an HCDR1 comprising the amino acid sequence of SEQ ID NO: 2, an HCDR2 comprising the amino acid sequence of SEQ ID NO: 12, and an HCDR3 comprising the amino acid sequence of SEQ ID NO: 22, and a LCDR1 comprising the amino acid sequence of SEQ ID NO: 32, a LCDR2 comprising the amino acid sequence of SEQ ID NO: 42, and a LCDR3 comprising the amino acid sequence of SEQ ID NO: 52.

In some more specific embodiments, the antibody or antigen binding fragment provided herein comprises an HCDR1 comprising the amino acid sequence of SEQ ID NO: 3, an HCDR2 comprising the amino acid sequence of SEQ ID NO: 13, and an HCDR3 comprising the amino acid sequence of SEQ ID NO: 23, and a LCDR1 comprising the amino acid sequence of SEQ ID NO: 33, a LCDR2 comprising the amino acid sequence of SEQ ID NO: 43, and a LCDR3 comprising the amino acid sequence of SEQ ID NO: 53.

In some more specific embodiments, the antibody or antigen binding fragment provided herein comprises an HCDR1 comprising the amino acid sequence of SEQ ID NO: 4, an HCDR2 comprising the amino acid sequence of SEQ ID NO: 14, and an HCDR3 comprising the amino acid sequence of SEQ ID NO: 24, and a LCDR1 comprising the amino acid sequence of SEQ ID NO: 34, a LCDR2 comprising the amino acid sequence of SEQ ID NO: 44, and a LCDR3 comprising the amino acid sequence of SEQ ID NO: 54.

In some more specific embodiments, the antibody or antigen binding fragment provided herein comprises an HCDR1 comprising the amino acid sequence of SEQ ID NO: 5, an HCDR2 comprising the amino acid sequence of SEQ ID NO: 15, and an HCDR3 comprising the amino acid sequence of SEQ ID NO: 25, and a LCDR1 comprising the amino acid sequence of SEQ ID NO: 35, a LCDR2 comprising the amino acid sequence of SEQ ID NO: 45, and a LCDR3 comprising the amino acid sequence of SEQ ID NO: 55.

In some more specific embodiments, the antibody or antigen binding fragment provided herein comprises an HCDR1 comprising the amino acid sequence of SEQ ID NO: 6, an HCDR2 comprising the amino acid sequence of SEQ ID NO: 16, and an HCDR3 comprising the amino acid sequence of SEQ ID NO: 26, and a LCDR1 comprising the amino acid sequence of SEQ ID NO: 36, a LCDR2 comprising the amino acid sequence of SEQ ID NO: 46, and a LCDR3 comprising the amino acid sequence of SEQ ID NO: 56.

In some more specific embodiments, the antibody or antigen binding fragment provided herein comprises an HCDR1 comprising the amino acid sequence of SEQ ID NO: 7, an HCDR2 comprising the amino acid sequence of SEQ ID NO: 17, and an HCDR3 comprising the amino acid sequence of SEQ ID NO: 27, and a LCDR1 comprising the amino acid sequence of SEQ ID NO: 37, a LCDR2 comprising the amino acid sequence of SEQ ID NO: 47, and a LCDR3 comprising the amino acid sequence of SEQ ID NO: 57.

In some more specific embodiments, the antibody or antigen binding fragment provided herein comprises an HCDR1 comprising the amino acid sequence of SEQ ID NO: 8, an HCDR2 comprising the amino acid sequence of SEQ ID NO: 18, and an HCDR3 comprising the amino acid sequence of SEQ ID NO: 28, and a LCDR1 comprising the amino acid sequence of SEQ ID NO: 38, a LCDR2 comprising the amino acid sequence of SEQ ID NO: 48, and a LCDR3 comprising the amino acid sequence of SEQ ID NO: 58.

In some more specific embodiments, the antibody or antigen binding fragment provided herein comprises an HCDR1 comprising the amino acid sequence of SEQ ID NO: 9, an HCDR2 comprising the amino acid sequence of SEQ ID NO: 19, and an HCDR3 comprising the amino acid sequence of SEQ ID NO: 29, and a LCDR1 comprising the amino acid sequence of SEQ ID NO: 39, a LCDR2 comprising the amino acid sequence of SEQ ID NO: 49, and a LCDR3 comprising the amino acid sequence of SEQ ID NO: 59.

In some more specific embodiments, the antibody or antigen binding fragment provided herein comprises an HCDR1 comprising the amino acid sequence of SEQ ID NO: 10, an HCDR2 comprising the amino acid sequence of SEQ ID NO: 20, and an HCDR3 comprising the amino acid sequence of SEQ ID NO: 30, and a LCDR1 comprising the amino acid sequence of SEQ ID NO: 40, a LCDR2 comprising the amino acid sequence of SEQ ID NO: 50, and a LCDR3 comprising the amino acid sequence of SEQ ID NO: 60.

In some embodiments, the antibody further comprises one or more framework regions of SEQ ID NOs: 61-80 and 117-125. In some embodiments, the antibody provided herein is a humanized antibody. In some embodiments, humanized antibodies can be generated using the method exemplified in the Section 6 below or the methods described in the section below. Framework regions described herein are determined based upon the boundaries of the CDR numbering system. In other words, if the CDRs are determined by, e.g., Kabat. IMGT, or Chothia, then the framework regions are the amino acid residues surrounding the CDRs in the variable region in the format, from the N-terminus to C-terminus: FR1-CDR1-FR2-CDR2-FR3-CDR3-FR4. For example FR1 is defined as the amino acid residues N-terminal to the CDR1 amino acid residues as defined by, e.g., the Kabat numbering system, the IMGT numbering system, or the Chothia numbering system. FR2 is defined as the amino acid residues between CDR1 and CDR2 amino acid residues as defined by, e.g., the Kabat numbering system, the IMGT numbering system, or the Chothia numbering system. FR3 is defined as the amino acid residues between CDR2 and CDR3 amino acid residues as defined by, e.g., the Kabat numbering system, the IMGT numbering system, or the Chothia numbering system, and FR4 is defined as the amino acid residues C-terminal to the CDR3 amino acid residues as defined by, e.g., the Kabat numbering system, the IMGT numbering system, or the Chothia numbering system.

In some embodiments, the antibody or antigen binding fragment provided herein comprises a VH domain comprising SEQ ID NO: 61 and a VL domain comprising SEQ ID NO: 71. In some embodiments, the antibody or antigen binding fragment provided herein comprises a VH domain comprising SEQ ID NO: 62 and a VL domain comprising SEQ ID NO: 72. In some embodiments, the antibody or antigen binding fragment provided herein comprises a VH domain comprising SEQ ID NO: 63 and a VL domain comprising SEQ ID NO: 73. In some embodiments, the antibody or antigen binding fragment provided herein comprises a VH domain comprising SEQ ID NO: 64 and a VL domain comprising SEQ ID NO: 74. In some embodiments, the antibody or antigen binding fragment provided herein comprises a VH domain comprising SEQ ID NO: 65 and a VL domain comprising SEQ ID NO: 75. In some embodiments, the antibody or antigen binding fragment provided herein comprises a VH domain comprising SEQ ID NO: 66 and a VL domain comprising SEQ ID NO: 76. In some embodiments, the antibody or antigen binding fragment provided herein comprises a VH domain comprising SEQ ID NO: 67 and a VL domain comprising SEQ ID NO: 77. In some embodiments, the antibody or antigen binding fragment provided herein comprises a VH domain comprising SEQ ID NO: 68 and a VL domain comprising SEQ ID NO: 78. In some embodiments, the antibody or antigen binding fragment provided herein comprises a VH domain comprising SEQ ID NO: 69 and a VL domain comprising SEQ ID NO: 79. In some embodiments, the antibody or antigen binding fragment provided herein comprises a VH domain comprising SEQ ID NO: 70 and a VL domain comprising SEQ ID NO: 80. In some embodiments, the antibody or antigen binding fragment provided herein comprises a VH domain comprising SEQ ID NO: 117 and a VL domain comprising SEQ ID NO: 123. In some embodiments, the antibody or antigen binding fragment provided herein comprises a VH domain comprising SEQ ID NO: 118 and a VL domain comprising SEQ ID NO: 123. In some embodiments, the antibody or antigen binding fragment provided herein comprises a VH domain comprising SEQ ID NO: 119 and a VL domain comprising SEQ ID NO: 123. In some embodiments, the antibody or antigen binding fragment provided herein comprises a VH domain comprising SEQ ID NO: 120 and a VL domain comprising SEQ ID NO: 123. In some embodiments, the antibody or antigen binding fragment provided herein comprises a VH domain comprising SEQ ID NO: 121 and a VL domain comprising SEQ ID NO: 123. In some embodiments, the antibody or antigen binding fragment provided herein comprises a VH domain comprising SEQ ID NO: 122 and a VL domain comprising SEQ ID NO: 123. In some embodiments, the antibody or antigen binding fragment provided herein comprises a VH domain comprising SEQ ID NO: 117 and a VL domain comprising SEQ ID NO: 124. In some embodiments, the antibody or antigen binding fragment provided herein comprises a VH domain comprising SEQ ID NO: 118 and a VL domain comprising SEQ ID NO: 124. In some embodiments, the antibody or antigen binding fragment provided herein comprises a VH domain comprising SEQ ID NO: 119 and a VL domain comprising SEQ ID NO: 124. In some embodiments, the antibody or antigen binding fragment provided herein comprises a VH domain comprising SEQ ID NO: 120 and a VL domain comprising SEQ ID NO: 124. In some embodiments, the antibody or antigen binding fragment provided herein comprises a VH domain comprising SEQ ID NO: 121 and a VL domain comprising SEQ ID NO: 124. In some embodiments, the antibody or antigen binding fragment provided herein comprises a VH domain comprising SEQ ID NO: 122 and a VL domain comprising SEQ ID NO: 124. In some embodiments, the antibody or antigen binding fragment provided herein comprises a VH domain comprising SEQ ID NO: 117 and a VL domain comprising SEQ ID NO: 125. In some embodiments, the antibody or antigen binding fragment provided herein comprises a VH domain comprising SEQ ID NO: 118 and a VL domain comprising SEQ ID NO: 125. In some embodiments, the antibody or antigen binding fragment provided herein comprises a VH domain comprising SEQ ID NO: 119 and a VL domain comprising SEQ ID NO: 125. In some embodiments, the antibody or antigen binding fragment provided herein comprises a VH domain comprising SEQ ID NO: 120 and a VL domain comprising SEQ ID NO: 125. In some embodiments, the antibody or antigen binding fragment provided herein comprises a VH domain comprising SEQ ID NO: 121 and a VL domain comprising SEQ ID NO: 125. In some embodiments, the antibody or antigen binding fragment provided herein comprises a VH domain comprising SEQ ID NO: 122 and a VL domain comprising SEQ ID NO: 125. In some embodiments, the antibody is a scFv.

In certain embodiments, an antibody described herein or an antigen binding fragment thereof comprises amino acid sequences with certain percent identity relative to any antibody provided herein, for example, those described in Section 6 below.

The determination of percent identity between two sequences (e.g., amino acid sequences or nucleic acid sequences) can be accomplished using a mathematical algorithm. A non-limiting example of a mathematical algorithm utilized for the comparison of two sequences is the algorithm of Karlin and Altschul. Proc. Natl. Acad. Sci. U.S.A. 87:2264 2268 (1990), modified as in Karlin and Altschul. Proc. Natl. Acad. Sci. U.S.A. 90:5873 5877 (1993). Such an algorithm is incorporated into the NBLAST and XBLAST programs of Altschul et al., J. Mol. Biol. 215:403 (1990). BLAST nucleotide searches can be performed with the NBLAST nucleotide program parameters set. e.g., for score=100, word length=12 to obtain nucleotide sequences homologous to a nucleic acid molecules described herein. BLAST protein searches can be performed with the XBLAST program parameters set. e.g., to score 50, word length=3 to obtain amino acid sequences homologous to a protein molecule described herein. To obtain gapped alignments for comparison purposes, Gapped BLAST can be utilized as described in Altschul et al., Nucleic Acids Res. 25:3389 3402 (1997). Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another non-limiting example of a mathematical algorithm utilized for the comparison of sequences is the algorithm of Myers and Miller, CABIOS 4:11-17 (1998). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In some embodiments, the antibody provide herein contains substitutions (e.g., conservative substitutions), insertions, or deletions relative to the reference sequence, but the anti-GPC3 antibody comprising that sequence retains the ability to bind to GPC3. In some embodiments, a total of 1 to 10 amino acids have been substituted, inserted and/or deleted in a reference amino acid sequence. In some embodiments, substitutions, insertions, or deletions occur in regions outside the CDRs (i.e., in the FRs). Optionally, the anti-GPC3 antibody provided herein includes post-translational modifications of a reference sequence.

In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 61 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 71, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 62 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 72, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 63 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 73, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 64 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 74, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 65 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 75, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 66 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 76, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 67 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 77, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 68 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 78, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 69 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 79, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 70 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 80, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 117 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 123, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 118 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 123, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 119 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 123, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 120 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 123, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 121 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 123, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 122 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 123, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 117 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 124, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 118 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 124, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 119 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 124, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 120 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 124, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 121 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 124, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 122 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 124, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 117 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 125, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 118 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 125, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 119 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 125, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 120 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 125, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 121 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 125, wherein the antibody binds to GPC3. In some embodiments, the antibody or antigen binding fragment provided herein comprises a VH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 122 and a VL domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 125, wherein the antibody binds to GPC3. In some embodiments, the antibody is a scFv.

In some embodiments, functional epitopes can be mapped, e.g., by combinatorial alanine scanning, to identify amino acids in the GPC3 protein that are necessary for interaction with anti-GPC3 antibodies provided herein. In some embodiments, conformational and crystal structure of anti-GPC3 antibody bound to GPC3 may be employed to identify the epitopes. In some embodiments, the present disclosure provides an antibody that specifically binds to the same epitope as any of the anti-GPC3 antibodies provided herein. For example, in some embodiments, an antibody is provided that binds to the same epitope as an anti-GPC3 antibody comprising a VH domain comprising SEQ ID NO: 61 and a VL domain comprising SEQ ID NO: 71. In some embodiments, an antibody is provided that binds to the same epitope as an anti-GPC3 antibody comprising a VH domain comprising SEQ ID NO: 62 and a VL domain comprising SEQ ID NO: 72. In some embodiments, an antibody is provided that binds to the same epitope as an anti-GPC3 antibody comprising a VH domain comprising SEQ ID NO: 63 and a VL domain comprising SEQ ID NO: 73. In some embodiments, an antibody is provided that binds to the same epitope as an anti-GPC3 antibody comprising a VH domain comprising SEQ ID NO: 64 and a VL domain comprising SEQ ID NO: 74. In some embodiments, an antibody is provided that binds to the same epitope as an anti-GPC3 antibody comprising a VH domain comprising SEQ ID NO: 65 and a VL domain comprising SEQ ID NO: 75. In some embodiments, an antibody is provided that binds to the same epitope as an anti-GPC3 antibody comprising a VH domain comprising SEQ ID NO: 66 and a VL domain comprising SEQ ID NO: 76. In some embodiments, an antibody is provided that binds to the same epitope as an anti-GPC3 antibody comprising a VH domain comprising SEQ ID NO: 67 and a VL domain comprising SEQ ID NO: 77. In some embodiments, an antibody is provided that binds to the same epitope as an anti-GPC3 antibody comprising a VH domain comprising SEQ ID NO: 68 and a VL domain comprising SEQ ID NO: 78. In some embodiments, an antibody is provided that binds to the same epitope as an anti-GPC3 antibody comprising a VH domain comprising SEQ ID NO: 69 and a VL domain comprising SEQ ID NO: 79. In some embodiments, an antibody is provided that binds to the same epitope as an anti-GPC3 antibody comprising a VH domain comprising SEQ ID NO: 70 and a VL domain comprising SEQ ID NO: 80. In some embodiments, an antibody is provided that binds to the same epitope as an anti-GPC3 antibody comprising a VH domain comprising SEQ ID NO: 117 and a VL domain comprising SEQ ID NO: 123. In some embodiments, an antibody is provided that binds to the same epitope as an anti-GPC3 antibody comprising a VH domain comprising SEQ ID NO: 118 and a VL domain comprising SEQ ID NO: 123. In some embodiments, an antibody is provided that binds to the same epitope as an anti-GPC3 antibody comprising a VH domain comprising SEQ ID NO: 119 and a VL domain comprising SEQ ID NO: 123. In some embodiments, an antibody is provided that binds to the same epitope as an anti-GPC3 antibody comprising a VH domain comprising SEQ ID NO: 120 and a VL domain comprising SEQ ID NO: 123. In some embodiments, an antibody is provided that binds to the same epitope as an anti-GPC3 antibody comprising a VH domain comprising SEQ ID NO: 121 and a VL domain comprising SEQ ID NO: 123. In some embodiments, an antibody is provided that binds to the same epitope as an anti-GPC3 antibody comprising a VH domain comprising SEQ ID NO: 122 and a VL domain comprising SEQ ID NO: 123. In some embodiments, an antibody is provided that binds to the same epitope as an anti-GPC3 antibody comprising a VH domain comprising SEQ ID NO: 117 and a VL domain comprising SEQ ID NO: 124. In some embodiments, an antibody is provided that binds to the same epitope as an anti-GPC3 antibody comprising a VH domain comprising SEQ ID NO: 118 and a VL domain comprising SEQ ID NO: 124. In some embodiments, an antibody is provided that binds to the same epitope as an anti-GPC3 antibody comprising a VH domain comprising SEQ ID NO: 119 and a VL domain comprising SEQ ID NO: 124. In some embodiments, an antibody is provided that binds to the same epitope as an anti-GPC3 antibody comprising a VH domain comprising SEQ ID NO: 120 and a VL domain comprising SEQ ID NO: 124. In some embodiments, an antibody is provided that binds to the same epitope as an anti-GPC3 antibody comprising a VH domain comprising SEQ ID NO: 121 and a VL domain comprising SEQ ID NO: 124. In some embodiments, an antibody is provided that binds to the same epitope as an anti-GPC3 antibody comprising a VH domain comprising SEQ ID NO: 122 and a VL domain comprising SEQ ID NO: 124. In some embodiments, an antibody is provided that binds to the same epitope as an anti-GPC3 antibody comprising a VH domain comprising SEQ ID NO: 117 and a VL domain comprising SEQ ID NO: 125. In some embodiments, an antibody is provided that binds to the same epitope as an anti-GPC3 antibody comprising a VH domain comprising SEQ ID NO: 118 and a VL domain comprising SEQ ID NO: 125. In some embodiments, an antibody is provided that binds to the same epitope as an anti-GPC3 antibody comprising a VH domain comprising SEQ ID NO: 119 and a VL domain comprising SEQ ID NO: 125. In some embodiments, an antibody is provided that binds to the same epitope as an anti-GPC3 antibody comprising a VH domain comprising SEQ ID NO: 120 and a VL domain comprising SEQ ID NO: 125. In some embodiments, an antibody is provided that binds to the same epitope as an anti-GPC3 antibody comprising a VH domain comprising SEQ ID NO: 121 and a VL domain comprising SEQ ID NO: 125. In some embodiments, an antibody is provided that binds to the same epitope as an anti-GPC3 antibody comprising a VH domain comprising SEQ ID NO: 122 and a VL domain comprising SEQ ID NO: 125. In some embodiments, the antibody is a scFv.

In some embodiments, provided herein is an anti-GPC3 antibody, or antigen binding fragment thereof, that specifically binds to GPC3 competitively with any one of the anti-GPC3 antibodies described herein. In some embodiments, an antibody is provided that specifically binds to GPC3 competitively with an anti-GPC3 antibody comprising a VH domain comprising SEQ ID NO: 61 and a VL domain comprising SEQ ID NO: 71. In some embodiments, an antibody is provided that specifically binds to GPC3 competitively with an anti-GPC3 antibody comprising a VH domain comprising SEQ ID NO: 62 and a VL domain comprising SEQ ID NO: 72. In some embodiments, an antibody is provided that specifically binds to GPC3 competitively with an anti-GPC3 antibody comprising a VH domain comprising SEQ ID NO: 63 and a VL domain comprising SEQ ID NO: 73. In some embodiments, an antibody is provided that specifically binds to GPC3 competitively with an anti-GPC3 antibody comprising a VH domain comprising SEQ ID NO: 64 and a VL domain comprising SEQ ID NO: 74. In some embodiments, an antibody is provided that specifically binds to GPC3 competitively with an anti-GPC3 antibody comprising a VH domain comprising SEQ ID NO: 65 and a VL domain comprising SEQ ID NO: 75. In some embodiments, an antibody is provided that specifically binds to GPC3 competitively with an anti-GPC3 antibody comprising a VH domain comprising SEQ ID NO: 66 and a VL domain comprising SEQ ID NO: 76. In some embodiments, an antibody is provided that specifically binds to GPC3 competitively with an anti-GPC3 antibody comprising a VH domain comprising SEQ ID NO: 67 and a VL domain comprising SEQ ID NO: 77. In some embodiments, an antibody is provided that specifically binds to GPC3 competitively with an anti-GPC3 antibody comprising a VH domain comprising SEQ ID NO: 68 and a VL domain comprising SEQ ID NO: 78. In some embodiments, an antibody is provided that specifically binds to GPC3 competitively with an anti-GPC3 antibody comprising a VH domain comprising SEQ ID NO: 69 and a VL domain comprising SEQ ID NO: 79. In some embodiments, an antibody is provided that specifically binds to GPC3 competitively with an anti-GPC3 antibody comprising a VH domain comprising SEQ ID NO: 70 and a VL domain comprising SEQ ID NO: 80. In some embodiments, an antibody is provided that specifically binds to GPC3 competitively with an anti-GPC3 antibody comprising a VH domain comprising SEQ ID NO: 117 and a VL domain comprising SEQ ID NO: 123. In some embodiments, an antibody is provided that specifically binds to GPC3 competitively with an anti-GPC3 antibody comprising a VH domain comprising SEQ ID NO: 118 and a VL domain comprising SEQ ID NO: 123. In some embodiments, an antibody is provided that specifically binds to GPC3 competitively with an anti-GPC3 antibody comprising a VH domain comprising SEQ ID NO: 119 and a VL domain comprising SEQ ID NO: 123. In some embodiments, an antibody is provided that specifically binds to GPC3 competitively with an anti-GPC3 antibody comprising a VH domain comprising SEQ ID NO: 120 and a VL domain comprising SEQ ID NO: 123. In some embodiments, an antibody is provided that specifically binds to GPC3 competitively with an anti-GPC3 antibody comprising a VH domain comprising SEQ ID NO: 121 and a VL domain comprising SEQ ID NO: 123. In some embodiments, an antibody is provided that specifically binds to GPC3 competitively with an anti-GPC3 antibody comprising a VH domain comprising SEQ ID NO: 122 and a VL domain comprising SEQ ID NO: 123. In some embodiments, an antibody is provided that specifically binds to GPC3 competitively with an anti-GPC3 antibody comprising a VH domain comprising SEQ ID NO: 117 and a VL domain comprising SEQ ID NO: 124. In some embodiments, an antibody is provided that specifically binds to GPC3 competitively with an anti-GPC3 antibody comprising a VH domain comprising SEQ ID NO: 118 and a VL domain comprising SEQ ID NO: 124. In some embodiments, an antibody is provided that specifically binds to GPC3 competitively with an anti-GPC3 antibody comprising a VH domain comprising SEQ ID NO: 119 and a VL domain comprising SEQ ID NO: 124. In some embodiments, an antibody is provided that specifically binds to GPC3 competitively with an anti-GPC3 antibody comprising a VH domain comprising SEQ ID NO: 120 and a VL domain comprising SEQ ID NO: 124. In some embodiments, an antibody is provided that specifically binds to GPC3 competitively with an anti-GPC3 antibody comprising a VH domain comprising SEQ ID NO: 121 and a VL domain comprising SEQ ID NO: 124. In some embodiments, an antibody is provided that specifically binds to GPC3 competitively with an anti-GPC3 antibody comprising a VH domain comprising SEQ ID NO: 122 and a VL domain comprising SEQ ID NO: 124. In some embodiments, an antibody is provided that specifically binds to GPC3 competitively with an anti-GPC3 antibody comprising a VH domain comprising SEQ ID NO: 117 and a VL domain comprising SEQ ID NO: 125. In some embodiments, an antibody is provided that specifically binds to GPC3 competitively with an anti-GPC3 antibody comprising a VH domain comprising SEQ ID NO: 118 and a VL domain comprising SEQ ID NO: 125. In some embodiments, an antibody is provided that specifically binds to GPC3 competitively with an anti-GPC3 antibody comprising a VH domain comprising SEQ ID NO: 119 and a VL domain comprising SEQ ID NO: 125. In some embodiments, an antibody is provided that specifically binds to GPC3 competitively with an anti-GPC3 antibody comprising a VH domain comprising SEQ ID NO: 120 and a VL domain comprising SEQ ID NO: 125. In some embodiments, an antibody is provided that specifically binds to GPC3 competitively with an anti-GPC3 antibody comprising a VH domain comprising SEQ ID NO: 121 and a VL domain comprising SEQ ID NO: 125. In some embodiments, an antibody is provided that specifically binds to GPC3 competitively with an anti-GPC3 antibody comprising a VH domain comprising SEQ ID NO: 122 and a VL domain comprising SEQ ID NO: 125. In some embodiments, the antibody is a scFv.

In some embodiments, provided herein is a GPC3 binding protein comprising any one of the anti-GPC3 antibodies described above. In some embodiments, the GPC3 binding protein is a monoclonal antibody, including a mouse, chimeric, humanized or human antibody. In some embodiments, the anti-GPC3 antibody is an antibody fragment, e.g., a scFv. In some embodiments, the GPC3 binding protein is a fusion protein comprising the anti-GPC3 antibody provided herein. In other embodiments, the GPC3 binding protein is a multispecific antibody comprising the anti-GPC3 antibody provided herein. Other exemplary GPC3 binding molecules are described in more detail in the following sections.

In some embodiments, the anti-GPC3 antibody or antigen binding protein according to any of the above embodiments may incorporate any of the features, singly or in combination, as described in Sections 5.2.2 to 5.2.8 below.

5.2.2. Antibody Fragments

As used herein, the term "antibody" also includes various antibody fragments thereof. Antibodies provided herein include, but are not limited to, immunoglobulin molecules and immunologically active portions of immunoglobulin molecules. The immunoglobulin molecules provided herein can be of any class (e.g., IgG, IgE, IgM, IgD, and IgA) or any subclass (e.g., IgG1, IgG2, IgG3, IgG4, IgAQ1, and IgA2) of immunoglobulin molecule. In some embodiments, the antibody is an IgG antibody. In some embodiments, the IgG antibody is an IgG1 antibody. In some embodiments, the IgG antibody is an IgG2, IgG3, or IgG4 antibody.

Variants and derivatives of antibodies include antibody functional fragments that retain the ability to bind to an antigen. Exemplary functional fragments include Fab fragments (e.g., an antibody fragment that contains the antigen-binding domain and comprises a light chain and part of a heavy chain bridged by a disulfide bond); Fab' (e.g., an antibody fragment containing a single antigen-binding domain comprising an Fab and an additional portion of the heavy chain through the hinge region); F(ab')2 (e.g., two Fab' molecules joined by interchain disulfide bonds in the hinge regions of the heavy chains; the Fab' molecules may be directed toward the same or different epitopes); a bispecific Fab (e.g., a Fab molecule having two antigen binding domains, each of which may be directed to a different epitope); a single chain comprising a variable region, also known as, scFv (e.g., the variable, antigen-binding determinative region of a single light and heavy chain of an antibody linked together by a chain of, e.g., 10-25 amino acids); a disulfide-linked Fv, or dsFv (e.g., the variable, antigen-binding determinative region of a single light and heavy chain of an antibody linked together by a disulfide bond); a camelized VH (e.g., the variable, antigen-binding determinative region of a single heavy chain of an antibody in which some amino acids at the VH interface are those found in the heavy chain of naturally occurring camel antibodies); a bispecific scFv (e.g., an scFv or a dsFv molecule having two antigen-binding domains, each of which may be directed to a different epitope); a diabody (e.g., a dimerized scFv formed when the VH domain of a first scFv assembles with the VL domain of a second scFv and the VL domain of the first scFv assembles with the VH domain of the second scFv; the two antigen-binding regions of the diabody may be directed towards the same or different epitopes); a triabody (e.g., a trimerized scFv, formed in a manner similar to a diabody, but in which three antigen-binding domains are created in a single complex; the three antigen binding domains may be directed towards the same or different epitopes); and a tetrabody (e.g., a tetramerized scFv, formed in a manner similar to a diabody, but in which four antigen-binding domains are created in a single complex; the four antigen binding domains may be directed towards the same or different epitopes).

Various techniques have been developed for the production of antibody fragments. Traditionally, these fragments were derived via proteolytic digestion of intact antibodies (see, e.g., Morimoto et al., 1992, J. Biochem. Biophys. Methods 24:107-17; and Brennan et al., 1985, Science 229:81-83). However, these fragments can now be produced directly by recombinant host cells. For example, Fab, Fv, and scFv antibody fragments can all be expressed in and secreted from *E. coli* or yeast cells, thus allowing the facile production of large amounts of these fragments. Antibody fragments can be isolated from the antibody phage libraries discussed above. Alternatively, Fab-SH fragments can be directly recovered from *E. coli* and chemically coupled to form F(ab')2 fragments (Carter et al., 1992, Bio/Technology 10:163-67). According to another approach, F(ab')2 fragments can be isolated directly from recombinant host cell culture. Fab and F(ab')2 fragment with increased in vivo half-life comprising salvage receptor binding epitope residues are described in, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894 and 5,587,458). Fv and scFv have intact combining sites that are devoid of constant regions; thus, they may be suitable for reduced nonspecific binding during in vivo use, scFv fusion proteins may be constructed to yield fusion of an effector protein at either the amino or the carboxy terminus of an scFv (See, e.g., Borrebaeck ed., supra). The antibody fragment may also be a "linear antibody." for example, as described in the references cited above. Such linear antibodies may be monospecific or multi-specific, such as bispecific.

In some specific embodiments, the antibody provided herein is a scFv comprising any one of the VH domains described above including, e.g., SEQ ID NOs: 61-70 and 117-122, and any one of the VL domains described above including, e.g., SEQ ID NOs: 71-80 and 123-125. More specifically, in some embodiments, provided herein is a scFv comprising the amino acid sequence of SEQ ID NO: 81. In some embodiments, provided herein is a scFv comprising the amino acid sequence of SEQ ID NO: 82. In some embodiments, provided herein is a scFv comprising the amino acid sequence of SEQ ID NO: 83. In some embodiments, provided herein is a scFv comprising the amino acid sequence of SEQ ID NO: 84. In some embodiments, provided herein is a scFv comprising the amino acid sequence of SEQ ID NO: 85. In some embodiments, provided herein is a scFv comprising the amino acid sequence of SEQ ID NO: 86. In some embodiments, provided herein is a scFv comprising the amino acid sequence of SEQ ID NO: 87. In some embodiments, provided herein is a scFv comprising the amino acid sequence of SEQ ID NO: 88. In some embodiments, provided herein is a scFv comprising the amino acid sequence of SEQ ID NO: 89. In some embodiments, provided herein is a scFv comprising the amino acid sequence of SEQ ID NO: 90. In some embodiments, provided herein is a scFv comprising the amino acid sequence of SEQ ID NO: 128. In some embodiments, provided herein is a scFv comprising the amino acid sequence of SEQ ID NO: 129.

In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 81. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 82. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 83. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 84. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 85. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 86. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 87. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 88. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 89. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 90. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 128. In some embodiments, provided herein is a scFv having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 129.

5.2.3. Humanized Antibodies

The antibodies described herein include humanized antibodies. Humanized antibodies, such as the humanized antibodies disclosed herein can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, Molecular Immunology 28(4/5):489-498 (1991); Studnicka et al., Protein Engineering 7(6):805-814 (1994); and Roguska et al., PNAS 91:969-973 (1994)), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

In some embodiments, antibodies provided herein can be humanized antibodies that bind to GPC3, including human GPC3. For example, humanized single chain antibodies of the present disclosure may comprise one or more CDRs set forth in SEQ ID NOs: 61-80 and 117-125. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., Nature 321:522-25 (1986); Riechmann et al., Nature 332:323-27 (1988); and Verhoeven et al., Science 239:1534-36 (1988)), by substituting hypervariable region sequences for the corresponding sequences of a human antibody. In a specific embodiment, humanization of the antibody provided herein is performed as described in Section 6 below.

In some cases, the humanized antibodies are constructed by CDR grafting, in which the amino acid sequences of the CDRs of the parent non-human antibody are grafted onto a human antibody framework. For example, Padlan et al. determined that only about one third of the residues in the CDRs actually contact the antigen, and termed these the "specificity determining residues," or SDRs (Padlan et al., FASEB J. 9:133-39 (1995)). In the technique of SDR grafting, only the SDR residues are grafted onto the human antibody framework (see. e.g., Kashmiri et al., Methods 36:25-34 (2005)).

The choice of human variable domains to be used in making the humanized antibodies can be important to reduce antigenicity. For example, according to the so-called "best-fit" method, the sequence of the variable domain of a non-human antibody is screened against the entire library of known human variable-domain sequences. The human sequence that is closest to that of the non-human antibody may be selected as the human framework for the humanized antibody (Sims et al., J. Immunol. 151:2296-308 (1993); and Chothia et al., J. Mol. Biol. 196:901-17 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA 89:4285-89 (1992); and Presta et al., J. Immunol. 151:2623-32 (1993)). In some cases, the framework is derived from the consensus sequences of the most abundant human subclasses, $V_L6$ subgroup I ($V_L6$I) and VH subgroup III ($V_H$III). In another method, human germline genes are used as the source of the framework regions.

In an alternative paradigm based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see. e.g., Tan et al., J. Immunol. 169:1119-25 (2002)).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, Protein Eng. 13:819-24 (2002)), Modeller (Sali and Blundell, J. Mol. Biol. 234:779-815 (1993)), and Swiss PDB Viewer (Guex and Peitsch, Electrophoresis 18:2714-23 (1997)). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., Mol. Immunol. 44:1986-98 (2007)).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see. e.g., Hoogenboom, Nat. Biotechnol. 23:1105-16 (2005); Dufner et al., Trends Biotechnol. 24:523-29 (2006); Feldhaus et al., Nat. Biotechnol. 21:163-70 (2003); and Schlapschy et al., Protein Eng. Des. Sel. 17:847-60) (2004)).

In the FR library approach, a collection of residue variants are introduced at specific positions in the FR followed by screening of the library to select the FR that best supports the grafted CDR. The residues to be substituted may include some or all of the "Vernier" residues identified as potentially contributing to CDR structure (see. e.g., Foote and Winter, J. Mol. Biol. 224:487-99 (1992)), or from the more limited set of target residues identified by Baca et al. J. Biol. Chem. 272:10678-84 (1997).

In FR shuffling, whole FRs are combined with the non-human CDRs instead of creating combinatorial libraries of selected residue variants (see. e.g., Dall'Acqua et al., Methods 36:43-60 (2005)). A one-step FR shuffling process may be used. Such a process has been shown to be efficient, as the resulting antibodies exhibited improved biochemical and physicochemical properties including enhanced expression, increased affinity, and thermal stability (see. e.g., Damschroder et al., Mol. Immunol. 44:3049-60 (2007)).

The "humaneering" method is based on experimental identification of essential minimum specificity determinants (MSDs) and is based on sequential replacement of non-human fragments into libraries of human FRs and assessment of binding. This methodology typically results in epitope retention and identification of antibodies from multiple subclasses with distinct human V-segment CDRs.

The "human engineering" method involves altering a non-human antibody or antibody fragment by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human antibody as "low risk." "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering 7:805-14 (1994); U.S. Pat. Nos. 5,766,886; 5,770,196; 5,821,123; and 5,869,619; and PCT Publication WO 93/11794.

A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody.

A deimmunized antibody is an antibody in which T-cell epitopes have been removed. Methods for making deimmunized antibodies have been described. See, e.g., Jones et al., Methods Mol Biol. 525:405-23 (2009), xiv, and De Groot et al., Cell. Immunol. 244:148-153 (2006)). Deimmunized antibodies comprise T-cell epitope-depleted variable regions and human constant regions. Briefly, variable regions of an antibody are cloned and T-cell epitopes are subsequently identified by testing overlapping peptides derived from the variable regions of the antibody in a T cell proliferation assay. T cell epitopes are identified via in silico methods to identify peptide binding to human MHC class II. Mutations are introduced in the variable regions to abrogate binding to human MHC class II. Mutated variable regions are then utilized to generate the deimmunized antibody.

5.2.4. Antibody Variants

In some embodiments, amino acid sequence modification (s) of the antibodies that bind to GPC3 described herein are contemplated. For example, it may be desirable to optimize the binding affinity and/or other biological properties of the antibody, including but not limited to specificity, thermostability, expression level, effector functions, glycosylation, reduced immunogenicity, or solubility. Thus, in addition to the antibodies that bind to GPC3 described herein, it is contemplated that variants of the antibodies that bind to GPC3 described herein can be prepared. For example, antibody variants can be prepared by introducing appropriate nucleotide changes into the encoding DNA, and/or by synthesis of the desired antibody or polypeptide. Those skilled in the art who appreciate that amino acid changes may alter post-translational processes of the antibody.

Chemical Modifications

In some embodiments, the antibodies provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, or conjugation to one or more immunoglobulin domains (e.g., Fc or a portion of an Fc). Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

When the antibody provided herein is fused to an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See. e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the binding molecules provided herein may be made in order to create variants with certain improved properties.

In other embodiments, when the antibody provided herein is fused to an Fc region, antibody variants provided herein may have a carbohydrate structure that lacks fucose attached (directly or indirectly) to said Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 and US 2004/0093621. Examples of publications related to "defucosylated" or "fucose-deficient" antibody variants include: US 2003/0157108: WO 2000/61739: WO 2001/29246; US 2003/0115614; US 2002/0164328; US 2004/0093621; US 2004/0132140; US 2004/0110704; US 2004/0110282; US 2004/0109865: WO 2003/085119: WO 2003/084570; WO 2005/035586: WO 2005/035778; WO2005/053742: WO2002/031140; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108; and WO 2004/056312, and knockout cell lines, such as alpha-1,6-fucosyltransferase gene, *FUT*8, knockout CHO cells (see. e.g., Yamane-Ohnuki et al. *Biotech. Bioeng.* 87:614 (2004); Kanda, Y. et al., *Biotechnol. Bioeng.,* 94(4): 680-688 (2006); and WO2003/085107).

The binding molecules comprising an antibody provided herein are further provided with bisected oligosaccharides, e.g., in which a biantennary oligosaccharide attached to the Fc region is bisected by GlcNAc. Such variants may have reduced fucosylation and/or improved ADCC function. Examples of such variants are described, e.g., in WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such variants may have improved CDC function. Such variants are described, e.g., in WO 1997/30087; WO 1998/58964; and WO 1999/22764.

In molecules that comprise the present antibody and an Fc region, one or more amino acid modifications may be introduced into the Fc region, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates variants that possesses some but not all effector functions, which make it a desirable candidate for applications in which the half-life of the binding molecule in vivo is important vet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the binding molecule lacks FcγR binding (hence likely lacking ADCC activity), but retains FcRn binding ability. Non-limiting examples of in vitro assays to assess ADCC activity of a molecule of interest is described in U.S. Pat. No. 5,500,362 (see. e.g. Hellstrom, I. et al. *Proc. Nat'l Acad. Sci. USA* 83:7059-7063 (1986)) and Hellstrom, I et al., Proc. *Nat'Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See. e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see. e.g., Petkova, S. B. et al., *Int'l. Immunol.* 18 (12); 1759-1769 (2006)).

Binding molecules with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain variants with improved or diminished binding to FcRs are described. (See. e.g., U.S. Pat. No. 6,737,056; WO 2004/056312, and Shields et al., *J. Biol. Chem.* 9 (2): 6591-6604 (2001).)

In some embodiments, a variant comprises an Fc region with one or more amino acid substitutions which improve ADCC, e.g., substitutions at positions 298, 333, and/or 334 of the Fc region (EU numbering of residues). In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164:4178-4184 (2000).

Binding molecules with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those molecules comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

In some embodiments, it may be desirable to create cysteine engineered antibodies, in which one or more residues of an antibody are substituted with cysteine residues. In some embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein.

Substitutions, Deletions, or Insertions

Variations may be a substitution, deletion, or insertion of one or more codons encoding the antibody or polypeptide that results in a change in the amino acid sequence as compared with the original antibody or polypeptide. Sites of interest for substitutional mutagenesis include the CDRs and FRs.

Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the parental antibodies.

Amino acid sequence insertions include amino- and/or carboxyl-terminal fusions ranging in length from one residue to polypeptides containing multiple residues, as well as intrasequence insertions of single or multiple amino acid residues. Examples of terminal insertions include an antibody with an N-terminal methionyl residue.

Antibodies generated by conservative amino acid substitutions are included in the present disclosure. In a conservative amino acid substitution, an amino acid residue is replaced with an amino acid residue having a side chain with a similar charge. As described above, families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined. Conservative (e.g., within an amino acid group with similar properties and/or side chains) substitutions may be made, so as to maintain or not significantly change the properties. Exemplary substitutions are shown in Table 2 below.

TABLE 2

Amino Acid Substitutions

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to similarities in the properties of their side chains (see. e.g., Lehninger, *Biochemistry* 73-75 (2d ed. 1975)); (1) non-polar: Ala (A), Val (V), Leu (L), Ile (I), Pro (P), Phe (F), Trp (W), Met (M); (2) uncharged polar: Gly (G), Ser(S), Thr (T), Cys (C), Tyr (Y), Asn (N), Gln (Q); (3) acidic: Asp (D), Glu (E); and (4) basic: Lys (K), Arg (R), His (H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. For example, any cysteine residue not involved in maintaining the proper conformation of the antibody also may be substituted, for example, with another amino acid, such as alanine or serine, to improve the oxidative stability of the molecule and to prevent aberrant crosslinking. Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see. e.g., Chowdhury, *Methods Mol. Biol.* 207:179-196 (2008)), and/or SDRs (a-CDRs), with the resulting variant antibody or fragment thereof being tested for binding affinity. Affinity maturation by constructing and reselecting from secondary libraries has been described, e.g., in Hoogenboom et al, in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. More detailed description regarding affinity maturation is provided in the section below.

In some embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In some embodiments of the variant antibody sequences provided herein, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells, Science, 244:1081-1085 (1989). In this method, a residue or group of target residues (e.g., charged residues such as Arg. Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

The variations can be made using methods known in the art such as oligonucleotide-mediated (site-directed) mutagenesis, alanine scanning, and PCR mutagenesis. Site-directed mutagenesis (see. e.g., Carter, Biochem J. 237:1-7 (1986); and Zoller et al., Nucl. Acids Res. 10:6487-500 (1982)), cassette mutagenesis (see. e.g., Wells et al., Gene 34:315-23 (1985)), or other known techniques can be performed on the cloned DNA to produce the antibody variant DNA.

5.2.5. In vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed on the surface of an organism (e.g., phage, bacteria, yeast, or mammalian cell) or in association (e.g., covalently or noncovalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Affinity matured antibodies can have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and used to infect bacteria to produce phage for further rounds of selection. For review; see, for example, Hoogenboom, Methods. Mol. Biol. 178:1-37 (2002); and Bradbury and Marks, J. Immunol. Methods 290:29-49 (2004).

In a yeast display system (see. e.g., Boder et al., Nat. Biotech. 15:553-57 (1997); and Chao et al., Nat. Protocols 1:755-68 (2006)), the antibody may be fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability.

Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the single chain antibody (e.g., scFv). Expression has been shown to correlate with the stability of the displayed protein, and thus antibodies can be selected for improved stability as well as affinity (see. e.g., Shusta et al., J. Mol. Biol. 292:949-56 (1999)). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently "titrated" while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., U.S. Pat. Publication 2003/0186374; and Blaise et al., Gene 342:211-18 (2004)).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reverse transcribed back into cDNA, which can then undergo mutagenesis and be used in the next round of selection (see. e.g., Fukuda et al., Nucleic Acids Res. 34:e127 (2006)). In mRNA display, a covalent bond between antibody and mRNA is established using puromycin as an adaptor molecule (Wilson et al., Proc. Natl. Acad. Sci. USA 98:3750-55 (2001)).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

In some embodiments, mammalian display systems may be used.

Diversity may also be introduced into the CDRs of the antibody libraries in a targeted manner or via random introduction. The former approach includes sequentially targeting all the CDRs of an antibody via a high or low level of mutagenesis or targeting isolated hot spots of somatic hypermutations (see. e.g., Ho et al., J. Biol. Chem. 280:607-17 (2005)) or residues suspected of affecting affinity on experimental basis or structural reasons. Diversity may also be introduced by replacement of regions that are naturally diverse via DNA shuffling or similar techniques (see. e.g., Lu et al., J. Biol. Chem. 278:43496-507 (2003); U.S. Pat. Nos. 5,565,332 and 6,989,250). Alternative techniques target hypervariable loops extending into framework-region residues (see. e.g., Bond et al., J. Mol. Biol. 348:699-709 (2005)) employ loop deletions and insertions in CDRs or use hybridization-based diversification (see. e.g., U.S. Pat. Publication No. 2004/0005709). Additional methods of generating diversity in CDRs are disclosed, for example, in U.S. Pat. No. 7,985,840. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

Screening of the libraries can be accomplished by various techniques known in the art. For example, antibodies can be immobilized onto solid supports, columns, pins, or cellulose/poly(vinylidene fluoride) membranes/other filters, expressed on host cells affixed to adsorption plates or used in cell sorting, or conjugated to biotin for capture with streptavidin-coated beads or used in any other method for panning display libraries.

For review of in vitro affinity maturation methods, see, e.g., Hoogenboom, Nature Biotechnology 23:1105-16 (2005); Quiroz and Sinclair, Revista Ingeneria Biomedia 4:39-51 (2010); and references therein.

5.2.6. Modifications of Antibodies

Covalent modifications of antibodies are included within the scope of the present disclosure. Covalent modifications include reacting targeted amino acid residues of an antibody with an organic derivatizing agent that is capable of reacting with selected side chains or the N- or C-terminal residues of the antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see. e.g., Creighton, *Proteins: Structure and Molecular Properties* 79-86 (1983)), acetylation of the N-terminal amine, and amidation of any C-terminal carboxyl group.

Other types of covalent modification of the antibody included within the scope of this present disclosure include altering the native glycosylation pattern of the antibody or polypeptide as described above (see. e.g., Beck et al., Curr. Pharm. Biotechnol. 9:482-501 (2008); and Walsh, Drug Discov. Today 15:773-80 (2010)), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192; or 4,179,337. The antibody that binds to GPC3 of the disclosure may also be genetically fused or conjugated to one or more immunoglobulin constant regions or portions thereof (e.g., Fc) to extend half-life and/or to impart known Fc-mediated effector functions.

The single chain antibody that binds to GPC3 of the present disclosure may also be modified to form chimeric molecules comprising the single chain antibody that binds to GPC3 fused to another, heterologous polypeptide or amino acid sequence, for example, an epitope tag (see. e.g., Terpe, *Appl. Microbiol. Biotechnol.* 60:523-33 (2003)) or the Fc region of an IgG molecule (see. e.g., Aruffo, Antibody Fusion Proteins 221-42 (Chamow and Ashkenazi eds., 1999)). The single chain antibody that binds to GPC3 may also be used to generate GPC3 binding chimeric antigen receptor (CAR), as described in more detail below.

Also provided herein are fusion proteins comprising the single chain antibody that binds to GPC3 of the disclosure and a heterologous polypeptide. In some embodiments, the heterologous polypeptide to which the antibody is genetically fused or chemically conjugated is useful for targeting the antibody to cells having cell surface-expressed GPC3.

Also provided herein are panels of antibodies that bind to a GPC3 antigen. In specific embodiments, the panels of antibodies have different association rates, different dissociation rates, different affinities for a GPC3 antigen, and/or different specificities for a GPC3 antigen. In some embodiments, the panels comprise or consist of about 10 to about 1000 antibodies or more. Panels of antibodies can be used, for example, in 96-well or 384-well plates, for assays such as ELISAs.

5.2.7. Preparation of Antibodies

Methods of preparing antibodies have been described. See, e.g., Els Pardon et al, *Nature Protocol,* 9(3); 674 (2014). Antibodies (such as scFv fragments) may be obtained using methods known in the art such as by immunizing a Camelid species (such as camel or llama) and obtaining hybridomas therefrom, or by cloning a library of antibodies using molecular biology techniques known in the art and subsequent selection by ELISA with individual clones of unselected libraries or by using phage display.

Antibodies provided herein may be produced by culturing cells transformed or transfected with a vector containing an antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells or B cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression, and purification are further described in Plückthun et al., *Antibody Engineering: Producing antibodies in Escherichia coli: From PCR to fermentation* 203-52 (McCafferty et al. eds., 1996); Kwong and Rader, *E. coli Expression and Purification of Fab Antibody Fragments, in Current Protocols in Protein Science* (2009); Tachibana and Takekoshi, *Production of Antibody Fab Fragments in Escherichia coli, in Antibody Expression and Production* (Al-Rubeai ed., 2011); and *Therapeutic Monoclonal Antibodies: From Bench to Clinic* (An ed., 2009).

It is, of course, contemplated that alternative methods, which are well known in the art, may be employed to prepare anti-GPC3 antibodies. For instance, the appropriate amino acid sequence, or portions thereof, may be produced by direct peptide synthesis using solid-phase techniques (see. e.g., Stewart et al., *Solid-Phase Peptide Synthesis* (1969); and Merrifield, J. Am. Chem. Soc. 85:2149-54 (1963)). In vitro protein synthesis may be performed using manual techniques or by automation. Various portions of the anti-GPC3 antibody may be chemically synthesized separately and combined using chemical or enzymatic methods to produce the desired anti-GPC3 antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

For example, the animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature.* 256:495 (1975), or may be made by recombinant DNA methods (U.S. Pat. No. 4,816,567).

In the hybridoma method, an appropriate host animal is immunized to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986).

The immunizing agent will typically include the antigenic protein or a fusion variant thereof. Goding, *Monoclonal Antibodies: Principles and Practice*, Academic Press (1986), pp. 59-103. Immortalized cell lines are usually transformed mammalian cells. The hybridoma cells thus prepared are seeded and grown in a suitable culture medium that preferably contains one or more substances that inhibit the growth or survival of the unfused, parental myeloma cells. Preferred immortalized myeloma cells are those that fuse efficiently, support stable high-level production of antibody by the selected antibody-producing cells, and are sensitive to a medium such as HAT medium.

Culture medium in which hybridoma cells are growing is assayed for production of monoclonal antibodies directed against the antigen. The culture medium in which the hybridoma cells are cultured can be assayed for the presence of monoclonal antibodies directed against the desired antigen. Such techniques and assays are known in the in art. For example, binding affinity may be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.,* 5:256-262 (1993) and Plückthun, *Immunol. Revs.* 130:151-188 (1992).

In a further embodiment, antibodies can be isolated from antibody phage libraries generated using the techniques described in McCafferty et al., *Nature.* 348:552-554 (1990). Clackson et al., *Nature.* 352:624-628 (1991) and Marks et al., *J. Mol. Biol.,* 222:581-597 (1991). Subsequent publications describe the production of high affinity (nM range) human antibodies by chain shuffling (Marks et al., *Bio/Technology.* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence (U.S. Pat. No. 4,816,567; Morrison, et al., *Proc. Natl Acad. Sci. USA.* 81:6851 (1984)), or by covalently joining to the coding sequence all or part of the coding sequence for a non-immunoglobulin polypeptide. Such non-immunoglobulin polypeptides can be substituted to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Recombinant Production in Prokaryotic Cells

Polynucleic acid sequences encoding the antibodies of the present disclosure can be obtained using standard recombinant techniques. Desired polynucleic acid sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to, an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as *E. coli* LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the present antibody by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the -galactose and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the target peptide (Siebenlist et al. *Cell* 20:269 (1980)) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence can be substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

In some embodiments, the production of the antibodies according to the present disclosure can occur in the cytoplasm of the host cell, and therefore does not require the presence of secretion signal sequences within each cistron. Certain host strains (e.g., the *E. coli* trxB$^{-}$ strains) provide cytoplasm conditions that are favorable for disulfide bond formation, thereby permitting proper folding and assembly of expressed protein subunits.

Prokaryotic host cells suitable for expressing the antibodies of the present disclosure include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium. Serratia marcescans. Klebsiella. Proteus. Shigella. Rhizobia. Vitreoscilla*, or *Paracoccus*. In some embodiments, gram-negative cells are used. In one embodiment, *E. coli* cells are used as hosts. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 AfhuA (AtonA) ptr3 lac Iq lacL8 AompT A (nmpc-fepE) degP41 kan$^{R}$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins.* 8:309-314 (1990). It is generally necessary to select the appropriate bacteria taking into consideration replicability of the replicon in the cells of a bacterium. For example, *E. coli. Serratia*, or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the antibodies of the present application are grown in media known in the art and suitable for culture of the selected host cells. Examples of suitable media include Luria Broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures and pHs.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* 263:133-147 (2002)). A variety of other inducers may be used, according to the vector construct employed, as is known in the art.

The expressed antibodies of the present disclosure are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. To improve the production yield and quality of the antibodies of the present disclosure, various fermentation conditions can be modified. For example, the chaperone proteins have been demonstrated to facilitate the proper folding and solubility of heterologous proteins produced in bacterial host cells. Chen et al. *J Bio Chem* 274:19601-19605 (1999); U.S. Pat. Nos. 6,083,715; 6,027,888; Bothmann and Pluckthun, J. Biol. Chem. 275: 17100-17105 (2000); Ramm and Pluckthun, *J. Biol. Chem.* 275:17106-17113 (2000); Arie et al., *Mol. Microbiol.* 39:199-210 (2001).

To minimize proteolysis of expressed heterologous proteins (especially those that are proteolytically sensitive), certain host strains deficient for proteolytic enzymes can be used for the present invention, as described in, for example, U.S. Pat. Nos. 5,264,365; 5,508,192; Hara et al., *Microbial Drug Resistance.* 2:63-72 (1996). *E. coli* strains deficient for proteolytic enzymes and transformed with plasmids over-expressing one or more chaperone proteins may be used as host cells in the expression system encoding the antibodies of the present application.

The antibodies produced herein can be further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75. Protein A immobilized on a solid phase for example can be used in some embodiments for immunoaffinity purification of binding molecules of the present disclosure. The solid phase to which Protein A is immobilized is preferably a column comprising a glass or silica surface, more preferably a controlled pore glass column or a silicic acid column. In some embodiments, the column has been coated with a reagent, such as glycerol, in an attempt to prevent nonspecific adherence of contaminants. The solid phase is then washed to remove contaminants non-specifically bound to the solid phase. Finally the antibodies of interest is recovered from the solid phase by elution.

Recombinant Production in Eukaryotic Cells

For eukaryotic expression, the vector components generally include, but are not limited to, one or more of the following, a signal sequence, an origin of replication, one or more marker genes, and enhancer element, a promoter, and a transcription termination sequence.

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region can be ligated in reading frame to DNA encoding the antibodies of the present application.

Generally, the origin of replication component is not needed for mammalian expression vectors (the SV40 origin may typically be used only because it contains the early promoter).

Expression and cloning vectors may contain a selection gene, also termed a selectable marker. Selection genes may encode proteins that confer resistance to antibiotics or other toxins, e.g., ampicillin, neomycin, methotrexate, or tetracycline; complement auxotrophic deficiencies; or supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application. For example, cells transformed with the DHFR selection gene are first identified by culturing all of the transformants in a culture medium that contains methotrexate (Mtx), a competitive antagonist of DHFR. An exemplary appropriate host cell when wild-type DHFR is employed is the Chinese hamster ovary (CHO) cell line deficient in DHFR activity. Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic.

Expression and cloning vectors usually contain a promoter that is recognized by the host organism and is operably linked to the nucleic acid encoding the desired polypeptide sequences. Eukaryotic genes have an AT-rich region located approximately 25 to 30 based upstream from the site where transcription is initiated. Another sequence found 70 to 80) bases upstream from the start of the transcription of many genes may be included. The 3' end of most eukaryotic may be the signal for addition of the poly A tail to the 3' end of the coding sequence. All of these sequences may be inserted into eukaryotic expression vectors.

Polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding the antibodies of the present disclosure by higher eukaryotes is often increased by inserting an enhancer sequence into the vector. Many enhancer sequences are now known from mammalian genes (globin, elastase, albumin, α-fetoprotein, and insulin). Examples include the SV40) enhancer on the late side of the replication origin (bp 100-270), the cytomegalovirus early promoter enhancer, the polyoma enhancer on the late side of the replication origin, and adenovirus enhancers. See also Yaniv. *Nature* 297:17-18 (1982) on enhancing elements for activation of eukaryotic promoters. The enhancer may be spliced into the vector at a position 5' or 3' to the polypeptide encoding sequence, but is preferably located at a site 5' from the promoter.

Expression vectors used in eukaryotic host cells (yeast, fungi, insect, plant, animal, human, or nucleated cells from other multicellular organisms) also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region.

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CVI line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980))); mouse sertoli cells (TM4, *Mather, Biol. Reprod.* 23:243-251 (1980))); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells can be transformed with the above-described expression or cloning vectors for antibodies production and cultured in conventional nutrient media modified as appropriate for inducing promoters, selecting transformants, or amplifying the genes encoding the desired sequences.

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing. SDS-PAGE, and ammonium sulfate precipitation are also available depending on the antibody to be recovered. Following any preliminary purification step(s), the mixture comprising the antibody of interest and contaminants may be subjected to low pH hydrophobic interaction chromatography.

5.2.8. Other Binding Molecules Comprising the Antibodies

In another aspect, provided herein is a binding molecule comprising an anti-GPC3 antibody provided herein. In addition to chimeric antigen receptors (CARs) provided herein as described in Section 5.3 below, in some embodiments, an antibody against GPC3 provided herein is part of other binding molecules. Exemplary binding molecules of the present disclosure are described herein.

Fusion Protein

In various embodiments, the antibody provided herein can be genetically fused or chemically conjugated to another agent, for example, protein-based entities. The antibody may be chemically-conjugated to the agent, or otherwise non-covalently conjugated to the agent. The agent can be a peptide or antibody (or a fragment thereof).

Thus, in some embodiments, provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, about 100, about 150, about 200, about 250, about 300, about 350, about 400, about 450) or about 500 amino acids, or over 500 amino acids) to generate fusion proteins, as well as uses thereof. In particular, provided herein are fusion proteins comprising an antigen binding fragment of the antibody provided herein (e.g., CDR1, CDR2, and/or CDR3) and a heterologous protein, polypeptide, or peptide.

Moreover, antibodies provided herein can be fused to marker or "tag" sequences, such as a peptide, to facilitate purification. In specific embodiments, the marker or tag amino acid sequence is a hexa-histidine peptide, hemagglutinin ("HA") tag, and "FLAG" tag.

Methods for fusing or conjugating moieties (including polypeptides) to antibodies are known (see, e.g., Arnon et al., Monoclonal Antibodies for Immunotargeting of Drugs in Cancer Therapy, in Monoclonal Antibodies and Cancer Therapy 243-56 (Reisfeld et al. eds., 1985); Hellstrom et al., Antibodies for Drug Delivery, in Controlled Drug Delivery 623-53 (Robinson et al. eds., 2d ed. 1987); Thorpe, Antibody Carriers of Cytotoxic Agents in Cancer Therapy: A Review, in Monoclonal Antibodies: Biological and Clinical Applications 475-506 (Pinchera et al. eds., 1985); Analysis, Results, and Future Prospective of the Therapeutic Use of Radiolabeled Antibody in Cancer Therapy, in Monoclonal Antibodies for Cancer Detection and Therapy 303-16 (Baldwin et al. eds., 1985); Thorpe et al., Immunol. Rev. 62:119-58 (1982); U.S. Pat. Nos. 5,336,603; 5,622,929; 5,359,046; 5,349,053; 5,447,851; 5,723,125; 5,783,181; 5,908,626; 5,844,095; and 5,112,946; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88:10535-39 (1991); Traunecker et al., Nature, 331:84-86 (1988); Zheng et al., J. Immunol. 154:5590-600 (1995); and Vil et al., Proc. Natl. Acad. Sci. USA 89:11337-41 (1992)).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the antibodies as provided herein, including, for example, antibodies with higher affinities and lower dissociation rates (see, e.g., U.S. Pat. Nos. 5,605,793; 5,811,238; 5,830,721; 5,834,252; and 5,837,458; Patten et al., Curr. Opinion Biotechnol. 8:724-33 (1997); Harayama, Trends Biotechnol. 16(2); 76-82 (1998); Hansson et al., J. Mol. Biol. 287:265-76 (1999); and Lorenzo and Blasco, Biotechniques 24(2); 308-13 (1998)). Antibodies, or the encoded antibodies, may be altered by being subjected to random mutagenesis by error-prone PCR, random nucleotide insertion, or other methods prior to recombination. A polynucleotide encoding an antibody provided herein may be recombined with one or more components, motifs, sections, parts, domains, fragments, etc. of one or more heterologous molecules.

In some embodiments, an antibody provided herein is conjugated to a second antibody to form an antibody heteroconjugate.

In various embodiments, the antibody is genetically fused to the agent. Genetic fusion may be accomplished by placing a linker (e.g., a polypeptide) between the antibody and the agent. The linker may be a flexible linker.

In various embodiments, the antibody is genetically conjugated to a therapeutic molecule, with a hinge region linking the antibody to the therapeutic molecule.

Also provided herein are methods for making the various fusion proteins provided herein. The various methods described in Section 5.2.7 above may also be utilized to make the fusion proteins provided herein.

In a specific embodiment, the fusion protein provided herein is recombinantly expressed. Recombinant expression of a fusion protein provided herein may require construction of an expression vector containing a polynucleotide that encodes the protein or a fragment thereof. Once a polynucleotide encoding a protein provided herein or a fragment thereof has been obtained, the vector for the production of the molecule may be produced by recombinant DNA technology using techniques well-known in the art. Thus, methods for preparing a protein by expressing a polynucleotide containing an encoding nucleotide sequence are described herein. Methods which are well known to those skilled in the art can be used to construct expression vectors containing coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding a fusion protein provided herein, or a fragment thereof, or a CDR, operably linked to a promoter.

The expression vector can be transferred to a host cell by conventional techniques and the transfected cells are then cultured by conventional techniques to produce a fusion protein provided herein. Thus, also provided herein are host cells containing a polynucleotide encoding a fusion protein provided herein or fragments thereof operably linked to a heterologous promoter.

A variety of host-expression vector systems may be utilized to express the fusion protein provided herein. Such host-expression systems represent vehicles by which the coding sequences of interest may be produced and subsequently purified, but also represent cells which may, when transformed or transfected with the appropriate nucleotide coding sequences, express a fusion protein provided herein in situ. These include but are not limited to microorganisms such as bacteria (e.g., *E. coli* and *B. subtilis*) transformed with recombinant bacteriophage DNA, plasmid DNA or cosmid DNA expression vectors containing coding sequences; yeast (e.g., *Saccharomyces Pichia*) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV, tobacco mosaic virus, TMV) or transformed with recombinant plasmid expression vectors (e.g., Ti plasmid) containing coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or, eukaryotic cells, especially for the expression of whole recombinant antibody molecule, can be used for the expression of a recombinant fusion protein. For example, mammalian cells such as Chinese hamster ovary cells (CHO), in conjunction with a vector such as the major intermediate early gene promoter element from human cytomegalovirus is an effective expression system for antibodies or variants thereof. In a specific embodiment, the expression of nucleotide sequences encoding the fusion proteins provided herein is regulated by a constitutive promoter, inducible promoter or tissue specific promoter.

In bacterial systems, a number of expression vectors may be advantageously selected depending upon the use intended for the fusion protein being expressed. For example, when a large quantity of such a fusion protein is to be produced, for the generation of pharmaceutical compositions of a fusion protein, vectors which direct the expression of high levels of fusion protein products that are readily purified may be desirable. Such vectors include, but are not limited to, the *E. coli* expression vector pUR278 (Ruther et al., *EMBO* 12:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fusion protein in infected hosts (e.g., see Logan & Shenk, Proc. Natl. Acad. Sci. USA 81:355-359 (1984)). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT20 and T47D, NS0 (a murine myeloma cell line that does not endogenously produce any immunoglobulin chains), CRL7030 and HsS78Bst cells.

For long-term, high-yield production of recombinant proteins, stable expression can be utilized. For example, cell lines which stably express the fusion proteins may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the fusion protein. Such engineered cell lines may be particularly useful in screening and evaluation of compositions that interact directly or indirectly with the binding molecule.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8-17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980)); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIB TECH 11 (5); 155-215 (1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds.), *Current Protocols in Human Genetics*, John Wiley & Sons, NY (1994); Colberre-Garapin et al., *J. Mol. Biol.* 150:1 (1981), which are incorporated by reference herein in their entireties.

The expression level of a fusion protein can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing a fusion protein is amplifiable, increase in the level of inhibitor present in culture of host cell will increase the number of copies of the marker gene. Since the amplified region is associated with the fusion protein gene, production of the fusion protein will also increase (Crouse et al., Mol. Cell. Biol. 3:257 (1983)).

The host cell may be co-transfected with multiple expression vectors provided herein. The vectors may contain identical selectable markers which enable equal expression of respective encoding polypeptides. Alternatively, a single vector may be used which encodes, and is capable of expressing multiple polypeptides. The coding sequences may comprise cDNA or genomic DNA.

Once a fusion protein provided herein has been produced by recombinant expression, it may be purified by any method known in the art for purification of a polypeptide (e.g., an immunoglobulin molecule), for example, by chromatography (e.g., ion exchange, affinity, particularly by affinity for the specific antigen after Protein A, sizing column chromatography, and Kappa select affinity chromatography), centrifugation, differential solubility, or by any other standard technique for the purification of proteins. Further, the fusion protein molecules provided herein can be fused to heterologous polypeptide sequences described herein or otherwise known in the art to facilitate purification.

Immunoconjugates

In some embodiments, the present disclosure also provides immunoconjugates comprising any of the anti-GPC3 antibodies described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0) 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In some embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $p^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocy anatobenzyl-3-methyldiethylene triaminepentaacetic acid (MX-DTPA) is an exemplary chelating agent for conjugation of radionucleotide to the antibody. See WO94/11026.

The linker may be a "cleavable linker" facilitating release of the conjugated agent in the cell, but non-cleavable linkers are also contemplated herein. Linkers for use in the conjugates of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers, thioether linkers, or hydrophilic linkers designed to evade multidrug transporter-mediated resistance.

The immunuoconjugates or ADCs herein contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

In other embodiments, antibodies provided herein are conjugated or recombinantly fused, e.g., to a diagnostic molecule. Such diagnosis and detection can be accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothiocynate, rhodamine, dichlorotriazinylamine fluorescein, dansyl chloride, or phycoerythrin; luminescent materials, such as, but not limited to, luminol; bioluminescent materials, such as, but not limited to, luciferase, luciferin, or aequorin; chemiluminescent material, such as, 225Acγ-emitting, Auger-emitting, β-emitting, an alpha-emitting or positron-emitting radioactive isotope.

5.3. Chimeric Antigen Receptors

In another aspect, provided herein is a chimeric antigen receptor (CAR) comprising an extracellular antigen binding domain comprising an antibody (e.g., scFv) provided herein that binds to GPC3. Exemplary CARs comprising the present scFv fragments are illustrated in Section 6 below.

In some embodiments, the chimeric antigen receptor (CAR) provided herein comprises a polypeptide comprising: (a) an extracellular antigen binding domain comprising one or more antibody specifically binding to GPC3 as provided herein, and optionally one or more additional binding domain(s); (b) a transmembrane domain; and (c) an intracellular signaling domain. Each components and additional regions are described in more detail below.

5.3.1. Extracellular Antigen Binding Domain

The extracellular antigen binding domain of the CARs described herein comprises one or more (such as any one of 1, 2, 3, 4, 5, 6 or more) antibodies. The antibodies can be fused to each other directly via peptide bonds, or via peptide linkers.

Antibodies

The CARs of the present disclosure comprise an extracellular antigen binding domain comprising one or more antibodies provided herein. The antibodies may be of the same or different origins, and of the same or different sizes. Exemplary antibodies include, but are not limited to, the scFv fragments described in Section 5.2 above.

In some embodiments, provided herein is a CAR comprising a polypeptide comprising: (a) an extracellular antigen binding domain comprising an anti-GPC3 antibody (e.g., scFv); (b) a transmembrane domain; and (c) an intracellular signaling domain, wherein the anti-GPC3 antibody is an anti-GPC3 antibody as described in Section 5.2 above, including, e.g., those comprising one or more CDRs in Table 3 and Table 4.

More specifically, in some embodiments, provided herein is a CAR comprising a polypeptide comprising: (a) an extracellular antigen binding domain comprising an anti-GPC3 antibody (e.g., a scFv fragment); (b) a transmembrane domain; and (c) an intracellular signaling domain, wherein the anti-GPC3 antibody (e.g., scFv) comprises (i) HCDR1 comprising the amino acid sequence of SEQ ID NO: 1, HCDR2 comprising the amino acid sequence of SEQ ID NO: 11, HCDR3 comprising the amino acid sequence of SEQ ID NO: 21, LCDR1 comprising the amino acid sequence of SEQ ID NO: 31, LCDR2 comprising the amino acid sequence of SEQ ID NO: 41, and LCDR3 comprising the amino acid sequence of SEQ ID NO: 51, or (ii) HCDR1 comprising the amino acid sequence of SEQ ID NO: 2, HCDR2 comprising the amino acid sequence of SEQ ID NO: 12, HCDR3 comprising the amino acid sequence of SEQ ID NO: 22, LCDR1 comprising the amino acid sequence of SEQ ID NO: 32, LCDR2 comprising the amino acid sequence of SEQ ID NO: 42, and LCDR3 comprising the amino acid sequence of SEQ ID NO: 52, or (iii) HCDR1 comprising the amino acid sequence of SEQ ID NO: 3, HCDR2 comprising the amino acid sequence of SEQ ID NO: 13, HCDR3 comprising the amino acid sequence of SEQ ID NO: 23, LCDR1 comprising the amino acid sequence of SEQ ID NO: 33, LCDR2 comprising the amino acid sequence of SEQ ID NO: 43, and LCDR3 comprising the amino acid sequence of SEQ ID NO: 53, or (iv) HCDR1 comprising the amino acid sequence of SEQ ID NO: 4, HCDR2 comprising the amino acid sequence of SEQ ID NO: 14, HCDR3 comprising the amino acid sequence of SEQ ID NO: 24, LCDR1 comprising the amino acid sequence of SEQ ID NO: 34, LCDR2 comprising the amino acid sequence of SEQ ID NO: 44, and LCDR3 comprising the amino acid sequence of SEQ ID NO: 54, or (v) HCDR1 comprising the amino acid sequence of SEQ ID NO: 5, HCDR2 comprising the amino acid sequence of SEQ ID NO: 15, HCDR3 comprising the amino acid sequence of SEQ ID NO: 25, LCDR1 comprising the amino acid sequence of SEQ ID NO: 35, LCDR2 comprising the amino acid sequence of SEQ ID NO: 45, and LCDR3 comprising the amino acid sequence of SEQ ID NO: 55, or (vi) HCDR1 comprising the amino acid sequence of SEQ ID NO: 6, HCDR2 comprising the amino acid sequence of SEQ ID NO: 16, HCDR3 comprising the amino acid sequence of SEQ ID NO: 26, LCDR1 comprising the amino acid sequence of SEQ ID NO: 36, LCDR2 comprising the amino acid sequence of SEQ ID NO: 46, and LCDR3 comprising the amino acid sequence of SEQ ID NO: 56, or (vii) HCDR1 comprising the amino acid sequence of SEQ ID NO: 7, HCDR2 comprising the amino acid sequence of SEQ ID NO: 17, HCDR3 comprising the amino acid sequence of SEQ ID NO: 27, LCDR1 comprising the amino acid sequence of SEQ ID NO: 37, LCDR2 comprising the amino acid sequence of SEQ ID NO: 47, and LCDR3 comprising the amino acid sequence of SEQ ID NO: 57, or (viii) HCDR1 comprising the amino acid sequence of SEQ ID NO: 8, HCDR2 comprising the amino acid sequence of SEQ ID NO: 18, HCDR3 comprising the amino acid sequence of SEQ ID NO: 28, LCDR1 comprising the amino acid sequence of SEQ ID NO: 38, LCDR2 comprising the amino acid sequence of SEQ ID NO: 48, and LCDR3 comprising the amino acid sequence of SEQ ID NO: 58, or (ix) HCDR1 comprising the amino acid sequence of SEQ ID NO: 9, HCDR2 comprising the amino acid sequence of SEQ ID NO: 19, HCDR3 comprising the amino acid sequence of SEQ ID NO: 29, LCDR1 comprising the amino acid sequence of SEQ ID NO: 39, LCDR2 comprising the amino acid sequence of SEQ ID NO: 49, and LCDR3 comprising the amino acid sequence of SEQ ID NO: 59, or (x) HCDR1 comprising the amino acid sequence of SEQ ID NO: 10, HCDR2 comprising the amino acid sequence of SEQ ID NO: 20, HCDR3 comprising the amino acid sequence of SEQ ID NO: 30, LCDR1 comprising the amino acid sequence of SEQ ID NO: 40, LCDR2 comprising the amino acid sequence of SEQ ID NO: 50, and LCDR3 comprising the amino acid sequence of SEQ ID NO: 60. In some embodiments, the antibody (e.g., scFv) comprises a VH domain selected from a group of SEQ ID NOs: 61-70 and 117-122 and a VL domain selected from a group of SEQ ID NOs.: 71-80 and 123-125. In more specific embodiments, the antibody is a scFv comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of any one of SEQ ID NOs.: 81-90, 128 and 129.

In other embodiments, the extracellular antigen binding domain further comprises one or more additional antigen binding domains. The one or more additional binding domain(s) that bind(s) to one or more additional antigen(s), e.g., 1, 2, 3, 4 or more additional antibody binding regions (antibodies) targeting one or more additional antigen(s).

In some embodiments, the additional antigen(s) targeted by the CARs of the present disclosure are cell surface molecules. The antibodies may be chosen to recognize an antigen that acts as a cell surface marker on target cells associated with a special disease state. In some embodiments, the antigen is a tumor antigen. In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

In addition to the antigen binding domains in the extracellular domain, the CAR provided herein may further comprise one or more of the following: a linker (e.g., a peptide linker), a transmembrane domain, a hinge region, a signal peptide, an intracellular signaling domain, a co-stimulatory signaling domain, each of which is described in more detail below.

For example, in some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the co-stimulatory signaling domain is derived from CD137. In some embodiments, the GPC3 CAR further comprises a hinge domain (such as a CD8α hinge domain) located between the C-terminus of the extracellular antigen binding domain and the N-terminus of the transmembrane domain. In some embodiments, the GPC3 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the GPC3 CAR is monospecific. In some embodiments, the GPC3 CAR is monovalent. In some embodiments, the GPC3 CAR is multispecific. In some embodiments, the GPC3 CAR is multivalent.

Peptide Linkers

In case multiple antibodies are present in the present CARs, the various antibodies may be fused to each other via peptide linkers. In some embodiments, the antibodies are directly fused to each other without any peptide linkers. The peptide linkers connecting different antibodies may be the same or different. Different domains of the CARs may also be fused to each other via peptide linkers.

Each peptide linker in a CAR may have the same or different length and/or sequence depending on the structural and/or functional features of the antibodies and/or the various domains. Each peptide linker may be selected and optimized independently. The length, the degree of flexibility and/or other properties of the peptide linker(s) used in the CARs may have some influence on properties, including but not limited to the affinity, specificity or avidity for one or more particular antigens or epitopes. For example, longer peptide linkers may be selected to ensure that two adjacent domains do not sterically interfere with one another. In some embodiments, a short peptide linker may be disposed between the transmembrane domain and the intracellular signaling domain of a CAR. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include but not limited to glycine polymers (G) n, glycine-serine polymers, glycine-alanine polymers, alanine-serine polymers, and other flexible linkers known in the art. Other linkers known in the art, for example, as described in WO2016014789, WO2015158671, WO2016102965, US20150299317, WO2018067992, U.S. Pat. No. 7,741,465, Colcher et al., *J. Nat. Cancer Inst.* 82:1191-1197 (1990), and Bird et al., *Science* 242:423-426 (1988) may also be included in the CARs provided herein, the disclosure of each of which is incorporated herein by reference.

5.3.2. Transmembrane Domain

The CARs of the present disclosure comprise a transmembrane domain that can be directly or indirectly fused to the extracellular antigen binding domain. The transmembrane domain may be derived either from a natural or from a synthetic source. As used herein, a "transmembrane domain" refers to any protein structure that is thermodynamically stable in a cell membrane, preferably an eukaryotic cell membrane. Transmembrane domains compatible for use in the CARs described herein may be obtained from a naturally occurring protein. Alternatively, it can be a synthetic, non-naturally occurring protein segment. e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times). Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the CAR described herein is derived from a Type I single-pass membrane protein. In some embodiments, transmembrane domains from multi-pass membrane proteins may also be compatible for use in the CARs described herein. Multi-pass membrane proteins may comprise a complex (at least 2, 3, 4, 5, 6, 7 or more) alpha helices or a beta sheet structure. In some embodiments, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side.

In some embodiments, the transmembrane domain of the CAR comprises a transmembrane domain chosen from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDlla, CD18), ICOS (CD278), 4-1BB (CD137), GITR, CD40, BAFFR, HVEM (LIGHTR), SLAMF7, NKp80 (KLRFl), CD160, GPC3, IL-2R beta, IL-2R gamma, IL-7R a, ITGA1, VLA1, CD49a, ITGA4, IA4, CD49D, ITGA6, VLA-6, CD49f, ITGAD, CDlld, ITGAE, CD103, ITGAL, CDlla, LFA-1, ITGAM, CDllb, ITGAX, CDllc, ITGB1, CD29, ITGB2, CD18, LFA-1, ITGB7, TNFR2, DNAMI (CD226), SLAMF4 (CD244, 2B4), CD84, CD96 (Tactile), CEACAM1, CRT AM, Ly9 (CD229), CD160) (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C. In some embodiments, the transmembrane domain is derived from a molecule selected from the group consisting of CD8α, CD4, CD28, CD137, CD80, CD86, CD152 and PD1.

In some specific embodiments, the transmembrane domain is derived from CD8α. In some embodiments, the transmembrane domain is a transmembrane domain of CD8α comprising the amino acid sequence of SEQ ID NO: 103.

Transmembrane domains for use in the CARs described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 and PCT Publication No. WO 2000/032776, the relevant disclosures of which are incorporated by reference herein.

The transmembrane domain provided herein may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane domain of the CAR provided herein comprises an artificial hydrophobic sequence. For example, a triplet of phenylalanine, tryptophan and valine may be present at the C terminus of the transmembrane domain. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence. The hydropathy, or hydrophobic or hydrophilic characteristics of a protein or protein segment, can be assessed by any method known in the art, for example the Kyte and Doolittle hydropathy analysis.

5.3.3. Intracellular Signaling Domain

The CARs of the present disclosure comprise an intracellular signaling domain (ISD). The intracellular signaling domain is responsible for activation of at least one of the normal effector functions of the immune effector cell expressing the CARs. The term "effector function" refers to a specialized function of a cell. Effector function of a T cell, for example, may be cytolytic activity or helper activity including the secretion of cytokines. Thus the term "cytoplasmic signaling domain" refers to the portion of a protein which transduces the effector function signal and directs the cell to perform a specialized function. While usually the entire cytoplasmic signaling domain can be employed, in many cases it is not necessary to use the entire chain. To the extent that a truncated portion of the cytoplasmic signaling domain is used, such truncated portion may be used in place of the intact chain as long as it transduces the effector function signal. The term cytoplasmic signaling domain is thus meant to include any truncated portion of the cytoplasmic signaling domain sufficient to transduce the effector function signal.

In some embodiments, the intracellular signaling domain comprises a primary intracellular signaling domain of an immune effector cell. In some embodiments, the CAR comprises an intracellular signaling domain consisting essentially of a primary intracellular signaling domain of an immune effector cell. "Primary intracellular signaling domain" refers to cytoplasmic signaling sequence that acts in a stimulatory manner to induce immune effector functions. In some embodiments, the primary intracellular signaling domain contains a signaling motif known as immunoreceptor tyrosine-based activation motif, or ITAM. An "ITAM." as used herein, is a conserved protein motif that is generally present in the tail portion of signaling molecules expressed in many immune cells. The motif may comprise two repeats of the amino acid sequence YxxL/I separated by 6-8 amino acids, wherein each x is independently any amino acid, producing the conserved motif YxxL/Ix (6-8) YxxL/I. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. Exemplary ITAM-containing primary cytoplasmic signaling sequences include those derived from CD3ζ, FcR gamma (FCERIG), FcR beta (Fc Epsilon Rib), CD3 gamma, CD3 delta, CD3 epsilon, CD5, CD22, CD79a, CD79b, and CD66d.

In some embodiments, the primary intracellular signaling domain is derived from CD3ζ. In some embodiments, the intracellular signaling domain consists of the cytoplasmic signaling domain of CD3ζ. In some embodiments, the primary intracellular signaling domain is a cytoplasmic signaling domain of wild-type CD3ζ. In some embodiments, the primary intracellular signaling domain of CD3ζ comprises the amino acid sequence of SEQ ID NO: 105. In some embodiments, the primary intracellular signaling domain of wild-type CD3ζ. In some embodiments, the primary intracellular signaling domain is a functional mutant of the cytoplasmic signaling domain of CD3ζ containing one or more mutations, such as Q65K.

5.3.4. Co-Stimulatory Signaling Domain

Many immune effector cells require co-stimulation, in addition to stimulation of an antigen-specific signal, to promote cell proliferation, differentiation and survival, as well as to activate effector functions of the cell. In some embodiments, the CAR comprises at least one co-stimulatory signaling domain. The term "co-stimulatory signaling domain," as used herein, refers to at least a portion of a protein that mediates signal transduction within a cell to induce an immune response such as an effector function. The co-stimulatory signaling domain of the chimeric receptor described herein can be a cytoplasmic signaling domain from a co-stimulatory protein, which transduces a signal and modulates responses mediated by immune cells, such as T cells, NK cells, macrophages, neutrophils, or eosinophils. "Co-stimulatory signaling domain" can be the cytoplasmic portion of a co-stimulatory molecule. The term "co-stimulatory molecule" refers to a cognate binding partner on an immune cell (such as T cell) that specifically binds with a co-stimulatory ligand, thereby mediating a co-stimulatory response by the immune cell, such as, but not limited to, proliferation and survival.

In some embodiments, the intracellular signaling domain comprises a single co-stimulatory signaling domain. In some embodiments, the intracellular signaling domain comprises two or more (such as about any of 2, 3, 4, or more) co-stimulatory signaling domains. In some embodiments, the intracellular signaling domain comprises two or more of the same co-stimulatory signaling domains. In some embodiments, the intracellular signaling domain comprises two or more co-stimulatory signaling domains from different co-stimulatory proteins, such as any two or more co-stimulatory proteins described herein. In some embodiments, the intracellular signaling domain comprises a primary intracellular signaling domain (such as cytoplasmic signaling domain of CD3ζ) and one or more co-stimulatory signaling domains. In some embodiments, the one or more co-stimulatory signaling domains and the primary intracellular signaling domain (such as cytoplasmic signaling domain of CD3ζ) are fused to each other via optional peptide linkers. The primary intracellular signaling domain, and the one or more co-stimulatory signaling domains may be arranged in any suitable order. In some embodiments, the one or more co-stimulatory signaling domains are located between the transmembrane domain and the primary intracellular signaling domain (such as cytoplasmic signaling domain of CD3ζ). Multiple co-stimulatory signaling domains may provide additive or synergistic stimulatory effects.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the CARs described herein. The type(s) of co-stimulatory signaling domain is selected based on factors such as the type of the immune effector cells in which the effector molecules would be expressed (e.g., T cells. NK cells, macrophages, neutrophils, or eosinophils) and the desired immune effector function (e.g., ADCC effect). Examples of co-stimulatory signaling domains for use in the CARs can be the cytoplasmic signaling domain of co-stimulatory proteins, including, without limitation, members of the B7/CD28 family (e.g., B7-1/CD80, B7-2/CD86, B7-H1/PD-L1. B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, and PDCD6); members of the TNF superfamily (e.g., 4-1BB/TNFSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40/TNFSF5, CD40) Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TNFRSF4, OX40 Ligand/TNFSF4, RELT/TNFRSF19L, TACI/TNFRSF13B, TL1A/TNFSF15, TNF-alpha, and TNF RII/TNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); and any other co-stimulatory molecules, such as CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C.

In some embodiments, the one or more co-stimulatory signaling domains are selected from the group consisting of CD27, CD28, CD137, OX40, CD30, CD40, CD3, lymphocyte function-associated antigen-1 (LFA-1), CD2, CD7, LIGHT, NKG2C, B7-H3 and ligands that specially bind to CD83 (such as CD83 and MD2).

In some embodiments, the intracellular signaling domain in the CAR of the present disclosure comprises a co-stimulatory signaling domain derived from CD137 (i.e., 4-1BB). In some embodiments, the intracellular signaling domain comprises a cytoplasmic signaling domain of CD3ζ and a co-stimulatory signaling domain of CD137. In some embodiments, the intracellular signaling domain comprises a co-stimulatory signaling domain of CD137 comprising the amino acid sequence of SEQ ID NO: 104.

Also within the scope of the present disclosure are variants of any of the co-stimulatory signaling domains described herein, such that the co-stimulatory signaling domain is capable of modulating the immune response of the immune cell. In some embodiments, the co-stimulatory signaling domains comprises up to 10 amino acid residue variations (e.g., 1, 2, 3, 4, 5, or 8) as compared to a wild-type counterpart. Such co-stimulatory signaling domains comprising one or more amino acid variations may be referred to as variants. Mutation of amino acid residues of the co-stimulatory signaling domain may result in an increase in signaling transduction and enhanced stimulation of immune responses relative to co-stimulatory signaling domains that do not comprise the mutation. Mutation of amino acid residues of the co-stimulatory signaling domain may result in a decrease in signaling transduction and reduced stimulation of immune responses relative to co-stimulatory signaling domains that do not comprise the mutation.

5.3.5. Hinge Region

The CARs of the present disclosure may comprise a hinge domain that is located between the extracellular antigen binding domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular antigen binding domain relative to the transmembrane domain of the effector molecule can be used.

The hinge domain may contain about 10-100 amino acids, e.g., about any one of 15-75 amino acids, 20-50 amino acids, or 30-60 amino acids. In some embodiments, the hinge domain may be at least about any one of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is derived from CD8α. In some embodiments, the hinge domain is a portion of the hinge domain of CD8α, e.g., a fragment containing at least 15 (e.g., 20, 25, 30, 35, or 40) consecutive amino acids of the hinge domain of CD8α. In some embodiments, the hinge domain of CD8α comprises the amino acid sequence of SEQ ID NO: 102.

Hinge domains of antibodies, such as an IgG, IgA, IgM, IgE, or IgD antibodies, are also compatible for use in the pH-dependent chimeric receptor systems described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptors described herein. In some embodiments, the hinge domain between the C-terminus of the extracellular ligand-binding domain of an Fc receptor and the N-terminus of the transmembrane domain is a peptide linker, such as a (GxS)n linker, wherein x and n, independently can be an integer between 3 and 12, including 3, 4, 5, 6, 7, 8, 9, 10, 11, 12, or more.

5.3.6. Signal Peptide

The CARs of the present disclosure may comprise a signal peptide (also known as a signal sequence) at the N-terminus of the polypeptide. In general, signal peptides are peptide sequences that target a polypeptide to the desired site in a cell. In some embodiments, the signal peptide targets the effector molecule to the secretory pathway of the cell and will allow for integration and anchoring of the effector molecule into the lipid bilayer. Signal peptides including signal sequences of naturally occurring proteins or synthetic, non-naturally occurring signal sequences, which are compatible for use in the CARs described herein will be evident to one of skill in the art. In some embodiments, the signal peptide is derived from a molecule selected from the group consisting of CD8α, GM-CSF receptor α, and IgG1 heavy chain. In some embodiments, the signal peptide is derived from CD8α. In some embodiments, the signal peptide of CD8α comprises the amino acid sequence of SEQ ID NO: 101.

5.3.7. Polypeptides Comprising a CAR and Additional Domain(s)

As shown in Section 6 below; engineered immune effector cells expressing a CAR and exogenously introduced p40 and CCL-19 produced surprisingly superior effects. For example, p40) and CCL-19 armored CAR-T cells exhibited higher efficacy than the corresponding naked CAR-T cells at lower doses.

Thus, in another aspect, provided herein is a polypeptide comprising a CAR provided herein, and at least one of p40 subunit of IL-12, and CCL-19. In some embodiments, provided herein is a polypeptide comprising a CAR provided herein and p40. In some embodiments, provided herein is a polypeptide comprising a CAR provided herein and CCL-19. In other embodiments, provided herein is a polypeptide comprising a CAR provided herein and both p40 and CCL-19. In some embodiments, p40) is human p40) comprising the amino acid sequence of SEQ ID NO: 135, and/or CCL-19 is human CCL-19 comprising the amino acid sequence of SEQ ID NO: 136.

In the present polypeptides, the CAR, p40) and/or CCL-19 can be arranged in any order. For example, in the case wherein CAR, p40 and CCL-19 are all present in a polypeptide, in some embodiments, the polypeptide provided herein comprises from N terminus to C terminus: the CAR, p40) and CCL-19; in some embodiments, the polypeptide provided herein comprises from N terminus to C terminus: the CAR, CCL-19, and p40; in some embodiments, the polypeptide provided herein comprises from N terminus to C terminus: CCL-19, p40, and the CAR; in some embodiments, the polypeptide provided herein comprises from N terminus to C terminus: p40, CCL-19 and the CAR; in some embodiments, the polypeptide provided herein comprises from N terminus to C terminus: p40, the CAR, and CCL-19; and in some embodiments, the polypeptide provided herein comprises from N terminus to C terminus: CCL-19, the CAR, and p40.

In some embodiments of the various polypeptides provided herein, the CAR, p40) and/or CCL-19 are linked with each other via a peptide linker. In some embodiments, the peptide linker is a self-cleaving peptide such as 2A self-cleaving peptide, so that the CAR, p40) and/or CCL-19 become separate polypeptides upon cleavage in cells. The members of 2A peptides are named after the virus in which they have been first described. For example, F2A, the first described 2A peptide, is derived from foot-and-mouth disease virus. The self-cleaving 18-22 amino acids long 2A peptides mediate ribosomal skipping between the proline and glycine residues and inhibit peptide bond formation without affecting downstream translation. These peptides allow multiple proteins to be encoded as polyproteins, which dissociate into component proteins upon translation. Self-cleaving peptides are found in members of the Picornaviridae virus family, including Aphthoviruses such as Foot-and-mouth disease virus (FMDV), Equine rhinitis A virus (ERAV), Thosea asigna virus (TaV) and Porcine teschovirus-1 (PTV-1) (see Donnelly et al., J. Gen. Virol., 82:1027-101 (2001); Ryan et al., J. Gen. Virol., 72:2727-2732 (2001)) and cardioviruses such as Theilovirus (e.g., Theiler's murine encephalomyelitis) and Encephalomyocarditis viruses. The 2A peptides derived from FMDV, ERAV, PTV-1, and TaV are sometimes referred to as "F2A," "E2A," "P2A," and "T2A," respectively, and are included in the present disclosure, e.g., as described in Donnelly et al., J. Gen. Virol., 78:13-21 (1997); Ryan and Drew, EMBO J., 13:928-933 (1994); Szymczak et al., Nature Biotech., 5:589-594 (2004); Hasegawa et al., Stem Cells, 25(7); 1707-12 (2007). In yet other embodiments, intein mediated protein splicing system is used herein, e.g., as described in Shah and Muir, Chem Sci., 5(1); 446-461 (2014) and Topilina and Mills, Mobile DNA, 5 (5) (2014). Other methods known in the art can also be used in the present constructs.

In some embodiments, the 2A self-cleaving peptide is selected from a group consisting of F2A, E2A, P2A, T2A, or variants thereof. In some embodiments, the self-cleaving peptide is a 2A self-cleaving peptide P2A fragment comprising the amino acid sequence of SEQ ID NO: 138. In a specific embodiment, the self-cleaving peptide is T2A fragment comprising the amino acid sequence of SEQ ID NO: 139.

In some specific embodiments, p40) and CCL-19 are linked by a first self-cleaving peptide. In some embodiments, the first self-cleaving peptide is a 19 self-cleaving peptide T2A fragment comprising the amino acid sequence of SEQ ID NO: 139. In some embodiments, a domain comprising p40) subunit of IL-12 and CCL-19 provided herein comprises the amino acid sequence of SEQ ID NO: 134. In some embodiments, the CAR is linked to the domain by a second self-cleaving peptide. In some embodiments, the second self-cleaving peptide is a 2A self-cleaving peptide P2A fragment comprising the amino acid sequence of SEQ ID NO: 138. In a specific embodiment, the CAR provided herein comprises the amino acid sequence of SEQ ID NO: 133.

In another aspect, provided herein is a nucleic acid encoding a polypeptide described above comprising a CAR provided herein, p40 subunit of IL-12, and/or CCL-19.

5.3.8. Exemplary CARs

Exemplary CARs are generated as shown in Section 6 below. In some embodiments, provided herein is a CAR comprising or consisting of the amino acid sequence of SEQ ID NO: 91. In some embodiments, provided herein is a CAR comprising or consisting of the amino acid sequence of SEQ ID NO: 92. In some embodiments, provided herein is a CAR comprising or consisting of the amino acid sequence of SEQ ID NO: 93. In some embodiments, provided herein is a CAR comprising or consisting of the amino acid sequence of SEQ ID NO: 94. In some embodiments, provided herein is a CAR comprising or consisting of the amino acid sequence of SEQ ID NO: 95. In some embodiments, provided herein is a CAR comprising or consisting of the amino acid sequence of SEQ ID NO: 96. In some embodiments, provided herein is a CAR comprising or consisting of the amino acid sequence of SEQ ID NO: 97. In some embodiments, provided herein is a CAR comprising or consisting of the amino acid sequence of SEQ ID NO: 98. In some embodiments, provided herein is a CAR comprising or consisting of the amino acid sequence of SEQ ID NO: 99. In some embodiments, provided herein is a CAR comprising or consisting of the amino acid sequence of SEQ ID NO: 100. In some embodiments, provided herein is a CAR comprising or consisting of the amino acid sequence of SEQ ID NO: 107. In some embodiments, provided herein is a CAR comprising or consisting of the amino acid sequence of SEQ ID NO: 108. In some embodiments, provided herein is a CAR comprising or consisting of the amino acid sequence of SEQ ID NO: 109. In some embodiments, provided herein is a CAR comprising or consisting of the amino acid sequence of SEQ ID NO: 110. In some embodiments, provided herein is a CAR comprising or consisting of the amino acid sequence of SEQ ID NO: 111. In some embodiments, provided herein is a CAR comprising or consisting of the amino acid sequence of SEQ ID NO: 112. In some embodiments, provided herein is a CAR comprising or consisting of the amino acid sequence of SEQ ID NO: 113. In some embodiments, provided herein is a CAR comprising or consisting of the amino acid sequence of SEQ ID NO: 114. In some embodiments, provided herein is a CAR comprising or consisting of the amino acid sequence of SEQ ID NO: 115. In some embodiments, provided herein is a CAR comprising or consisting of the amino acid sequence of SEQ ID NO: 116. In some embodiments, provided herein is a CAR comprising or consisting of the amino acid sequence of SEQ ID NO: 130. In some embodiments, provided herein is a CAR comprising or consisting of the amino acid sequence of SEQ ID NO: 131. In some embodiments, provided herein is a CAR comprising or consisting of the amino acid sequence of SEQ ID NO: 133.

In certain embodiments, the CAR provided herein comprises amino acid sequences with certain percent identity relative to any one of the CARs exemplified in the Section 6 below. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 91. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 92. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 93. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 94. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 95. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 96. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 97. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 98. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 99. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 100. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 107. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 108. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 109. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 110. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 111. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 112. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 113. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 114. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 115. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 116. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 130. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 131. In some embodiments, provided herein is a GPC3 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 133.

In some embodiments, provided herein is an isolated nucleic acid encoding any of the GPC3 CARs provided herein. More detailed description regarding nucleic acid sequences and vectors are provided below.

5.4. Engineered Immune Effector Cells

In yet another aspect, provided herein are host cells (such as immune effector cells) comprising any one of the CARs described herein.

Thus, in some embodiments, provided herein is an engineered immune effector cell (such as T cell) comprising a CAR which comprises a polypeptide comprising: (a) an extracellular antigen binding domain comprising one or more anti-GPC3 antibody(s); (b) a transmembrane domain; and (c) an intracellular signaling domain, wherein the anti-GPC3 antibody is an anti-GPC3 antibody as described in Section 5.2 above, including, e.g., those comprising one or more CDRs in Table 3 and Table 4, and more specifically, in some embodiments, the anti-GPC3 antibody (e.g., scFv) comprises (i) HCDR1 comprising the amino acid sequence of SEQ ID NO: 1, HCDR2 comprising the amino acid sequence of SEQ ID NO: 11, HCDR3 comprising the amino acid sequence of SEQ ID NO: 21, LCDR1 comprising the amino acid sequence of SEQ ID NO: 31, LCDR2 comprising the amino acid sequence of SEQ ID NO: 41, and LCDR3 comprising the amino acid sequence of SEQ ID NO: 51, or (ii) HCDR1 comprising the amino acid sequence of SEQ ID NO: 2, HCDR2 comprising the amino acid sequence of SEQ ID NO: 12, HCDR3 comprising the amino acid sequence of SEQ ID NO: 22, LCDR1 comprising the amino acid sequence of SEQ ID NO: 32, LCDR2 comprising the amino acid sequence of SEQ ID NO: 42, and LCDR3 comprising the amino acid sequence of SEQ ID NO: 52, or (iii) HCDR1 comprising the amino acid sequence of SEQ ID NO: 3, HCDR2 comprising the amino acid sequence of SEQ ID NO: 13. HCDR3 comprising the amino acid sequence of SEQ ID NO: 23, LCDR1 comprising the amino acid sequence of SEQ ID NO: 33, LCDR2 comprising the amino acid sequence of SEQ ID NO: 43, and LCDR3 comprising the amino acid sequence of SEQ ID NO: 53, or (iv) HCDR1 comprising the amino acid sequence of SEQ ID NO: 4, HCDR2 comprising the amino acid sequence of SEQ ID NO: 14, HCDR3 comprising the amino acid sequence of SEQ ID NO: 24, LCDR1 comprising the amino acid sequence of SEQ ID NO: 34, LCDR2 comprising the amino acid sequence of SEQ ID NO: 44, and LCDR3 comprising the amino acid sequence of SEQ ID NO: 54, or (v) HCDR1 comprising the amino acid sequence of SEQ ID NO: 5, HCDR2 comprising the amino acid sequence of SEQ ID NO: 15, HCDR3 comprising the amino acid sequence of SEQ ID NO: 25, LCDR1 comprising the amino acid sequence of SEQ ID NO: 35, LCDR2 comprising the amino acid sequence of SEQ ID NO: 45, and LCDR3 comprising the amino acid sequence of SEQ ID NO: 55, or (vi) HCDR1 comprising the amino acid sequence of SEQ ID NO: 6, HCDR2 comprising the amino acid sequence of SEQ ID NO: 16, HCDR3 comprising the amino acid sequence of SEQ ID NO: 26, LCDR1 comprising the amino acid sequence of SEQ ID NO: 36, LCDR2 comprising the amino acid sequence of SEQ ID NO: 46, and LCDR3 comprising the amino acid sequence of SEQ ID NO: 56, or (vii) HCDR1 comprising the amino acid sequence of SEQ ID NO: 7. HCDR2 comprising the amino acid sequence of SEQ ID NO: 17, HCDR3 comprising the amino acid sequence of SEQ ID NO: 27, LCDR1 comprising the amino acid sequence of SEQ ID NO: 37, LCDR2 comprising the amino acid sequence of SEQ ID NO: 47, and LCDR3 comprising the amino acid sequence of SEQ ID NO: 57, or (viii) HCDR1 comprising the amino acid sequence of SEQ ID NO: 8, HCDR2 comprising the amino acid sequence of SEQ ID NO: 18, HCDR3 comprising the amino acid sequence of SEQ ID NO: 28, LCDR1 comprising the amino acid sequence of SEQ ID NO: 38, LCDR2 comprising the amino acid sequence of SEQ ID NO: 48, and LCDR3 comprising the amino acid sequence of SEQ ID NO: 58, or (ix) HCDR1 comprising the amino acid sequence of SEQ ID NO: 9, HCDR2 comprising the amino acid sequence of SEQ ID NO: 19, HCDR3 comprising the amino acid sequence of SEQ ID NO: 29, LCDR1 comprising the amino acid sequence of SEQ ID NO: 39, LCDR2 comprising the amino acid sequence of SEQ ID NO: 49, and LCDR3 comprising the amino acid sequence of SEQ ID NO: 59, or (x) HCDR1 comprising the amino acid sequence of SEQ ID NO: 10, HCDR2 comprising the amino acid sequence of SEQ ID NO: 20, HCDR3 comprising the amino acid sequence of SEQ ID NO: 30, LCDR1 comprising the amino acid sequence of SEQ ID NO: 40, LCDR2 comprising the amino acid sequence of SEQ ID NO: 50, and LCDR3 comprising the amino acid sequence of SEQ ID NO: 60. In some embodiments, the antibody (e.g., scFv) in the CAR expressed in the present immune effector cells comprises a VH domain selected from a group of SEQ ID NOs: 61-70 and 117-122 and a VL domain selected from a group of SEQ ID NOs.: 71-80 and 123-125. In more specific embodiments, the antibody in the CAR of the present immune effector cells is a scFv comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of any one of SEQ ID NOs.: 81-90, 128 and 129. In some embodiments, the transmembrane domain is selected from the group consisting of CD8α. CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the CAR further comprises a hinge domain (such as a CD8α hinge domain) located between the C-terminus of the extracellular antigen binding domain and the N-terminus of the transmembrane domain. In some embodiments, the CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In other specific embodiments, provided herein is an engineered immune effector cell (such as T cell) comprising a CAR which comprises a polypeptide comprising an amino acid sequence of SEQ ID NOs: 91-100, 107-116 and 130-131, or an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NOs: 91-100, 107-116 and 130-131.

In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

Also provided are engineered immune effector cells comprising (or expressing) two or more different CARs. Any two or more of the CARs described herein may be expressed in combination. The CARs may target different antigens, thereby providing synergistic or additive effects. The two or more CARs may be encoded on the same vector or different vectors.

The engineered immune effector cell may further express one or more therapeutic proteins and/or immunomodulators, such as immune checkpoint inhibitors. See, e.g., International Patent Application NOs. PCT/CN2016/073489 and PCT/CN2016/087855, which are incorporated herein by reference in their entirety.

5.4.1. Vectors

The present disclosure provides vectors for cloning and expressing any one of the CARs described herein. In some embodiments, the vector is suitable for replication and integration in eukaryotic cells, such as mammalian cells. In some embodiments, the vector is a viral vector. Examples of viral vectors include, but are not limited to, adenoviral vectors, adeno-associated virus vectors, lentiviral vector, retroviral vectors, vaccinia vector, herpes simplex viral vector, and derivatives thereof. Viral vector technology is well known in the art and is described, for example, in Sambrook et al. (2001, Molecular Cloning: A Laboratory Manual, Cold Spring Harbor Laboratory, New York), and in other virology and molecular biology manuals.

A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex vivo. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying the immunomodulator (such as immune checkpoint inhibitor) coding sequence and/or self-inactivating lentiviral vectors carrying chimeric antigen receptors can be packaged with protocols known in the art. The resulting lentiviral vectors can be used to transduce a mammalian cell (such as primary human T cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce non-proliferating cells.

In some embodiments, the vector comprises any one of the nucleic acids encoding a CAR described herein. The nucleic acid can be cloned into the vector using any known molecular cloning methods in the art, including, for example, using restriction endonuclease sites and one or more selectable markers. In some embodiments, the nucleic acid is operably linked to a promoter. Varieties of promoters have been explored for gene expression in mammalian cells, and any of the promoters known in the art may be used in the present disclosure. Promoters may be roughly categorized as constitutive promoters or regulated promoters, such as inducible promoters.

In some embodiments, the nucleic acid encoding the CAR is operably linked to a constitutive promoter. Constitutive promoters allow heterologous genes (also referred to as transgenes) to be expressed constitutively in the host cells. Exemplary constitutive promoters contemplated herein include, but are not limited to, Cytomegalovirus (CMV)

promoters, human elongation factors-1 alpha (hEF1α), ubiquitin C promoter (UbiC), phosphoglycerokinase promoter (PGK), simian virus 40 early promoter (SV40), and chicken β-Actin promoter coupled with CMV early enhancer (CAGG). The efficiencies of such constitutive promoters on driving transgene expression have been widely compared in a huge number of studies. For example, Michael C. Milone et al compared the efficiencies of CMV, hEF1α, UbiC and PGK to drive chimeric antigen receptor expression in primary human T cells, and concluded that hEF1α promoter not only induced the highest level of transgene expression, but was also optimally maintained in the CD4 and CD8 human T cells (Molecular Therapy, 17(8); 1453-1464 (2009)). In some embodiments, the nucleic acid encoding the CAR is operably linked to a hEF1α promoter.

In some embodiments, the nucleic acid encoding the CAR is operably linked to an inducible promoter. Inducible promoters belong to the category of regulated promoters. The inducible promoter can be induced by one or more conditions, such as a physical condition, microenvironment of the engineered immune effector cell, or the physiological state of the engineered immune effector cell, an inducer (i.e., an inducing agent), or a combination thereof.

In some embodiments, the inducing condition does not induce the expression of endogenous genes in the engineered mammalian cell, and/or in the subject that receives the pharmaceutical composition. In some embodiments, the inducing condition is selected from the group consisting of: inducer, irradiation (such as ionizing radiation, light), temperature (such as heat), redox state, tumor environment, and the activation state of the engineered mammalian cell.

In some embodiments, the vector also contains a selectable marker gene or a reporter gene to select cells expressing the CAR from the population of host cells transfected through lentiviral vectors. Both selectable markers and reporter genes may be flanked by appropriate regulatory sequences to enable expression in the host cells. For example, the vector may contain transcription and translation terminators, initiation sequences, and promoters useful for regulation of the expression of the nucleic acid sequences.

In some embodiments, the vector comprises more than one nucleic acid encoding CARs. In some embodiments, the vector comprises a nucleic acid comprising a first nucleic acid sequence encoding a first CAR and a second nucleic acid sequence encoding a second CAR, wherein the first nucleic acid is operably linked to the second nucleic acid via a third nucleic acid sequence encoding a self-cleaving peptide. In some embodiments, the self-cleaving peptide is selected from the group consisting of T2A, P2A and F2A.

5.4.2. Immune Effector Cells

"Immune effector cells" are immune cells that can perform immune effector functions. In some embodiments, the immune effector cells express at least FcγRIII and perform ADCC effector function. Examples of immune effector cells which mediate ADCC include peripheral blood mononuclear cells (PBMC), natural killer (NK) cells, monocytes, cytotoxic T cells, neutrophils, and eosinophils.

In some embodiments, the immune effector cells are T cells. In some embodiments, the T cells are CD4+/CD8−, CD4−/CD8+, CD4+/CD8+, CD4−/CD8−, or combinations thereof. In some embodiments, the T cells produce IL-2, TFN, and/or TNF upon expressing the CAR and binding to the target cells, such as GPC3+ tumor cells. In some embodiments, the CD8+ T cells lyse antigen-specific target cells upon expressing the CAR and binding to the target cells.

In some embodiments, the immune effector cells are NK cells. In other embodiments, the immune effector cells can be established cell lines, for example, NK-92 cells.

In some embodiments, the immune effector cells are differentiated from a stem cell, such as a hematopoietic stem cell, a pluripotent stem cell, an iPS, or an embryonic stem cell.

The engineered immune effector cells are prepared by introducing the CARs into the immune effector cells, such as T cells. In some embodiments, the CAR is introduced to the immune effector cells by transfecting any one of the isolated nucleic acids or any one of the vectors described above. In some embodiments, the CAR is introduced to the immune effector cells by inserting proteins into the cell membrane while passing cells through a microfluidic system, such as CELL SQUEEZER (see, e.g., U.S. Patent Application Publication No. 20140287509).

Methods of introducing vectors or isolated nucleic acids into a mammalian cell are known in the art. The vectors described can be transferred into an immune effector cell by physical, chemical, or biological methods.

Physical methods for introducing the vector into an immune effector cell include calcium phosphate precipitation, lipofection, particle bombardment, microinjection, electroporation, and the like. Methods for producing cells comprising vectors and/or exogenous nucleic acids are well-known in the art. See, e.g., Sambrook et al. (2001) Molecular Cloning: A Laboratory Manual, Cold Spring Harbor Laboratory, New York. In some embodiments, the vector is introduced into the cell by electroporation.

Biological methods for introducing the vector into an immune effector cell include the use of DNA and RNA vectors. Viral vectors have become the most widely used method for inserting genes into mammalian, e.g., human cells.

Chemical means for introducing the vector into an immune effector cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro is a liposome (e.g., an artificial membrane vesicle).

In some embodiments, RNA molecules encoding any of the CARs described herein may be prepared by a conventional method (e.g., in vitro transcription) and then introduced into the immune effector cells via known methods such as mRNA electroporation. See, e.g., Rabinovich et al., Human Gene Therapy 17:1027-1035 (2006).

In some embodiments, the transduced or transfected immune effector cell is propagated ex vivo after introduction of the vector or isolated nucleic acid. In some embodiments, the transduced or transfected immune effector cell is cultured to propagate for at least about any of 1 day, 2 days, 3 days, 4 days, 5 days, 6 days, 7 days, 10 days, 12 days, or 14 days. In some embodiments, the transduced or transfected immune effector cell is further evaluated or screened to select the engineered mammalian cell.

Reporter genes may be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. FEBS Letters 479:79-82 (2000)). Suitable expression systems are well known and may be prepared using known techniques or obtained commercially.

Other methods to confirm the presence of the nucleic acid encoding the CARs in the engineered immune effector cell, include, for example, molecular biological assays well known to those of skill in the art, such as Southern and Northern blotting, RT-PCR and PCR; biochemical assays, such as detecting the presence or absence of a particular peptide, e.g., by immunological methods (such as ELISAs and Western blots).

5.4.3. Sources of T Cells

In some embodiments, prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. Initial activation steps in the absence of calcium may lead to magnified activation. As those of ordinary skill in the art would readily appreciate a washing step may be accomplished by methods known to those in the art, such as by using a semi-automated "flow-through" centrifuge (for example, the Cobe™ 2991 cell processor, the Baxter CytoMate, or the Haemonetics R Cell Saver (R) 5 autotransfusion system) according to the manufacturer's instructions. After washing, the cells may be resuspended in a variety of biocompatible buffers, such as, for example, Ca2-free, Mg2-free PBS, PlasmaLyte A solution, or other saline solution with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+T cells, can be further isolated by positive or negative selection techniques. For example, in some embodiments, T cells are isolated by incubation with anti-CD3/anti-CD28 (i.e., 3×28)-conjugated beads, such as DYNABEADS® M-450) CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, in some embodiments, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In vet another embodiment, a concentration of cells from 75, 80, 85, 90, 95, or 100 million cells/ml is used. In further embodiments, concentrations of 125 or 150 million cells/ml can be used. Using high concentrations may result in increased cell yield, cell activation, and cell expansion. Further, use of high cell concentrations may allow more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. In some embodiments, using high concentration of cells allows more efficient selection of CD8+ T cells that normally have weaker CD28 expression.

In some embodiments, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5\times10^6$/mL. In some embodiments, the concentration used can be from about $1\times10^5$/mL to $1\times10^6$/mL, and any integer value in between.

In some embodiments, the cells may be incubated on a rotator for varying lengths of time at varying speeds at either 2-10° C., or at room temperature.

T cells for stimulation can also be frozen after a washing step. Without being bound by theory, the freeze and subsequent thaw step may provide a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% dextran 40 and 5% dextrose, 20% human serum albumin and 7.5% DMSO, or 31.25% Plasma-Lyte A solution, 31.25% dextrose 5%, 0.45% NaCl, 10% dextran 40 and 5% dextrose, 20% human serum albumin, and 7.5% DMSO or other suitable cell freezing media containing for example, Hespan R solution and Plasma-Lyte A solution. The cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation.

Also contemplated in the present disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815 (1991); Henderson et al., Immun 73:316-321 (1991); Bierer et al., Curr. Opin. Immun. 5:763-773 (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH.

In some embodiments, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

5.4.4. Activation and Expansion of T Cells

In some embodiments, prior to or after genetic modification of the T cells with the CARs described herein, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, T cells can be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD3 antibody include UCHT1, OKT3, HIT3a (BioLegend, San Diego, US) can be used as can other methods commonly known in the art (Graves J, et al., J. Immunol. 146:2102 (1991); Li B, et al., Immunology 116:487 (2005); Rivollier A, et al., Blood 104:4029 (2004)). Examples of an anti-CD28 antibody include 9.3, B-T3, XR-CD28 (Diaclone, Besancon, France) can be used as can other methods commonly known in the art (Berg et al., Transplant Proc. 30(8):3975-3977 (1998); Haanen et al., J. Exp. Med. 190 (9):13191328 (1999); Garland et al., J. Immunol Meth. 227(1-2):53-63 (1999)).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example U.S. Patent Application Publication Nos. 20040101519 and 20060034810 for artificial antigen presenting cells (aAPCs) that are contemplated for use in activating and expanding T cells in certain embodiments in the present disclosure.

In some embodiments, the T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment, the cells (for example, $10^4$ to $4\times10^8$ T cells) and beads (for example, anti-CD3/CD28 MACSiBead particles at a recommended titer of 1:100) are combined in a buffer, preferably PBS (without divalent cations such as, calcium and magnesium). Those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/mL is used. In another embodiment, greater than 100 million cells/mL is used. In a further embodiment, a concentration of cells of 10, 15, 20, 25, 30, 35, 40, 45, or 50 million cells/mL is used. In yet another embodiment, a concentration of cells from 75, 80, 85, 90, 95, or 100 million cells/mL is used. In further embodiments, concentrations of 125 or 150 million cells/mL can be used. Using high concentrations may result in increased cell yield, cell activation, and cell expansion. Further, use of high cell concentrations may allow more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments, the mixture may be cultured for several hours (about 3 hours) to about 14 days or any hourly integer value in between. In another embodiment, the mixture may be cultured for 21 days. In one embodiment, the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640) or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFB, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

5.4.5. CAR-T Cells Expressing Exogenously Introduced p40 and CCL-19

In certain embodiments, the T cells provided herein further express an exogenously introduced p40) and CCL-19. As described above and in Section 6 below, such CAR-T cells demonstrated surprisingly superior effects.

Such CAR-T cells can be produced by introducing into a T cell a polypeptide described in Section 5.3.7 above.

More specifically, in some embodiments, CAR-T cells expressing exogenously introduced p40 and CCL-19 can be produced by introducing one or more nucleic acid(s) encoding a polypeptide described in Section 5.3.7.

The CAR, p40) and CCL-19 can each be introduced into T cells separately as separately polypeptides. For example, a nucleic acid encoding a CAR provided herein, a nucleic acid encoding p40, and a nucleic acid encoding CCL-19 are introduced into T cells separately.

Alternatively, any two of the three or all three of them can be introduced into T cell together as single polypeptide via one nucleic acid which will be cleaved upon translation in cells. For example, a nucleic acid encoding a polypeptide comprising a CAR provided herein and p40) linked via a self-cleaving peptide linker is introduced into the T cells, and separately a nucleic acid encoding CCL-19 is introduced into the T cells. Similarly, a nucleic acid encoding a polypeptide comprising a CAR provided herein and CCL-19 linked via a self-cleaving peptide linker is introduced into the T cells, and separately a nucleic acid encoding p40 is introduced into the T cells. In some embodiments, a nucleic acid encoding a polypeptide comprising all three of the CAR, p40) and CCL-19 linked to each other via self-cleaving peptide linkers can be introduced into T cells. Self-cleaving peptide linkers are described in more detail above. In some embodiments, the 2A self-cleaving peptide is selected from a group consisting of F2A, E2A, P2A, T2A, or variants thereof. In some embodiments, the self-cleaving peptide is a 2A self-cleaving peptide P2A fragment comprising the amino acid sequence of SEQ ID NO: 138. In a specific embodiment, the self-cleaving peptide is T2A fragment comprising the amino acid sequence of SEQ ID NO: 139.

Alternatively, the CAR-T cells provided herein can be produced by a polynucleotide comprising multiple regions, for example, a region encoding a CAR, a region encoding p40, and/or a region encoding CCL-19. Different regions can be controlled by the same promoter. For example, in some embodiments, internal ribosomal entry sites (IRES) are used herein to express multiple genes from one promoter. In other embodiments, different regions are controlled by separate promoters.

Among other properties, the CAR-T cells expressing exogenously introduced p40) and CCL-19 have higher level of IL-23 as compared to CAR-T cells without exogenously introduced p40) and CCL-19. In some embodiments, the level of IL-23 is at least 20% higher. In some embodiments, the level of IL-23 is at least 50% higher. In some embodiments, the level of IL-23 is at least 80% higher.

5.5. Polynucleotides

In certain embodiments, the disclosure provides polynucleotides that encode the present antibodies that bind to GPC3 and fusion proteins comprising the antibodies that bind to GPC3 described herein. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is in the form of cDNA. In some embodiments, the polynucleotide is a synthetic polynucleotide.

In certain embodiments, the disclosure provides polynucleotides that encode the GPC3 CAR provided herein. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is in the form of cDNA. In some embodiments, the polynucleotide is a synthetic polynucleotide.

The present disclosure further relates to variants of the polynucleotides described herein, wherein the variant encodes, for example, fragments, analogs, and/or derivatives of the antibody or CAR that binds GPC3 of the disclosure. In certain embodiments, the present disclosure provides a polynucleotide comprising a polynucleotide having a nucleotide sequence at least about 75% identical, at least about 80% identical, at least about 85% identical, at least about 90% identical, at least about 95% identical, and in some embodiments, at least about 96%, 97%, 98% or 99% identical to a polynucleotide encoding the antibody or CAR that binds GPC3 of the disclosure. As used herein, the phrase "a polynucleotide having a nucleotide sequence at least, for example, 95% "identical" to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

Also provided are vectors comprising the nucleic acid molecules described herein. In an embodiment, the nucleic acid molecules can be incorporated into a recombinant expression vector. The present disclosure provides recombinant expression vectors comprising any of the nucleic acids of the disclosure. As used herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors described herein are not naturally-occurring as a whole; however, parts of the vectors can be naturally-occurring. The described recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. The non-naturally occurring or altered nucleotides or internucleotide linkages do not hinder the transcription or replication of the vector.

In an embodiment, the recombinant expression vector of the disclosure can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as AGT10, λGT11, λEMBL4, and λNM1149, λZapII (Stratagene) can be used. Examples of plant expression vectors include pBI01, pBI01.2, pBI121, pBI101.3, and pBIN19 (Clontech). Examples of animal expression vectors include pEUK-Cl, pMAM, and pMAMneo (Clontech). The recombinant expression vector may be a viral vector, e.g., a retroviral vector, e.g., a gamma retroviral vector.

In an embodiment, the recombinant expression vectors are prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, SV40, 2μ plasmid, λ, bovine papilloma virus, and the like.

The recombinant expression vector may comprise regulatory sequences, such as transcription and translation initiation and termination codons, which are specific to the type of host (e.g., bacterium, plant, fungus, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the described expression vectors include, for instance, neomycin/G418 resistance genes, histidinol x resistance genes, histidinol resistance genes, tetracycline resistance genes, and ampicillin resistance genes.

The recombinant expression vector can comprise a native or normative promoter operably linked to the nucleotide sequence of the disclosure. The selection of promoters, e.g., strong, weak, tissue-specific, inducible and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an RSV promoter, an SV40) promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

In certain embodiments, a polynucleotide is isolated. In certain embodiments, a polynucleotide is substantially pure.

Also provided are host cells comprising the nucleic acid molecules described herein. The host cell may be any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURER Competent Cells, and SOLOPACK Gold Cells, can be used as host cells for vector replication and/or expression. Additionally, bacterial cells such as *E. coli* LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, Saos, PC12, SP2/0) (American Type Culture Collection (ATCC), Manassas, VA, CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATCC CRL-TIB-196). Other useful cell lines include those derived from Chinese Hamster Ovary (CHO) cells such as CHO-K1SV (Lonza Biologics, Walkersville, MD), CHO-K1 (ATCC CRL-61) or DG44.

5.6. Pharmaceutical Compositions

In one aspect, the present disclosure further provides pharmaceutical compositions comprising an antibody, a binding molecule or therapeutic molecule comprising an antibody, or an engineered immune effector cell of the present disclosure. In some embodiments, a pharmaceutical composition comprises a therapeutically effective amount of the antibody, the binding molecule or therapeutic molecule comprising the antibody, or the engineered immune effector cell of the present disclosure and a pharmaceutically acceptable excipient.

In some embodiments, provided herein is a pharmaceutical composition comprising a therapeutically effective amount of the antibody provided herein and a pharmaceutically acceptable excipient.

In some embodiments, provided herein is a pharmaceutical composition comprising a therapeutically effective amount of the therapeutic molecule (such as a fusion protein, immunoconjugate, and a multispecific binding molecule) comprising the antibody provided herein and a pharmaceutically acceptable excipient.

In other embodiments, provided herein is a pharmaceutical composition comprising a therapeutically effective amount of CAR comprising the antibody provided herein and a pharmaceutically acceptable excipient.

In other embodiments, provided herein is a pharmaceutical composition comprising a therapeutically effective amount of engineered immune effector cells provided herein and a pharmaceutically acceptable excipient.

In other embodiments, provided herein is a pharmaceutical composition comprising a therapeutically effective amount of a nucleic acid provided herein, e.g., in a vector, and a pharmaceutically acceptable excipient, e.g., suitable for gene therapy.

In a specific embodiment, the term "excipient" can also refer to a diluent, adjuvant (e.g., Freunds' adjuvant (complete or incomplete), carrier or vehicle. Pharmaceutical excipients can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid excipients. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical excipients are described in *Remington's Pharmaceutical Sciences* (1990) Mack Publishing Co., Easton, PA. Such compositions will contain a prophylactically or therapeutically effective amount of the active ingredient provided herein, such as in purified form, together with a suitable amount of excipient so as to provide the form for proper administration to the patient. The formulation should suit the mode of administration.

In some embodiments, the choice of excipient is determined in part by the particular cell, binding molecule, and/or antibody, and/or by the method of administration. Accordingly, there are a variety of suitable formulations.

Typically, acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers may be used to control the pH in a range which optimizes the therapeutic effectiveness, especially if stability is pH dependent. Suitable buffering agents for use with the present disclosure include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives may be added to retard microbial growth. Suitable preservatives for use with the present disclosure include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Exemplary tonicity agents include polyhydric sugar alcohols, trihydric or higher sugar alcohols, such as glycerin, erythritol, arabitol, xylitol, sorbitol and mannitol.

Additional exemplary excipients include: (1) bulking agents, (2) solubility enhancers, (3) stabilizers and (4) agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") may be present to help solubilize the therapeutic agent as well as to protect the therapeutic protein against agitation-induced aggregation, which also permits the formulation to be exposed to shear surface stress without causing denaturation of the active therapeutic protein or antibody. Suitable non-ionic surfactants include, e.g., polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they are preferably sterile. The pharmaceutical composition may be rendered sterile by filtration through sterile filtration membranes. The pharmaceutical compositions herein generally can be placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

In another embodiment, a pharmaceutical composition can be provided as a controlled release or sustained release system. In one embodiment, a pump may be used to achieve controlled or sustained release (see. e.g., Sefton, Crit. Ref. Biomed. Eng. 14:201-40 (1987); Buchwald et al., Surgery 88:507-16 (1980); and Saudek et al., N. Engl. J. Med. 321:569-74 (1989)). In another embodiment, polymeric materials can be used to achieve controlled or sustained release of a prophylactic or therapeutic agent (e.g., a fusion protein as described herein) or a composition provided herein (see. e.g., *Medical Applications of Controlled Release* (Langer and Wise eds., 1974); *Controlled Drug Bioavailability, Drug Product Design and Performance* (Smolen and Ball eds., 1984); Ranger and Peppas, J. Macromol. Sci. Rev. Macromol. Chem. 23:61-126 (1983); Levy et al., Science 228:190-92 (1985); During et al., Ann. Neurol. 25:351-56 (1989); Howard et al., J. Neurosurg. 71:105-12 (1989); U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. In yet another embodiment, a controlled or sustained release system can be placed in proximity of a particular target tissue, for example, the nasal passages or lungs, thus requiring only a fraction of the systemic dose (see. e.g., Goodson, *Medical Applications of Controlled Release* Vol. 2, 115-38 (1984)). Controlled release systems are discussed, for example, by Langer, Science 249:1527-33 (1990). Any technique known to one of skill in the art can be used to produce sustained release formulations comprising one or more agents as described herein (see. e.g., U.S. Pat. No. 4,526,938, PCT publication Nos. WO 91/05548 and WO 96/20698, Ning et al., Radiotherapy & Oncology 39:179-89 (1996); Song et al., PDA J. of Pharma. Sci. & Tech. 50:372-97 (1995); Cleek et al., Pro. Int'l. Symp. Control. Rel. Bioact. Mater. 24:853-54 (1997); and Lam et al., Proc. Int'l. Symp. Control Rel. Bioact. Mater. 24:759-60 (1997)).

The pharmaceutical compositions described herein may also contain more than one active compound or agent as necessary for the particular indication being treated. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

Various compositions and delivery systems are known and can be used with the therapeutic agents provided herein, including, but not limited to, encapsulation in liposomes, microparticles, microcapsules, recombinant cells capable of expressing the antibody or therapeutic molecule provided herein, construction of a nucleic acid as part of a retroviral or other vector, etc.

In some embodiments, the pharmaceutical composition provided herein contains the binding molecules and/or cells in amounts effective to treat or prevent the disease or disorder, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined.

5.7. Methods and Uses

In another aspect, provided herein are methods for using and uses of the GPC3 binding molecules provided herein, including the anti-GPC3 antibodies, chimeric antigen receptors (CARs), and/or engineered cells expressing the recombinant receptors.

5.7.1. Therapeutic Methods and Uses

Such methods and uses include therapeutic methods and uses, for example, involving administration of the molecules, cells, or compositions containing the same, to a subject having a disease, condition, or disorder expressing or associated with GPC3 expression, and/or in which cells or tissues express GPC3. In some embodiments, the molecule, cell, and/or composition is administered in an effective amount to effect treatment of the disease or disorder. Uses include uses of the antibodies and cells in such methods and treatments, and in the preparation of a medicament in order to carry out such therapeutic methods. In some embodiments, the methods are carried out by administering the antibodies or cells, or compositions comprising the same, to the subject having or suspected of having the disease or condition. In some embodiments, the methods thereby treat the disease or disorder in the subject.

In some embodiments, the treatment provided herein cause complete or partial amelioration or reduction of a disease or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms include, but do not imply, complete curing of a disease or complete elimination of any symptom or effect(s) on all symptoms or outcomes.

As used herein, in some embodiments, the treatment provided herein delay development of a disease or disorder, e.g., defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease or disorder. For example, a late stage cancer, such as development of metastasis, may be delayed. In other embodiments, the method or the use provided herein prevents a disease or disorder.

In some embodiments, the disease or disorder is a GPC3 associated disease or disorder. In some embodiments, the disease or disorder is a GPC3-positive cancer, i.e., a cancer that expresses or overexpresses GPC3. Examples of GPC3-positive cancers include, but are not limited to, HCC, melanoma, ovarian clear-cell carcinomas, volk sac tumors (YST), neuroblastoma, hepatoblastoma, nephroblastomas (Wilms' tumors), squamous cell carcinoma of the lung, adenocarcinoma of the lung, large-cell lung carcinoma, small cell lung cancer, testicular nonseminomatous germ cell tumors, liposarcoma, cervical intraepithelial neoplasia, adenoma of the adrenal gland, schwannoma, embryonal tumors, gastric cancers (such as gastric cancers that produce α-fetoprotein), colorectal carcinoma, esophageal cancer, and thyroid cancer. In some embodiments, the disease or disorder is HCC. In some embodiments, the disease or disorder is melanoma. In some embodiments, the disease or disorder is ovarian clear-cell carcinoma. In some embodiments, the disease or disorder is yolk sac tumor (YST). In some embodiments, the disease or disorder is neuroblastoma. In some embodiments, the disease or disorder is hepatoblastoma. In some embodiments, the disease or disorder is nephroblastoma (Wilms' tumor). In some embodiments, the disease or disorder is squamous cell carcinoma of the lung. In some embodiments, the disease or disorder is adenocarcinoma of the lung. In some embodiments, the disease or disorder is large-cell lung carcinoma. In some embodiments, the disease or disorder is small cell lung cancer. In some embodiments, the disease or disorder is testicular nonseminomatous germ cell tumor. In some embodiments, the disease or disorder is liposarcoma. In some embodiments, the disease or disorder is cervical intraepithelial neoplasia. In some embodiments, the disease or disorder is adenoma of the adrenal gland. In some embodiments, the disease or disorder is schwannoma. In some embodiments, the disease or disorder is embryonal tumor. In some embodiments, the disease or disorder is gastric carcinoma (such as a gastric cancer that produce α-fetoprotein). In some embodiments, the disease or disorder is colorectal carcinoma. In some embodiments, the disease or disorder is esophageal cancer. In some embodiments, the disease or disorder is thyroid cancer.

In some embodiments, the methods include adoptive cell therapy, whereby genetically engineered cells expressing the provided GPC3-targeted CARs are administered to a subject. Such administration can promote activation of the cells (e.g., T cell activation) in a GPC3-targeted manner, such that the cells of the disease or disorder are targeted for destruction.

In some embodiments, the methods include administration of the cells or a composition containing the cells to a subject, tissue, or cell, such as one having, at risk for, or suspected of having the disease or disorder. In some embodiments, the cells, populations, and compositions are administered to a subject having the particular disease or disorder to be treated, e.g., via adoptive cell therapy, such as adoptive T cell therapy. In some embodiments, the cells or compositions are administered to the subject, such as a subject having or at risk for the disease or disorder. In some embodiments, the methods thereby treat, e.g., ameliorate one or more symptom of the disease or disorder, such as by lessening tumor burden in a GPC3-expressing cancer.

Methods for administration of cells for adoptive cell therapy are known, as described, e.g., in US Patent Application Publication No. 2003/0170238; U.S. Pat. No. 4,690, 915; Rosenberg, *Nat Rev Clin Oncol.* 8 (10); 577-85 (2011); Themeli et al., Nat Biotechnol. 31 (10); 928-933 (2013); Tsukahara et al., Biochem Biophys Res Commun 438 (1); 84-9 (2013); and Davila et al., PLOS ONE 8 (4); e61338 (2013). These methods may be used in connection with the methods and compositions provided herein.

In some embodiments, the cell therapy (e.g., adoptive T cell therapy) is carried out by autologous transfer, in which the cells are isolated and/or otherwise prepared from the subject who is to receive the cell therapy, or from a sample derived from such a subject. Thus, in some aspects, the cells are derived from a subject in need of a treatment and the cells, following isolation and processing are administered to the same subject. In other embodiments, the cell therapy (e.g., adoptive T cell therapy) is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. In other embodiments, the cell therapy (e.g., adoptive T cell therapy) is carried out by allogeneic transfer.

In some embodiments, the subject, to whom the cells, cell populations, or compositions are administered is a primate, such as a human. The subject can be male or female and can be any suitable age, including infant, juvenile, adolescent, adult, and geriatric subjects. In some examples, the subject is a validated animal model for disease, adoptive cell therapy, and/or for assessing toxic outcomes.

The GPC3-binding molecules, such as antibodies and chimeric antigen receptors that bind to GPC3 and cells expressing the same, can be administered by any suitable means, for example, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

The amount of a prophylactic or therapeutic agent provided herein that will be effective in the prevention and/or treatment of a disease or condition can be determined by standard clinical techniques. Effective doses may be extrapolated from dose-response curves derived from in vitro or animal model test systems. For the prevention or treatment of disease, the appropriate dosage of the binding molecule or cell may depend on the type of disease or disorder to be treated, the type of binding molecule, the severity and course of the disease or disorder, whether the therapeutic agent is administered for preventive or therapeutic purposes, previous therapy, the patient's clinical history and response to the agent, and the discretion of the attending physician. The compositions, molecules and cells are in some embodiments suitably administered to the patient at one time or over a series of treatments.

For example, depending on the type and severity of the disease, dosages of antibodies may include about 10 μg/kg to 100 mg/kg or more. Multiple doses may be administered intermittently. An initial higher loading dose, followed by one or more lower doses may be administered. In some embodiments, wherein the pharmaceutical composition comprises any one of the antibodies described herein, the pharmaceutical composition is administered at a dosage of about 10 ng/kg up to about 100 mg/kg of body weight of the individual or more per day, for example, at about 1 mg/kg/day to 10 mg/kg/day, depending upon the route of administration. Guidance as to particular dosages and methods of delivery is provided in the literature (see, e.g., U.S. Pat. Nos. 4,657,760; 5,206,344; and 5,225,212).

In the context of genetically engineered cells containing the binding molecules, in some embodiments, a subject may be administered the range of about one million to about 100 billion cells and/or that amount of cells per kilogram of body weight. In some embodiments, wherein the pharmaceutical composition comprises any one of the engineered immune cells described herein, the pharmaceutical composition is administered at a dosage of at least about any of $10^4$, $10^5$, $10^6$, $10^7$, $10^8$, or $10^9$ cells/kg of body weight of the individual. Dosages may vary depending on attributes particular to the disease or disorder and/or patient and/or other treatments.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once or multiple times during a dosing cycle. A dosing cycle can be, e.g., 1, 2, 3, 4, 5 or more week(s), or 1, 2, 3, 4, 5, or more month(s). The optimal dosage and treatment regime for a particular patient can be determined by one skilled in the art of medicine by monitoring the patient for signs of disease and adjusting the treatment accordingly.

In some embodiments, the cells or antibodies are administered as part of a combination treatment, such as simultaneously with or sequentially with, in any order, another therapeutic intervention, such as another antibody or engineered cell or receptor or agent, such as a cytotoxic or therapeutic agent.

In some embodiments, the cells or antibodies are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents.

In certain embodiments, once the cells are administered to a mammal (e.g., a human), the biological activity of the engineered cell populations and/or antibodies is measured by any of a number of known methods. Parameters to assess include specific binding of an engineered or natural T cell or other immune cell to antigen, in vivo, e.g., by imaging, or ex vivo. e.g., by ELISA or flow cytometry. In certain embodiments, the ability of the engineered cells to destroy target cells can be measured using any suitable method known in the art, such as cytotoxicity assays described in, for example. Kochenderfer et al., J. Immunotherapy, 32(7); 689-702 (2009), and Herman et al. J. Immunological Methods, 285 (1); 25-40 (2004). In certain embodiments, the biological activity of the cells also can be measured by assaying expression and/or secretion of certain cytokines, such as CD107a. IFNγ, IL-2, and TNF. In some aspects the biological activity is measured by assessing clinical outcome, such as reduction in tumor burden or load.

In some specific embodiments, provided herein is a method for treating a disease or disorder in a subject comprising administering to the subject a binding molecule comprising an antibody that binds to GPC3 as described in Section 5.2 above, including. e.g., those with CDRs in Table 3 and Table 4, and more specifically the anti-GPC3 antibody that comprises (i) HCDR1 comprising the amino acid sequence of SEQ ID NO: 1, HCDR2 comprising the amino acid sequence of SEQ ID NO: 11, HCDR3 comprising the amino acid sequence of SEQ ID NO: 21, LCDR1 comprising the amino acid sequence of SEQ ID NO: 31, LCDR2 comprising the amino acid sequence of SEQ ID NO: 41, and LCDR3 comprising the amino acid sequence of SEQ ID NO: 51, or (ii) HCDR1 comprising the amino acid sequence of SEQ ID NO: 2, HCDR2 comprising the amino acid sequence of SEQ ID NO: 12, HCDR3 comprising the amino acid sequence of SEQ ID NO: 22, LCDR1 comprising the amino acid sequence of SEQ ID NO: 32, LCDR2 comprising the amino acid sequence of SEQ ID NO: 42, and LCDR3 comprising the amino acid sequence of SEQ ID NO: 52, or (iii) HCDR1 comprising the amino acid sequence of SEQ ID NO: 3, HCDR2 comprising the amino acid sequence of SEQ ID NO: 13, HCDR3 comprising the amino acid sequence of SEQ ID NO: 23, LCDR1 comprising the amino acid sequence of SEQ ID NO: 33, LCDR2 comprising the amino acid sequence of SEQ ID NO: 43, and LCDR3 comprising the amino acid sequence of SEQ ID NO: 53, or (iv) HCDR1 comprising the amino acid sequence of SEQ ID NO: 4. HCDR2 comprising the amino acid sequence of SEQ ID NO: 14, HCDR3 comprising the amino acid sequence of SEQ ID NO: 24, LCDR1 comprising the amino acid sequence of SEQ ID NO: 34, LCDR2 comprising the amino acid sequence of SEQ ID NO: 44, and LCDR3 comprising the amino acid sequence of SEQ ID NO: 54, or (v) HCDR1 comprising the amino acid sequence of SEQ ID NO: 5, HCDR2 comprising the amino acid sequence of SEQ ID NO: 15, HCDR3 comprising the amino acid sequence of SEQ ID NO: 25, LCDR1 comprising the amino acid sequence of SEQ ID NO: 35, LCDR2 comprising the amino acid sequence of SEQ ID NO: 45, and LCDR3 comprising the amino acid sequence of SEQ ID NO: 55, or (vi) HCDR1 comprising the amino acid sequence of SEQ ID NO: 6, HCDR2 comprising the amino acid sequence of SEQ ID NO: 16, HCDR3 comprising the amino acid sequence of SEQ ID NO: 26, LCDR1 comprising the amino acid sequence of SEQ ID NO: 36, LCDR2 comprising the amino acid sequence of SEQ ID NO: 46, and LCDR3 comprising the amino acid sequence of SEQ ID NO: 56, or (vii) HCDR1 comprising the amino acid sequence of SEQ ID NO: 7, HCDR2 comprising the amino acid sequence of SEQ ID NO: 17. HCDR3 comprising the amino acid sequence of SEQ ID NO: 27, LCDR1 comprising the amino acid sequence of SEQ ID NO: 37, LCDR2 comprising the amino acid sequence of SEQ ID NO: 47, and LCDR3 comprising the amino acid sequence of SEQ ID NO: 57, or (viii) HCDR1 comprising the amino acid sequence of SEQ ID NO: 8, HCDR2 comprising the amino acid sequence of SEQ ID NO: 18, HCDR3 comprising the amino acid sequence of SEQ ID NO: 28, LCDR1 comprising the amino acid sequence of SEQ ID NO: 38, LCDR2 comprising the amino acid sequence of SEQ ID NO: 48, and LCDR3 comprising the amino acid sequence of SEQ ID NO: 58, or (ix) HCDR1 comprising the amino acid sequence of SEQ ID NO: 9, HCDR2 comprising the amino acid sequence of SEQ ID NO: 19, HCDR3 comprising the amino acid sequence of SEQ ID NO: 29, LCDR1 comprising the amino acid sequence of SEQ ID NO: 39, LCDR2 comprising the amino acid sequence of SEQ ID NO: 49, and LCDR3 comprising the amino acid sequence of SEQ ID NO: 59, or (x) HCDR1 comprising the amino acid sequence of SEQ ID NO: 10, HCDR2 comprising the amino acid sequence of SEQ ID NO: 20, HCDR3 comprising the amino acid sequence of SEQ ID NO: 30, LCDR1 comprising the amino acid sequence of SEQ ID NO: 40, LCDR2 comprising the amino acid sequence of SEQ ID NO: 50, and LCDR3 comprising the amino acid sequence of SEQ ID NO: 60. In some embodiments, the antibody comprises a VH domain selected from a group of SEQ ID NOs: 61-70 and 117-122 and a VL domain selected from a group of SEQ ID NOs.: 71-80 and 123-125. In some embodiments, the disease or disorder is a GPC3 associated disease or disorder. In some embodiments, the disease or disorder is a GPC3-positive cancer, i.e., a cancer that expresses or overexpresses GPC3. Examples of GPC3-positive cancers include, but are not limited to, HCC, melanoma, ovarian clear-cell carcinomas, volk sac tumors (YST), neuroblastoma, hepatoblastoma, nephroblastomas (Wilms' tumors), squamous cell carcinoma of the lung, adenocarcinoma of the lung, large-cell lung carcinoma, small cell lung cancer, testicular nonseminomatous germ cell tumors, liposarcoma, cervical intraepithelial neoplasia, adenoma of the adrenal gland, schwannoma, embryonal tumors, gastric cancers (such as gastric cancers that produce α-fetoprotein), colorectal carcinoma, esophageal cancer, and thyroid cancer. In some embodiments, the disease or disorder is HCC. In some embodiments, the disease or disorder is melanoma. In some embodiments, the disease or disorder is ovarian clear-cell carcinoma. In some embodiments, the disease or disorder is yolk sac tumor (YST). In some embodiments, the disease or disorder is neuroblastoma. In some embodiments, the disease or disorder is hepatoblastoma. In some embodiments, the disease or disorder is nephroblastoma (Wilms' tumor). In some embodiments, the disease or disorder is squamous cell carcinoma of the lung. In some embodiments, the disease or disorder is adenocarcinoma of the lung. In some embodiments, the disease or disorder is large-cell lung carcinoma. In some embodiments, the disease or disorder is small cell lung cancer. In some embodiments, the disease or disorder is testicular nonseminomatous germ cell tumor. In some embodiments, the disease or disorder is liposarcoma. In some embodiments, the disease or disorder is cervical intraepithelial neoplasia. In some embodiments, the disease or disorder is adenoma of the adrenal gland. In some embodiments, the disease or disorder is schwannoma. In some embodiments, the disease or disorder is embryonal tumor. In some embodiments, the disease or disorder is gastric carcinoma (such as a gastric cancer that produce α-fetoprotein). In some embodiments, the disease or disorder is colorectal carcinoma. In some embodiments, the disease or disorder is esophageal cancer. In some embodiments, the disease or disorder is thyroid cancer.

In other specific embodiments, provided herein is a method for treating a disease or disorder in a subject comprising administering to the subject an engineered immune effector cell expressing a CAR provided herein, for example, a CAR comprising an antibody (such as scFv) that binds to GPC3 as described in Section 5.2 above, including, e.g., those with CDRs in Table 3 and Table 4, and those comprising a VH domain selected from a group of SEQ ID NOs: 61-70 and 117-122 and a VL domain selected from a group of SEQ ID NOs.: 71-80 and 123-125. In more specific embodiments, the antibody in the CAR of the present immune effector cells for treating a disease or disorder is a scFv comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of any one of SEQ ID NOs.: 81-90, 128 and 129. In other specific embodiments, the engineered immune effector cell (such as T cell) for treating a disease or disorder comprises a CAR which comprises a polypeptide comprising an amino acid sequence of SEQ ID NOs: 91-100, 107-116 and 130-131, or an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NOs: 91-100, 107-116 and 130-131. In some embodiments, the disease or disorder is a GPC3 associated disease or disorder. In some embodiments, the disease or disorder is a GPC3-positive cancer, i.e., a cancer that expresses or overexpresses GPC3. Examples of GPC3-positive cancers include, but are not limited to, HCC, melanoma, ovarian clear-cell carcinomas, volk sac tumors (YST), neuroblastoma, hepatoblastoma, nephroblastomas (Wilms' tumors), squamous cell carcinoma of the lung, adenocarcinoma of the lung, large-cell lung carcinoma, small cell lung cancer, testicular nonseminomatous germ cell tumors, liposarcoma, cervical intraepithelial neoplasia, adenoma of the adrenal gland, schwannoma, embryonal tumors, gastric cancers (such as gastric cancers that produce α-fetoprotein), colorectal carcinoma, esophageal cancer, and thyroid cancer. In some embodiments, the disease or disorder is HCC. In some embodiments, the disease or disorder is melanoma. In some embodiments, the disease or disorder is ovarian clear-cell carcinoma. In some embodiments, the disease or disorder is volk sac tumor (YST). In some embodiments, the disease or disorder is neuroblastoma. In some embodiments, the disease or disorder is hepatoblastoma. In some embodiments, the disease or disorder is nephroblastoma (Wilms' tumor). In some embodiments, the disease or disorder is squamous cell carcinoma of the lung. In some embodiments, the disease or disorder is adenocarcinoma of the lung. In some embodiments, the disease or disorder is large-cell lung carcinoma. In some embodiments, the disease or disorder is small cell lung cancer. In some embodiments, the disease or disorder is testicular nonseminomatous germ cell tumor. In some embodiments, the disease or disorder is liposarcoma. In some embodiments, the disease or disorder is cervical intraepithelial neoplasia. In some embodiments, the disease or disorder is adenoma of the adrenal gland. In some embodiments, the disease or disorder is schwannoma. In some embodiments, the disease or disorder is embryonal tumor. In some embodiments, the disease or disorder is gastric carcinoma (such as a gastric cancer that produce α-fetoprotein). In some embodiments, the disease or disorder is colorectal carcinoma. In some embodiments, the disease or disorder is esophageal cancer. In some embodiments, the disease or disorder is thyroid cancer.

5.7.2. Diagnostic and Detection Methods and Uses

In another aspect, provided herein are methods involving use of the binding molecules provided herein, e.g., antibodies that binds GPC3 and molecules (such as conjugates and complexes) containing such antibodies, for detection, prognosis, diagnosis, staging, determining binding of a particular treatment to one or more tissues or cell types, and/or informing treatment decisions in a subject, such as by the detection of GPC3 and/or the presence of an epitope thereof recognized by the antibody.

In some embodiments, an anti-GPC3 antibody (such as any one of the anti-GPC3 antibodies described herein) for use in a method of diagnosis or detection is provided. In a further aspect, a method of detecting the presence of GPC3 in a biological sample is provided. In certain embodiments, the method comprises detecting the presence of GPC3 protein in a biological sample. In certain embodiments, GPC3 is human GPC3. In some embodiments, the methods are diagnostic and/or prognostic methods in association with a GPC3-expressing disease or disorder. The methods in some embodiments include incubating and/or probing a biological sample with the antibody and/or administering the antibody to a subject. In certain embodiments, a biological sample includes a cell or tissue or portion thereof, such as tumor or cancer tissue or biopsy or section thereof. In certain embodiments, the contacting is under conditions permissive for binding of the anti-GPC3 antibody to GPC3 present in the sample. In some embodiments, the methods further include detecting whether a complex is formed between the anti-GPC3 antibody and GPC3 in the sample, such as detecting the presence or absence or level of such binding. Such a method may be an in vitro or in vivo method. In one embodiment, an anti-GPC3 antibody is used to select subjects eligible for therapy with an anti-GPC3 antibody or engineered antigen receptor, e.g., where GPC3 is a biomarker for selection of patients.

In some embodiments, a sample, such as a cell, tissue sample, lysate, composition, or other sample derived therefrom is contacted with the anti-GPC3 antibody and binding or formation of a complex between the antibody and the sample (e.g., GPC3 in the sample) is determined or detected. When binding in the test sample is demonstrated or detected as compared to a reference cell of the same tissue type, it may indicate the presence of an associated disease or disorder, and/or that a therapeutic containing the antibody will specifically bind to a tissue or cell that is the same as or is of the same type as the tissue or cell or other biological material from which the sample is derived. In some embodiments, the sample is from human tissues and may be from diseased and/or normal tissue, e.g., from a subject having the disease or disorder to be treated and/or from a subject of the same species as such subject but that does not have the disease or disorder to be treated. In some cases, the normal tissue or cell is from a subject having the disease or disorder to be treated but is not itself a diseased cell or tissue, such as a normal tissue from the same or a different organ than a cancer that is present in a given subject.

Various methods known in the art for detecting specific antibody-antigen binding can be used. Exemplary immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be used so as to meet the needs of various uses of the method which are often dictated by the availability of assay equipment and compatible immunoassay procedures. Exemplary labels include radionuclides (e.g. $^{125}I$, $^{131}I$, $^{35}S$, $^{3}H$, or $^{32}P$ and/or chromium ($^{51}Cr$), cobalt ($^{57}Co$), fluorine ($^{18}F$), gadolinium ($^{153}Gd$, $^{159}Gd$), germanium ($^{68}Ge$), holmium ($^{166}Ho$), indium ($^{115}In$, $^{113}In$, $^{112}In$, $^{111}In$), iodine ($^{125}I$, $^{123}I$, $^{121}I$), lanthanium ($^{140}La$), lutetium ($^{177}Lu$), manganese ($^{54}Mn$), molybdenum ($^{99}Mo$), palladium ($^{103}Pd$), phosphorous ($^{32}P$), praseodymium ($^{142}Pr$), promethium ($^{149}Pm$), rhenium ($^{186}Re$, $^{188}Re$), rhodium ($^{105}Rh$), rutheroium ($^{97}Ru$), samarium ($^{153}Sm$), scandium ($^{47}Sc$), selenium ($^{75}Se$), ($^{85}Sr$), sulphur ($^{35}S$), technetium ($^{99}Tc$), thallium ($^{201}Ti$) tin ($^{113}Sn$, $^{117}Sn$), tritium ($^{3}H$), xenon ($^{133}Xe$), ytterbium ($^{169}Yb$, $^{175}Yb$), yttrium ($^{90}Y$),), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Various general techniques to be used in performing the various immunoassays noted above are known.

In certain embodiments, labeled antibodies (such as anti-GPC3 antibodies) are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. In other embodiments, antibodies are not labeled, and the presence thereof can be detected using a labeled antibody which binds to any of the antibodies.

5.8. Kits and Articles of Manufacture

Further provided are kits, unit dosages, and articles of manufacture comprising any of the antibodies, the chimeric antigen receptors, or the engineered immune effector cells described herein. In some embodiments, a kit is provided which contains any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

For the sake of conciseness, certain abbreviations are used herein. One example is the single letter abbreviation to represent amino acid residues. The amino acids and their corresponding three letter and single letter abbreviations are as follows:

| Amino acid | Three letter | One letter |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The disclosure is generally disclosed herein using affirmative language to describe the numerous embodiments. The disclosure also specifically includes embodiments in which particular subject matter is excluded, in full or in part, such as substances or materials, method steps and conditions, protocols, procedures, assays or analysis. Thus, even though the disclosure is generally not expressed herein in terms of what the disclosure does not include, aspects that are not expressly included in the disclosure are nevertheless disclosed herein.

A number of embodiments of the disclosure have been described. Nevertheless, it will be understood that various modifications may be made without departing from the spirit and scope of the disclosure. Accordingly, the following examples are intended to illustrate but not limit the scope of disclosure described in the claims.

6. EXAMPLES

The following is a description of various methods and materials used in the studies, and are put forth so as to provide those of ordinary skill in the art with a complete disclosure and description of how to make and use the present disclosure, and are not intended to limit the scope of what the inventors regard as their disclosure nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present disclosure. Efforts have been made to ensure accuracy with respect to numbers used (e.g., amounts, percentages, etc.), but some experimental errors and deviations should be accounted for.

6.1. Example 1—Generation of Anti-GPC3 Antibodies

Animal Immunization and Immune Response Testing

Antibodies against GPC3 were developed by hybridoma platform through a service order from GenScript. Human recombinant protein GPC3 (ACRO, Cat. No. GP3-H5223) was modified by ImmunoPlus™ technology by Genscript. Female Balb/c and C57bl/6 mice were subcutaneously immunized with 1:1 emulsion containing 200 μL Freund's complete adjuvant (Sigma, Cat. No. F5881) and 50 μg GPC3 fusion protein (SEQ ID NO: 106). Then, to enhance the immunity, the intraperitoneal injection alternating with subcutaneous was adopted in the mice with 1:1 emulsion containing Freund's incomplete adjuvant (Sigma, Cat. No. F5506) and 25 μg GPC3 fusion protein every two weeks. Except for No. 409 and No. 416, the serum titers of other mice were above 105 after five time immunizations.

Two mice (No. 410 and No. 412) with the highest antibody titer received intraperitoneal boost with 25 μg GPC3 fusion protein (without adjuvant) and were selected for hybridoma fusion. The serum of two immunized mice also showed significant binding activity against typical GPC3 HepG2 cells (ATCC, Cat. No. HB-8065). The antibodies in the Test-bleeding serum showed binding to HepG2 cells, starting from 19.1 to 112 for No. 410 mouse and from 19.1 to 62.9 for No. 412 mouse.

Screening of Anti-GPC3 Antibodies

Full length human, mouse or cynomolgus monkey GPC3 encoding cDNA (NM_004484.3, NM_016697.3 or XM_005594608.2, respectively) was synthesized into plasmid PLVX-puro (Clontech, Cat. No. 632164) through a service from GenScript, then the plasmids were named PLVX-huGPC3, PLVX-muGPC3 or PLVX-cmGPC3, respectively.

High-titer recombinant lentivirus were produced and were transduced to SK-HEP-1 cells (ATCC, Cat. No. HTB-52). 100 μL Lentivirus supernatant (100)×concentrated) was added to 0.5 million target cells in 6-well plates and the mixture was incubated through centrifuges (1200 g, 32° C., 90 min). After screening with puromycin, in vitro extracellular expression of GPC3 was monitored via flow cytometry. PE conjugated anti-GPC3 specific monoclonal antibody (R&D, Cat. No. FAB2119P) was used as the detection antibody. Following this method, the mean fluorescence intensity (MFI) of labeled SK-HEP-1-huGPC3 was 7.67 folds higher than that of SK-HEP-1 cells (MFI values 1350, 176 respectively). The MFI of labeled SK-HEP-1-cmGPC3 was 4.36 folds higher than that of SK-HEP-1 cells (MFI values 768, 176 respectively). At the same time, the MFI of labeled SK-HEP-1-muGPC3 was also higher than that of SK-HEP-1 cells.

Three days after the last boost, splenocytes from the mice with good titers were prepared sterilely and fused with sp2/0 cells following a standard hybridoma generation protocol. The human or cynomolgus GPC3 transfected SK-HEP-1 cells were plated in 96-well U-bottom plates (BD) at a density of $1\times10^5$ cells/well. Hybridoma supernatants were transferred to the plates and incubated with cells for 1 hour at 4° C. The cells were then washed twice with staining buffer (BSA/1×PBS). PE-conjugated goat anti-mouse IgG Fc antibody (Jackson, Cat. No. 115115164), was added and incubated at 4° C. in the dark for 30 min. The cells were then washed twice and re-suspended in 100 μL staining buffer. The fluorescence intensity was measured by flow cytometry and analyzed by the FlowJo™ software.

Hybridoma supernatant was used for primary screen. The primary binding screen identified 30 hybridomas which could produce antigen-specific binding antibodies. The positive binders were selected for subcloning. Hybridoma cells of each selected lines were plated in 96-well plates at the density of 1 cell/well. The plates were kept in a humidified incubator at 37° C., 5% $CO_2$ for 10-12 days. The single clones were picked and tested by FACS. The selected subclones were purified and further evaluated in binding assay, cross-family binding assay and binning assay.

Monoclonal antibodies were identified by the rapid ELISA SBA Clonotyping System-HRP Kit (Southern Biotech, Cat. No. 5300-05). Total RNA was extracted from hybridoma cells by the TRIzol™ reagent and reverse transcribed into cDNA by using specific and universal primers of antibody subtypes (Takara, Cat. No. 6210A). The heavy chain and light chain V-region fragments of mouse immunoglobulin were amplified by RACE-PCR (Takara, Cat. No. 28001488) and subcloned into pMD18-T vector system (Takara, Cat. No. D101A). The inserted fragments were sequenced by vector-specific primers. Finally, the unique V-region nucleotide/protein sequences of Lab19301, Lab19302, Lab19303, Lab19304, Lab19305, Lab19306, Lab19307, Lab19308, Lab19309 and Lab19310 were obtained. Antibody isotypes were determined using Clonotyping System-HRP (SouthernBiotech). CDR sequences of selected antigen specific clones are shown in Table 3 and Table 4 as below.

TABLE 3

Amino acid sequences of heavy chain CDR regions from selected clones

| Clone ID | HCDR1 | HCDR2 | HCDR3 |
|---|---|---|---|
| LAb19301 | SGFSWH (SEQ ID NO: 1) | FMQYSGNTNYNPSLKS (SEQ ID NO: 11) | REEGAWFAY (SEQ ID NO: 21) |
| LAb19302 | TYGMS (SEQ ID NO: 2) | YISSGGATTYYPDSVKG (SEQ ID NO: 12) | LSIMIRGWFAY (SEQ ID NO: 22) |
| LAb19303 | DYEMH (SEQ ID NO: 3) | AIDPETGATAYNQKFKG (SEQ ID NO: 13) | YYSFAY (SEQ ID NO: 23) |
| LAb19304 | AYEMH (SEQ ID NO: 4) | GIDPETGNTAYSQKFKG (SEQ ID NO: 14) | YYSFAY (SEQ ID NO: 24) |
| LAb19305 | AYEMH (SEQ ID NO: 5) | GIDPETGNTAYSQNFKG (SEQ ID NO: 15) | YYSFAY (SEQ ID NO: 25) |
| LAb19306 | TYDMS (SEQ ID NO: 6) | YISSGGATTYYPDSVKG (SEQ ID NO: 16) | LSLMIRGWFAY (SEQ ID NO: 26) |
| LAb19307 | TYDMS (SEQ ID NO: 7) | YISSGGNSPYYPQTVKG (SEQ ID NO: 17) | QNIARRGAMDF (SEQ ID NO: 27) |
| LAb19308 | TYGMS (SEQ ID NO: 8) | YISSGGANTYYPDSVKG (SEQ ID NO: 18) | LSTLVRGWFAY (SEQ ID NO: 28) |
| LAb19309 | DYEMH (SEQ ID NO: 9) | GIDPETGNTAYSQKFKG (SEQ ID NO: 19) | YYSFAY (SEQ ID NO: 29) |
| LAb19310 | VSPMT (SEQ ID NO: 10) | LIHPYNGDTTYNQKFKG (SEQ ID NO: 20) | WGNYYPYAMDY (SEQ ID NO: 30) |

TABLE 4

Amino acid sequences of light chain CDR regions from selected clones

| Clone ID | LCDR1 | LCDR2 | LCDR3 |
|---|---|---|---|
| LAb19301 | GSSQSLVHSNGNTYLH (SEQ ID NO: 31) | KVSNRFS (SEQ ID NO: 41) | SQSTHFPFT (SEQ ID NO: 51) |
| LAb19302 | RSSQSLVHSNGNTYLH (SEQ ID NO: 32) | KVSNRFS (SEQ ID NO: 42) | SQSTHVPYT (SEQ ID NO: 52) |
| LAb19303 | RSSQSFVHSNGNTYLQ (SEQ ID NO: 33) | KVSNRFS (SEQ ID NO: 43) | FQGSHVPYT (SEQ ID NO: 53) |
| LAb19304 | RSSQTIVHSNGNTYLE (SEQ ID NO: 34) | KVSNRFS (SEQ ID NO: 44) | FQVSHVPYT (SEQ ID NO: 54) |
| LAb19305 | RSSQTIVHSNGNTYLE (SEQ ID NO: 35) | KVSNRFS (SEQ ID NO: 45) | FQVSHVPYT (SEQ ID NO: 55) |

TABLE 4-continued

Amino acid sequences of light chain CDR regions from selected clones

| Clone ID | LCDR1 | LCDR2 | LCDR3 |
|---|---|---|---|
| LAb19306 | RSSQSLVHSNGNTYLH (SEQ ID NO: 36) | KVSNRFS (SEQ ID NO: 46) | SQSTHVPYT (SEQ ID NO: 56) |
| LAb19307 | TSSQSLLHSNGNTYLH (SEQ ID NO: 37) | KVSNRFS (SEQ ID NO: 47) | SQSTHVPPT (SEQ ID NO: 57) |
| LAb19308 | RSSQSLVHSNGNTYLH (SEQ ID NO: 38) | KVSNRFS (SEQ ID NO: 48) | SQSTHVPYT (SEQ ID NO: 58) |
| LAb19309 | RSSQTIVHSNGNTYLE (SEQ ID NO: 39) | KVSNRFS (SEQ ID NO: 49) | FQVSHVPYT (SEQ ID NO: 59) |
| LAb19310 | KASQNVRSTVA (SEQ ID NO: 40) | LTSNRHT (SEQ ID NO: 50) | LQHWNYPYT (SEQ ID NO: 60) |

Purification of Anti-GPC3 Antibodies

Harvested hybridoma supernatants were loaded to Protein A column (GE Healthcare, Cat. No. 17040201) after adjusting pH to 7.0. Antibodies were eluted by Glycine followed with immediately neutralization using 1 M Tris. Antibody concentration was tested by Nano Drop. The purity of proteins was evaluated by SDS-PAGE (GenScript Cat. No. M42012). The concentration was determined by A280 method. Representative data of protein expression was summarized in Table 5.

TABLE 5

Antibodies expression information

| Sample code | Purity | Concentration (mg/mL) |
|---|---|---|
| LAb19301 | ~92% | 0.607 |
| LAb19302 | ~97% | 1.407 |
| LAb19303 | ~92% | 1.299 |
| LAb19304 | ~95% | 1.407 |
| LAb19305 | ~98% | 1.458 |
| LAb19306 | ~91% | 1.779 |
| LAb19307 | ~93% | 0.607 |
| LAb19308 | ~93% | 1.710 |
| LAb19309 | ~93% | 1.279 |
| LAb19310 | ~93% | 0.607 |

Affinity of Anti-GPC3 Antibodies

The binding kinetics of the antibodies to recombinant human GPC3 were measured by the surface plasmon resonance (SPR) (e.g., the Biacore™ SPR system). Binding rate ($K_a$) and dissociation rates ($K_d$) were calculated using a simple one-to-one Langmuir binding model (Biacore™ Evaluation Software). The equilibrium dissociation constant ($K_D$) is calculated as the ratio $K_d/K_a$. The measured binding affinities of anti-human GPC3 antibodies are shown In Table 6.

TABLE 6

Affinity measurement of GPC3 antibodies to proteins

| Ligand | Analyte | Chi$^2$ (RU$^2$) | $K_a$ (1/Ms) | $K_d$ (1/s) | $K_D$ (M) | Rmax (RU) |
|---|---|---|---|---|---|---|
| LAb19301 | hGPC3 | 0.0976 | 1.69E+04 | 2.07E−03 | 1.22E−07 | 31.63 |
| LAb19302 | hGPC3 | 0.28 | 2.58E+04 | 0.001835 | 7.12E−08 | 45.74 |
| LAb19303 | hGPC3 | 0.449 | 3.34E+04 | 4.60E−04 | 1.38E−08 | 41.41 |
| LAb19304 | hGPC3 | 0.35 | 2.70E+04 | 1.38E−04 | 5.11E−09 | 56.51 |
| LAb19305 | hGPC3 | 0.0782 | 3.11E+04 | 1.30E−04 | 4.19E−09 | 32.97 |
| LAb19306 | hGPC3 | 0.216 | 2.71E+04 | 7.70E−04 | 2.84E−08 | 16.7 |

TABLE 6-continued

Affinity measurement of GPC3 antibodies to proteins

| Ligand | Analyte | Chi$^2$ (RU$^2$) | $K_a$ (1/Ms) | $K_d$ (1/s) | $K_D$ (M) | Rmax (RU) |
|---|---|---|---|---|---|---|
| LAb19307 | hGPC3 | 0.347 | 3.02E+04 | 0.001776 | 5.87E−08 | 64.69 |
| LAb19308 | hGPC3 | 0.0532 | 2.47E+04 | 0.001022 | 4.14E−08 | 33.46 |
| LAb19309 | hGPC3 | 0.268 | 2.33E+04 | 1.95E−04 | 8.38E−09 | 60.01 |
| LAb19310 | hGPC3 | 1.4 | 3.69E+04 | 4.65E−04 | 1.26E−08 | 70.87 |

Binding to GPC3 Cell Lines by FACS

The SK-HEP-1-huGPC3 cells and SK-HEP-1-cmGPC3 were plated in 96-well U-bottom plates (BD) at a density of $1\times10^5$ cells/well. The purified antibodies were diluted in the staining buffer and incubated with cells for 1 hour at 4° C. The cells were then washed twice with staining buffer (BSA/1×PBS). PE-conjugated goat anti-mouse IgG Fc antibody was added and incubated at 4° C. in the dark for 30 minutes. The cells were then washed twice and re-suspended in 100 μL staining buffer. The fluorescence intensity was measured by flow cytometry and analyzed by the FlowJo™ software.

As shown in Table 7, all antibodies can specifically bind to SK-HEP-1-huGPC3, but not to empty SK-HEP-1 cells. In addition, some GPC3 antibodies can also cross-react with mouse GPC3, which will provide a potential safety evaluation method.

TABLE 7

Binding capacity of antibody to GPC3 cell lines

| Protein code | Positive population, % | | | |
|---|---|---|---|---|
| | Binding on SK-HEP-1 | Binding on SK-HEP-1-huGPC3 | Binding on SK-HEP-1-muGPC3 | Binding on SK-HEP-1-cmGPC3 |
| LAb19301 | n.s. | 72.6 | 17.5 | 18.5 |
| LAb19302 | n.s. | 91.5 | 81.8 | 12.3 |
| LAb19303 | n.s. | 92.6 | 0.72 | 83.1 |
| LAb19304 | n.s. | 91.9 | 25.6 | 94.6 |
| LAb19305 | n.s. | 92.6 | 17.0 | 94.2 |
| LAb19306 | n.s. | 86.2 | 75.8 | 3.32 |
| LAb19307 | n.s. | 92.9 | 83.3 | 11.6 |
| LAb19308 | n.s. | 91.4 | 82.4 | 9.55 |
| LAb19309 | n.s. | 92.7 | 1.02 | 91.9 |
| LAb19310 | n.s. | 91.3 | 83.9 | 22.3 |
| ISOTYPE | n.s. | 0.85 | 0.91 | 0.43 |

6.2. Example 2—Preparation of Monospecific scFv Based Chimeric Antigen Receptors (CARs) and In Vitro Screening A CAR backbone sequence encoding a CAR backbone polypeptide comprising from the N-terminus to the C-terminus: a CD8α hinge domain (SEQ ID NO: 102), a CD8α transmembrane domain (SEQ ID NO: 103), a CD137 co-stimulatory signaling domain (SEQ ID NO: 104), and a CD3ζ cytoplasmic signaling domain (SEQ ID NO: 105) was chemically synthesized and cloned into a pre-modified PT7 vector downstream and operably linked to a constitutive T7 promoter. The resulting CAR backbone vector was named "PT7-T7-LB193." Multi-cloning sites (MCS) in the vector allowed insertion of a nucleic acid sequence comprising a Kozak sequence operably linked to a nucleic acid sequence encoding a CD8α signal peptide (SEQ ID NO: 101) fused to the N-terminus of an anti-GPC3 scFv fragment into the CAR backbone vector, upstream and operably linked to the CAR backbone sequence. The nucleic acid sequence encoding the CD8α signal peptide and the anti-GPC3 scFv fragment was chemically synthesized and cloned into the PT7-T7-LB193 via the MluI (5'-ACGCGT-3') (SEQ ID NO: 140) and SpeI (5'-ACTAGT-3') (SEQ ID NO: 141) restriction sites by molecular cloning techniques known in the art. PT7-T7-LB193 vector was constructed by cloning the elements required for in vitro transcribing of RNA to the pUC57 vector (GenScript, Cat. No. SD1176).

Ten anti-GPC3 scFvs, 1Ab19301-1Ab19310 scFvs, were generated by combining the VH and VL of 1Ab19301-1Ab19310 monoclonal antibodies (SEQ ID NOs: 81-90), respectively, to construct monospecific CARs into the PT7-T7-LB193 vector backbone. Each anti-GPC3 scFv was further modified by fusing the human CD8α leader sequence, human CD8α transmembrane domain, and the intracellular signaling domain of the CD137 and CD3 zeta chain of the human T cell receptor to generate a chimeric antigen receptor. A nucleic acid sequence encoding the selected scFv clone was operably linked to the 3' of the nucleic acid sequence encoding the CD8α signal peptide. The fusion nucleic acid sequence was chemically synthesized and cloned into the PT7-T7-LB193 CAR backbone via the MluI (5'-ACGCGT-3') (SEQ ID NO: 140) and SpeI (5'-ACTAGT-3') (SEQ ID NO: 141) restriction sites by molecular cloning techniques known in the art.

The GPC3 CAR DNA was linearized, and then a mMESSAGE mMACHINE™ T7 RNA transcription kit (ThermoFisher #AM1344) was used to synthesize the RNA. Transcription kit was used to generate all RNA. For the polyadenylation of invitro transcribed RNA to enhance translation initiation efficiency, all mRNA was added a poly(A) tail of at least 150 nucleotides in length to the 3' termini of RNA using poly(A) Tailing Kit (ThermoFisher #AM1350). RNA was purified with the rNeasy® Mini Kit (QIAGEN #74104) after capping and poly(A) tailing.

T Cell Purification

PBMCs were purchased from Hemacare (#17044560). Human T cells were purified from PBMCs using Pan T cell isolation kit (Miltenyi #130-096-535), following manufacturer's protocol as described below. Cell number was determined and the cell suspension was centrifuged at 300 g for 10 minutes. The supernatant was then aspirated completely, and the cell pellets were re-suspended in 40 μL buffer per 107 total cells. 10 μL of Pan T Cell Biotin-Antibody Cocktail was added per 107 total cells, mixed thoroughly and incubated for about 5 minutes in the refrigerator (2-8° C.). 30 μL of buffer was then added per $10^7$ cells. 20 μL of Pan T Cell MicroBead Cocktail was added per $10^7$ cells. The cell suspension mixture was mixed well and incubated for an additional 10 minutes in the refrigerator (2-8° C.). A minimum of 500 μL was required for magnetic separation. For magnetic separation, an LS column was placed in the magnetic field of a suitable MACS Separator. The column was prepared by rinsing with 3 mL of buffer. The cell suspension was then applied onto the column, and flow-through containing the unlabeled cells was collected, which represented the enriched T cell fractions. Additional T cells were collected by washing the column with 3 mL of buffer and collecting unlabeled cells that pass through. These unlabeled cells again represented the enriched T cells, and were combined with the flow-through from previous step. The pooled enriched T cells were then centrifuged and re-suspended in RPMI-1640+300 IU/mL IL-2.

The prepared T cells were subsequently pre-activated for 48 hours with human T cell TransAct™ kit (Miltenyi #130-111-160) according to manufacturer's protocol in which anti-CD3/CD28 MACSiBead particles were added at a bead-to-cell ratio of 10 μL/million.

Figure 1:
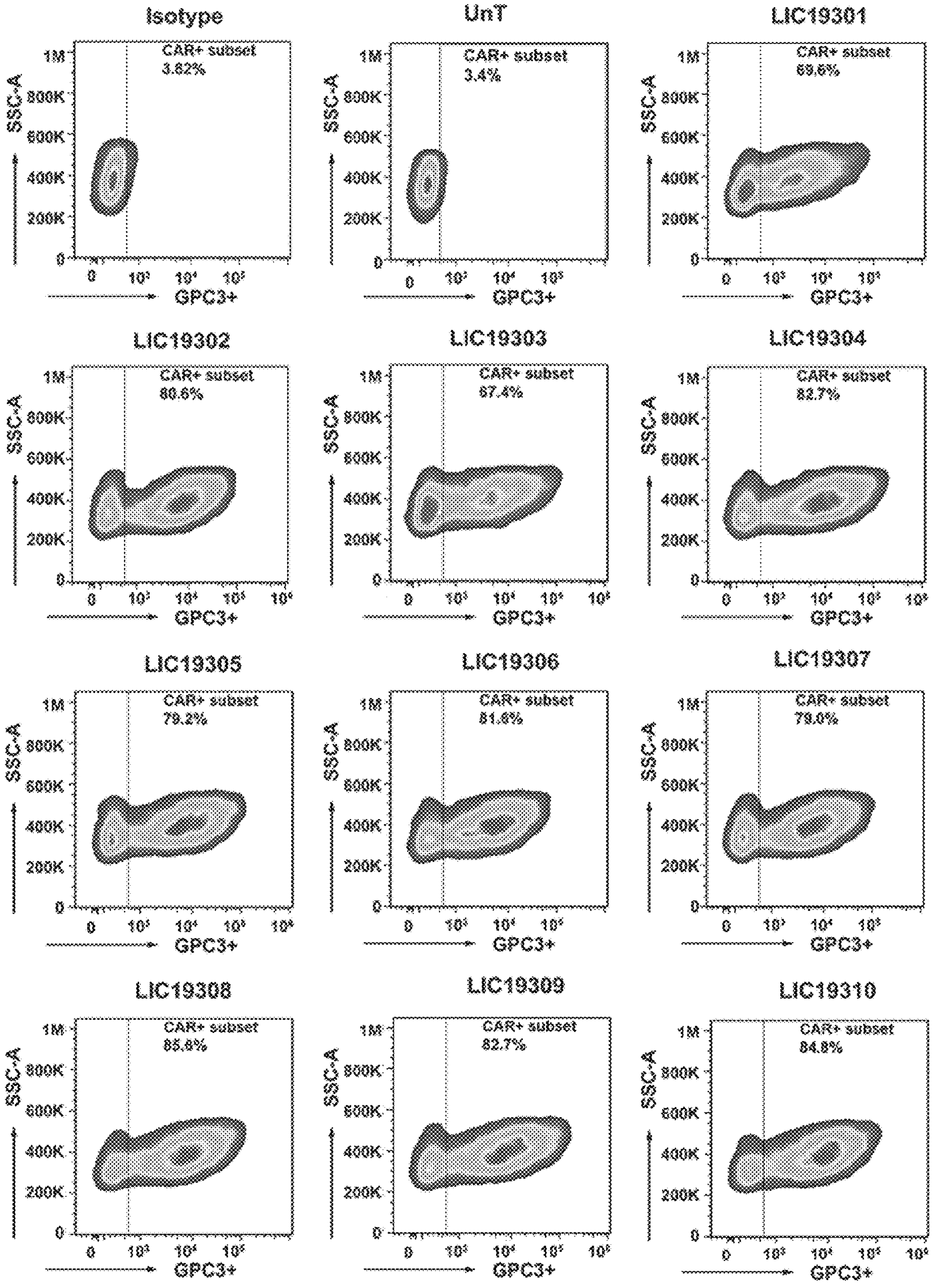

For CAR-T cells preparation, the pre-activated T cells were re-suspended at 5× 10) 6 cells in 130 μL electroporation buffer (Celetrix #13-0104) and 10 μg of mRNA was added for electroporation. Un-electroporated T lymphocytes was used as a negative control and the positive rates of electroporated T cells expressing different anti-GPC3 scFv CARs were 67.4%-85.6% (FIG. 1).

Cytotoxicity Assay

Target cells were either GPC3 positive human hepatocellular carcinoma (HCC) cell line HepG2.Luc (ATCC #HB-8065), Huh7.Luc (Cobioer #CBP60202) or GPC3 negative cell line SK-HEP1. Luc (ATCC #HTB-52), A549.Luc (ATCC #CRM-CCL-185) cell line. All the cell lines were engineered to express firefly luciferase with the techniques known in the art. GPC3 CAR-T cells and target cells were mixed at different ratio (2×10) 3 cells/well each), cultured in 384-well plates for 24 hours. To assay the cytotoxicity of CAR-T on tumor cells, One-glo luminescent luciferase assay reagents (Promega #E6110) were prepared according to manufacturer's protocol and added to the co-cultured cells to detect the remaining luciferase activity in the well. Since luciferase is expressed only in tumor cells, the remaining luciferase activity in the well correlates directly to the number of viable target cells in the well. The maximum luciferase activity was obtained by adding culture media to target cells in the absence of effector cells. The minimum luciferase activity was determined by adding Triton X-100 at a final concentration of 1% at the time when the cytotoxicity assays were initiated. The specific cytotoxicity was calculated by the formula: Specific Cytotoxicity %=100%×(1-(RLUsample−RLUmin)/(RLUmax−RLUmin)).

Figure 2:
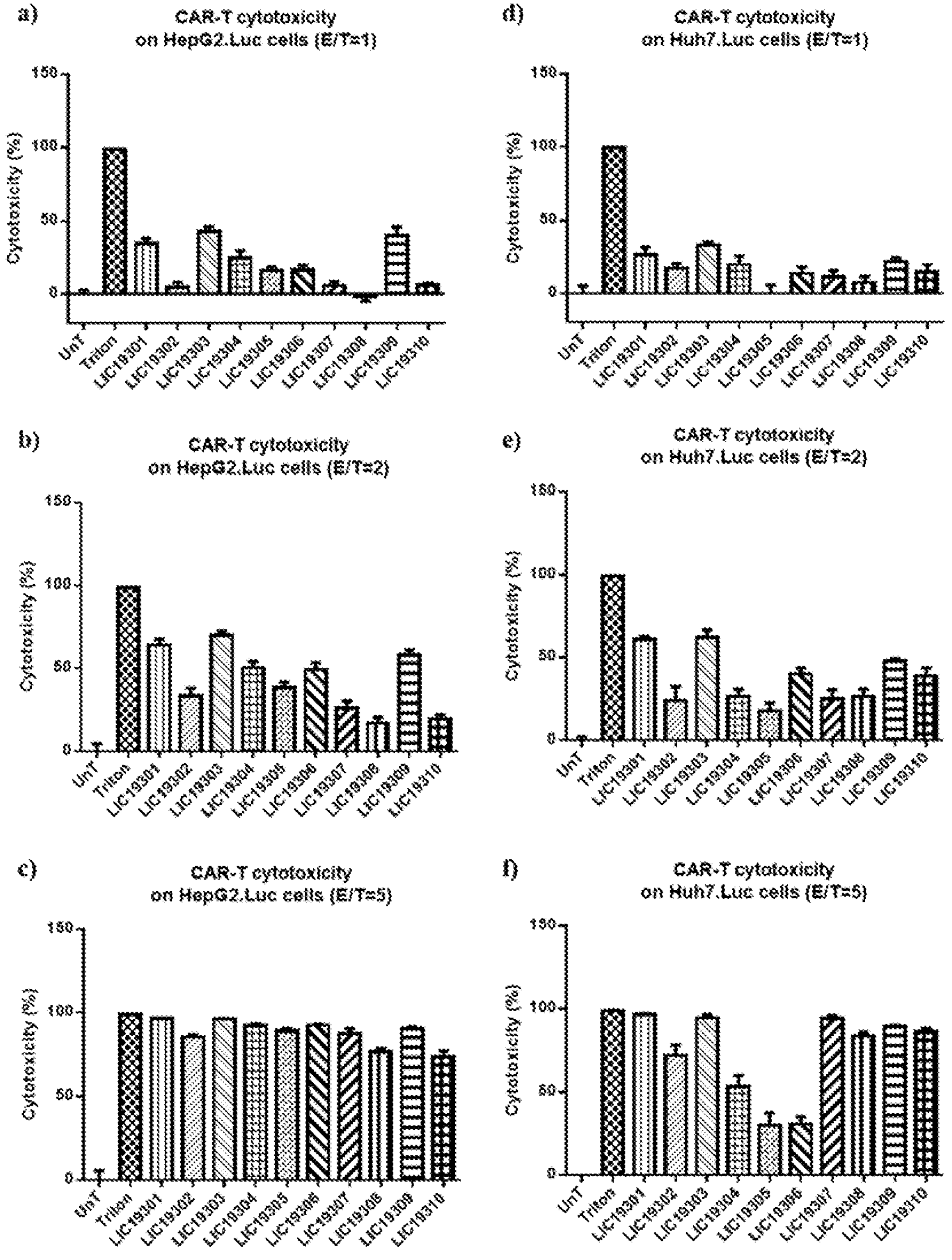
Figure 3:
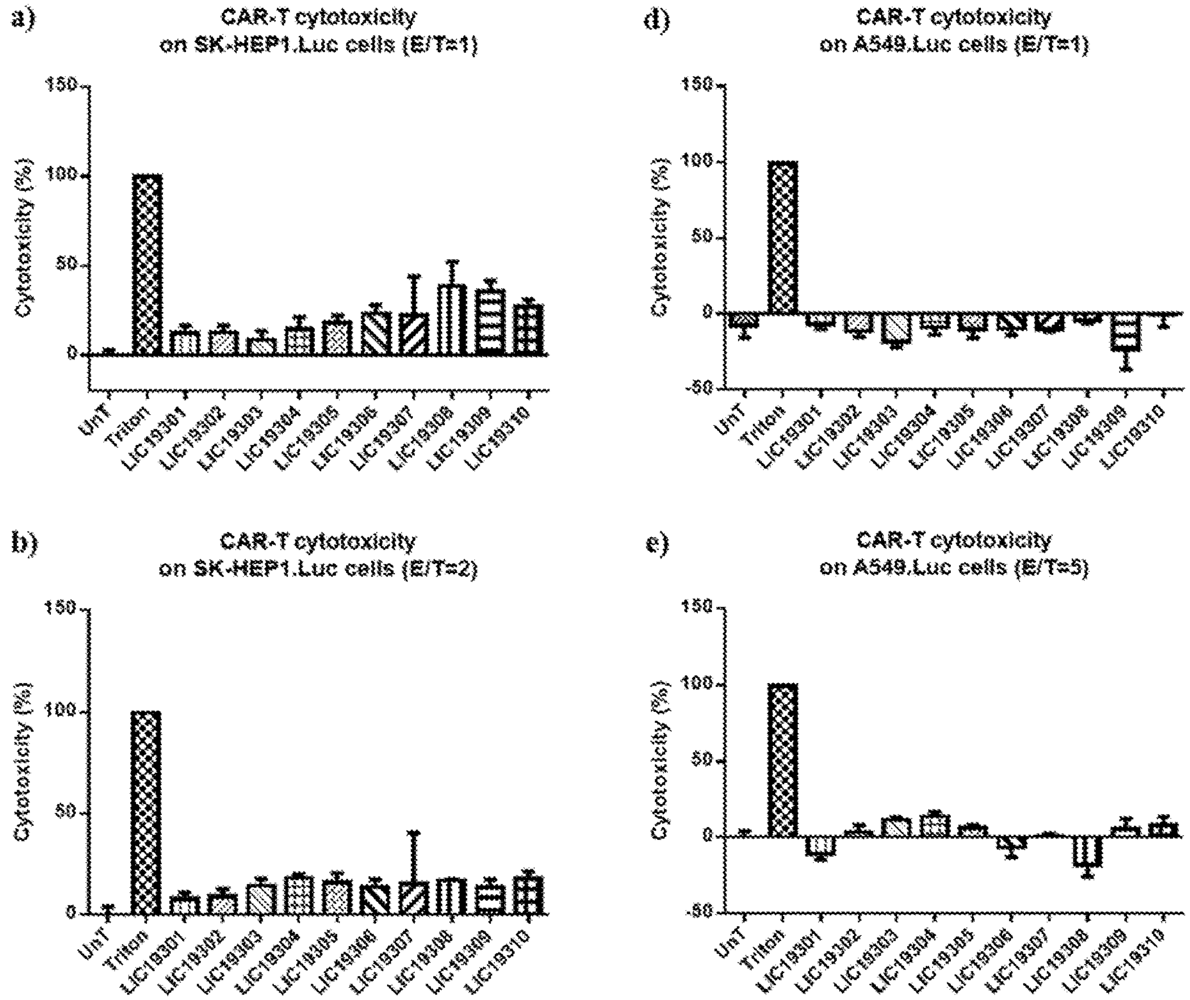

As shown in FIGS. 2-3, GPC3 CAR-T cells exhibited different levels of cytotoxicity on GPC3 positive-HCC cell line HepG2. Luc and Huh7.Luc cells in a dose dependent manner. But no CAR-T cells showed potent cytotoxicity on GPC3 negative cell line SK-HEP1. Luc and A549. Luc, as compared with UnT. Among these clones, LIC19301 CAR-T cells, LIC19303 CAR-T cells and LIC19309 CAR-T cells were most potent according to the cytotoxicity data. LIC19301 CAR-T cells, LIC19303 CAR-T cells and LIC19309 CAR-T cells showed nearly 100% cytotoxicity on both HepG2. Luc and Huh7.Luc cells at an E/T ratio of 5:1.

IFN-Gamma and TNF-Alpha Release

Figure 4:
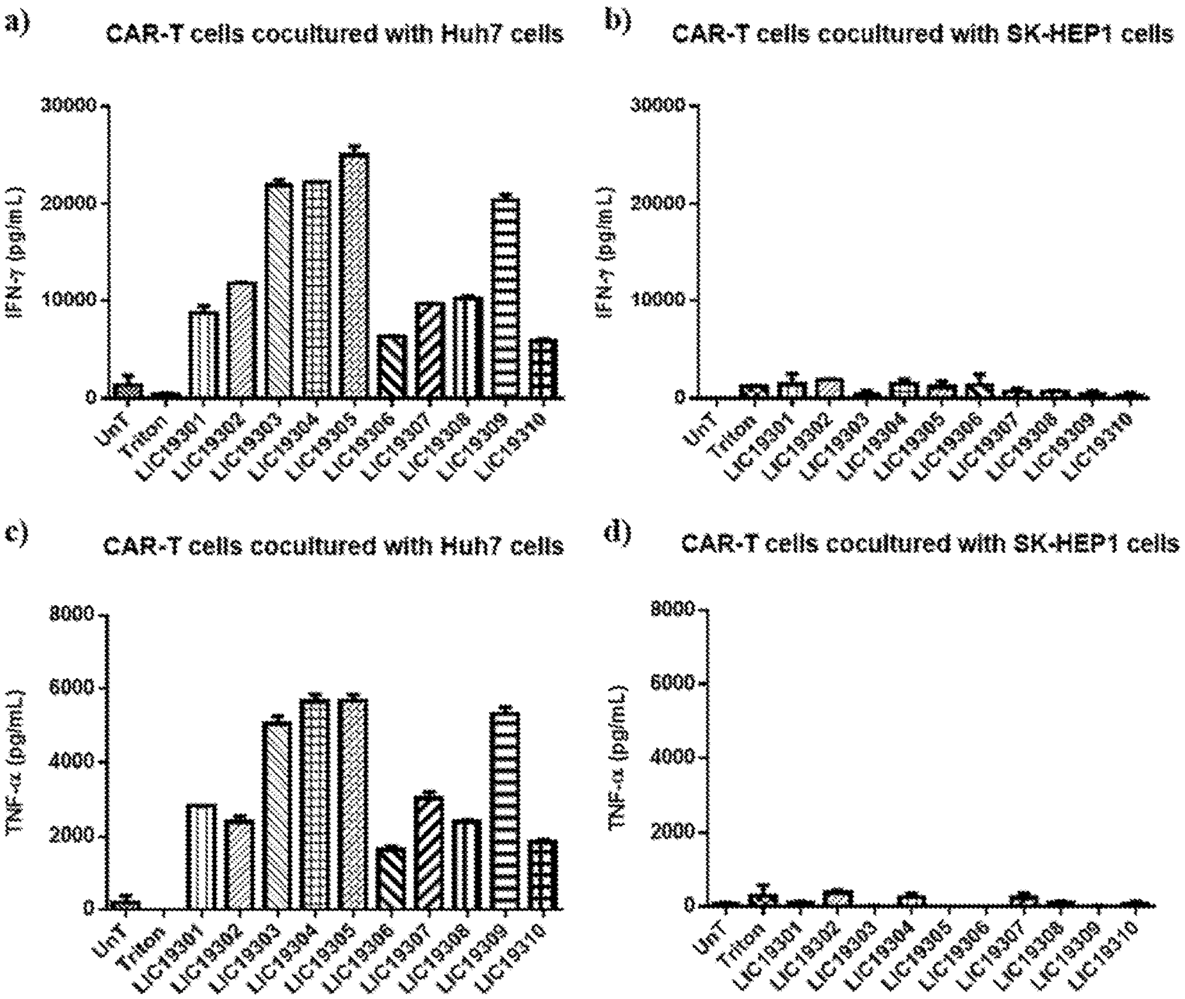
FIG. 4 shows cytokine secretion of CAR-T cells of LIC19301-LIC19310 after being co-cultured with Huh7 or SK-HEP1 for 24 hours. UnT refers to T cells un-electroporated with CAR.

In addition to the cytotoxic activity against GPC3 positive cancer cells, the ability of GPC3 CAR-T cells to produce IFN-γ and TNF-α was analyzed. GPC3 CAR-T cells and target cells (Huh7 or SK-HEP1) were mixed at the E/T ratio of 2 (2×10) 3 target cells/well each), cultured in a 384-well plate for 24 hours, and the concentration of IFN-γ and TNF-α produced in the culture supernatant was measured by ELISA. As a result, all of the GPC3 CAR-T cells derived from the above 10 types of scFv clones showed the ability to produce IFN-γ and TNF-α dependent on the expression of GPC3. IFN-γ and TNF-α release were both CAR and GPC3 antigen specific, but varied among different CAR-T cells and showed no significant correlation with cytotoxicity potency. As shown in FIG. 4, the concentration of IFN-γ and TNF-α secreted by CAR-T cells significantly increased after GPC3-based activation, within the range of 5809.7-24997.2 pg/mL (IFN-γ) and 1638.1-5667.9 pg/mL (TNF-α). LIC19303 CAR-T cells, LIC19304 CAR-T cells, LIC19305 CAR-T cells and LIC19309 CAR-T cells exhibited the highest cytokine release level among all the CAR-T cells tested after being co-cultured with GPC3 positive Huh7 cells, while all anti-GPC3 CAR-T cells showed no specific activation and cytokine secretion co-cultured with GPC3 negative SK-HEP1 cells.

6.3. Example 3-Anti-Tumor Effect of GPC3 CAR-T Cells after Adoptive Transfer In Vivo In vivo anti-tumor efficacy of LIC19309 CAR-T cells were evaluated in NCG mouse xenograft model. This model was created by sequential CRISPR/Cas9 editing of the Prkdc and Il2rg loci in the NOD/Nju mouse, generating a mouse coisogenic to the NOD/Nju. The NOD/Nju carries a mutation in the Sirpa (SIRP α) gene that allows for engrafting of foreign hematopoietic stem cells (Schuler et al., Cell, 1986, 46(7): 963-97 2; Sugamura et al., Annual review of immunology, 1996, 14(1): 179-20 5; Yamauchi et al., The Journal of the American Society of Hematology, 2013, 121(8): 1316-1325).

The Prkdc knockout generates a SCID-like phenotype lacking proper T-cell and B-cell formation. The knockout of the Il2rg gene further exacerbates the SCID-like phenotype while additionally resulting in a decrease of NK cell production. This "triple-immunodeficient" mouse strain is more immunocompromised than commonly used immunodeficient mouse strains including SCID and nude mice. Prkdc and Il2rg are part of the SCID (severe combined immunodeficiency) family of genes affecting maturation and formation of T cells, B cells, NK cells and, to a lesser degree, dendritic cells. Disrupting the Prkdc gene, encoding for the catalytic subunit of the DNA-dependent protein kinase enzyme, reduces function required for V(D)J recombination necessary in propagating antibody diversity of maturing T and B cells. Disrupting Il2rg, encoding of the common gamma subunit found in IL-2 and multiple IL receptors (IL-4, IL-7, IL-9, IL-15 and IL-21), prevents immature lymphocytes (T, B and NK cells) and other leukocytes from reaching maturation as the receptor are required to bind and induce cytokine-mediated signaling. The NCG mouse strain is similar to other triple-immunodeficient models capable of hosting xenograft cells, tissue and human immune systems components, thus enabling studies of tumor biology and immune-oncology, infectious disease, graft-versus-host disease (GvHD), hematopoiesis, and tissue transplant studies.

This strain was further transferred to Charles River in 2016, and now is available for North American customers, with nomenclatures as NOD-Prkdc$^{em26Cd52}$Il2rg$^{em26Cd22}$/NjuCrl and Strain Code: 572. Performance data of the NCG model were described in, e.g., Shultz et al., The Journal of Immunology, 1995, 154(1): 180-191; Covassin et al., Clinical & Experimental Immunology, 2011, 166(2): 269-280; and Ma and Huang, The FEBS journal, 2014, 281(23): 5186-5193.

For the subcutaneous xenograft model, 40 NCG mice aged 6-7 weeks were inoculated with Huh7 cells subcutaneously in the right foreleg ($1\times10^7$ cells/mouse). When the average tumor volume approached to 100 mm$^3$ (day 6 after the xenograft inoculation), mice were randomized into 3 groups and treated with LIC19309 CAR-T cells (2 M/mouse), un-electroporated T cells (2 M/mouse) and solvent only, respectively, by tail vein injection. Tumor size was measured with digital calipers twice per week. Tumor volume was calculated according to the following formula:

$$\text{Tumor volume} = \frac{(\text{length})\times(\text{width})2}{2}.$$

Human CD3 positive T cells in mouse blood were also detected by FACS on the day 7, 14 and 21 after the adoptive transfer.

Figure 5:
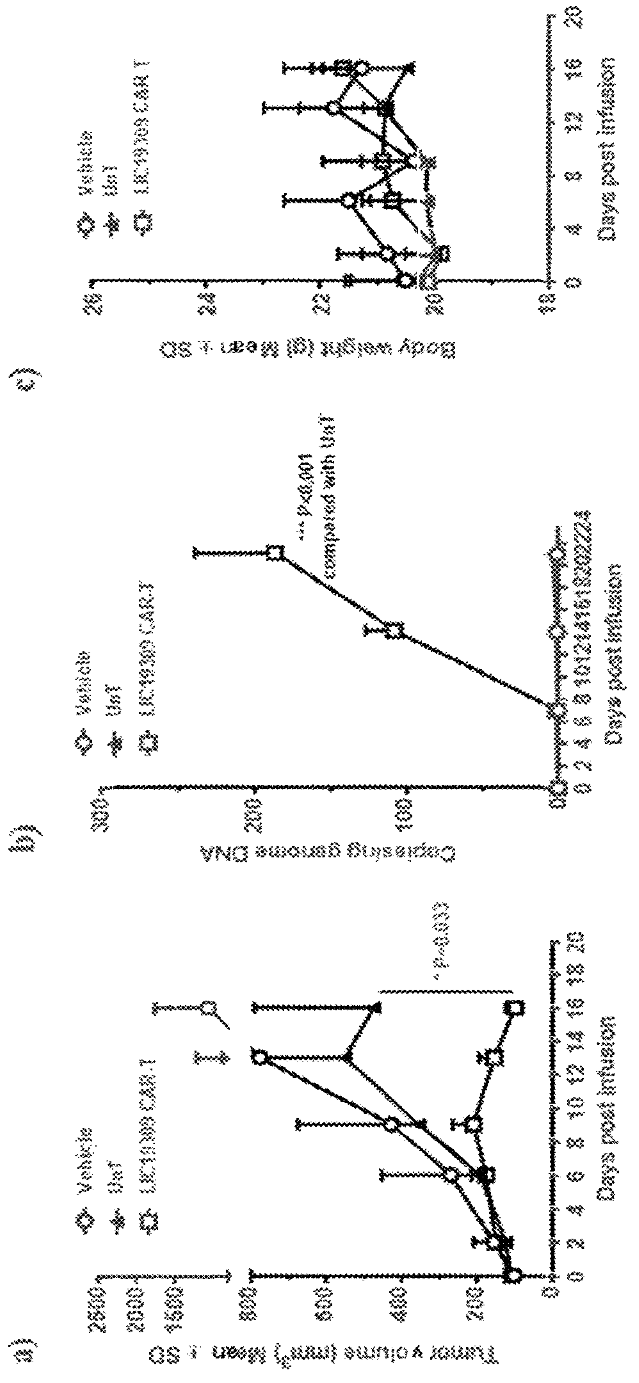
FIG. 5 shows the antitumor activity of LIC19309 CAR-T cells following administration to NCG mice engrafted with Huh7 cells.

As shown in FIG. 5 (part a), compared to the UnT group, mice having been administered adoptive transfer of LIC19309 CAR-T cells were observed to have a 78.9% reduction in tumor size (100.0 mm$^3$ VS 474.8 mm$^3$) at day 16, which suggested LIC19309 CAR-T cells are potent in tumor regression. As shown in FIG. 5 (part b), CAR gene copy number in mouse peripheral blood cells was detected by digital PCR, and LIC19309 CAR-T exhibited target-dependent significant expansion from day 7 and continuous for at least 2 weeks. The copy number of LIC19309 CAR-T cells at day 14 was 281.4 folds than that at day 0 (107.888 vs 0.3833). No mouse bodyweight loss was observed in all the three groups during this experiment (FIG. 5, part c).

6.4. Example 4—Generation of Anti-GPC3 Humanized Antibodies

Humanization Design of Mouse Antibody

Antibodies 1Ab19309 and 1Ab19305 were selected to perform antibody humanization. The variable domain sequences of anti-GPC3 mAb were searched against the human IgG germline database. Three human framework sequences with high homology to each antibody were chosen as human acceptors for both light and heavy chains. A humanized VH chain or VL chain was prepared by grafting CDRs of a murine antibody to FRs of a human germline. In some instances, backmutations can match the murine germline, but in other cases it cannot (as in the case with somatic mutations). The humanized Ab19309 and 1Ab19305 variable domains of three heavy chains were denoted as 9VH1, 9VH2, 9VH3 and 5VH1, 5VH2, 5VH3, respectively, while the humanized variable domains of three light chains were denoted as VL1, VL2, VL3. Sequence information of humanized VHs and VLs, as well as corresponding human germlines are shown in Table 8.

TABLE 8

Humanization antibodies variable domains

| Humanized variable chain code | Humanized variable chain SEQ ID NO. |
|---|---|
| 9VH1 | SEQ ID NO: 117 |
| 9VH2 | SEQ ID NO: 118 |
| 9VH3 | SEQ ID NO: 119 |

TABLE 8-continued

| Humanization antibodies variable domains | |
|---|---|
| Humanized variable chain code | Humanized variable chain SEQ ID NO. |
| 5VH1 | SEQ ID NO: 120 |
| 5VH2 | SEQ ID NO: 121 |
| 5VH3 | SEQ ID NO: 122 |
| VL1 | SEQ ID NO: 123 |
| VL2 | SEQ ID NO: 124 |
| VL3 | SEQ ID NO: 125 |

Production and Affinity of Humanized Antibodies

The humanized variable heavy chains and humanized variable light chains were designed as described above. Chimeric light chains (LC) were constructed by fusing humanized VL domains to human kappa constant regions (hIgKCL, SEQ ID NO: 126) and chimeric heavy chains (HC) were constructed by fusing humanized VH domains to human IgG1 constant regions (hIgG1CH, SEQ ID NO: 127). The designed plasmid of the heavy chain and the light chain were inserted into pTT5 vector to construct expression plasmids of full-length human IgGs, which was outsourced through GenScript's services. The humanized heavy chain (i.e., 9VH1-hIgG1CH, 9VH2-hIgG1CH, 9VH3-hIgG1CH, 5VH1-hIgG1CH, 5VH2-hIgG1CH, 5VH3-hIgG1CH) expression sequences including a leader sequence are shown in SEQ ID NO: 144-149. The humanized light chain (i.e., VL1-hIgKCL, VL2-hIgKCL. VL3-hIgKCL) expression sequences including a leader sequence are shown in SEQ ID NO: 150-152.

Entire anti-GPC3 humanized antibodies with full length of heavy chain and light chain were generated by HC and LC plasmid co-transduction. Chimeric 1Ab19309-hIgG1 and 1Ab19305-hIgG1 comprising chimeric heavy chain by fusing mouse VH with hIgG1CH and chimeric light chain by fusing mouse VL with hIgKCL were also generated as positive control.

Humanized antibodies were expressed in 10 mL HEK293-6E cell culture. Cells were spin down and the supernatant was kept. Affinity ranking was performed using the crude antibodies secreted to the medium by the Biacore™ SPR system. For affinity ranking, antibodies were immobilized on the sensor chip through Fc capture method. GPC3 was used as the analyte. Then several binders were selected to express in HEK293 or CHO-S cell culture. The recombinant IgGs secreted to the medium were purified using resin A affinity chromatography. The purified IgGs migrated as ~150 kDa band in SDS-PAGE under non-reducing condition, ~50 kDa and ~25 kDa bands under reducing condition. Judging from the SDS-PAGE, the purity of humanized IgGs were all over 90%.

The affinity of purified antibodies binding to GPC3 was individually confirmed using the Biacore™ T200 SPR system. Antibodies were immobilized on the sensor chip through Fc capture method. GPC3 was used as the analyte. The surface was regenerated before the injection of another antibody. The process was repeated until all antibodies are analyzed. The off-rates of antibodies were obtained from fitting the experimental data locally to 1:1 interaction model using the Biacore™ T200 evaluation software. The data of dissociation (kd) and association (ka) rate constants (KD) were calculated from the ration of kd over ka. The affinity of GPC3 to antibodies was summarized in Table 9 and Table 10.

TABLE 9

The affinity of GPC3 to purified humanized LAb19309 antibodies

| Name | Analyte | ka(1/Ms) | kd(1/s) | KD(M) | Rmax(RU) | $Chi^2(RU^2)$ |
|---|---|---|---|---|---|---|
| Chimeric LAb19309-hIgG1 | GPC3 | 6.71E+04 | 2.39E−04 | 3.56E−09 | 62.95 | 0.0911 |
| 9VH1VL3-hIgG1 | GPC3 | 9.13E+04 | 1.40E−04 | 1.53E−09 | 78.8 | 0.299 |
| 9VH3VL2-hIgG1 | GPC3 | 1.34E+05 | 9.01E−05 | 6.72E−10 | 71.14 | 0.237 |
| 9VH3VL3-hIgG1 | GPC3 | 1.29E+05 | 1.45E−04 | 1.13E−09 | 72.9 | 0.389 |

TABLE 10

The affinity of GPC3 to purified humanized LAb19305 antibodies

| Ligand | Analyte | ka(1/Ms) | kd(1/s) | KD(M) | Rmax(RU) | $Chi^2(RU^2)$ |
|---|---|---|---|---|---|---|
| 5VH2VL3-hIgG1 | GPC3 | 1.61E+05 | 8.76E−05 | 5.44E−10 | 61.3 | 0.0401 |
| 5VH2VL2-hIgG1 | GPC3 | 1.56E+05 | 8.91E−05 | 5.72E−10 | 78.55 | 0.0665 |
| Chimeric LAb19305-hIgG1 | GPC3 | 1.23E+05 | 1.03E−04 | 8.40E−10 | 107.4 | 0.0675 |
| 5VH1VL2-hIgG1 | GPC3 | 1.07E+05 | 1.17E−04 | 1.10E−09 | 80.25 | 0.0252 |

6.5. Example 5—Preparation of Humanized Monospecific scFv Based CARs and In Vitro Screening Based on affinity ranking of humanized antibodies, the VH chain and VL chain of 9VH1VL3-hIgG1 mAb and 9VH3VL2-hIgG1 mAb were selected to construct chimeric antigen receptors, named as huLIC19309a and huLIC19309b, respectively.

For huLIC19309a CAR, LAb9VH1VL3 scFv (SEQ ID NO: 128) was constructed by fusing 9VL3 and 9VH1 regions via a linker peptide (SEQ ID NO: 132). The resulting CAR (huLIC19309a CAR) comprises SEQ ID NO: 130. Similarly, for huLIC19309b CAR, LAb9VH3VL2 scFv (SEQ ID NO: 129) was constructed by fusing 9VL2 and 9VH3 sequence with the linker (SEQ ID NO: 132). The resulting CAR (huLIC19309b CAR) comprises SEQ ID NO: 131.

A CAR backbone sequence encoding a CAR backbone polypeptide comprising from the N-terminus to the C-terminus: a CD8α hinge domain (SEQ ID NO: 102), a CD8α transmembrane domain (SEQ ID NO: 103), a CD137 co-stimulatory signaling domain (SEQ ID NO: 104), and a CD3ζ cytoplasmic signaling domain (SEQ ID NO: 105) was chemically synthesized and cloned into a pre-modified lentiviral vector (pLSINK-BBzBB) downstream and operably linked to a constitutive hEF1α promoter for in vitro transcription. Multi-cloning sites (MCS) in the vector allowed insertion of a nucleic acid sequence comprising a Kozak sequence operably linked to a nucleic acid sequence encoding a CD8α signal peptide (SEQ ID NO: 101) fused to the N-terminus of an anti-GPC3 humanized scFv fragment into the CAR backbone vector, upstream and operably linked to the CAR backbone sequence. The nucleic acid sequence encoding the CD8α signal peptide and the anti-GPC3 humanized scFv fragment was chemically synthesized and cloned into pLSINK-BBBB CAR backbone via the EcoRI (5'-GAATTC-3) (SEQ ID NO: 142) and SpeI (5'-ACTAGT-3') (SEQ ID NO: 141) restriction sites by molecular cloning techniques known in the art.

The lentivirus packaging plasmid mixture containing pMDLg.pRRE (Addgene #12251), pRSV-REV (Addgene #12253) and pMD2.G (Addgene #12259) were pre-mixed with the vectors expressing CAR constructs at a pre-optimized ratio with polyetherimide (PEI), then incubated at 25° C. for 5 min. Then HEK293 cells were added into the transfection mix. Afterwards, cells were incubated overnight in a cell incubator with 5% CO2 at 37° C. The supernatants were collected after centrifuged at 4° C. and 3000 g for 15 min, and filtered through a 0.45 μm PES filter followed by ultra-centrifugation for lentivirus concentration. Then the supernatants were carefully discarded and the virus pellets were rinsed cautiously with pre-chilled DPBS. The viruses were liquated properly, and stored at −80° C. The virus titer was determined by a titration method via transduction of CHO (Chinese hamster ovarian) cell line.

CAR-T Cell Preparation

PBMCs were purchased from Allcells (#LP190116). Human T cells were purified from PBMCs and pre-activated using the method in Example 2.

Figure 6:
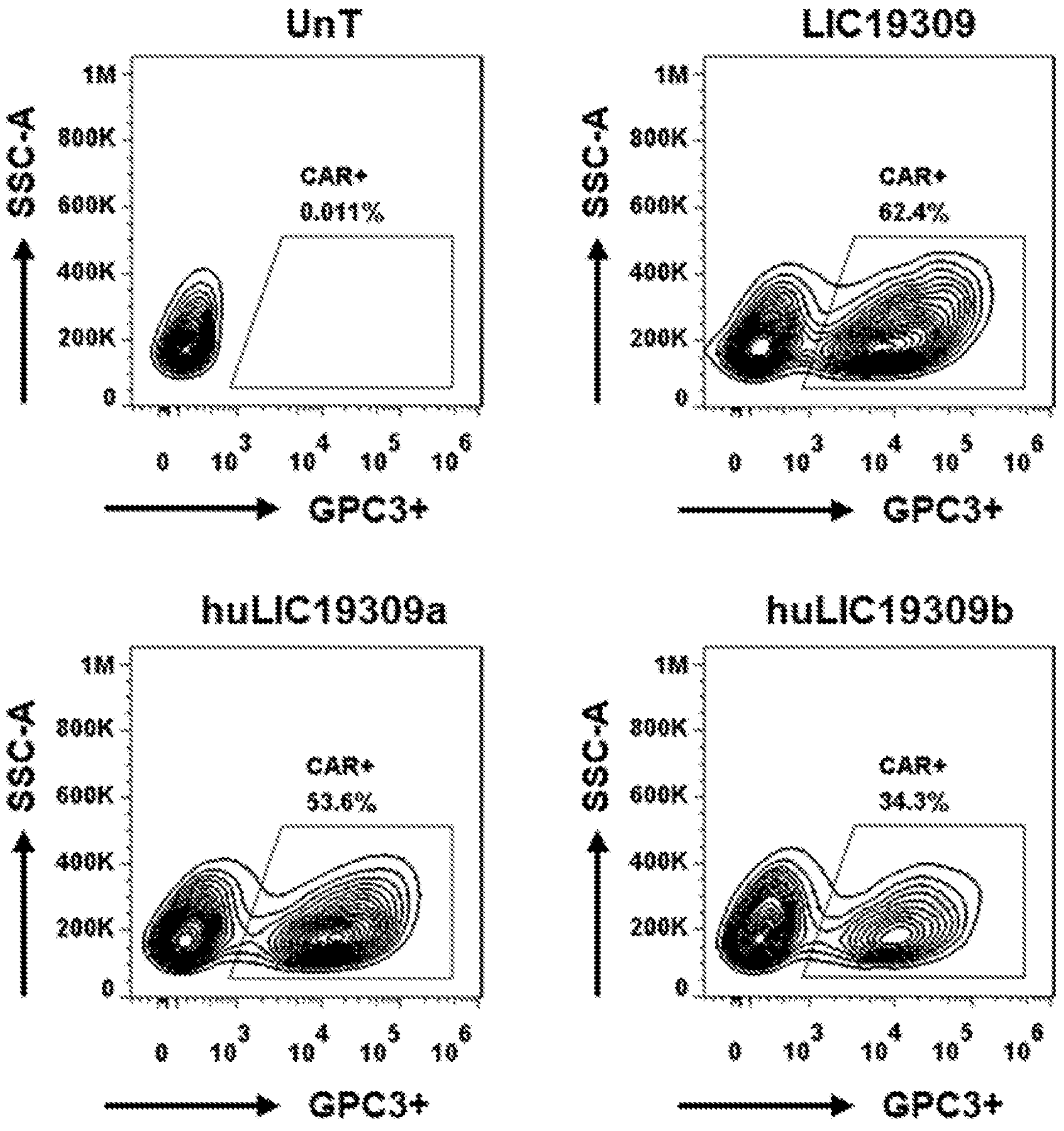
FIG. 6 shows the expression levels of humanized CAR-T cells.

For CAR-T cells preparation, the pre-activated T cells were re-suspended at 1× 10) 6 cells/mL in 1 mL complete medium (Tex MACS GMP Medium+300 IU/mL IL-2), and different lentivirus (MOI=10) was added for transfection. Un-transfected T lymphocytes (UnT) was used as a negative control. The positive rates of LIC19309, huLIC19309a and huLIC19309b CAR-T were 62.4%, 53.6% and 34.3%, respectively (FIG. 6).

Cytotoxicity Assay

Target cells were either GPC3 positive human hepatocellular carcinoma (HCC) cell line HepG2 (ATCC #HB-8065), Huh7 (Cobioer #CBP60202), PLC/PRF/5 (ATCC #CRL-8024) or GPC3 negative cell line K562 (ATCC #CCL-243), Kato III (ATCC #HTB-103), A549 (ATCC #CRM-CCL-185), NUGC4 (JCRB #0) 1262018). All the cell lines were engineered to express firefly luciferase with the techniques known in the art. GPC3 CAR-T cells and target cells were mixed at different ratio ($2\times10^3$ cells/well each), cultured in 384-well plates for 24 hours. To assay the cytotoxicity of CAR-T on tumor cells, One-glo luminescent luciferase assay reagents (Promega #E6110) were prepared according to manufacturer's protocol.

As shown in FIG. 7 and FIG. 8, humanized GPC3 CAR-T cells exhibited different levels of cytotoxicity on GPC3 positive-HCC cell line HepG2. Luc, Huh7.Luc and PLC/PRF/5.Luc cells in a dose dependent manner. At an E/T ratio of 3:1, LIC19309 CAR-T cells showed a potent killing efficiency of 98.30%, 94.06% and 82.33% on HepG2 cells, Huh7 cells and PLC/PRF/5 cells, respectively. At the same condition, both of huLIC19309a CAR-T cells and huLIC19309b CAR-T cells showed a comparative cytotoxicity potency of 93.75%, 97.47%, 73.51% and 97.00%, 94.06%, 72.21% on these three cell lines, indicating no potency compromise of CAR-T cells by antibody humanization. None of the CAR-T cells showed significant cytotoxicity on GPC3 negative cell lines as compared with UnT (FIG. 8).

IFN-Gamma and TNF-Alpha Release

In addition to the cytotoxic activity against GPC3 positive cancer cells, the ability of humanized GPC3 CAR-T cells to produce IFN-γ and TNF-α was analyzed. GPC3 CAR-T cells only or GPC3 CAR-T cells mixed with target cells (HepG2, Huh7 or PLC/PRF/5) at the different E/T ratio (2×10) 3 target cells/well each, E/T=3:1, 1:1, 1:3), cultured in 384-well plate for 20 hours, and the concentration of IFN-γ and TNF-α produced in the two culture supernatant were measured by HTRF. IFN-γ and TNF-α release were both CAR and GPC3 antigen specific, but varied among different CAR-T cells and showed no significant correlation with cytotoxicity potency. As shown in FIG. 9 and FIG. 10, the release level of IFN-γ and TNF-α significantly increased with antigen-specific CAR-T activation. IFN-γ release level increased from 1015.99 pg/mL to 31037.50 pg/mL and TNF-α from 21.51 pg/mL to 5447.91 pg/mL after huLIC19039a CAR-T cells co-cultured with GPC3 positive HepG2 cells for 20 h at an E/T of 3:1. At the same condition, the IFN-γ release level of huLIC19309b CAR-T cells and LIC19309 CAR-T cells after 20 hours' co-culture with HepG2 was 24848.92 pg/mL and 29339.66 pg/mL, respectively, while the TNF-α release level was 6080.85 pg/mL and 5256.41 pg/mL, respectively (FIG. 9 and FIG. 10). In a comprehensive perspective, humanized huLIC19309a CAR-T cells and huLIC19309b CAR-T cells exhibited a comparative cytokine release level with non-humanized LIC19309 CAR-T cells.

6.6. Example 6—Anti-Tumor Effect of Humanized GPC3 CAR-T Cells after Adoptive Transfer In Vivo LIC19309 CAR-T cells and huLIC19309b CAR-T cells were selected to perform the in vivo efficacy study. For the subcutaneous xenograft model, 28 NCG mice aged 6-7 weeks were inoculated with Huh7 cells subcutaneously in the right foreleg ($1\times10^7$ cells/mouse). When the average tumor volume approached to 100 $mm^3$ (day 6 after the xenograft inoculation), mice were randomized into 7 groups and treated with huLIC19309b CAR-T cells (0.33, 1, 3 M/mouse), LIC19309 CAR-T cells (0.33, 1, 3 M/mouse) and solvent only (Vehicle), respectively, by tail vein injection. Tumor size was measured with digital calipers twice per week. Tumor volume was calculated according to the following formula:

$$\text{Tumor volume} = \frac{(\text{length}) \times (\text{width})2}{2}.$$

As shown in FIG. 11 (part a), compared to the control group (Vehicle) with an average volume of 1747.02 $mm^3$, G7 group mice with 3 M huLIC19309b CAR-T cells treatment were observed to have a 97.4% reduction in tumor size with an average volume of 45.41 $mm^3$ at day 17, and two mice are in the tumor free state, which showed potent anti-tumor efficacy of huLIC19309b CAR-T cells. Mice treated with 3 M LIC19309 CAR-T cells in G4 showed a 67.7% tumor reduction with a volume of 564.75 $mm^3$. Based on the tumor volume data, humanized huLIC19309b CAR-T cells showed a significant in vivo efficacy advantage over LIC19309 CAR-T cells at all three doses of 0.33 M, 1 M and 3 M.

To analyze the CAR-T expansion potency, CAR copy number in mouse blood were also detected by ddPCR (Droplet Digital PCR) on the day 7, 14, 21 and 28 after the adoptive transfer. As shown in FIG. 11 (part b), huLIC19309b CAR-T exhibited target-dependent significant expansion from day 7 to day 14, and reached the highest copy numbers of 119.09 copies/ng. After reaching the peak, it has maintained about 50 copies/ng for 2 weeks.

The mouse bodyweight showed a negative correlation with tumor burden. As the tumor burden increased and general behavioral status deteriorated, the bodyweight of mice in control group (Vehicle) decreased simultaneously. At day 17, the average bodyweight of control group was 19.50 g, while the average bodyweight of LIC19309 CAR-T cells treated mice was 19.95 g, 22.61 g and 23.34 g at the dose of 0.33 M, 1 M and 3 M. Compared with vehicle or LIC19309 CAR-T cells treated mice, huLIC19309b CAR-T cells treated mice showed a higher bodyweight of 21.41 g, 23.21 g, and 25.57 g at the dose of 0.33 M, 1 M and 3 M at day 17, indicating a more potent efficacy of huLIC19309b CAR-T cells and more healthy mouse status (FIG. 11, part c).

6.7. Example 7—Preparation of CAR-T Cells Over-Expressing Human IL12p40 and Human CCL-19

6.7.1. Construction of Chimeric Antigen Receptors

To construct humanized anti-GPC3 scFv CAR (H93 CAR), a CAR backbone sequence encoding a CAR backbone polypeptide comprising from the N-terminus to the C-terminus: a CD8α hinge domain (SEQ ID NO: 102), a CD8α transmembrane domain (SEQ ID NO: 103), a CD137 co-stimulatory signaling domain (SEQ ID NO: 104), and a CD3ζ cytoplasmic signaling domain (SEQ ID NO: 105) was chemically synthesized and cloned into a pre-modified lentiviral vector (pLSINK-BBBB) downstream and operably linked to a constitutive hEF1α promoter for in vitro transcription. Multi-cloning sites (MCS) in the vector allowed insertion of a nucleic acid sequence comprising a Kozak sequence operably linked to a nucleic acid sequence encoding a CD8α signal peptide (SEQ ID NO: 101) fused to the N-terminus of an anti-GPC3 humanized scFv fragment (i.e., LAb9VH3VL2 scFv described above comprising the amino acid sequence of SEQ ID NO: 129) into the CAR backbone vector, upstream and operably linked to the CAR backbone sequence. The nucleic acid sequence encoding the CD8α signal peptide and the anti-GPC3 humanized scFv fragment was chemically synthesized and cloned into pLSINK-BBzBB CAR backbone via the EcoRI (5'-GAATTC-3') and SpeI (5'-ACTAGT-3') restriction sites by molecular cloning techniques known in the art. The amino acid sequence of the resulting H93 CAR is SEQ ID NO: 131. H93 CAR is another name of huLIC19309b CAR described above. The CAR coding region is presented in the top part of FIG. 12.

Based on H93 CAR backbone. MCS in H93M CAR vector allowed insertion of a nucleic acid sequence comprising a nucleic acid sequence encoding human IL12p40 (SEQ ID NO: 135) and human CCL-19 (SEQ ID NO: 136) linked by a 2A self-cleaving peptide (e.g., a T2A peptide shown in SEQ ID NO: 139) fused to the C-terminus of another 2A self-cleaving peptide (e.g., a P2A fragment shown in SEQ ID NO: 138), upstream and operably linked to the C-terminus of CD3ζ cytoplasmic signaling domain. The nucleic acid sequence encoding the P2A peptide and IL12p40-T2A-CCL-19 peptide was chemically synthesized and cloned into pLSINK-BBzBB CAR backbone via the HpaI (5'-GTTAAC-3') (SEQ ID NO: 143) and MluI (5'-ACGCGT-3') (SEQ ID NO: 140) restriction sites. The amino acid sequence of the resulting H93M CAR is SEQ ID NO: 133 and the nucleic acid sequence encoding H93M CAR is shown in SEQ ID NO: 137. The CAR coding region of H93M is presented in the middle part of FIG. 12. Without being bound to any theory, the overexpressed IL 12p40 in H93M CAR-T cells could form IL-23 with the endogenous IL-23a p19 subunit which was reported to being upregulated by T cells upon TCR stimulation. See e.g., Ma, et al., Interleukin-23 engineering improves CAR T cell function in solid tumors. Nat Biotechnol. 2020 April; 38(4):448-459.

The lentivirus packaging plasmid mixture containing pMDLg.pRRE (Addgene #12251), pRSV-REV (Addgene #12253) and pMD2.G (Addgene #12259) were pre-mixed with the vectors expressing CAR constructs at a pre-optimized ratio with polyetherimide (PEI), then incubated at 25° C. for 5 min. Then HEK293 cells were added into the transfection mix. Afterwards, cells were incubated overnight in a cell incubator with 5% $CO_2$ at 37° C. The supernatants were collected after centrifuged at 4° C. and 3000 g for 15 min, and filtered through a 0.45 μm PES filter followed by ultra-centrifugation for lentivirus concentration. The supernatants were carefully discarded and the virus pellets were rinsed cautiously with pre-chilled DPBS. The viruses were liquated properly, and stored at −80° C. The virus titer was determined by a titration method via transduction of CHO (Chinese hamster ovarian) cell line.

6.7.2. CAR-T Cell Preparation

PBMCs were purchased from TPCS (#A19Z284097). Human T cells were purified from PBMCs using Pan T cell isolation kit (Miltenyi #130-096-535) and pre-activated using the method in Example 2.

For CAR-T cells preparation, the pre-activated T cells were plated in 24-well plates at a density of $0.5\times10^6$ cells/well. Then, the purified virus were added into the wells. After overnight, the transduced cells were placed into a 24-well G-Rex (Wilson Wolf #80192M) after collecting, centrifugation and re-suspended with fresh RPMI-1640+300 IU/mL IL-2. Un-transduced T cells (UnT) were used as a negative control. On day 7, the CAR positive rates of naked H93 CAR-T cells and H93M CAR-T cells were 39.3% and 32.5%, respectively (FIG. 13).

6.7.3. IL-23 and CCL-19 Expression

In order to verify the structure of H93M CAR, the CAR-T cells were cultured in normal condition (RPMI-1640+300 IU/mL IL-2) and the secretion of IL-23 and CCL-19 were analyzed. Briefly, cells were cultured at $1\times10^6$ cells/mL in 6-well plates and supernatants were harvested on day 12, 14 and 17, respectively. The human IL-23 kit (CISBIO #62HIL23PEG) and CCL-19 ELISA kit (Abcam #ab100601) were used to determine the amount of IL-23 and CCL-19 according to manufacturer's protocol. As shown in FIG. 14, only H93M CAR-T cells had the secretion of IL-23 (286.9 pg per $10^6$ cells-570.3 pg per $10^6$ cells) and CCL-19 (65.4 pg per $10^6$ cells-237.2 pg per $10^6$ cells) compared with H93 CAR-T cells and UnT (Neither IL-23 nor CCL-19 expression was detected).

6.8. Example 8—In Vitro CAR-T Cells Repeat Challenge Assay

To evaluate the persistence and exhaustion of CAR-T cells in vitro. CAR-T cells repeat challenge model was set up. CAR-T cells were constantly stimulated by GPC3 positive tumor cells for several rounds to gain an exhaustion phenotype of CAR-T cells. There were three groups of treatment in the re-challenge assay: H93 CAR-T group (the initial CAR-T cells were H93 CAR-T cells). H93M CAR-T group (the initial CAR-T cells were H93M CAR-T cells) and UnT (the initial T cells were T cells un-transduced with CAR). For the first round (round 1) of re-challenge. CAR-T cells were co-cultured with tumor cells at 1:1 E/T ratio in a 6-well plate. After overnight. CAR-T cells in the well were gently collected, centrifuged, and re-suspended in fresh CAR-T culture medium (RPMI-1640+300 IU/mL IL-2). Then CAR-T cells were added to a new plate for another 2 days. Where after. CAR-T cells in the well were collected, re-suspended in fresh medium again and added to a new plate seeded with fresh tumor cells (round 2). The number of fresh tumor cells added was calculated by the positive ratio of CAR-T cells at the end of the former round. This procedure could be repeated for several rounds depending on the cell number and viability of the remaining CAR-T cells. Exhaustion markers PD-1 and LAG3 of CD4+ T cells and CD8+ T cells in CAR+ T cells were analyzed 24 hours after each round's tumor cell re-challenge. T cells were counted at the end of each round and the cytotoxicity assay was performed on GPC3 positive HCC cell line PLC/PRF/5 72 hours after stimulation.

6.8.1. Expansion of T Cells

To determine the benefits of the expansion function of H93M CAR-T cells, the cell number and viability of total T cells were recorded at the end of each round of re-challenge.

As shown in FIG. 15A, repeat stimulations with PLC/PRF/5 cells resulted in a significant expansion of cells in H93M CAR-T group (138.4 folds at round 6) in comparison with that in H93 CAR-T group (10.5 folds at round 6) and that in UnT group (0.2 folds at round 6). In parallel, the cell viability of H93M CAR-T group was remained high, as a comparison, the H93 CAR-T group and UnT group were gradually reduced after each stimulation (FIG. 15B).

6.8.2. Cytotoxicity Assay and Cytokine Release

The cytotoxicity of CAR-T cells was also assessed at the end of every two rounds in CAR-T re-challenge assay at total T cells:target cells ratio of 1:1. The target cell was GPC3 positive PLC/PRF/5 cell, which was engineered to express firefly luciferase with the techniques known in the art. The cells collected at the end of every two rounds and the target cells were mixed (2×10) 3 cells/well each), cultured in 384-well plates for 24 hours. To assay the cytotoxicity of CAR-T cells on tumor cells, One-glo luminescent luciferase assay reagents (Promega #E6110) were prepared according to manufacturer's protocol and added to the co-cultured cells to detect the remaining luciferase activity in the well. Since luciferase is expressed only in tumor cells, the remaining luciferase activity in the well correlates directly to the number of viable target cells in the well. The maximum luciferase activity was obtained by adding culture media to target cells in the absence of effector cells. The minimum luciferase activity was determined by adding Triton X-100 at a final concentration of 1% at the time when the cytotoxicity assays were initiated. The specific cytotoxicity was calculated by the formula: Specific Cytotoxicity %=100%×(1−(RLUsample−RLUmin)/(RLUmax−RLUmin)).

As shown in FIG. 16A, H93M CAR-T group showed higher cytotoxicity than H93 CAR-T group after round 3, except that after the round 1 showed equal cytotoxicity (21.1% vs 22.4%). Concretely, H93M CAR-T group exhibited average cytotoxicity of 74.4% after round 3, and increased slightly after round 5 (80.7%) and round 7 (83.4%). While the relative lower cytotoxicity were observed in H93 CAR-T group, which showed average cytotoxicity of 52.7% (round 3), 57.9% (round 5) and 47.0% (round 7), respectively. Indicating H93M CAR-T group had a sustained high levels of cytotoxicity on GPC3 positive-HCC cell line PLC/PRF/5.Luc cells.

To further verify the sustained cytotoxic activity of H93M CAR-T cells against GPC3 positive tumor cells in comparison with H93 CAR-T cells in the re-challenge assay, TNF-α and IFN-γ production were analyzed by ELISA after coculturing CAR-T cells with PLC/PRF/5.Luc cells at 1:1 E/T ratio (total T cells:target cells) for 24 hours. As a result, the ability to produce TNF-α and IFN-γ of H93M CAR-T group were significant higher compared with H93 CAR-T group, and showed significant correlation with cytotoxicity potency in all rounds. As shown in FIGS. 16B and 16C, the concentration of TNF-α and IFN-γ secreted by cells in H93M CAR-T group significantly increased after round 3 to round 5, within the range of 451.2-1151.1 pg/mL (TNF-α) and 18353.7-37072.7 pg/mL (IFN-γ), while the concentration of TNF-α and IFN-γ secreted by cells in H93 CAR-T group were gradually reduced after round 3 to round 7, within the range of 197.1-129.2 pg/mL (TNF-α) and 4993.1-1672.1 pg/mL (IFN-γ).

6.8.3. Rates Change of Positive CAR-T Cells

The positive rates of H93 CAR-T cells and H93M CAR-T cells were calculated after each two rounds, which were almost identical increasing with the rounds of stimulation, within the range of 30%-86%. Finally, the positive rates of H93 CAR-T cells and H93M CAR-T cells were not increased after round 5 (FIG. 17). H93M CAR-T cells showed high cytotoxicity comparing the increasing cytotoxicity (FIG. 16A) with the flat CAR+% (FIG. 17) after round 5 re-challenge.

6.8.4. Exhaustion of T Cells

Figure 18A:
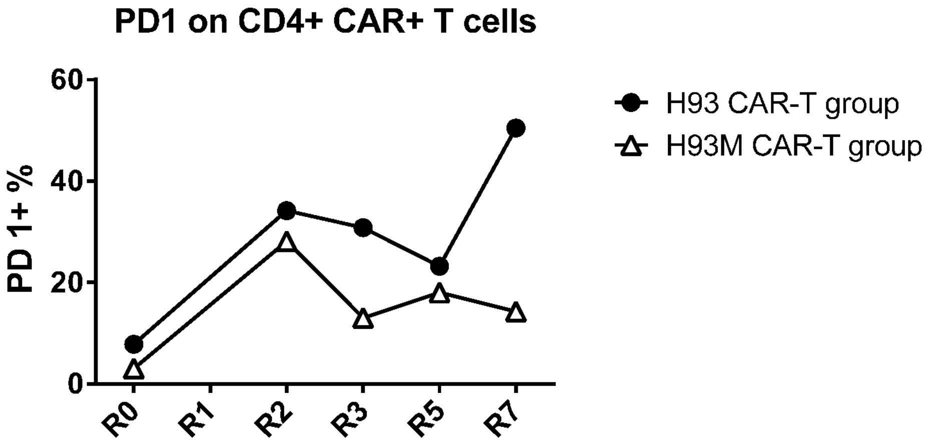
Figure 18B:
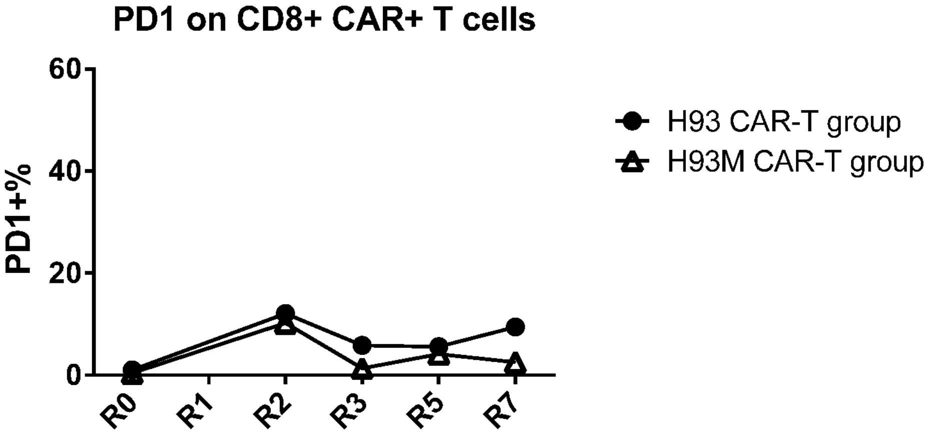
Figure 18C:
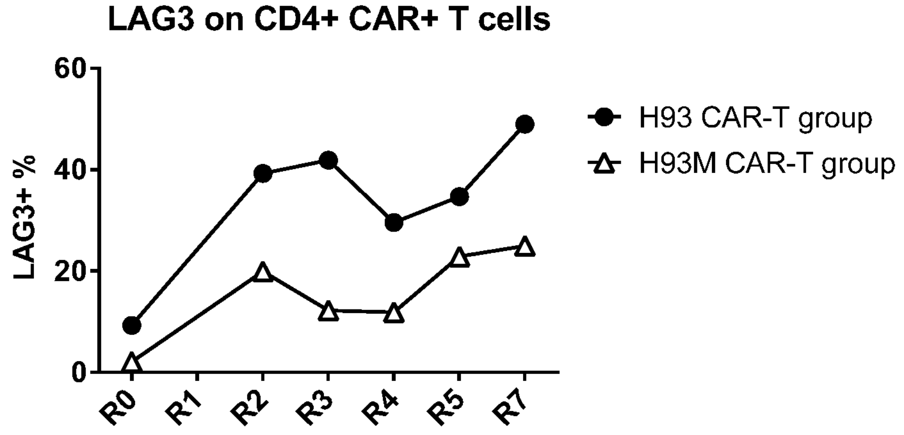
Figure 18D:
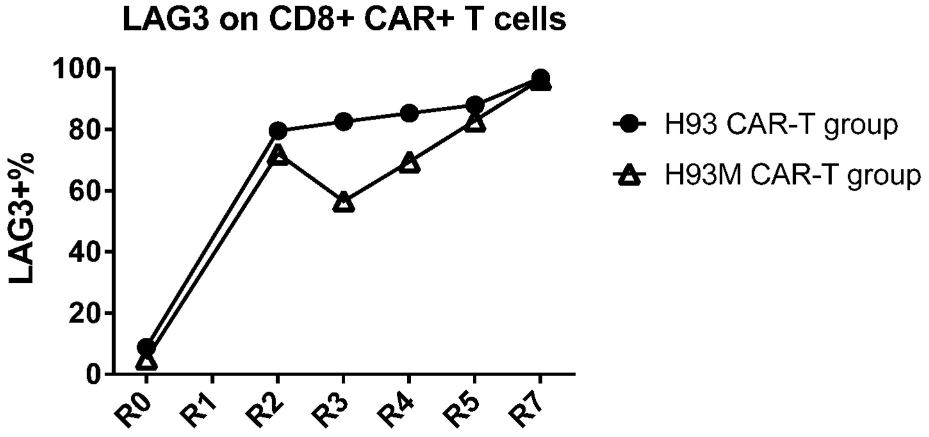

T cell exhaustion was evaluated 24 hours after each round in the re-challenge assay. PD-1 and LAG-3 as two exhaustion markers were marked using anti-human PD-1 antibody (Biolegend #329908) and anti-LAG-3 antibody (Invitrogen #17-2239-42), respectively and the expression levels of CD4+CAR+ T cells and CD8+CAR+ T cells double positive subsets were analyzed. As shown in FIGS. 18A-18D. H93M CAR-T group showed reduced expression of the exhaustion markers PD-1 and LAG3, as compared to H93 CAR-T group in all rounds. Especially in rounds 3 to 5, the PD-1 expression of CD4+CAR+ double positive subset in H93M CAR-T group was between 13% and 18%, while H93 CAR-T group was above 30% (FIG. 18A). H93M CAR-T group had significant lower LAG-3 expression (12%-25%) than H93 CAR-T group (30%-49%) in CD4+CAR+ double positive subset in all rounds (R2-R7) (FIG. 18C). In CD8+CAR+ double positive subset, the expression level of PD-1 in H93M CAR-T group still lower than H93 CAR-T group (1.3%-4.1% vs 5.6%-9.4% in round 3 to round 7) (FIG. 18B), and the LAG3 expression level of H93M CAR-T group was between 56.6% and 82.9% that was lower than that of the H93 CAR-T group (82.7%-88.1%) in round 3 to round 5 (FIG. 18D), indicating H93M CAR-T cells have the ability of resistance to exhaustion.

6.9. Example 9—Cell Migration Assay

To evaluate the chemotactic function of CCL-19, cell migration assay was performed. Chemotaxis of the responder T cells was measured by migration through a polycarbonate filter of 5-μm pore-size in 96-well transwell chambers (Corning). CAR-T cells and UnT cells were stimulated with GPC3 positive human HCC cell line PLC/PRF/5 cells and the co-culture supernatant was collected after 30 hours. Then 125 μL of supernatant was placed in the lower chambers, and 75 μL untreated T cells (0.075 M) were incubated in the upper chambers. After 4, 6 and 8 hours, the T cells migrated from the upper chamber to the lower chamber were counted by blood counting chamber. There were three groups of treatment in cell migration assay: H93 CAR-T group (the supernatant in the lower chamber was from H93 CAR-T cells co-cultured with PLC/PRF/5 cells). H93M CAR-T group (the supernatant in the lower chamber was from H93M CAR-T cells co-cultured with PLC/PRF/5 cells) and UnT group (the supernatant in the lower chamber was from UnT cells co-cultured with PLC/PRF/5 cells).

As shown in FIG. 19A, more T cells were attracted into the supernatant of H93M CAR-T cells (with secretion of CCL-19) co-cultured with PLC/PRF/5 cells than that of H93 CAR-T cells co-cultured with PLC/PRF/5 cells and that of UnT cells co-cultured with PLC/PRF/5 cells at different timing (H93M CAR-T group vs H93 CAR-T group: $P<0.0001$). Concretely. H93M CAR-T group could completely attract all T cells of upper chambers on 6 hours (0.104 M), while H93 CAR-T group and UnT group with no production of CCL-19 only migrated fewer T cells even on 8 hours, 0.032 M and 0.026 M respectively. In addition, the concentration of CCL-19 in co-culture supernatant was measured by CCL-19 ELISA (Abcam #ab100601). This result indicated that the supernatant from H93M CAR-T cells co-cultured with PLC/PRF/5 cells had secretion of CCL-19 (4590.15+380.85 pg/mL) that further verify the chemotactic function of H93M CAR-T cells (FIG. 19B).

6.10. Example 10—Anti-Tumor Effect of CAR-T Cells after Adoptive Transfer In Vivo In vivo anti-tumor efficacy of CAR-T cells were evaluated in NCG mouse xenograft model. For the subcutaneous xenograft model. NCG mice aged 6-7 weeks were inoculated with Huh7 cells subcutaneously in the right foreleg ($1.5\times10^6$ cells/mouse). When the average tumor volume approached to 100 $mm^3$ (day 11 after the xenograft inoculation), mice were randomized into 6 groups and treated with H93 CAR-T cells (at 0.2 M or 0.6 M dosage). H93M CAR-T cells (at 0.2 M or 0.6 M dosage). UnT (at 2.3 M dosage, same cell number of total T cells with CAR-T groups) and solvent only (Vehicle), respectively, by tail vein injection. Tumor size was measured with digital calipers twice per week. Tumor volume was calculated according to the following formula: Tumor volume=((length)×(width)$^2$)/2. The copy number of CAR-T cells in mouse blood were also detected by digital PCR on the day 0, 7, 14, 21 and 28 after the adoptive transfer, respectively.

Figure 20A:
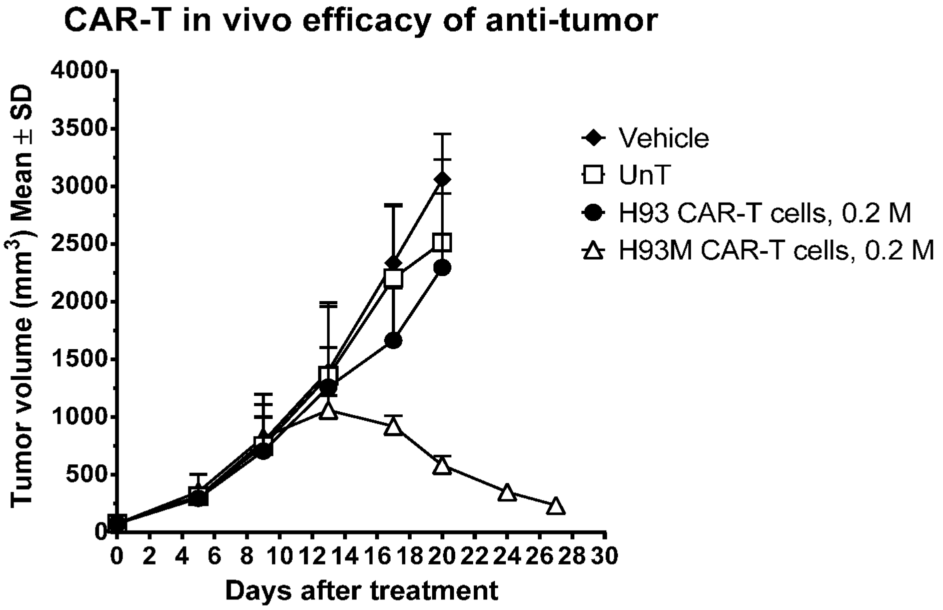
Figure 20B:
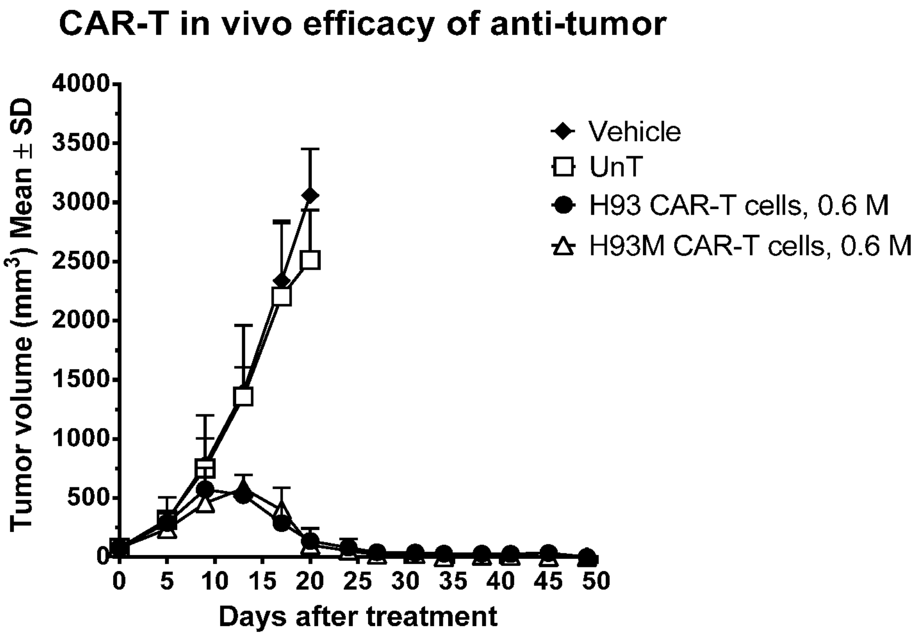

Mice treated with Vehicle. UnT and H93 CAR-T cells were sacrificed on day 20 because of animal ethics and the tumor volume of these three groups had reached more than 2000 $mm^3$. Mice treated with H93M CAR-T cells were continued to record until day 27 (dosage: 0.2 M) and day 49 (dosage: 0.6 M). As shown in FIG. 20A, compared to the UnT and H93 CAR-T cells groups, mice administered with the adoptive transfer of H93M CAR-T cells were observed to have a 76.8% and 74.6% reduction respectively in tumor size (584.3 $mm^3$ vs 2514.7 $mm^3$, 2297.3 $mm^3$) at day 20, and after day 20, the tumor size still gradually reduced, which suggested H93M CAR-T cells had better therapeutic potential than H93 CAR-T cells at lower dosage (0.2 M/mouse). When the dosage were increased to 0.6 M/mouse, as shown in FIG. 20B, administration of H93M CAR-T cells had an obvious inhibitory effect on tumor growth with a growth inhibition rate of 96.0% in comparison with UnT (101.6 $mm^3$ vs 2514.7 $mm^3$) at day 20, but similar tumor regression were observed in the H93M CAR-T cells treatment group and H93 CAR-T cells treatment group (101.6 $mm^3$ vs 137.3 $mm^3$). On day 34, the mice treated with H93M CAR-T cells had almost tumor free.

Figure 20C:
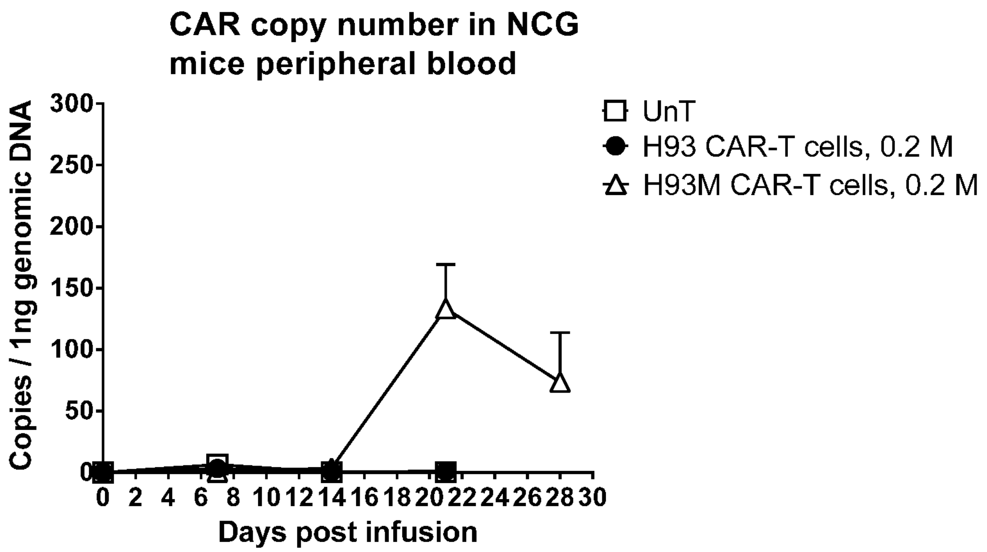
Figure 20D:
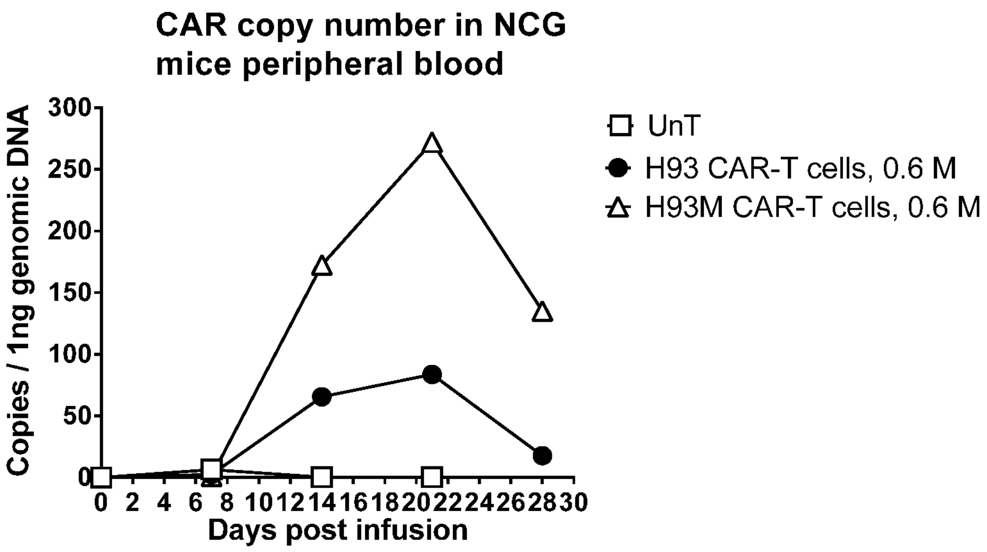

CAR gene copy number in mouse peripheral blood cells was detected by digital PCR, and H93M CAR-T cells exhibited significant expansion on day 21 and reduced subsequently at 0.2 M dosage, while there were no obvious expansion in the mice treated with H93 CAR-T cells and UnT throughout the treatment (FIG. 20C). At 0.2 M dosage, the copy number of H93M CAR-T cells at day 21 was 335.6 folds than that at day 0 (133.4175 copies vs 0.3975 copies). H93M CAR-T cells and H93 CAR-T cells both showed significant expansion after day 7 at 0.6 M dosage, and H93M CAR-T cells had a better ability of expansion than H93 CAR-T cells (272.2850) copies vs 83.6275 copies on day 21) (FIG. 20D).

No mouse bodyweight loss was observed in all the three groups whether 0.2 M dosage or 0.6 M dosage during this experiment (FIGS. 21A and 21B). But the mice treated with H93 CAR-T cells showed such symptoms as bristling, arched back and emaciation on day 20 at 0.2 M dosage, while the mice treated with H93M CAR-T cells were normal. At 0.6 M dosage, the mice of both groups had normal appearance.

Figure 22A:
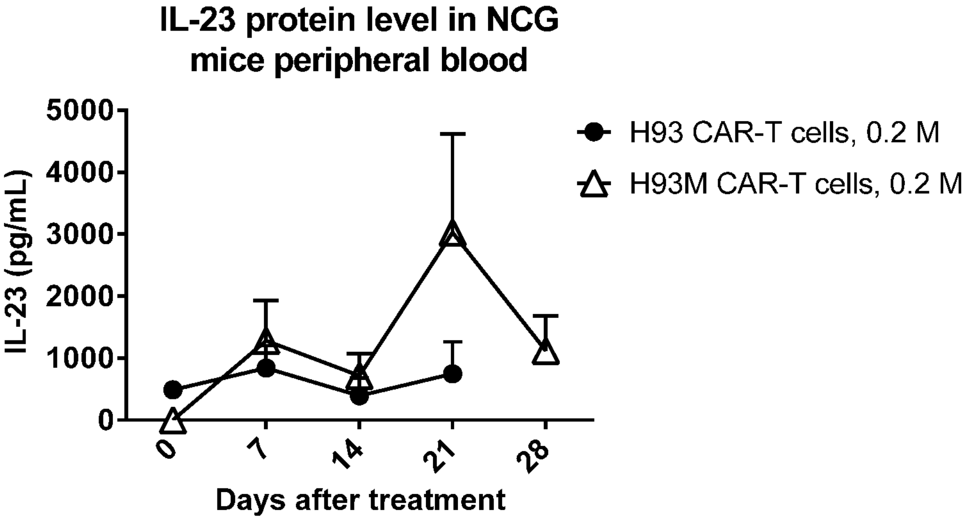
Figure 22B:
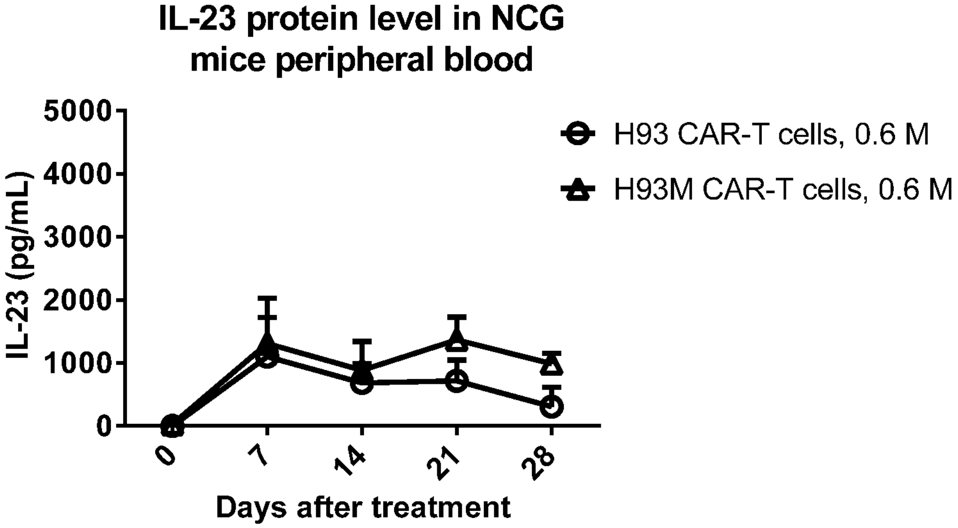
Figure 22C:
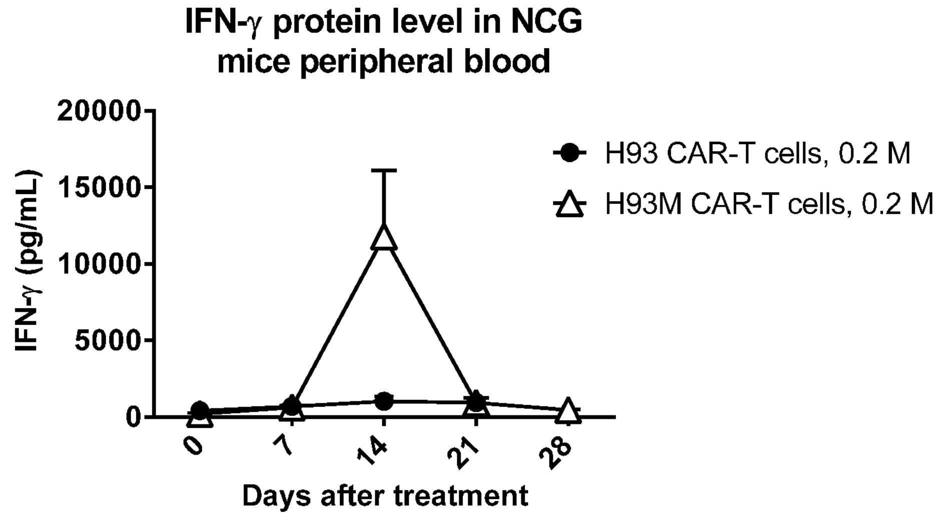
Figure 22D:
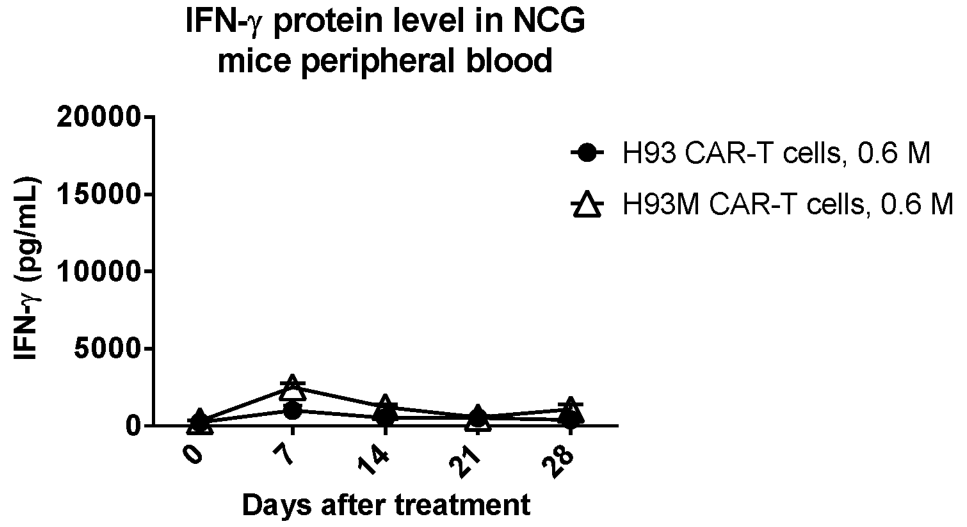

In order to verify the activation-dependent production of IL-23 in H93M CAR-T cells, the secretion level of IL-23 and IFN-γ in NCG mice peripheral blood after treated with CAR-T cells were analyzed by using human IL-23 kits (CISBIO #62HIL23PEG) and human IFN-γ kits (CISBIO #62HIFNGPEG). As shown in FIG. 22A. H93M CAR-T cells treatment group showed up to 3 folds higher secretion level of IL-23 at low dose (0.2 M, day 21), compared with H93 CAR-T cells treatment group. H93M CAR-T cells treated mice and H93 CAR-T cells treated mice at high dose (0.6 M) showed similar levels of IL-23 secretion (FIG. 22B). In parallel, the secretory behavior of IFN-γ that was activation-dependent production in mice peripheral blood were similar with IL-23 (FIGS. 22C and 22D), indicating the activation-dependent production of IL-23 in H93M CAR-T cells. To investigate the anti-tumor effects of H93M CAR-T cells in vivo.

immunohistochemistry (IHC) was used to study the infiltration of T cells and the recruitment of macrophages and dendritic cells (DCs) in the tumor site. In brief, the tissue paraffin section slides were heated at 60° C. for 60 minutes, and then dewaxed three times in xylene for 10 minutes each and rehydrated in 100%, 100%, 95%, 90%, 80%, 70% alcohols and water for 5 minutes each. The antigen retrieval were performed by boiling the slides in the antigen retrieval buffer for 20 minutes, and the slides were then treated with 3% hydrogen peroxide in methanol for 10 minutes to deprive the endogenous peroxidase activity after the slides were immersed in the antigen retrieval buffer and cooled to Room Temperature (RT). To reduce nonspecific background staining the slides were incubated with blocking buffers (5% goat serum diluted with DPBS) at 2-8° C. overnight.

After overnight, the slides were incubated at RT for 30 minutes, and then incubated with diluted primary antibody at 37° C. for 2 hours and second antibody HRP conjugated anti-mouse IgG antibody (Fuzhou Maixin Biotech. Co., Ltd. #KIT-5002) at RT for 15 minutes in the dark. The DAB substrate was prepared according to the Manufacturer's instructions, and 200-500 μL DAB substrate was added to the slides and incubate for 2 minutes in the dark. The staining were stopped by washing with distilled water for 5 minutes. Finally, the slides were added neutral balsam and mounted after counterstained with hematoxylin, differentiated in 1% hydrochloric acid alcohol and dehydrated in alcohols.

To elucidate the mechanisms of enhanced antitumor ability of H93M CAR-T cells at a lower dosage (0.2 M), T cell infiltration was investigated in tumor tissues of treated mice by IHC using TCRα (H-1) (SANTA CRUZ BIOTECHNOLOGY #sc-515719). As shown in FIG. 23, there was improved T cell infiltration into tumor sites of all three mice in the H93M CAR-T cells treatment group compared to the H93 CAR-T cells and UnT treatment groups. More T cells infiltrated into the central tumor nest in H93M CAR-T cells treatment group, while only one mouse among three H93 CAR-T cells treated mice had fewer T cell infiltration in the tumor marginal region, and other mice had very few T cells in the tumor site. In UnT treatment group, there was no T cell infiltration observed in tumor site among three mice.

In addition, macrophage and DC recruitment in tumor tissues were investigated. Anti-CD68 antibody (Abcam #ab125212) and Anti-CD11c antibody (Cell signaling technology #97585S) were used to detect mouse macrophages and DCs in tumor tissues. As shown in FIG. 24, CD68+ macrophages (left column) and CD11c+ DCs (right column) were stained by DAB. Macrophage and DC recruitment to the tumor site were significantly higher in the H93M CAR-T cells treatment group, while the UnT and H93 CAR-T cells treatment groups only had macrophage recruitment in a margin of tumor tissues. These data reveal that H93M CAR-T cells can induce more macrophage and DC recruitment in the tumor tissues compared to H93 CAR-T cells and UnT, and are more potent to elicit innate immune responses in tumor tissue.

The teachings of all patents, published applications and references cited herein are incorporated by reference in their entirety. While example embodiments have been particularly shown and described, it will be understood by those skilled in the art that various changes in form and details may be made therein without departing from the scope of the embodiments encompassed by the appended claims.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed:

1. An antibody or antigen binding fragment thereof that binds glypican-3 (GPC3), comprising an HCDR1, an HCDR2, an HCDR3, a LCDR1, a LCDR2, and a LCDR3, wherein:

(i) the HCDR1 comprises the amino acid sequence of SEQ ID NO: 1, the HCDR2 comprises the amino acid sequence of SEQ ID NO: 11, the HCDR3 comprises the amino acid sequence of SEQ ID NO: 21, the LCDR1 comprises the amino acid sequence of SEQ ID NO: 31, the LCDR2 comprises the amino acid sequence of SEQ ID NO: 41, and the LCDR3 comprises the amino acid sequence of SEQ ID NO: 51, or (ii) the HCDR1 comprises the amino acid sequence of SEQ ID NO: 2, the HCDR2 comprises the amino acid sequence of SEQ ID NO: 12, the HCDR3 comprises the amino acid sequence of SEQ ID NO: 22, the LCDR1 comprises the amino acid sequence of SEQ ID NO: 32, the LCDR2 comprises the amino acid sequence of SEQ ID NO: 42, and the LCDR3 comprises the amino acid sequence of SEQ ID NO: 52, or (iii) the HCDR1 comprises the amino acid sequence of SEQ ID NO: 3, the HCDR2 comprises the amino acid sequence of SEQ ID NO: 13, the HCDR3 comprises the amino acid sequence of SEQ ID NO: 23, the LCDR1 comprises the amino acid sequence of SEQ ID NO: 33, the LCDR2 comprises the amino acid sequence of SEQ ID NO: 43, and the LCDR3 comprises the amino acid sequence of SEQ ID NO: 53, or (iv) the HCDR1 comprises the amino acid sequence of SEQ ID NO: 4, the HCDR2 comprises the amino acid sequence of SEQ ID NO: 14, the HCDR3 comprises the amino acid sequence of SEQ ID NO: 24, the LCDR1 comprises the amino acid sequence of SEQ ID NO: 34, the LCDR2 comprises the amino acid sequence of SEQ ID NO: 44, and the LCDR3 comprises the amino acid sequence of SEQ ID NO: 54, or (v) the HCDR1 comprises the amino acid sequence of SEQ ID NO: 5, the HCDR2 comprises the amino acid sequence of SEQ ID NO: 15, the HCDR3 comprises the amino acid sequence of SEQ ID NO: 25, the LCDR1 comprises the amino acid sequence of SEQ ID NO: 35, the LCDR2 comprises the amino acid sequence of SEQ ID NO: 45, and the LCDR3 comprises the amino acid sequence of SEQ ID NO: 55, or (vi) the HCDR1 comprises the amino acid sequence of SEQ ID NO: 6, the HCDR2 comprises the amino acid sequence of SEQ ID NO: 16, the HCDR3 comprises the amino acid sequence of SEQ ID NO: 26, the LCDR1 comprises the amino acid sequence of SEQ ID NO: 36, the LCDR2 comprises the amino acid sequence of SEQ ID NO: 46, and the LCDR3 comprises the amino acid sequence of SEQ ID NO: 56, or (vii) the HCDR1 comprises the amino acid sequence of SEQ ID NO: 7, the HCDR2 comprises the amino acid sequence of SEQ ID NO: 17, the HCDR3 comprises the amino acid sequence of SEQ ID NO: 27, the LCDR1 comprises the amino acid sequence of SEQ ID NO: 37 the LCDR2 comprises the amino acid sequence of SEQ ID NO: 47, and the LCDR3 comprises the amino acid sequence of SEQ ID NO: 57, or (viii) the HCDR1 comprises the amino acid sequence of SEQ ID NO: 8, the HCDR2 comprises the amino acid sequence of SEQ ID NO: 18, the HCDR3 comprises the amino acid sequence of SEQ ID NO: 28, the LCDR1 comprises the amino acid sequence of SEQ ID NO: 38, the LCDR2 comprises the amino acid sequence of SEQ ID NO: 48, and the LCDR3 comprises the amino acid sequence of SEQ ID NO: 58, or (ix) the HCDR1 comprises the amino acid sequence of SEQ ID NO: 9, the HCDR2 comprises the amino acid sequence of SEQ ID NO: 19, the HCDR3 comprises the amino acid sequence of SEQ ID NO: 29, the LCDR1 comprises the amino acid sequence of SEQ ID NO: 39, the LCDR2 comprises the amino acid sequence of SEQ ID NO: 49, and the LCDR3 comprises the amino acid sequence of SEQ ID NO: 59, or (x) the HCDR1 comprises the amino acid sequence of SEQ ID NO: 10, the HCDR2 comprises the amino acid sequence of SEQ ID NO: 20, the HCDR3 comprises the amino acid sequence of SEQ ID NO: 30, the LCDR1 comprises the amino acid sequence of SEQ ID NO: 40, the LCDR2 comprises the amino acid sequence of SEQ ID NO: 50, and the LCDR3 comprises the amino acid sequence of SEQ ID NO: 60.

2. The antibody or antigen binding fragment of claim 1, wherein the antibody or antigen binding fragment comprises (i) a VH domain comprising an amino acid sequence having at least 80% identity to the amino acid sequence of SEQ ID NO: 61 and a VL domain comprising an amino acid sequence having at least 80% identity to the amino acid sequence of SEQ ID NO: 71, or (ii) a VH domain comprising an amino acid sequence having at least 80% identity to the amino acid sequence of SEQ ID NO: 62 and a VL domain comprising an amino acid sequence having at least 80% identity to the amino acid sequence of SEQ ID NO: 72, or (iii) a VH domain comprising an amino acid sequence having at least 80% identity to the amino acid sequence of SEQ ID NO: 63 and a VL domain comprising an amino acid sequence having at least 80% identity to the amino acid sequence of SEQ ID NO: 73, or (iv) a VH domain comprising an amino acid sequence having at least 80% identity to the amino acid sequence of SEQ ID NO: 64 and a VL domain comprising an amino acid sequence having at least 80% identity to the amino acid sequence of SEQ ID NO: 74, or (v) a VH domain comprising an amino acid sequence having at least 80% identity to the amino acid sequence of SEQ ID NO: 65 and a VL domain comprising an amino acid sequence having at least 80% identity to the amino acid sequence of SEQ ID NO: 75, or (vi) a VH domain comprising an amino acid sequence having at least 80% identity to the amino acid sequence of SEQ ID NO: 66 and a VL domain comprising an amino acid sequence having at least 80% identity to the amino acid sequence of SEQ ID NO: 76, or (vii) a VH domain comprising an amino acid sequence having at least 80% identity to the amino acid sequence of SEQ ID NO: 67 and a VL domain comprising an amino acid sequence having at least 80% identity to the amino acid sequence of SEQ ID NO: 77, or (viii) a VH domain comprising an amino acid sequence having at least 80% identity to the amino acid sequence of SEQ ID NO: 68 and a VL domain comprising an amino acid sequence having at least 80% identity to the amino acid sequence of SEQ ID NO: 78, or (ix) a VH domain comprising an amino acid sequence having at least 80% identity to the amino acid sequence of SEQ ID NO: 69 and a VL domain comprising an amino acid sequence having at least 80% identity to the amino acid sequence of SEQ ID NO: 79, or (x) a VH domain comprising an amino acid sequence having at least 80% identity to the amino acid sequence of SEQ ID NO: 70 and a VL domain comprising an amino acid sequence having at least 80% identity to the amino acid sequence of SEQ ID NO: 80, or (xi) a VH domain comprising an amino acid sequence having at least 80% identity to the amino acid sequence of SEQ ID NO: 117 and a VL domain comprising an amino acid sequence having at least 80% identity to the amino acid sequence of SEQ ID NO: 123, or (xii) a VH domain comprising an amino acid sequence having at least 80% identity to the amino acid sequence of SEQ ID NO: 118 and a VL domain comprising an amino acid sequence having at least 80% identity to the amino acid sequence of SEQ ID NO: 123, or (xiii) a VH domain comprising an amino acid sequence having at least 80% identity to the amino acid sequence of SEQ ID NO: 119 and a VL domain comprising an amino acid sequence having at least 80% identity to the amino acid sequence of SEQ ID NO: 123, or (xiv) a VH domain comprising an amino acid sequence having at least 80% identity to the amino acid sequence of SEQ ID NO: 120 and a VL domain comprising an amino acid sequence having at least 80% identity to the amino acid sequence of SEQ ID NO: 123, or (xv) a VH domain comprising an amino acid sequence having at least 80% identity to the amino acid sequence of SEQ ID NO: 121 and a VL domain comprising an amino acid sequence having at least 80% identity to the amino acid sequence of SEQ ID NO: 123, or (xvi) a VH domain comprising an amino acid sequence having at least 80% identity to the amino acid sequence of SEQ ID NO: 122 and a VL domain comprising an amino acid sequence having at least 80% identity to the amino acid sequence of SEQ ID NO: 123, or (xvii) a VH domain comprising an amino acid sequence having at least 80% identity to the amino acid sequence of SEQ ID NO: 117 and a VL domain comprising an amino acid sequence having at least 80% identity to the amino acid sequence of SEQ ID NO: 124, or (xviii) a VH domain comprising an amino acid sequence having at least 80% identity to the amino acid sequence of SEQ ID NO: 118 and a VL domain comprising an amino acid sequence having at least 80% identity to the amino acid sequence of SEQ ID NO: 124, or (xix) a VH domain comprising an amino acid sequence having at least 80% identity to the amino acid sequence of SEQ ID NO: 119 and a VL domain comprising an amino acid sequence having at least 80% identity to the amino acid sequence of SEQ ID NO: 124, or (xx) a VH domain comprising an amino acid sequence having at least 80% identity to the amino acid sequence of SEQ ID NO: 120 and a VL domain comprising an amino acid sequence having at least 80% identity to the amino acid sequence of SEQ ID NO: 124, or (xxi) a VH domain comprising an amino acid sequence having at least 80% identity to the amino acid sequence of SEQ ID NO: 121 and a VL domain comprising an amino acid sequence having at least 80% identity to the amino acid sequence of SEQ ID NO: 124, or (xxii) a VH domain comprising an amino acid sequence having at least 80% identity to the amino acid sequence of SEQ ID NO: 122 and a VL domain comprising an amino acid sequence having at least 80% identity to the amino acid sequence of SEQ ID NO: 124, or (xxiii) a VH domain comprising an amino acid sequence having at least 80% identity to the amino acid sequence of SEQ ID NO: 117 and a VL domain comprising an amino acid sequence having at least 80% identity to the amino acid sequence of SEQ ID NO: 125, or (xxiv) a VH domain comprising an amino acid sequence having at least 80% identity to the amino acid sequence of SEQ ID NO: 118 and a VL domain comprising an amino acid sequence having at least 80% identity to the amino acid sequence of SEQ ID NO: 125, or (xxv) a VH domain comprising an amino acid sequence having at least 80% identity to the amino acid sequence of SEQ ID NO: 119 and a VL domain comprising an amino acid sequence having at least 80% identity to the amino acid sequence of SEQ ID NO: 125, or (xxvi) a VH domain comprising an amino acid sequence having at least 80% identity to the amino acid sequence of SEQ ID NO: 120 and a VL domain comprising an amino acid sequence having at least 80% identity to the amino acid sequence of SEQ ID NO: 125, or (xxvii) a VH domain comprising an amino acid sequence having at least 80% identity to the amino acid sequence of SEQ ID NO: 121 and a VL domain comprising an amino acid sequence having at least 80% identity to the amino acid sequence of SEQ ID NO: 125, or (xxviii) a VH domain comprising an amino acid sequence having at least 80% identity to the amino acid sequence of SEQ ID NO: 122 and a VL domain comprising an amino acid sequence having at least 80% identity to the amino acid sequence of SEQ ID NO: 125.

3. The antibody or antigen binding fragment of claim 1, wherein the antibody or antigen binding fragment comprises (i) a VH domain comprising the amino acid sequence of SEQ ID NO: 61 and a VL domain comprising the amino acid sequence of SEQ ID NO: 71, or (ii) a VH domain comprising the amino acid sequence of SEQ ID NO: 62 and a VL domain comprising the amino acid sequence of SEQ ID NO: 72, or (iii) a VH domain comprising the amino acid sequence of SEQ ID NO: 63 and a VL domain comprising the amino acid sequence of SEQ ID NO: 73, or (iv) a VH domain comprising the amino acid sequence of SEQ ID NO: 64 and a VL domain comprising the amino acid sequence of SEQ ID NO: 74, or (v) a VH domain comprising the amino acid sequence of SEQ ID NO: 65 and a VL domain comprising the amino acid sequence of SEQ ID NO: 75, or (vi) a VH domain comprising the amino acid sequence of SEQ ID NO: 66 and a VL domain comprising the amino acid sequence of SEQ ID NO: 76, or (vii) a VH domain comprising the amino acid sequence of SEQ ID NO: 67 and a VL domain comprising the amino acid sequence of SEQ ID NO: 77, or (viii) a VH domain comprising the amino acid sequence of SEQ ID NO: 68 and a VL domain comprising the amino acid sequence of SEQ ID NO: 78, or (ix) a VH domain comprising the amino acid sequence of SEQ ID NO: 69 and a VL domain comprising the amino acid sequence of SEQ ID NO: 79, or (x) a VH domain comprising the amino acid sequence of SEQ ID NO: 70 and a VL domain comprising the amino acid sequence of SEQ ID NO: 80, or (xi) a VH domain comprising the amino acid sequence of SEQ ID NO: 117 and a VL domain comprising the amino acid sequence of SEQ ID NO: 123, or (xii) a VH domain comprising the amino acid sequence of SEQ ID NO: 118 and a VL domain comprising the amino acid sequence of SEQ ID NO: 123, or (xiii) a VH domain comprising the amino acid sequence of SEQ ID NO: 119 and a VL domain comprising the amino acid sequence of SEQ ID NO: 123, or (xiv) a VH domain comprising the amino acid sequence of SEQ ID NO: 120 and a VL domain comprising the amino acid sequence of SEQ ID NO: 123, or (xv) a VH domain comprising the amino acid sequence of SEQ ID NO: 121 and a VL domain comprising the amino acid sequence of SEQ ID NO: 123, or (xvi) a VH domain comprising the amino acid sequence of SEQ ID NO: 122 and a VL domain comprising the amino acid sequence of SEQ ID NO: 123, or (xvii) a VH domain comprising the amino acid sequence of SEQ ID NO: 117 and a VL domain comprising the amino acid sequence of SEQ ID NO: 124, or (xviii) a VH domain comprising the amino acid sequence of SEQ ID NO: 118 and a VL domain comprising the amino acid sequence of SEQ ID NO: 124, or (xix) a VH domain comprising the amino acid sequence of SEQ ID NO: 119 and a VL domain comprising the amino acid sequence of SEQ ID NO: 124, or (xx) a VH domain comprising the amino acid sequence of SEQ ID NO: 120 and a VL domain comprising the amino acid sequence of SEQ ID NO: 124, or (xxi) a VH domain comprising the amino acid sequence of SEQ ID NO: 121 and a VL domain comprising the amino acid sequence of SEQ ID NO: 124, or (xxii) a VH domain comprising the amino acid sequence of SEQ ID NO: 122 and a VL domain comprising the amino acid sequence of SEQ ID NO: 124, or (xxiii) a VH domain comprising the amino acid sequence of SEQ ID NO: 117 and a VL domain comprising the amino acid sequence of SEQ ID NO: 125, or (xxiv) a VH domain comprising the amino acid sequence of SEQ ID NO: 118 and a VL domain comprising the amino acid sequence of SEQ ID NO: 125, or (xxv) a VH domain comprising the amino acid sequence of SEQ ID NO: 119 and a VL domain comprising the amino acid sequence of SEQ ID NO: 125, or (xxvi) a VH domain comprising the amino acid sequence of SEQ ID NO: 120 and a VL domain comprising the amino acid sequence of SEQ ID NO: 125, or (xxvii) a VH domain comprising the amino acid sequence of SEQ ID NO: 121 and a VL domain comprising the amino acid sequence of SEQ ID NO: 125, or (xxviii) a VH domain comprising the amino acid sequence of SEQ ID NO: 122 and a VL domain comprising the amino acid sequence of SEQ ID NO: 125.

4. The antibody or antigen binding fragment of claim 1, wherein the antibody or antigen binding fragment is a Fab fragment, a Fab' fragment, a F(ab)'2 fragment, a single chain variable fragment (scFv), or a disulfide stabilized variable fragment (dsFv).

5. The antibody or antigen binding fragment of claim 1, comprising an amino acid sequence having at least 80% identity to any one of SEQ ID NOs: 81-90, 128, and 129.

6. A nucleic acid molecule encoding the antibody or antigen binding fragment of claim 1.

7. A vector comprising the nucleic acid molecule of claim 6.

8. A host cell transformed with the vector of claim 7.

9. A composition comprising a therapeutically effective amount of the antibody or antigen binding fragment of claim 1, and a pharmaceutically acceptable carrier.

10. A method of treating a patient who has cancer that expresses GPC3, comprising administering to the patient the composition of claim 9, wherein optionally the cancer is selected from the group consisting of hepatocellular carcinoma (HCC), melanoma, ovarian clear cell carcinoma (OCCC), yolk sac tumor (YST), neuroblastoma, hepatoblastoma, nephroblastoma (Wilms' tumor), squamous cell carcinoma of the lung, testicular nonseminomatous germ cell tumor, liposarcoma, cervical intraepithelial neoplasia, adenoma of the adrenal gland, schwannoma, embryonal tumor, gastric carcinoma, colorectal carcinoma, and thyroid cancer.

11. A method of detecting GPC3 in a tissue sample, comprising contacting the tissue sample with the antibody or antigen binding fragment of claim 1; and detecting binding of the antibody to the tissue sample, wherein an increase in binding of the antibody to the tissue sample as compared to binding of the antibody to a control sample detects GPC3 in the tissue sample.

12. A chimeric antigen receptor (CAR), comprising a polypeptide comprising:

(a) an extracellular antigen binding domain comprising the antibody or antigen binding fragment of claim 1;

(b) a transmembrane domain; and (c) an intracellular signaling domain.

13. The CAR of claim 12, comprising a polypeptide comprising (i) the amino acid sequence of SEQ ID NO: 91, or (ii) the amino acid sequence of SEQ ID NO: 92, or (iii) the amino acid sequence of SEQ ID NO: 93, or (iv) the amino acid sequence of SEQ ID NO: 94, or (v) the amino acid sequence of SEQ ID NO: 95, or (vi) the amino acid sequence of SEQ ID NO: 96, or (vii) the amino acid sequence of SEQ ID NO: 97, or (viii) the amino acid sequence of SEQ ID NO: 98, or (ix) the amino acid sequence of SEQ ID NO: 99, or (x) the amino acid sequence of SEQ ID NO: 100, or xi) the amino acid sequence of SEQ ID NO: 107, or (xii) the amino acid sequence of SEQ ID NO: 108, or (xiii) the amino acid sequence of SEQ ID NO: 109, or (xiv) the amino acid sequence of SEQ ID NO: 110, or (xv) the amino acid sequence of SEQ ID NO: 111, or (xvi) the amino acid sequence of SEQ ID NO: 112, or (xvii) the amino acid sequence of SEQ ID NO: 113, or (xviii) the amino acid sequence of SEQ ID NO: 114, or (xix) the amino acid sequence of SEQ ID NO: 115, or (xx) the amino acid sequence of SEQ ID NO: 116, or (xxi) the amino acid sequence of SEQ ID NO: 130, or (xxii) the amino acid sequence of SEQ ID NO: 131.

14. A polypeptide comprising the CAR of claim 12, wherein the polypeptide further comprises p40 subunit of IL-12 and/or CCL-19.

15. The polypeptide of claim 14, wherein p40 and CCL-19 are linked by a first self-cleaving peptide.

16. The polypeptide of claim 15, wherein the CAR is linked to the domain by a second self-cleaving peptide.

17. An immune effector cell expressing (i) the CAR of claim 12, (ii) exogenously introduced p40, and (iii) exogenously introduced CCL-19.

18. A composition comprising a therapeutically effective amount of the immune effector cell of claim 17, and a pharmaceutically acceptable carrier.

19. A method of treating a patient who has cancer that expresses GPC3, comprising administering to the patient the composition of claim 18, wherein the cancer is optionally selected from the group consisting of hepatocellular carcinoma (HCC), melanoma, ovarian clear cell carcinoma (OCCC), yolk sac tumor (YST), neuroblastoma, hepatoblastoma, nephroblastoma (Wilms' tumor), squamous cell carcinoma of the lung, adenocarcinoma of the lung, large-cell lung carcinoma, small cell lung cancer, testicular nonseminomatous germ cell tumor, liposarcoma, cervical intraepithelial neoplasia, adenoma of the adrenal gland, schwannoma, embryonal tumor, gastric carcinoma, colorectal carcinoma, thyroid cancer, and esophageal cancer.

20. A nucleic acid molecule comprising a sequence encoding the CAR of claim 12.

21. A vector comprising the nucleic acid molecule of claim 20.

22. A cell comprising the nucleic acid molecule of claim 20.

23. An antibody or antigen binding fragment thereof that binds glypican-3 (GPC3), comprising:

(i) HCDR1, HCDR2, and HCDR3 that are identical to HCDR1, HCDR2, and HCDR3 in SEQ ID NO: 61 and LCDR1, LCDR2, and LCDR3 that are identical to LCDR1, LCDR2, and LCDR3 in SEQ ID NO: 71;

(ii) HCDR1, HCDR2, and HCDR3 that are identical to HCDR1, HCDR2, and HCDR3 in SEQ ID NO: 62 and LCDR1, LCDR2, and LCDR3 that are identical to LCDR1, LCDR2, and LCDR3 in SEQ ID NO: 72;

(iii) HCDR1, HCDR2, and HCDR3 that are identical to HCDR1, HCDR2, and HCDR3 in SEQ ID NO: 63 and LCDR1, LCDR2, and LCDR3 that are identical to LCDR1, LCDR2, and LCDR3 in SEQ ID NO: 73;

(iv) HCDR1, HCDR2, and HCDR3 that are identical to HCDR1, HCDR2, and HCDR3 in SEQ ID NO: 64 and LCDR1, LCDR2, and LCDR3 that are identical to LCDR1, LCDR2, and LCDR3 in SEQ ID NO: 74;

(v) HCDR1, HCDR2, and HCDR3 that are identical to HCDR1, HCDR2, and HCDR3 in SEQ ID NO: 65 and LCDR1, LCDR2, and LCDR3 that are identical to LCDR1, LCDR2, and LCDR3 in SEQ ID NO: 75;

(vi) HCDR1, HCDR2, and HCDR3 that are identical to HCDR1, HCDR2, and HCDR3 in SEQ ID NO: 66 and LCDR1, LCDR2, and LCDR3 that are identical to LCDR1, LCDR2, and LCDR3 in SEQ ID NO: 76;

(vii) HCDR1, HCDR2, and HCDR3 that are identical to HCDR1, HCDR2, and HCDR3 in SEQ ID NO: 67 and LCDR1, LCDR2, and LCDR3 that are identical to LCDR1, LCDR2, and LCDR3 in SEQ ID NO: 77;

(viii) HCDR1, HCDR2, and HCDR3 that are identical to HCDR1, HCDR2, and HCDR3 in SEQ ID NO: 68 and LCDR1, LCDR2, and LCDR3 that are identical to LCDR1, LCDR2, and LCDR3 in SEQ ID NO: 78;

(ix) HCDR1, HCDR2, and HCDR3 that are identical to HCDR1, HCDR2, and HCDR3 in SEQ ID NO: 69 and LCDR1, LCDR2, and LCDR3 that are identical to LCDR1, LCDR2, and LCDR3 in SEQ ID NO: 79;

(x) HCDR1, HCDR2, and HCDR3 that are identical to HCDR1, HCDR2, and HCDR3 in SEQ ID NO: 70 and LCDR1, LCDR2, and LCDR3 that are identical to LCDR1, LCDR2, and LCDR3 in SEQ ID NO: 80;

(xi) HCDR1, HCDR2, and HCDR3 that are identical to HCDR1, HCDR2, and HCDR3 in SEQ ID NO: 117 and LCDR1, LCDR2, and LCDR3 that are identical to LCDR1, LCDR2, and LCDR3 in SEQ ID NO: 123;

(xii) HCDR1, HCDR2, and HCDR3 that are identical to HCDR1, HCDR2, and HCDR3 in SEQ ID NO: 118 and LCDR1, LCDR2, and LCDR3 that are identical to LCDR1, LCDR2, and LCDR3 in SEQ ID NO: 123;

(xiii) HCDR1, HCDR2, and HCDR3 that are identical to HCDR1, HCDR2, and HCDR3 in SEQ ID NO: 119 and LCDR1, LCDR2, and LCDR3 that are identical to LCDR1, LCDR2, and LCDR3 in SEQ ID NO: 123;

(xiv) HCDR1, HCDR2, and HCDR3 that are identical to HCDR1, HCDR2, and HCDR3 in SEQ ID NO: 120 and LCDR1, LCDR2, and LCDR3 that are identical to LCDR1, LCDR2, and LCDR3 in SEQ ID NO: 123;

(xv) HCDR1, HCDR2, and HCDR3 that are identical to HCDR1, HCDR2, and HCDR3 in SEQ ID NO: 121 and LCDR1, LCDR2, and LCDR3 that are identical to LCDR1, LCDR2, and LCDR3 in SEQ ID NO: 123;

(xvi) HCDR1, HCDR2, and HCDR3 that are identical to HCDR1, HCDR2, and HCDR3 in SEQ ID NO: 122 and LCDR1, LCDR2, and LCDR3 that are identical to LCDR1, LCDR2, and LCDR3 in SEQ ID NO: 123;

(xvii) HCDR1, HCDR2, and HCDR3 that are identical to HCDR1, HCDR2, and HCDR3 in SEQ ID NO: 117 and LCDR1, LCDR2, and LCDR3 that are identical to LCDR1, LCDR2, and LCDR3 in SEQ ID NO: 124;

(xviii) HCDR1, HCDR2, and HCDR3 that are identical to HCDR1, HCDR2, and HCDR3 in SEQ ID NO: 118 and LCDR1, LCDR2, and LCDR3 that are identical to LCDR1, LCDR2, and LCDR3 in SEQ ID NO: 124;

(xix) HCDR1, HCDR2, and HCDR3 that are identical to HCDR1, HCDR2, and HCDR3 in SEQ ID NO: 119 and LCDR1, LCDR2, and LCDR3 that are identical to LCDR1, LCDR2, and LCDR3 in SEQ ID NO: 124;

(xx) HCDR1, HCDR2, and HCDR3 that are identical to HCDR1, HCDR2, and HCDR3 in SEQ ID NO: 120 and LCDR1, LCDR2, and LCDR3 that are identical to LCDR1, LCDR2, and LCDR3 in SEQ ID NO: 124;

(xxi) HCDR1, HCDR2, and HCDR3 that are identical to HCDR1, HCDR2, and HCDR3 in SEQ ID NO: 121 and LCDR1, LCDR2, and LCDR3 that are identical to LCDR1, LCDR2, and LCDR3 in SEQ ID NO: 124;

(xxii) HCDR1, HCDR2, and HCDR3 that are identical to HCDR1, HCDR2, and HCDR3 in SEQ ID NO: 122 and LCDR1, LCDR2, and LCDR3 that are identical to LCDR1, LCDR2, and LCDR3 in SEQ ID NO: 124;

(xxiii) HCDR1, HCDR2, and HCDR3 that are identical to HCDR1, HCDR2, and HCDR3 in SEQ ID NO: 117 and LCDR1, LCDR2, and LCDR3 that are identical to LCDR1, LCDR2, and LCDR3 in SEQ ID NO: 125;

(xxiv) HCDR1, HCDR2, and HCDR3 that are identical to HCDR1, HCDR2, and HCDR3 in SEQ ID NO: 118 and LCDR1, LCDR2, and LCDR3 that are identical to LCDR1, LCDR2, and LCDR3 in SEQ ID NO: 125;

(xxv) HCDR1, HCDR2, and HCDR3 that are identical to HCDR1, HCDR2, and HCDR3 in SEQ ID NO: 119 and LCDR1, LCDR2, and LCDR3 that are identical to LCDR1, LCDR2, and LCDR3 in SEQ ID NO: 125;

(xxvi) HCDR1, HCDR2, and HCDR3 that are identical to HCDR1, HCDR2, and HCDR3 in SEQ ID NO: 120 and LCDR1, LCDR2, and LCDR3 that are identical to LCDR1, LCDR2, and LCDR3 in SEQ ID NO: 125;

(xxvii) HCDR1, HCDR2, and HCDR3 that are identical to HCDR1, HCDR2, and HCDR3 in SEQ ID NO: 121 and LCDR1, LCDR2, and LCDR3 that are identical to LCDR1, LCDR2, and LCDR3 in SEQ ID NO: 125; or (xxviii) HCDR1, HCDR2, and HCDR3 that are identical to HCDR1, HCDR2, and HCDR3 in SEQ ID NO: 122 and LCDR1, LCDR2, and LCDR3 that are identical to LCDR1, LCDR2, and LCDR3 in SEQ ID NO: 125;

wherein the CDR sequences are determined according to IMGT numbering, Kabat numbering, AbM numbering, Chothia numbering, or Contact numbering.

* * * * *